US007183403B2

(12) United States Patent
Hirano et al.

(10) Patent No.: US 7,183,403 B2
(45) Date of Patent: Feb. 27, 2007

(54) GENES FOR HEAT RESISTANT ENZYMES OF AMINO ACID BIOSYNTHETIC PATHWAY DERIVED FROM THERMOPHILIC CORYNEFORM BACTERIA

(75) Inventors: Seiko Hirano, Kawasaki (JP); Eiichiro Kimura, Kawasaki (JP); Tsuyoshi Osumi, Kawasaki (JP); Kazuhiko Matsui, Kawasaki (JP); Yoshio Kawahara, Kawasaki (JP); Gen Nonaka, Kawasaki (JP); Yumi Matsuzaki, Kawasaki (JP); Naoki Akiyoshi, Kawasaki (JP); Kanae Nakamura, Ho Chiminh (VN); Osamu Kurahashi, Kawasaki (JP); Tsuyoshi Nakamatsu, Tokyo (JP); Shinichi Sugimoto, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 11/073,560

(22) Filed: Mar. 8, 2005

(65) Prior Publication Data

US 2005/0239176 A1 Oct. 27, 2005

Related U.S. Application Data

(62) Division of application No. 10/089,057, filed as application No. PCT/JP00/06913 on Oct. 4, 2000, now Pat. No. 6,995,250.

(30) Foreign Application Priority Data

Oct. 4, 1999 (JP) ................................ 11-282716
Nov. 1, 1999 (JP) ................................ 11-311147
Apr. 21, 2000 (JP) ............................ 2000-120687

(51) Int. Cl.
*C07H 21/04* (2006.01)
*C12P 21/06* (2006.01)

(52) U.S. Cl. .................................... 536/23.7; 435/69.1

(58) Field of Classification Search ............... 536/23.7; 435/69.1
See application file for complete search history.

(56) References Cited

U.S. PATENT DOCUMENTS

| | | | | |
|---|---|---|---|---|
| 5,250,423 | A | 10/1993 | Murakami et al. | |
| 5,250,434 | A | 10/1993 | Yamada et al. | |
| 6,696,561 | B1 * | 2/2004 | Pompejus et al. | 536/23.7 |

FOREIGN PATENT DOCUMENTS

| | | |
|---|---|---|
| AU | 616168 | 2/1988 |
| JP | 61-268185 | 11/1986 |
| JP | 63-119688 | 5/1988 |
| JP | 63-214189 | 9/1988 |
| JP | 2-291276 | 4/1990 |
| JP | 4-4887 | 1/1992 |
| JP | 5-56782 | 3/1993 |
| JP | 5-244958 | 9/1993 |
| JP | 6-504548 | 3/1994 |
| JP | 7-63383 | 7/1995 |
| JP | 7-121227 | 12/1995 |
| JP | 8-66189 | 3/1996 |
| JP | 8-196280 | 8/1996 |
| JP | 10-165180 | 6/1998 |
| JP | 10-234371 | 9/1998 |
| JP | 11-196887 | 7/1999 |
| WO | 92/18635 | 10/1992 |
| WO | 94/08016 | 4/1994 |
| WO | 95/23224 | 8/1995 |
| WO | 95/34672 | 12/1995 |
| WO | 96/32484 | 10/1996 |
| WO | 97/48790 | 12/1997 |
| WO | 99/18228 | 4/1999 |

OTHER PUBLICATIONS

K. Takai, et al., "PPC, The Gene for Phosphoenolpyruvate Carboxylase From an Extremely Thermophilic Bacterium, Rhodothermus Obamensis: Cloning, Sequencing and Overexpression in *Escherichia coli*", Microbiology, vol. 144, No. 5, pp. 1423-1434, 1989.

D. Wereecke, et al., "Cloning and Sequence Analysis of the Gene Encoding Isocitrate Lyase From Rhodococcus Fascians", Gene, vol. 145, No. 1, pp. 109-114, 1994.

W. Jager, et al., "A Corynebacterium Glutamicum Gene Encoding a Two-Domain Protein Similar to Biotin Carboxylases and Biotin-Carboxyl-Carrier Proteins", Arch. Microbiol., vol. 166, No. 2, pp. 977-984, 1996.

S. Donadio. et al., "Erythromycin Production in Saccharopolyspora Erythraea Does Not Require a Functional Propionyl-COA Carboxylase", Mol. Microbiol., vol. 19, pp. 977-984, 1996.

E. Kumura, et al., "Molecular Cloning of a Novel Gene, DTSR, Which Rescues the Detergent Sensitivity of a Mutant Derived From Brevibacterium Lactofermentum", Biosci. Biotechnol. Biochem., vol. 60, pp. 1565-1570, 1996.

(Continued)

*Primary Examiner*—Mark Navarro
(74) *Attorney, Agent, or Firm*—Oblon, Spivak, McClelland, Maier & Neustadt, P.C.

(57) ABSTRACT

A plurality of primer sets are designed based on a region where conservation at the amino acid level is observed among various microorganisms for known gene sequences corresponding to a gene coding for an enzyme of the L-amino acid biosynthetic pathway derived from *Corynebacterium thermoaminogenes*, preferably an enzyme that functions at a higher temperature compared with that of *Corynebacterium glutamicum*. PCR is performed by using the primers and chromosomal DNA of *Corynebacterium thermoaminogenes* as a template. The primers with which an amplification fragment has been obtained are used as primers for screening to select a clone containing a target DNA fragment from a plasmid library of chromosomal DNA of *Corynebacterium thermoaminogenes*.

21 Claims, 15 Drawing Sheets

OTHER PUBLICATIONS

A.M. Alves, et al., "Characterization and Phylogeny of the PFP Gene of Amycolatopsis Methanolica Encoding PPI-Dependent Phosphofructokinase", J. Bacteriol., vol. 178, pp. 149-155, 1996.

A.M.C.R. Alves, et al., "Identification of ATP-Dependent Phosphofructokinase as a Regulatory Step in the Glycolytic Pathway of the Acnomycete Streptomyces Coelicolor", Appl. Environ. Microbiol., vol. 63, pp. 951-956, 1997.

W. Kronemeyer, et al., "Structure of the Gluabcd Cluster Encoding the Glutamate Uptake System of Corynebacterium Glutamicum", J. Bacteriol., vol. 177, pp. 1152-1158, 1995.

C. Rollin, et al, "13C-NMR Studies of Corynebacterium Melassecola Metabolic Pathways", Eur. J. Biochem., vol. 227, No. 1-2, pp. 488-493, 1995.

S.Hein, et al., "Biochemical and Molecular Characterization of the Alcaligenes Eutrophus Pyruvate Dehydrogenase Complex and Identification of New Type of Dihydrolipoamide Dehydrogenase", J. Bacteriol., vol. 176, pp. 4394-4408, 1994.

P.E. Stephens, et al., "The Pyruvate Dehydrogenase Complex of *Escherichia coli* K12. Nucleotide Sequence Encoding the Pyruvate Dehydrogenase Component", Euro. J. Biochem., vol. 133, pp. 155-162, 1983.

M.P. Ruklish, et al., "The Functioning of the Tricarboxylic Acid Cycle in Brevibacterium Flavum and Micrococcus Glutamicus", Mikrobiologia, vol. 56, No. 5, pp. 759-763, 1987.

J.M. Mengaud, et al., "The Major Iron-Containing Protein of Legionella Pneumophila is an Aconitase Homologous With the Human Iron-Responsive Element-Binding Protein", J. Bacteriol., vol. 175, pp. 5666-5676, 1993.

C. Prodromou, et al., "The Aconitase of *Escherichia coli.* Nucleotide Sequence of the Aconitase Gene and Amino Sequence Similarity With Mitochondrial Isopropylmalate Isomerases", Eur. J. Biochem., vol. 204, pp. 599-609, 1992.

B.J. Eikmanns, et al., "Cloning, Sequence Analysis, Expression, and Inactivation of the Corynebacterium Glutamicum ICD Gene Encoding Isocitrate Dehydrogenase and Biochemical Characterization of the Enzyme", J. Bacteriol., vol. 177, pp. 774-782, 1993.

A. Ishi, et al., "Genes Encoding Two Isocitrate Dehydrogenase Isozymes of a Psychrophilic Bacterium, Vinrio sp. Strain Abe-1", J. Bacteriol., vol. 175, pp. 6873-6880, 1993.

B.J. Eikmanns, et al., "Corynebacterium Glutamicum LPD Gene, Complete CDS", Genbank Acc. No. Y16642, Feb. 1, 1999.

E.R. Boermann, et al., "Molecular Analysis of the Corynebacterium Glutamicum GDH Gene Encoding Glutmade Dehydrogenase", Mol. Microbiol., vol. 6, pp. 317-326, 1992.

B.J. Eikmanns, et al., "Nucleotide Sequence, Expression and Transcriptional Analysis of the Corynebacterium Glutamicum GLTA Gene Encoding Citrate Syntase", Microbiology, vol. 140, pp. 1817-1828, 1994.

M.A. Pardo, et al., "Nodulationg Ability of Rhizobium Tropici is Conditioned by Plasmid-Encoded Citrate Syntase", Mol. Microbil., vol. 11, pp. 315-321, 1994.

D.J. Reinscheid, et al., "Characterization of the Isocitrate Lyase Gene From Corynebacterium Glutamicum and Biochemical Analysis of the Enzyme", Journal of Bacteriology, vol. 176, No. 12, XP-009014047, pp. 3474-3483, Jun. 1994.

R.M. Chell, et al., "Isolation and Characterization of Isocitrate Lyase From a Thermophilic Bacillus sp", Biochemical Journal, vol. 173, No. 1, XP-001156125, pp. 165-177, 1978.

J.M. Muir, et al., "Citrate Synthase From the Hyperthermophilic Archaeon, Pyrocococcus Furiosus", Protein Engineering, vol. 8, No. 6, XP-009020603, pp. 583-892, 1995.

K.L. Britton, et al., "Insights into Thermal Stability From a Comparison of the Glutamate Dehydrogenases From Pyrococcus Furiosus and the Thermococcus Litoralis", European Journal of Biochemistry, vol. 229, No. 3, XP-009027920, pp. 688-695, 1995.

J.H.G. Lebbink, et al., "Glutamate Dehydrogenase From Hyperthermophilic Bacteria and Archaea: Determinants of Thermostability and Catalysis at Extremely High Temperatures", Journal of Molecular Catalysis B: Enzymatic, vol. 7, No. 1-4, XP-001180258, pp. 133-145, Sep. 15, 1999.

Rudinger (Peptide Hormones, University Park Press, Jun. 1976, pp. 1-7).

Y. Usuda, et al., "Molecular Cloning of the Corynebacterium Glutamicum ('Brevibacterium Lactofermentum' AJ12036) ODHA Gene Encoding a Novel Type of 2-Oxoglutarate Dehydrogenase", Microbiology, 1996, 142, pp. 3347-3354.

Kawarabayasi, Y., et al., " Complete Genome Sequence of an Aerobic Hyper-thermophilic Crenarchaeon, Aeropyrum pernix K1," DNA Research 6, pp. 83-101, 1999, XP-002395273.

Sutherland, K. J., et al., "Citrate Synthase from the Thermophilic Archaebacterium Thermoplasma acidophilium Cloning and Sequencing of the Gene," European Journal of Biochemistry, vol. 194, No. 3, 1990, pp. 839-844, XP002395031.

* cited by examiner (a)

(b)

SEQUENCE LISTING

<160> NUMBER OF SEQ ID NOS: 129

<210> SEQ ID NO 1
<211> LENGTH: 1980
<212> TYPE: DNA
<213> ORGANISM: Corynebacterium thermoaminogenes
<220> FEATURE:
<221> NAME/KEY: CDS
<222> LOCATION: (577)..(1869)
<223> OTHER INFORMATION:

-continued

<400> SEQUENCE: 1

```
tgcattccac cgacggtcac gcgttcggtc ttgtcagcgg cgtcaatctg ctgatggttc      60

atgcaaagct ccttcgaagc aagagatcgg gtgtgtgcgg gcacctatcg ggggaagccc     120

tcgctgcgcc ccagggggag ctggcgatgt gaccaggtta agtgataacc atcaccttgc     180

caatgggttt gcgaacttta ccgtgacgct acccccgctt ttgtttgatc acaccagctc     240

gaaggctgtc gcttttccga agatgcacgt gaagtggcaa atccttgcca cccgaggttt     300

tcccagtaca aacgtactag tgatgaggat cacggggaac attgtggaga ttgcactttg     360

caatatttgc aaaaggggtg actacccccg cgcaaaactt aaaaacccaa atccgttgac     420

ggacccatgc ccgatgaagc aatgtgtgaa gcacgccacc ggaacacagg ttgtggatca     480

ctcaccatga tgtgggggat tcgcatcaca cagtgtgcag ggcggcacct ctaccgaatg     540

cgccttacag cagcaccaag aagaagtgac tcttag atg tca aac gtt gga acg       594
                                        Met Ser Asn Val Gly Thr
                                        1               5

cca cgt acc gca cag gaa atc cag cag gat tgg gac acc aac cca cgc       642
Pro Arg Thr Ala Gln Glu Ile Gln Gln Asp Trp Asp Thr Asn Pro Arg
            10                  15                  20

tgg aac gga atc acc cgc gac tac acc gct gag cag gta gct gag ctc       690
Trp Asn Gly Ile Thr Arg Asp Tyr Thr Ala Glu Gln Val Ala Glu Leu
        25                  30                  35

cag ggc agc gtc gtc gag gag cac acc ctc gca aag cgc ggc gcc gag       738
Gln Gly Ser Val Val Glu Glu His Thr Leu Ala Lys Arg Gly Ala Glu
    40                  45                  50

atc ctg tgg gat gca gtt tcc gca gag ggc gac gac tac atc aac gca       786
Ile Leu Trp Asp Ala Val Ser Ala Glu Gly Asp Asp Tyr Ile Asn Ala
55                  60                  65                  70

ctg ggc gcc ctt acc ggt aac cag gct gtc cag cag gtc cgt gcc ggc       834
Leu Gly Ala Leu Thr Gly Asn Gln Ala Val Gln Gln Val Arg Ala Gly
                75                  80                  85

ctg aag gct gtc tac ctc tcc ggc tgg cag gtc gca ggt gac gcc aac       882
Leu Lys Ala Val Tyr Leu Ser Gly Trp Gln Val Ala Gly Asp Ala Asn
            90                  95                  100

ctc gcc ggt cac acc tac ccc gac cag tcc ctg tac ccg gcg aac tcc       930
Leu Ala Gly His Thr Tyr Pro Asp Gln Ser Leu Tyr Pro Ala Asn Ser
        105                 110                 115

gtc ccg aac gtt gtc cgt cgc atc aac aac gca ctg ctg cgc gcc gat       978
Val Pro Asn Val Val Arg Arg Ile Asn Asn Ala Leu Leu Arg Ala Asp
    120                 125                 130

gag atc gca cgc gtc gag ggt gac acc tcc gtc gac aac tgg ctc gtc      1026
Glu Ile Ala Arg Val Glu Gly Asp Thr Ser Val Asp Asn Trp Leu Val
135                 140                 145                 150

ccg atc gtc gcc gac ggc gag gcc ggc ttc ggt ggc gcc ctc aac gtc      1074
Pro Ile Val Ala Asp Gly Glu Ala Gly Phe Gly Gly Ala Leu Asn Val
                155                 160                 165

tac gag ctc cag aag ggc atg atc acc gct ggt gcc gca ggc acc cac      1122
Tyr Glu Leu Gln Lys Gly Met Ile Thr Ala Gly Ala Ala Gly Thr His
            170                 175                 180

tgg gag gat cag ctc gct tcc gag aag aag tgt ggc cac ctc ggt ggc      1170
Trp Glu Asp Gln Leu Ala Ser Glu Lys Lys Cys Gly His Leu Gly Gly
        185                 190                 195

aag gtc ctc atc ccg acc cag cag cac atc cgc acc ctg aac tcc gcc      1218
Lys Val Leu Ile Pro Thr Gln Gln His Ile Arg Thr Leu Asn Ser Ala
    200                 205                 210

cgc ctg gca gct gac gtg gcc aac acc ccg acc gtc gtc atc gcc cgc      1266
Arg Leu Ala Ala Asp Val Ala Asn Thr Pro Thr Val Val Ile Ala Arg
215                 220                 225                 230
```

-continued

```
acc gac gca gag gcc gcc acc ctg atc acc tct gat gtt gat gag cgc      1314
Thr Asp Ala Glu Ala Ala Thr Leu Ile Thr Ser Asp Val Asp Glu Arg
                235                 240                 245

gac cgc cca ttc atc acc ggc gag cgc acc gcc gag ggc tac tac cac      1362
Asp Arg Pro Phe Ile Thr Gly Glu Arg Thr Ala Glu Gly Tyr Tyr His
            250                 255                 260

gtc aag ccg ggt ctc gag ccc tgc atc gca cgt gcg aag tcc tac gct      1410
Val Lys Pro Gly Leu Glu Pro Cys Ile Ala Arg Ala Lys Ser Tyr Ala
        265                 270                 275

ccc tac gca gac atg atc tgg atg gag acc ggc acc cct gac ctc gag      1458
Pro Tyr Ala Asp Met Ile Trp Met Glu Thr Gly Thr Pro Asp Leu Glu
    280                 285                 290

ctg gcc aag aag ttc gcc gag ggc gtc cgc agc gag ttc ccg gac cag      1506
Leu Ala Lys Lys Phe Ala Glu Gly Val Arg Ser Glu Phe Pro Asp Gln
295                 300                 305                 310

ctg ctg tcc tac aac tgc tcc ccg tcc ttc aac tgg tct gca cac ctc      1554
Leu Leu Ser Tyr Asn Cys Ser Pro Ser Phe Asn Trp Ser Ala His Leu
                315                 320                 325

gag gcc gac gag atc gct aag ttc cag aag gaa ctg ggt gcc atg ggc      1602
Glu Ala Asp Glu Ile Ala Lys Phe Gln Lys Glu Leu Gly Ala Met Gly
            330                 335                 340

ttc aag ttc cag ttc atc acc ctg gct ggc ttc cac tcc ctc aac tac      1650
Phe Lys Phe Gln Phe Ile Thr Leu Ala Gly Phe His Ser Leu Asn Tyr
        345                 350                 355

ggt atg ttc gac ctg gct tac ggc tac gcc cgt gaa ggc atg ccc gcc      1698
Gly Met Phe Asp Leu Ala Tyr Gly Tyr Ala Arg Glu Gly Met Pro Ala
    360                 365                 370

ttc gtc gac ctg cag aac cgt gag ttc aag gca gct gag gag cgc ggc      1746
Phe Val Asp Leu Gln Asn Arg Glu Phe Lys Ala Ala Glu Glu Arg Gly
375                 380                 385                 390

ttc acc gcc gtc aag cac cag cgt gag gtc ggc gcc ggc tac ttc gac      1794
Phe Thr Ala Val Lys His Gln Arg Glu Val Gly Ala Gly Tyr Phe Asp
                395                 400                 405

acc atc gcc acc acc gtt gac ccg aac tcc tcc acc acc gcg ctg aag      1842
Thr Ile Ala Thr Thr Val Asp Pro Asn Ser Ser Thr Thr Ala Leu Lys
            410                 415                 420

ggt tcc acc gag gaa tgc cag ttc cac taggaaccac ctgatgcggt           1889
Gly Ser Thr Glu Glu Cys Gln Phe His
        425                 430

gccgtatggc ctgacggcac cgcccctccc tttgcactcc agtactcctt tgtgcacatc   1949

ggccatctcc acaccgcgcg ccccgccacc t                                  1980


<210> SEQ ID NO 2
<211> LENGTH: 431
<212> TYPE: PRT
<213> ORGANISM: Corynebacterium thermoaminogenes

<400> SEQUENCE: 2

Met Ser Asn Val Gly Thr Pro Arg Thr Ala Gln Glu Ile Gln Gln Asp
1               5                   10                  15

Trp Asp Thr Asn Pro Arg Trp Asn Gly Ile Thr Arg Asp Tyr Thr Ala
            20                  25                  30

Glu Gln Val Ala Glu Leu Gln Gly Ser Val Val Glu Glu His Thr Leu
        35                  40                  45

Ala Lys Arg Gly Ala Glu Ile Leu Trp Asp Ala Val Ser Ala Glu Gly
    50                  55                  60

Asp Asp Tyr Ile Asn Ala Leu Gly Ala Leu Thr Gly Asn Gln Ala Val
65                  70                  75                  80
```

```
Gln Gln Val Arg Ala Gly Leu Lys Ala Val Tyr Leu Ser Gly Trp Gln
                85                  90                  95

Val Ala Gly Asp Ala Asn Leu Ala Gly His Thr Tyr Pro Asp Gln Ser
            100                 105                 110

Leu Tyr Pro Ala Asn Ser Val Pro Asn Val Val Arg Arg Ile Asn Asn
        115                 120                 125

Ala Leu Leu Arg Ala Asp Glu Ile Ala Arg Val Glu Gly Asp Thr Ser
    130                 135                 140

Val Asp Asn Trp Leu Val Pro Ile Val Ala Asp Gly Glu Ala Gly Phe
145                 150                 155                 160

Gly Gly Ala Leu Asn Val Tyr Glu Leu Gln Lys Gly Met Ile Thr Ala
                165                 170                 175

Gly Ala Ala Gly Thr His Trp Glu Asp Gln Leu Ala Ser Glu Lys Lys
            180                 185                 190

Cys Gly His Leu Gly Gly Lys Val Leu Ile Pro Thr Gln Gln His Ile
        195                 200                 205

Arg Thr Leu Asn Ser Ala Arg Leu Ala Ala Asp Val Ala Asn Thr Pro
    210                 215                 220

Thr Val Val Ile Ala Arg Thr Asp Ala Glu Ala Ala Thr Leu Ile Thr
225                 230                 235                 240

Ser Asp Val Asp Glu Arg Asp Arg Pro Phe Ile Thr Gly Glu Arg Thr
                245                 250                 255

Ala Glu Gly Tyr Tyr His Val Lys Pro Gly Leu Glu Pro Cys Ile Ala
            260                 265                 270

Arg Ala Lys Ser Tyr Ala Pro Tyr Ala Asp Met Ile Trp Met Glu Thr
        275                 280                 285

Gly Thr Pro Asp Leu Glu Leu Ala Lys Lys Phe Ala Glu Gly Val Arg
    290                 295                 300

Ser Glu Phe Pro Asp Gln Leu Leu Ser Tyr Asn Cys Ser Pro Ser Phe
305                 310                 315                 320

Asn Trp Ser Ala His Leu Glu Ala Asp Glu Ile Ala Lys Phe Gln Lys
                325                 330                 335

Glu Leu Gly Ala Met Gly Phe Lys Phe Gln Phe Ile Thr Leu Ala Gly
            340                 345                 350

Phe His Ser Leu Asn Tyr Gly Met Phe Asp Leu Ala Tyr Gly Tyr Ala
        355                 360                 365

Arg Glu Gly Met Pro Ala Phe Val Asp Leu Gln Asn Arg Glu Phe Lys
    370                 375                 380

Ala Ala Glu Glu Arg Gly Phe Thr Ala Val Lys His Gln Arg Glu Val
385                 390                 395                 400

Gly Ala Gly Tyr Phe Asp Thr Ile Ala Thr Thr Val Asp Pro Asn Ser
                405                 410                 415

Ser Thr Thr Ala Leu Lys Gly Ser Thr Glu Glu Cys Gln Phe His
            420                 425                 430
```

<210> SEQ ID NO 3
<211> LENGTH: 2381
<212> TYPE: DNA
<213> ORGANISM: Corynebacterium thermoaminogenes
<220> FEATURE:
<221> NAME/KEY: CDS
<222> LOCATION: (577)..(2349)
<223> OTHER INFORMATION:

<400> SEQUENCE: 3

-continued

```
agcaggccgt gttgccgaac ggcaacttcc gcagccgcaa ggagatcgag gaggtgtact     60

cgcacctcaa ccctgccgag gacaccgtgg tgtactgccg cgtgggtgac cgcgcggccc    120

acacctggtt cgtgttgaag tacctgctgg ggtttgaaaa cgtccgcaac tatgacggtt    180

cctggtccga gtggggcaac atggtgcgca tgcccatcgt ccagggtgat gagccgggct    240

cactctagtc accccggggt cacctccctg gtcacccccg taccctcccg ggtacacccc    300

ggggacgggg tgtgacctgg atctcccctg catgtggaca ccgggaaact ttgcctggga    360

aatgaccatc cagtaccgta atgcgggtat gttaacgcgg tcacagggta caccagaatc    420

cggatcgtct aacccccttta gcgggattcg ctaaaagatc accgagttag tgtgcaagaa    480

taatgctgat cgcaggggca ctgtcatacg ctgtcatgca gtcaatgaac agtgcggtgc    540

tctgtcgtga agaaaatcaa aaccaggagg gtttta gtg tca gtc gag acc agg      594
                                        Val Ser Val Glu Thr Arg
                                        1               5

aag atc acc aag gta ctt gtc gcc aac cgt ggt gaa atc gca atc cgt      642
Lys Ile Thr Lys Val Leu Val Ala Asn Arg Gly Glu Ile Ala Ile Arg
            10                  15                  20

gtt ttc cgc gca gca cgg gat gaa ggc atc gcc tct gtc gcc gtc tac      690
Val Phe Arg Ala Ala Arg Asp Glu Gly Ile Ala Ser Val Ala Val Tyr
        25                  30                  35

gcg gag ccg gac gca gat gcc cct ttc gtc gag tat gcc gat gag gcc      738
Ala Glu Pro Asp Ala Asp Ala Pro Phe Val Glu Tyr Ala Asp Glu Ala
    40                  45                  50

ttc gca ctc ggt ggc cag act tcc gca gag tcc tac ctc gtc att gac      786
Phe Ala Leu Gly Gly Gln Thr Ser Ala Glu Ser Tyr Leu Val Ile Asp
55                  60                  65                  70

aag atc att gac gca gca cgc aag tcc ggt gca gac gct gtc cac ccc      834
Lys Ile Ile Asp Ala Ala Arg Lys Ser Gly Ala Asp Ala Val His Pro
                75                  80                  85

ggc tac ggc ttc ctc gcc gag aac gcc gat ttc gct gaa gct gtc atc      882
Gly Tyr Gly Phe Leu Ala Glu Asn Ala Asp Phe Ala Glu Ala Val Ile
            90                  95                  100

aac gag ggc ctg atc tgg atc gga cca tcc cct gag tcc atc cgt tcc      930
Asn Glu Gly Leu Ile Trp Ile Gly Pro Ser Pro Glu Ser Ile Arg Ser
        105                 110                 115

ctc ggt gac aag gtc acc gca cgc cac atc gcc aac aac gcc aac gca      978
Leu Gly Asp Lys Val Thr Ala Arg His Ile Ala Asn Asn Ala Asn Ala
    120                 125                 130

ccg atg gca ccg ggc acc aag gag cct gtc aag gac gcc gct gag gtt     1026
Pro Met Ala Pro Gly Thr Lys Glu Pro Val Lys Asp Ala Ala Glu Val
135                 140                 145                 150

gtc gcc ttc gcc gag gag ttc ggt ctc ccc atc gcc atc aag gct gcc     1074
Val Ala Phe Ala Glu Glu Phe Gly Leu Pro Ile Ala Ile Lys Ala Ala
                155                 160                 165

ttc ggt ggc ggc gga cgt ggc atg aag gtc gcc tac gag atg gac gag     1122
Phe Gly Gly Gly Gly Arg Gly Met Lys Val Ala Tyr Glu Met Asp Glu
            170                 175                 180

gtc gcc gac ctc ttc gaa tcc gcc acc cgt gag gcc acc gcc gcc ttc     1170
Val Ala Asp Leu Phe Glu Ser Ala Thr Arg Glu Ala Thr Ala Ala Phe
        185                 190                 195

ggt cgt ggt gag tgc ttc gtg gag cgc tac ctg gac aag gcc cgc cac     1218
Gly Arg Gly Glu Cys Phe Val Glu Arg Tyr Leu Asp Lys Ala Arg His
    200                 205                 210

gtc gag gca cag gtc atc gcc gac aag cac ggc aac gtt gtg gtc gcc     1266
Val Glu Ala Gln Val Ile Ala Asp Lys His Gly Asn Val Val Val Ala
215                 220                 225                 230

ggt acc cgt gac tgc tcc ctg cag cgt cgt ttc cag aag ctc gtc gag     1314
```

-continued

```
Gly Thr Arg Asp Cys Ser Leu Gln Arg Arg Phe Gln Lys Leu Val Glu
                235                 240                 245

gag gca ccg gca ccg ttc ctc acc gat gag cag cgt gac cgc atc cac      1362
Glu Ala Pro Ala Pro Phe Leu Thr Asp Glu Gln Arg Asp Arg Ile His
            250                 255                 260

tcc tcc gcc aag gct atc tgc cgc gag gcc ggt tac tac ggt gcc ggc      1410
Ser Ser Ala Lys Ala Ile Cys Arg Glu Ala Gly Tyr Tyr Gly Ala Gly
        265                 270                 275

acc gtg gag tac ctg gtc ggt tcc gac gga ctg atc tcc ttc ctg gag      1458
Thr Val Glu Tyr Leu Val Gly Ser Asp Gly Leu Ile Ser Phe Leu Glu
    280                 285                 290

gtc aac acc cgc ctg cag gtg gag cac ccc gtc acc gag gag acc acc      1506
Val Asn Thr Arg Leu Gln Val Glu His Pro Val Thr Glu Glu Thr Thr
295                 300                 305                 310

ggc atc gac ctg gtg cgc gag atg ttc cgc atc gcc gag ggc gcc gag      1554
Gly Ile Asp Leu Val Arg Glu Met Phe Arg Ile Ala Glu Gly Ala Glu
                315                 320                 325

ctc tcc atc aag gag gac ccg acc cca cgc ggc cac gcc ttc gag ttc      1602
Leu Ser Ile Lys Glu Asp Pro Thr Pro Arg Gly His Ala Phe Glu Phe
            330                 335                 340

cgc atc aac ggc gag gac gca ggc tcc aac ttc atg ccc gca ccg ggc      1650
Arg Ile Asn Gly Glu Asp Ala Gly Ser Asn Phe Met Pro Ala Pro Gly
        345                 350                 355

aag atc acc cgc tac cgt gag ccc gcc ggc ccg ggt gtc cgc atg gac      1698
Lys Ile Thr Arg Tyr Arg Glu Pro Ala Gly Pro Gly Val Arg Met Asp
    360                 365                 370

tcc ggc gtt gtc gag ggt tcc gag atc tcc ggc cag ttc gac tcc atg      1746
Ser Gly Val Val Glu Gly Ser Glu Ile Ser Gly Gln Phe Asp Ser Met
375                 380                 385                 390

ctg gcc aag ctg atc gtc tgg ggc cag acc cgt gag cag gcc ctg gag      1794
Leu Ala Lys Leu Ile Val Trp Gly Gln Thr Arg Glu Gln Ala Leu Glu
                395                 400                 405

cgt tcc cgt cgt gcg ctc ggc gag tac atc gtc gag ggc atg ccg acc      1842
Arg Ser Arg Arg Ala Leu Gly Glu Tyr Ile Val Glu Gly Met Pro Thr
            410                 415                 420

gtc atc ccg ttc cac tcc cac atc gtc tcc aac ccg gca ttc gtc ggt      1890
Val Ile Pro Phe His Ser His Ile Val Ser Asn Pro Ala Phe Val Gly
        425                 430                 435

gac ggc gag ggc ttc gag gtc tac acc aag tgg atc gag gag gtc tgg      1938
Asp Gly Glu Gly Phe Glu Val Tyr Thr Lys Trp Ile Glu Glu Val Trp
    440                 445                 450

gac aac ccg atc gag ccg ttc gtc gat gca gcc gac ctc gac gac gag      1986
Asp Asn Pro Ile Glu Pro Phe Val Asp Ala Ala Asp Leu Asp Asp Glu
455                 460                 465                 470

gag aag acc ccg tcg cag aag gtc atc gtc gag atc gac ggc cgc cgc      2034
Glu Lys Thr Pro Ser Gln Lys Val Ile Val Glu Ile Asp Gly Arg Arg
                475                 480                 485

gtc gag gtg gct ctc ccg ggc gac ctc gct ctc ggc ggt ggc gca ggt      2082
Val Glu Val Ala Leu Pro Gly Asp Leu Ala Leu Gly Gly Gly Ala Gly
            490                 495                 500

gcc gcc aag aag aag ccg aag aag cgt cgc gca ggt ggc gcc aag gcc      2130
Ala Ala Lys Lys Lys Pro Lys Lys Arg Arg Ala Gly Gly Ala Lys Ala
        505                 510                 515

ggt gtc tcc ggt gac tcc gtc gca gcc ccg atg cag ggc acc gtc atc      2178
Gly Val Ser Gly Asp Ser Val Ala Ala Pro Met Gln Gly Thr Val Ile
    520                 525                 530

aag gtc aac gtt gag gac ggc gcc gag gtc tcc gag ggt gac acc gtc      2226
Lys Val Asn Val Glu Asp Gly Ala Glu Val Ser Glu Gly Asp Thr Val
535                 540                 545                 550
```

-continued

```
gtg gtt ctc gag gcc atg aag atg gag aac ccg gtc aag gcc cac aag      2274
Val Val Leu Glu Ala Met Lys Met Glu Asn Pro Val Lys Ala His Lys
                555                 560                 565

tcc ggt acc gtc tcc ggt ctg acc atc gcc gcg ggt gag ggc gtg acc      2322
Ser Gly Thr Val Ser Gly Leu Thr Ile Ala Ala Gly Glu Gly Val Thr
            570                 575                 580

aag ggt cag gtt ctc ctg gag atc aag taatcccttc agggaacaga            2369
Lys Gly Gln Val Leu Leu Glu Ile Lys
        585                 590

cagccctgtt ct                                                        2381


<210> SEQ ID NO 4
<211> LENGTH: 591
<212> TYPE: PRT
<213> ORGANISM: Corynebacterium thermoaminogenes

<400> SEQUENCE: 4

Val Ser Val Glu Thr Arg Lys Ile Thr Lys Val Leu Val Ala Asn Arg
1               5                   10                  15

Gly Glu Ile Ala Ile Arg Val Phe Arg Ala Ala Arg Asp Glu Gly Ile
            20                  25                  30

Ala Ser Val Ala Val Tyr Ala Glu Pro Asp Ala Asp Ala Pro Phe Val
        35                  40                  45

Glu Tyr Ala Asp Glu Ala Phe Ala Leu Gly Gly Gln Thr Ser Ala Glu
    50                  55                  60

Ser Tyr Leu Val Ile Asp Lys Ile Ile Asp Ala Ala Arg Lys Ser Gly
65                  70                  75                  80

Ala Asp Ala Val His Pro Gly Tyr Gly Phe Leu Ala Glu Asn Ala Asp
                85                  90                  95

Phe Ala Glu Ala Val Ile Asn Glu Gly Leu Ile Trp Ile Gly Pro Ser
            100                 105                 110

Pro Glu Ser Ile Arg Ser Leu Gly Asp Lys Val Thr Ala Arg His Ile
        115                 120                 125

Ala Asn Asn Ala Asn Ala Pro Met Ala Pro Gly Thr Lys Glu Pro Val
    130                 135                 140

Lys Asp Ala Ala Glu Val Val Ala Phe Ala Glu Glu Phe Gly Leu Pro
145                 150                 155                 160

Ile Ala Ile Lys Ala Ala Phe Gly Gly Gly Gly Arg Gly Met Lys Val
                165                 170                 175

Ala Tyr Glu Met Asp Glu Val Ala Asp Leu Phe Glu Ser Ala Thr Arg
            180                 185                 190

Glu Ala Thr Ala Ala Phe Gly Arg Gly Glu Cys Phe Val Glu Arg Tyr
        195                 200                 205

Leu Asp Lys Ala Arg His Val Glu Ala Gln Val Ile Ala Asp Lys His
    210                 215                 220

Gly Asn Val Val Val Ala Gly Thr Arg Asp Cys Ser Leu Gln Arg Arg
225                 230                 235                 240

Phe Gln Lys Leu Val Glu Glu Ala Pro Ala Pro Phe Leu Thr Asp Glu
                245                 250                 255

Gln Arg Asp Arg Ile His Ser Ser Ala Lys Ala Ile Cys Arg Glu Ala
            260                 265                 270

Gly Tyr Tyr Gly Ala Gly Thr Val Glu Tyr Leu Val Gly Ser Asp Gly
        275                 280                 285

Leu Ile Ser Phe Leu Glu Val Asn Thr Arg Leu Gln Val Glu His Pro
    290                 295                 300
```

-continued

```
Val Thr Glu Glu Thr Thr Gly Ile Asp Leu Val Arg Glu Met Phe Arg
305                 310                 315                 320

Ile Ala Glu Gly Ala Glu Leu Ser Ile Lys Glu Asp Pro Thr Pro Arg
                325                 330                 335

Gly His Ala Phe Glu Phe Arg Ile Asn Gly Glu Asp Ala Gly Ser Asn
            340                 345                 350

Phe Met Pro Ala Pro Gly Lys Ile Thr Arg Tyr Arg Glu Pro Ala Gly
        355                 360                 365

Pro Gly Val Arg Met Asp Ser Gly Val Val Glu Gly Ser Glu Ile Ser
    370                 375                 380

Gly Gln Phe Asp Ser Met Leu Ala Lys Leu Ile Val Trp Gly Gln Thr
385                 390                 395                 400

Arg Glu Gln Ala Leu Glu Arg Ser Arg Arg Ala Leu Gly Glu Tyr Ile
                405                 410                 415

Val Glu Gly Met Pro Thr Val Ile Pro Phe His Ser His Ile Val Ser
            420                 425                 430

Asn Pro Ala Phe Val Gly Asp Gly Glu Gly Phe Glu Val Tyr Thr Lys
        435                 440                 445

Trp Ile Glu Glu Val Trp Asp Asn Pro Ile Glu Pro Phe Val Asp Ala
    450                 455                 460

Ala Asp Leu Asp Asp Glu Glu Lys Thr Pro Ser Gln Lys Val Ile Val
465                 470                 475                 480

Glu Ile Asp Gly Arg Arg Val Glu Val Ala Leu Pro Gly Asp Leu Ala
                485                 490                 495

Leu Gly Gly Gly Ala Gly Ala Ala Lys Lys Lys Pro Lys Lys Arg Arg
            500                 505                 510

Ala Gly Gly Ala Lys Ala Gly Val Ser Gly Asp Ser Val Ala Ala Pro
        515                 520                 525

Met Gln Gly Thr Val Ile Lys Val Asn Val Glu Asp Gly Ala Glu Val
    530                 535                 540

Ser Glu Gly Asp Thr Val Val Val Leu Glu Ala Met Lys Met Glu Asn
545                 550                 555                 560

Pro Val Lys Ala His Lys Ser Gly Thr Val Ser Gly Leu Thr Ile Ala
                565                 570                 575

Ala Gly Glu Gly Val Thr Lys Gly Gln Val Leu Leu Glu Ile Lys
            580                 585                 590
```

<210> SEQ ID NO 5
<211> LENGTH: 2128
<212> TYPE: DNA
<213> ORGANISM: Corynebacterium thermoaminogenes
<220> FEATURE:
<221> NAME/KEY: CDS
<222> LOCATION: (339)..(1967)
<223> OTHER INFORMATION:

<400> SEQUENCE: 5

```
gctgtcattc cgaccacatt cgccccggga tccgggctcc accacctccc ggacccatgc      60

cccatacctg cggaaaccac gggaaacacg ggaaaaaccg atctcattca gaccggcggg     120

atccacctgt ggaacagtca gcggcgcggc catggagggc agcgacaggt gacgtccgag     180

cacccggttc cccaccgtgg acacggcatt gatccgacac ggtggggata gtttcatgct     240

gaaaaactat cgctgtgcag ggaggatccg gaatgtgacc tatttcatgg agaaatgatt     300

gtggacgata cccccgggta cggctaccat tccaaaac atg acc att tcc tca cct     356
                                          Met Thr Ile Ser Ser Pro
                                          1               5
```

-continued

```
ttg att gac gtc gct aac ctg cca gac atc aac acc acc gcc ggc aag      404
Leu Ile Asp Val Ala Asn Leu Pro Asp Ile Asn Thr Thr Ala Gly Lys
            10                  15                  20

atc gcc gac ctg aag gcc cgc cgg gcg gaa gcc cac ttc ccc atg ggt      452
Ile Ala Asp Leu Lys Ala Arg Arg Ala Glu Ala His Phe Pro Met Gly
        25                  30                  35

gaa aag gcc gta gag aag gtc cac gcg gcc aac cgc ctc acc gcg cgc      500
Glu Lys Ala Val Glu Lys Val His Ala Ala Asn Arg Leu Thr Ala Arg
    40                  45                  50

gaa cga ctt gac tac ctg ctc gat gaa ggc tcc ttc atc gaa acc gat      548
Glu Arg Leu Asp Tyr Leu Leu Asp Glu Gly Ser Phe Ile Glu Thr Asp
55                  60                  65                  70

cag ctc gca cgc cac cgc acc acc gcg ttc ggc ctg ggc aac aag cga      596
Gln Leu Ala Arg His Arg Thr Thr Ala Phe Gly Leu Gly Asn Lys Arg
                75                  80                  85

ccg gcc acc gac ggc atc gtc acc ggc tgg ggc acc atc gac ggc cgc      644
Pro Ala Thr Asp Gly Ile Val Thr Gly Trp Gly Thr Ile Asp Gly Arg
            90                  95                  100

gag gtc tgc atc ttc tcc cag gac ggc acc gtc ttc ggt ggc gca ctc      692
Glu Val Cys Ile Phe Ser Gln Asp Gly Thr Val Phe Gly Gly Ala Leu
        105                 110                 115

ggt gag gtc tac ggc gag aag atg atc aag atc atg gag ctg gcc atc      740
Gly Glu Val Tyr Gly Glu Lys Met Ile Lys Ile Met Glu Leu Ala Ile
    120                 125                 130

gac acc ggc cgc cca ctc atc ggc ctg tac gag ggt gca ggt gcc cgc      788
Asp Thr Gly Arg Pro Leu Ile Gly Leu Tyr Glu Gly Ala Gly Ala Arg
135                 140                 145                 150

atc cag gac ggt gcg gtc tcc ctc gac ttc atc tcc cag acc ttc tat      836
Ile Gln Asp Gly Ala Val Ser Leu Asp Phe Ile Ser Gln Thr Phe Tyr
                155                 160                 165

cag aac atc cag gcc tcc ggc gtg atc ccg cag atc tcc gtg atc atg      884
Gln Asn Ile Gln Ala Ser Gly Val Ile Pro Gln Ile Ser Val Ile Met
            170                 175                 180

ggt gcc tgc gcc ggt ggc aac gcc tac ggc ccg gcc ctg acc gac ttc      932
Gly Ala Cys Ala Gly Gly Asn Ala Tyr Gly Pro Ala Leu Thr Asp Phe
        185                 190                 195

gtg gtc atg gtg gac aag acc tcg aag atg ttc gtc acc ggc ccc gat      980
Val Val Met Val Asp Lys Thr Ser Lys Met Phe Val Thr Gly Pro Asp
    200                 205                 210

gtg atc aag acc gtc acc ggc gag gag atc acc cag gag gag ctc ggc     1028
Val Ile Lys Thr Val Thr Gly Glu Glu Ile Thr Gln Glu Glu Leu Gly
215                 220                 225                 230

gga gca acc acc cac atg gtc acc gcc ggc aac tcc cac tac acc gtc     1076
Gly Ala Thr Thr His Met Val Thr Ala Gly Asn Ser His Tyr Thr Val
                235                 240                 245

gcc acc gat gag gag gcc ctc gac tgg gtc cag gac ctc atc tcc ttc     1124
Ala Thr Asp Glu Glu Ala Leu Asp Trp Val Gln Asp Leu Ile Ser Phe
            250                 255                 260

ctg ccc tcc aac aat cgc tcc tac gcc ccg gtg gag gag ttc gac gag     1172
Leu Pro Ser Asn Asn Arg Ser Tyr Ala Pro Val Glu Glu Phe Asp Glu
        265                 270                 275

gag gac ggt ggc atc gcc gag aac atc acc gcc gat gac ctg aag ctg     1220
Glu Asp Gly Gly Ile Ala Glu Asn Ile Thr Ala Asp Asp Leu Lys Leu
    280                 285                 290

gat gag atc atc ccg gat tcc gcc acc gtg ccc tat gat gtc cgc gac     1268
Asp Glu Ile Ile Pro Asp Ser Ala Thr Val Pro Tyr Asp Val Arg Asp
295                 300                 305                 310

gtc atc cag tgc ctg acc gac gac ggt gag tac ctg gag atc cag gcc     1316
Val Ile Gln Cys Leu Thr Asp Asp Gly Glu Tyr Leu Glu Ile Gln Ala
```

-continued

```
            315                 320                 325

gac cga gcc gag aat gtc gtc atc gcc ttc ggc cgc atc gag ggc cag     1364
Asp Arg Ala Glu Asn Val Val Ile Ala Phe Gly Arg Ile Glu Gly Gln
            330                 335                 340

tcc gtc ggt ttc gtc gcc aac cag ccg acc cag ttc gcc ggc tgc ctg     1412
Ser Val Gly Phe Val Ala Asn Gln Pro Thr Gln Phe Ala Gly Cys Leu
        345                 350                 355

gac atc gac tcc tcc gag aag gca gcc cgc ttc gtc cgc acc tgc gat     1460
Asp Ile Asp Ser Ser Glu Lys Ala Ala Arg Phe Val Arg Thr Cys Asp
    360                 365                 370

gcc ttc aac atc ccg atc gtc atg ctt gtc gac gtc ccc ggc ttc ctc     1508
Ala Phe Asn Ile Pro Ile Val Met Leu Val Asp Val Pro Gly Phe Leu
375                 380                 385                 390

ccc ggt gcc ggc cag gag tac ggc ggc atc ctg cgt cgt ggc gcc aaa     1556
Pro Gly Ala Gly Gln Glu Tyr Gly Gly Ile Leu Arg Arg Gly Ala Lys
                395                 400                 405

ctg ctc tac gcc tac ggt gag gcc acc gtc ccg aag atc acc gtg acc     1604
Leu Leu Tyr Ala Tyr Gly Glu Ala Thr Val Pro Lys Ile Thr Val Thr
            410                 415                 420

atg cgc aag gcc tac ggc ggt gcg tac tgt gtc atg gga tcc aag ggt     1652
Met Arg Lys Ala Tyr Gly Gly Ala Tyr Cys Val Met Gly Ser Lys Gly
        425                 430                 435

ctg ggc gca gac atc aac ctg gcc tgg ccg acc gcg cag atc gcc gtc     1700
Leu Gly Ala Asp Ile Asn Leu Ala Trp Pro Thr Ala Gln Ile Ala Val
    440                 445                 450

atg ggt gcc gcc ggc gcg gtc cag ttc atc tac cgc aag gag ctc atg     1748
Met Gly Ala Ala Gly Ala Val Gln Phe Ile Tyr Arg Lys Glu Leu Met
455                 460                 465                 470

gcc gct gat gcc aag ggc ctg gac acc gtc gcc ctg gcc cag tcc ttc     1796
Ala Ala Asp Ala Lys Gly Leu Asp Thr Val Ala Leu Ala Gln Ser Phe
                475                 480                 485

gag cgt gag tac gag gac cac atg ctc aac ccg tac ctg gcg gcc gag     1844
Glu Arg Glu Tyr Glu Asp His Met Leu Asn Pro Tyr Leu Ala Ala Glu
            490                 495                 500

cgt ggc ctc atc gac gcg gtg atc ctg ccg tcc gag acc cgt ggc cag     1892
Arg Gly Leu Ile Asp Ala Val Ile Leu Pro Ser Glu Thr Arg Gly Gln
        505                 510                 515

atc gca cgc aac ctg cgt ctg ctc aag cac aag aat gtc tcc cgc cct     1940
Ile Ala Arg Asn Leu Arg Leu Leu Lys His Lys Asn Val Ser Arg Pro
    520                 525                 530

gcc cgc aag cac ggc aac atg cca ctg taagcacccg ggaccacccc           1987
Ala Arg Lys His Gly Asn Met Pro Leu
535                 540

ctacgcccgc acccacggcc ctttgctggc aggtgcgggc gctgtgcgtt ttccgcgcct   2047

gccgacgccc ggccccctgc cctgtgatgc gatctgcgga tgtgatctgc gcccgcgcca   2107

actcccctgg ttgaaccctg c                                             2128


<210> SEQ ID NO 6
<211> LENGTH: 543
<212> TYPE: PRT
<213> ORGANISM: Corynebacterium thermoaminogenes

<400> SEQUENCE: 6

Met Thr Ile Ser Ser Pro Leu Ile Asp Val Ala Asn Leu Pro Asp Ile
1               5                   10                  15

Asn Thr Thr Ala Gly Lys Ile Ala Asp Leu Lys Ala Arg Arg Ala Glu
            20                  25                  30

Ala His Phe Pro Met Gly Glu Lys Ala Val Glu Lys Val His Ala Ala
```

-continued

```
        35                  40                  45

Asn Arg Leu Thr Ala Arg Glu Arg Leu Asp Tyr Leu Leu Asp Glu Gly
    50                  55                  60

Ser Phe Ile Glu Thr Asp Gln Leu Ala Arg His Arg Thr Thr Ala Phe
65                  70                  75                  80

Gly Leu Gly Asn Lys Arg Pro Ala Thr Asp Gly Ile Val Thr Gly Trp
                85                  90                  95

Gly Thr Ile Asp Gly Arg Glu Val Cys Ile Phe Ser Gln Asp Gly Thr
            100                 105                 110

Val Phe Gly Gly Ala Leu Gly Glu Val Tyr Gly Glu Lys Met Ile Lys
        115                 120                 125

Ile Met Glu Leu Ala Ile Asp Thr Gly Arg Pro Leu Ile Gly Leu Tyr
    130                 135                 140

Glu Gly Ala Gly Ala Arg Ile Gln Asp Gly Ala Val Ser Leu Asp Phe
145                 150                 155                 160

Ile Ser Gln Thr Phe Tyr Gln Asn Ile Gln Ala Ser Gly Val Ile Pro
                165                 170                 175

Gln Ile Ser Val Ile Met Gly Ala Cys Ala Gly Gly Asn Ala Tyr Gly
            180                 185                 190

Pro Ala Leu Thr Asp Phe Val Val Met Val Asp Lys Thr Ser Lys Met
        195                 200                 205

Phe Val Thr Gly Pro Asp Val Ile Lys Thr Val Thr Gly Glu Glu Ile
    210                 215                 220

Thr Gln Glu Glu Leu Gly Gly Ala Thr Thr His Met Val Thr Ala Gly
225                 230                 235                 240

Asn Ser His Tyr Thr Val Ala Thr Asp Glu Glu Ala Leu Asp Trp Val
                245                 250                 255

Gln Asp Leu Ile Ser Phe Leu Pro Ser Asn Asn Arg Ser Tyr Ala Pro
            260                 265                 270

Val Glu Glu Phe Asp Glu Glu Asp Gly Gly Ile Ala Glu Asn Ile Thr
        275                 280                 285

Ala Asp Asp Leu Lys Leu Asp Glu Ile Ile Pro Asp Ser Ala Thr Val
    290                 295                 300

Pro Tyr Asp Val Arg Asp Val Ile Gln Cys Leu Thr Asp Asp Gly Glu
305                 310                 315                 320

Tyr Leu Glu Ile Gln Ala Asp Arg Ala Glu Asn Val Val Ile Ala Phe
                325                 330                 335

Gly Arg Ile Glu Gly Gln Ser Val Gly Phe Val Ala Asn Gln Pro Thr
            340                 345                 350

Gln Phe Ala Gly Cys Leu Asp Ile Asp Ser Ser Glu Lys Ala Ala Arg
        355                 360                 365

Phe Val Arg Thr Cys Asp Ala Phe Asn Ile Pro Ile Val Met Leu Val
    370                 375                 380

Asp Val Pro Gly Phe Leu Pro Gly Ala Gly Gln Glu Tyr Gly Gly Ile
385                 390                 395                 400

Leu Arg Arg Gly Ala Lys Leu Leu Tyr Ala Tyr Gly Glu Ala Thr Val
                405                 410                 415

Pro Lys Ile Thr Val Thr Met Arg Lys Ala Tyr Gly Gly Ala Tyr Cys
            420                 425                 430

Val Met Gly Ser Lys Gly Leu Gly Ala Asp Ile Asn Leu Ala Trp Pro
        435                 440                 445

Thr Ala Gln Ile Ala Val Met Gly Ala Ala Gly Ala Val Gln Phe Ile
    450                 455                 460
```

-continued

```
Tyr Arg Lys Glu Leu Met Ala Ala Asp Ala Lys Gly Leu Asp Thr Val
465                 470                 475                 480

Ala Leu Ala Gln Ser Phe Glu Arg Glu Tyr Glu Asp His Met Leu Asn
                485                 490                 495

Pro Tyr Leu Ala Ala Glu Arg Gly Leu Ile Asp Ala Val Ile Leu Pro
            500                 505                 510

Ser Glu Thr Arg Gly Gln Ile Ala Arg Asn Leu Arg Leu Leu Lys His
        515                 520                 525

Lys Asn Val Ser Arg Pro Ala Arg Lys His Gly Asn Met Pro Leu
    530                 535                 540


<210> SEQ ID NO 7
<211> LENGTH: 2076
<212> TYPE: DNA
<213> ORGANISM: Corynebacterium thermoaminogenes
<220> FEATURE:
<221> NAME/KEY: CDS
<222> LOCATION: (412)..(2022)
<223> OTHER INFORMATION:

<400> SEQUENCE: 7

acgcccggcc ccctgccctg tgatgcgatc tgcggatgtg atctgcgccc gcgccaactc     60

ccctggttga accctgccac ataccctgag tcgcacctgg gtggggtcac tttccacctc    120

acggggggga ggaggtcaca taggccatac gctgcacttt tgatgaagtg tgggcagatc    180

gaccgggcaa atctgggaaa taaggggcct ggtgaactag cattcccctt agcgaagggt    240

gagcatcgcg gaccccgcga tgtcccaacc ggtcgtaaat tcatgtgccg ccacagtccc    300

ctcaccaggg gatcggaacc agcccagcct gattccggcg tgacggacct caccgtgaac    360

aagtccccgc attactcaca gaactcacac caggatttag actaagaaac c atg act     417
                                                         Met Thr
                                                         1

gca gca acg aca gca cct gat ctg acc acc acc gcc ggc aaa ctc gcg      465
Ala Ala Thr Thr Ala Pro Asp Leu Thr Thr Thr Ala Gly Lys Leu Ala
        5                   10                  15

gat ctc cgc gcc cgc ctt tcc gag acc cag gcc ccc atg ggt cag gcc      513
Asp Leu Arg Ala Arg Leu Ser Glu Thr Gln Ala Pro Met Gly Gln Ala
    20                  25                  30

tcc gtg gag aag gtg cac gag gca ggg aag aag acc gca cgc gag cgc      561
Ser Val Glu Lys Val His Glu Ala Gly Lys Lys Thr Ala Arg Glu Arg
35                  40                  45                  50

atc gag tac ctg ctc gat gag ggc tcc ttc gtt gag gtc gat gcc ctc      609
Ile Glu Tyr Leu Leu Asp Glu Gly Ser Phe Val Glu Val Asp Ala Leu
                55                  60                  65

gcc cgc cac cgt tcc aag aac ttc ggc ctg gac tcc aag cgc ccg gtc      657
Ala Arg His Arg Ser Lys Asn Phe Gly Leu Asp Ser Lys Arg Pro Val
            70                  75                  80

acc gac ggt gtg gtc acc ggt tac ggc acc atc gac gga cgc aag gtc      705
Thr Asp Gly Val Val Thr Gly Tyr Gly Thr Ile Asp Gly Arg Lys Val
        85                  90                  95

tgc gtc ttc tcc cag gac ggc gct atc ttc ggc ggt gcc ctc ggt gag      753
Cys Val Phe Ser Gln Asp Gly Ala Ile Phe Gly Gly Ala Leu Gly Glu
    100                 105                 110

gtc tac ggc gag aag atc gtc aag atc atg gac ctg gcc atc aag acc      801
Val Tyr Gly Glu Lys Ile Val Lys Ile Met Asp Leu Ala Ile Lys Thr
115                 120                 125                 130

ggt gtc ccc ctc atc ggc atc aac gag ggc gcc ggc gcc cgc atc cag      849
Gly Val Pro Leu Ile Gly Ile Asn Glu Gly Ala Gly Ala Arg Ile Gln
                135                 140                 145
```

-continued

```
gaa ggc gtt gtc tcc ctg ggc ctg tac tcc cag atc ttc tac cgc aac      897
Glu Gly Val Val Ser Leu Gly Leu Tyr Ser Gln Ile Phe Tyr Arg Asn
            150                 155                 160

acc cag gca tcc ggt gtc atc cca cag atc tcc ctc atc atg ggt gcc      945
Thr Gln Ala Ser Gly Val Ile Pro Gln Ile Ser Leu Ile Met Gly Ala
        165                 170                 175

tgc gcc ggt ggc cat gtg tac tcc ccc gcc ctg acc gac ttc atc atc      993
Cys Ala Gly Gly His Val Tyr Ser Pro Ala Leu Thr Asp Phe Ile Ile
    180                 185                 190

atg gtg gac aag acc tcc aag atg ttc atc acc ggc ccc gac gtg atc     1041
Met Val Asp Lys Thr Ser Lys Met Phe Ile Thr Gly Pro Asp Val Ile
195                 200                 205                 210

aag acc gtc acc ggc gag gag gtc acc cag gag gaa ctg ggt ggt gcc     1089
Lys Thr Val Thr Gly Glu Glu Val Thr Gln Glu Glu Leu Gly Gly Ala
            215                 220                 225

tac acc cac atg gcc cag tcc ggc acc tcg cac tac acc gca gcc gat     1137
Tyr Thr His Met Ala Gln Ser Gly Thr Ser His Tyr Thr Ala Ala Asp
            230                 235                 240

gac tcc gat gcc ctc gac tgg gtc cgt gag ctg gtc agc tac ctg ccg     1185
Asp Ser Asp Ala Leu Asp Trp Val Arg Glu Leu Val Ser Tyr Leu Pro
        245                 250                 255

tcc aac aac cgt gcg gag acc cca cgc cag gac gcc gac atc atg gtg     1233
Ser Asn Asn Arg Ala Glu Thr Pro Arg Gln Asp Ala Asp Ile Met Val
    260                 265                 270

ggc tcc atc aag gag aac atc acc gag acc gac ctc gaa ctc gac acc     1281
Gly Ser Ile Lys Glu Asn Ile Thr Glu Thr Asp Leu Glu Leu Asp Thr
275                 280                 285                 290

ctg atc ccg gat tcc ccg aac cag ccg tac gac atg aag gac gtc atc     1329
Leu Ile Pro Asp Ser Pro Asn Gln Pro Tyr Asp Met Lys Asp Val Ile
                295                 300                 305

acc cgc atc gtc gat gat gcc gag ttc ttc gag atc cag gag ggt tac     1377
Thr Arg Ile Val Asp Asp Ala Glu Phe Phe Glu Ile Gln Glu Gly Tyr
            310                 315                 320

gcc gag aac atc atc tgc ggt ttc gcc cgc gtc gag ggt cgt gcc gtg     1425
Ala Glu Asn Ile Ile Cys Gly Phe Ala Arg Val Glu Gly Arg Ala Val
        325                 330                 335

ggt atc gtg gcc aac cag ccg atg cag ttc gcc ggc tgc ctg gac atc     1473
Gly Ile Val Ala Asn Gln Pro Met Gln Phe Ala Gly Cys Leu Asp Ile
    340                 345                 350

aag gca tcc gag aag gcc gcc cgc ttc atc cgc acc tgt gac gcc ttc     1521
Lys Ala Ser Glu Lys Ala Ala Arg Phe Ile Arg Thr Cys Asp Ala Phe
355                 360                 365                 370

aac atc ccg atc atc gag ctt gtc gac gtc cca ggc ttc ctc ccg ggc     1569
Asn Ile Pro Ile Ile Glu Leu Val Asp Val Pro Gly Phe Leu Pro Gly
            375                 380                 385

acc aac cag gag ttc gac ggc atc atc cgt cgc ggc gcg aag ctg ctc     1617
Thr Asn Gln Glu Phe Asp Gly Ile Ile Arg Arg Gly Ala Lys Leu Leu
            390                 395                 400

tac gcc tac gcc gag gcc acc gtc ggc aag atc acc gtg atc acc cgc     1665
Tyr Ala Tyr Ala Glu Ala Thr Val Gly Lys Ile Thr Val Ile Thr Arg
        405                 410                 415

aag tcc tac ggc ggt gcc tac tgc gtg atg ggc tcc aag gac atg ggt     1713
Lys Ser Tyr Gly Gly Ala Tyr Cys Val Met Gly Ser Lys Asp Met Gly
    420                 425                 430

gcg gac ctc gtc ttc gca tgg ccc acc gcg cag atc gcc gtc atg ggt     1761
Ala Asp Leu Val Phe Ala Trp Pro Thr Ala Gln Ile Ala Val Met Gly
435                 440                 445                 450

gcc tcc ggt gcc gtc ggc ttc atc tac cgc aag gag ctc aag cag gct     1809
Ala Ser Gly Ala Val Gly Phe Ile Tyr Arg Lys Glu Leu Lys Gln Ala
```

-continued

```
            455                 460                 465

gca gcg gcc ggc gag gat gtc acc gcg ctg atg aag aag tac gag cag     1857
Ala Ala Ala Gly Glu Asp Val Thr Ala Leu Met Lys Lys Tyr Glu Gln
            470                 475                 480

gag tac gag gag acc ctg gtc aac ccg tac atg gct gca gag cgt ggc     1905
Glu Tyr Glu Glu Thr Leu Val Asn Pro Tyr Met Ala Ala Glu Arg Gly
        485                 490                 495

tac gtc gac gcc gtc atc cca cca tcc gag acc cgt ggt cag atc atc     1953
Tyr Val Asp Ala Val Ile Pro Pro Ser Glu Thr Arg Gly Gln Ile Ile
    500                 505                 510

gag ggt ctg cgt ctg ctc gac cgc aag gtg gtc aac gtc ccg gcc aag     2001
Glu Gly Leu Arg Leu Leu Asp Arg Lys Val Val Asn Val Pro Ala Lys
515                 520                 525                 530

aag cac ggt aac atc ccg ctg taaaccgtct tcccctccgg caccacgccg        2052
Lys His Gly Asn Ile Pro Leu
            535

gagaaggctt tgtccgcagc tgtc                                          2076


<210> SEQ ID NO 8
<211> LENGTH: 537
<212> TYPE: PRT
<213> ORGANISM: Corynebacterium thermoaminogenes

<400> SEQUENCE: 8

Met Thr Ala Ala Thr Thr Ala Pro Asp Leu Thr Thr Thr Ala Gly Lys
1               5                   10                  15

Leu Ala Asp Leu Arg Ala Arg Leu Ser Glu Thr Gln Ala Pro Met Gly
            20                  25                  30

Gln Ala Ser Val Glu Lys Val His Glu Ala Gly Lys Lys Thr Ala Arg
        35                  40                  45

Glu Arg Ile Glu Tyr Leu Leu Asp Glu Gly Ser Phe Val Glu Val Asp
    50                  55                  60

Ala Leu Ala Arg His Arg Ser Lys Asn Phe Gly Leu Asp Ser Lys Arg
65                  70                  75                  80

Pro Val Thr Asp Gly Val Val Thr Gly Tyr Gly Thr Ile Asp Gly Arg
                85                  90                  95

Lys Val Cys Val Phe Ser Gln Asp Gly Ala Ile Phe Gly Gly Ala Leu
            100                 105                 110

Gly Glu Val Tyr Gly Glu Lys Ile Val Lys Ile Met Asp Leu Ala Ile
        115                 120                 125

Lys Thr Gly Val Pro Leu Ile Gly Ile Asn Glu Gly Ala Gly Ala Arg
    130                 135                 140

Ile Gln Glu Gly Val Val Ser Leu Gly Leu Tyr Ser Gln Ile Phe Tyr
145                 150                 155                 160

Arg Asn Thr Gln Ala Ser Gly Val Ile Pro Gln Ile Ser Leu Ile Met
                165                 170                 175

Gly Ala Cys Ala Gly Gly His Val Tyr Ser Pro Ala Leu Thr Asp Phe
            180                 185                 190

Ile Ile Met Val Asp Lys Thr Ser Lys Met Phe Ile Thr Gly Pro Asp
        195                 200                 205

Val Ile Lys Thr Val Thr Gly Glu Glu Val Thr Gln Glu Glu Leu Gly
    210                 215                 220

Gly Ala Tyr Thr His Met Ala Gln Ser Gly Thr Ser His Tyr Thr Ala
225                 230                 235                 240

Ala Asp Asp Ser Asp Ala Leu Asp Trp Val Arg Glu Leu Val Ser Tyr
                245                 250                 255
```

```
Leu Pro Ser Asn Asn Arg Ala Glu Thr Pro Arg Gln Asp Ala Asp Ile
            260                 265                 270

Met Val Gly Ser Ile Lys Glu Asn Ile Thr Glu Thr Asp Leu Glu Leu
        275                 280                 285

Asp Thr Leu Ile Pro Asp Ser Pro Asn Gln Pro Tyr Asp Met Lys Asp
    290                 295                 300

Val Ile Thr Arg Ile Val Asp Asp Ala Glu Phe Phe Glu Ile Gln Glu
305                 310                 315                 320

Gly Tyr Ala Glu Asn Ile Ile Cys Gly Phe Ala Arg Val Glu Gly Arg
                325                 330                 335

Ala Val Gly Ile Val Ala Asn Gln Pro Met Gln Phe Ala Gly Cys Leu
            340                 345                 350

Asp Ile Lys Ala Ser Glu Lys Ala Ala Arg Phe Ile Arg Thr Cys Asp
        355                 360                 365

Ala Phe Asn Ile Pro Ile Ile Glu Leu Val Asp Val Pro Gly Phe Leu
    370                 375                 380

Pro Gly Thr Asn Gln Glu Phe Asp Gly Ile Ile Arg Arg Gly Ala Lys
385                 390                 395                 400

Leu Leu Tyr Ala Tyr Ala Glu Ala Thr Val Gly Lys Ile Thr Val Ile
                405                 410                 415

Thr Arg Lys Ser Tyr Gly Gly Ala Tyr Cys Val Met Gly Ser Lys Asp
            420                 425                 430

Met Gly Ala Asp Leu Val Phe Ala Trp Pro Thr Ala Gln Ile Ala Val
        435                 440                 445

Met Gly Ala Ser Gly Ala Val Gly Phe Ile Tyr Arg Lys Glu Leu Lys
    450                 455                 460

Gln Ala Ala Ala Ala Gly Glu Asp Val Thr Ala Leu Met Lys Lys Tyr
465                 470                 475                 480

Glu Gln Glu Tyr Glu Glu Thr Leu Val Asn Pro Tyr Met Ala Ala Glu
                485                 490                 495

Arg Gly Tyr Val Asp Ala Val Ile Pro Pro Ser Glu Thr Arg Gly Gln
            500                 505                 510

Ile Ile Glu Gly Leu Arg Leu Leu Asp Arg Lys Val Val Asn Val Pro
        515                 520                 525

Ala Lys Lys His Gly Asn Ile Pro Leu
    530                 535


<210> SEQ ID NO 9
<211> LENGTH: 1643
<212> TYPE: DNA
<213> ORGANISM: Corynebacterium thermoaminogenes
<220> FEATURE:
<221> NAME/KEY: CDS
<222> LOCATION: (326)..(1363)
<223> OTHER INFORMATION:

<400> SEQUENCE: 9

agcgcgccgg cagccaccag tgggatcgtg cccagcggac ggatgccgga ttcacggcgg      60

tcagccaccc gccgatgaga cctgcagcga caacggtggc ggtgctgacc tggtcagcgt     120

ctttgagttt catatccatg tcagacagtc taaccactct ctccgacgcg tccgaacatg     180

ctggggtggc ggacaccatg tccgttcggg cgttgccccg acgggggaaa atcgcaggca     240

gatgtgtccg atgtgggata aacccaccgg ttcgggcgtg tcttcgggat caatggcaca     300

gcattaaccg tgtggggggt ttaat atg gga gcc atg cga att gcc act ctc       352
                            Met Gly Ala Met Arg Ile Ala Thr Leu
```

-continued

```
                        1             5

acg tca ggc ggc gac tgc ccc gga ctc aat gct gtc atc agg gga atc      400
Thr Ser Gly Gly Asp Cys Pro Gly Leu Asn Ala Val Ile Arg Gly Ile
10                  15                  20                  25

gtc cgt acc gca agt aat gaa ttc ggt tcc acc gtc gtg ggt tat cag      448
Val Arg Thr Ala Ser Asn Glu Phe Gly Ser Thr Val Val Gly Tyr Gln
                30                  35                  40

gac ggc tgg gag ggc ctg ctg gcg gac cga cgt gtt cag ctc tat gac      496
Asp Gly Trp Glu Gly Leu Leu Ala Asp Arg Arg Val Gln Leu Tyr Asp
            45                  50                  55

gat gag gac atc gac cgc atc ctg ctc cgc ggt gga aca atc ctg ggc      544
Asp Glu Asp Ile Asp Arg Ile Leu Leu Arg Gly Gly Thr Ile Leu Gly
        60                  65                  70

acc ggt cgt ctc cac ccc gac aag ttc aga gcc gga atc gac cag gtc      592
Thr Gly Arg Leu His Pro Asp Lys Phe Arg Ala Gly Ile Asp Gln Val
    75                  80                  85

aag gcg aat ctc gcc gat gcg gga att gac gca ctc atc ccg atc ggt      640
Lys Ala Asn Leu Ala Asp Ala Gly Ile Asp Ala Leu Ile Pro Ile Gly
90                  95                  100                 105

ggc gag ggc acc ctc aag gga gcg aag tgg ctc gcc gac aac ggc atc      688
Gly Glu Gly Thr Leu Lys Gly Ala Lys Trp Leu Ala Asp Asn Gly Ile
                110                 115                 120

ccc gtg gtc ggt gtc ccg aaa acc atc gac aat gat gtc aac ggc acg      736
Pro Val Val Gly Val Pro Lys Thr Ile Asp Asn Asp Val Asn Gly Thr
            125                 130                 135

gat ttc acc ttc ggt ttc gat tcc gcg gtc tct gtg gcc acc gac gcc      784
Asp Phe Thr Phe Gly Phe Asp Ser Ala Val Ser Val Ala Thr Asp Ala
        140                 145                 150

atc gac cgg ctg cac acc acg gcg gaa tcc cac aac cgt gtg atg atc      832
Ile Asp Arg Leu His Thr Thr Ala Glu Ser His Asn Arg Val Met Ile
    155                 160                 165

gtc gag gtc atg ggc cgc cac gtc ggt tgg atc gca ctg cat gcc ggc      880
Val Glu Val Met Gly Arg His Val Gly Trp Ile Ala Leu His Ala Gly
170                 175                 180                 185

atg gcc ggt gga gcc cac tac acc gtc atc ccc gag gtg ccc ttc gac      928
Met Ala Gly Gly Ala His Tyr Thr Val Ile Pro Glu Val Pro Phe Asp
                190                 195                 200

atc tcg gag atc tgc aag cgt atg gaa cgt cgc ttc cag atg ggg gag      976
Ile Ser Glu Ile Cys Lys Arg Met Glu Arg Arg Phe Gln Met Gly Glu
            205                 210                 215

aag tac ggc atc atc gtc gtc gcg gag ggt gcc ctg ccc aag gag gga     1024
Lys Tyr Gly Ile Ile Val Val Ala Glu Gly Ala Leu Pro Lys Glu Gly
        220                 225                 230

acc atg gag ctg cgt gag ggg gag gtg gat cag ttc ggt cac aag acc     1072
Thr Met Glu Leu Arg Glu Gly Glu Val Asp Gln Phe Gly His Lys Thr
    235                 240                 245

ttc acc ggc atc ggc cag cag atc gcc gac gag gtg cac agg cgt ctg     1120
Phe Thr Gly Ile Gly Gln Gln Ile Ala Asp Glu Val His Arg Arg Leu
250                 255                 260                 265

ggt cat gat gtc cgc acc acg gtc ctg ggc cat atc cag cgt ggt ggc     1168
Gly His Asp Val Arg Thr Thr Val Leu Gly His Ile Gln Arg Gly Gly
                270                 275                 280

acc ccc acc gcc ttc gac cgt gtc ctg gcc acc cgg tac ggt gtc cgc     1216
Thr Pro Thr Ala Phe Asp Arg Val Leu Ala Thr Arg Tyr Gly Val Arg
            285                 290                 295

gcc gcg cgt gcc tgc cac gag ggt cag ttc aac acc gtg gtc gcg ctc     1264
Ala Ala Arg Ala Cys His Glu Gly Gln Phe Asn Thr Val Val Ala Leu
        300                 305                 310

aag ggg gag cgc atc cgg atg atc tcc ttc gat gag gcc gtg ggc acc     1312
```

-continued

```
Lys Gly Glu Arg Ile Arg Met Ile Ser Phe Asp Glu Ala Val Gly Thr
    315                 320                 325

ctg aag aag gtg ccg atg gaa cgc tgg gtg acc gcc cag gct atg ttc     1360
Leu Lys Lys Val Pro Met Glu Arg Trp Val Thr Ala Gln Ala Met Phe
330                 335                 340                 345

ggt tagtcaggcc gcattcccgg ttccgcgccc gcggggccgg gttttttcat          1413
Gly

gccccggaac acatcggtat gaaatcgtga tatgcattac ttgacgggga agtgggggat   1473

ccgtcacctc gcgttgtcca actacagccc gcagcgcctg cgggaattct tcgagcaatc   1533

cgccgattcc ccggcccgtc ccgtcgccgt ccaaccgcag tacaatctgc tggcccgccg   1593

ggattatgag accggtatcc gcccggtcgt ggacgagttc ggtcccgcgg              1643


<210> SEQ ID NO 10
<211> LENGTH: 346
<212> TYPE: PRT
<213> ORGANISM: Corynebacterium thermoaminogenes

<400> SEQUENCE: 10

Met Gly Ala Met Arg Ile Ala Thr Leu Thr Ser Gly Gly Asp Cys Pro
1               5                   10                  15

Gly Leu Asn Ala Val Ile Arg Gly Ile Val Arg Thr Ala Ser Asn Glu
            20                  25                  30

Phe Gly Ser Thr Val Val Gly Tyr Gln Asp Gly Trp Glu Gly Leu Leu
        35                  40                  45

Ala Asp Arg Arg Val Gln Leu Tyr Asp Asp Glu Asp Ile Asp Arg Ile
    50                  55                  60

Leu Leu Arg Gly Gly Thr Ile Leu Gly Thr Gly Arg Leu His Pro Asp
65                  70                  75                  80

Lys Phe Arg Ala Gly Ile Asp Gln Val Lys Ala Asn Leu Ala Asp Ala
                85                  90                  95

Gly Ile Asp Ala Leu Ile Pro Ile Gly Gly Glu Gly Thr Leu Lys Gly
            100                 105                 110

Ala Lys Trp Leu Ala Asp Asn Gly Ile Pro Val Val Gly Val Pro Lys
        115                 120                 125

Thr Ile Asp Asn Asp Val Asn Gly Thr Asp Phe Thr Phe Gly Phe Asp
    130                 135                 140

Ser Ala Val Ser Val Ala Thr Asp Ala Ile Asp Arg Leu His Thr Thr
145                 150                 155                 160

Ala Glu Ser His Asn Arg Val Met Ile Val Glu Val Met Gly Arg His
                165                 170                 175

Val Gly Trp Ile Ala Leu His Ala Gly Met Ala Gly Gly Ala His Tyr
            180                 185                 190

Thr Val Ile Pro Glu Val Pro Phe Asp Ile Ser Glu Ile Cys Lys Arg
        195                 200                 205

Met Glu Arg Arg Phe Gln Met Gly Glu Lys Tyr Gly Ile Ile Val Val
    210                 215                 220

Ala Glu Gly Ala Leu Pro Lys Glu Gly Thr Met Glu Leu Arg Glu Gly
225                 230                 235                 240

Glu Val Asp Gln Phe Gly His Lys Thr Phe Thr Gly Ile Gly Gln Gln
                245                 250                 255

Ile Ala Asp Glu Val His Arg Arg Leu Gly His Asp Val Arg Thr Thr
            260                 265                 270

Val Leu Gly His Ile Gln Arg Gly Gly Thr Pro Thr Ala Phe Asp Arg
        275                 280                 285
```

-continued

```
Val Leu Ala Thr Arg Tyr Gly Val Arg Ala Ala Arg Ala Cys His Glu
    290                 295                 300

Gly Gln Phe Asn Thr Val Val Ala Leu Lys Gly Glu Arg Ile Arg Met
305                 310                 315                 320

Ile Ser Phe Asp Glu Ala Val Gly Thr Leu Lys Lys Val Pro Met Glu
                325                 330                 335

Arg Trp Val Thr Ala Gln Ala Met Phe Gly
            340                 345


<210> SEQ ID NO 11
<211> LENGTH: 498
<212> TYPE: DNA
<213> ORGANISM: Corynebacterium thermoaminogenes
<220> FEATURE:
<221> NAME/KEY: CDS
<222> LOCATION: (1)..(498)
<223> OTHER INFORMATION:

<400> SEQUENCE: 11

tac tac cag cac gat cca ggt ttc ccc ttc gca cca aag cgc acc ggt       48
Tyr Tyr Gln His Asp Pro Gly Phe Pro Phe Ala Pro Lys Arg Thr Gly
1               5                   10                  15

tgg gct cac acc acc acg ccg ttg acc gga ccg cag cga ttg cag tgg       96
Trp Ala His Thr Thr Thr Pro Leu Thr Gly Pro Gln Arg Leu Gln Trp
            20                  25                  30

acg cac ctg ccc gat gct ctt tac ccg gat gta tcc tat gac ctg gat      144
Thr His Leu Pro Asp Ala Leu Tyr Pro Asp Val Ser Tyr Asp Leu Asp
        35                  40                  45

gga tgc tat tcc ggc gga gcc gta ttt tct gac ggc acg ctt aaa ctt      192
Gly Cys Tyr Ser Gly Gly Ala Val Phe Ser Asp Gly Thr Leu Lys Leu
    50                  55                  60

ttc tac acc ggc aac cga aaa att gac ggc aag cgc cgc gcc acc caa      240
Phe Tyr Thr Gly Asn Arg Lys Ile Asp Gly Lys Arg Arg Ala Thr Gln
65                  70                  75                  80

aac ctc gtc gaa gtc gag gac cca act ggg ctg atg ggc ggc att cat      288
Asn Leu Val Glu Val Glu Asp Pro Thr Gly Leu Met Gly Gly Ile His
                85                  90                  95

cgc cgc tcg cct aaa aat ccg ctt atc gac gga ccc gcc agc ggt ttt      336
Arg Arg Ser Pro Lys Asn Pro Leu Ile Asp Gly Pro Ala Ser Gly Phe
            100                 105                 110

acg ccc cac tac cgc gat ccc atg atc agc cct gat ggg gat ggt tgg      384
Thr Pro His Tyr Arg Asp Pro Met Ile Ser Pro Asp Gly Asp Gly Trp
        115                 120                 125

aag atg gtt ctt ggg gct cag cgc gaa aac ctc acc ggt gca gcg gtt      432
Lys Met Val Leu Gly Ala Gln Arg Glu Asn Leu Thr Gly Ala Ala Val
    130                 135                 140

cta tac cgc tcg gca gat ctt gaa aac tgg gaa ttc tcc ggt gaa atc      480
Leu Tyr Arg Ser Ala Asp Leu Glu Asn Trp Glu Phe Ser Gly Glu Ile
145                 150                 155                 160

acc ttt gac ctc agc gac                                              498
Thr Phe Asp Leu Ser Asp
                165


<210> SEQ ID NO 12
<211> LENGTH: 166
<212> TYPE: PRT
<213> ORGANISM: Corynebacterium thermoaminogenes

<400> SEQUENCE: 12

Tyr Tyr Gln His Asp Pro Gly Phe Pro Phe Ala Pro Lys Arg Thr Gly
1               5                   10                  15
```

-continued

```
Trp Ala His Thr Thr Thr Pro Leu Thr Gly Pro Gln Arg Leu Gln Trp
            20                  25                  30

Thr His Leu Pro Asp Ala Leu Tyr Pro Asp Val Ser Tyr Asp Leu Asp
        35                  40                  45

Gly Cys Tyr Ser Gly Gly Ala Val Phe Ser Asp Gly Thr Leu Lys Leu
    50                  55                  60

Phe Tyr Thr Gly Asn Arg Lys Ile Asp Gly Lys Arg Arg Ala Thr Gln
65                  70                  75                  80

Asn Leu Val Glu Val Glu Asp Pro Thr Gly Leu Met Gly Gly Ile His
                85                  90                  95

Arg Arg Ser Pro Lys Asn Pro Leu Ile Asp Gly Pro Ala Ser Gly Phe
            100                 105                 110

Thr Pro His Tyr Arg Asp Pro Met Ile Ser Pro Asp Gly Asp Gly Trp
        115                 120                 125

Lys Met Val Leu Gly Ala Gln Arg Glu Asn Leu Thr Gly Ala Ala Val
    130                 135                 140

Leu Tyr Arg Ser Ala Asp Leu Glu Asn Trp Glu Phe Ser Gly Glu Ile
145                 150                 155                 160

Thr Phe Asp Leu Ser Asp
                165
```

<210> SEQ ID NO 13
<211> LENGTH: 479
<212> TYPE: DNA
<213> ORGANISM: Corynebacterium thermoaminogenes
<220> FEATURE:
<221> NAME/KEY: CDS
<222> LOCATION: (1)..(477)
<223> OTHER INFORMATION:

<400> SEQUENCE: 13

```
tac tac cag cac gat cca ggt ttc ccc ttc gca cca aag cgc acc ggc       48
Tyr Tyr Gln His Asp Pro Gly Phe Pro Phe Ala Pro Lys Arg Thr Gly
1               5                   10                  15

tgg gct cac acc acc acg ccg ttg acc gga ccg cag cga ttg cag tgg       96
Trp Ala His Thr Thr Thr Pro Leu Thr Gly Pro Gln Arg Leu Gln Trp
            20                  25                  30

acg cac ctg ccc gac gct ctt tac ccg gat gca tcc tat gac ctg gat      144
Thr His Leu Pro Asp Ala Leu Tyr Pro Asp Ala Ser Tyr Asp Leu Asp
        35                  40                  45

gga tgc tat tcc ggt gga gcc gta ttt act gac ggc aca ctt aaa ctt      192
Gly Cys Tyr Ser Gly Gly Ala Val Phe Thr Asp Gly Thr Leu Lys Leu
    50                  55                  60

ttc tac acc ggc aac cta aaa att gac ggc aag cgc cgc gcc acc caa      240
Phe Tyr Thr Gly Asn Leu Lys Ile Asp Gly Lys Arg Arg Ala Thr Gln
65                  70                  75                  80

aac ctc gtc gaa gtc gag gac cca act ggg ctg atg ggc ggc att cat      288
Asn Leu Val Glu Val Glu Asp Pro Thr Gly Leu Met Gly Gly Ile His
                85                  90                  95

cgc cgt tcg cct aaa aat ccg ctt atc gac gga ccc gcc agc ggt ttc      336
Arg Arg Ser Pro Lys Asn Pro Leu Ile Asp Gly Pro Ala Ser Gly Phe
            100                 105                 110

aca ccc cat tac cgc gat ccc atg atc agc cct gat ggt gat ggt tgg      384
Thr Pro His Tyr Arg Asp Pro Met Ile Ser Pro Asp Gly Asp Gly Trp
        115                 120                 125

aaa atg gtt ctt ggg gcc caa cgc gaa aac ctc acc ggt gca gcg gtt      432
Lys Met Val Leu Gly Ala Gln Arg Glu Asn Leu Thr Gly Ala Ala Val
    130                 135                 140
```

-continued

```
cta tac cgc tcg aca gat ctt gaa aac tgg gaa ttc tcc ggt gaa at       479
Leu Tyr Arg Ser Thr Asp Leu Glu Asn Trp Glu Phe Ser Gly Glu
145                 150                 155


<210> SEQ ID NO 14
<211> LENGTH: 159
<212> TYPE: PRT
<213> ORGANISM: Corynebacterium thermoaminogenes

<400> SEQUENCE: 14

Tyr Tyr Gln His Asp Pro Gly Phe Pro Phe Ala Pro Lys Arg Thr Gly
1               5                   10                  15

Trp Ala His Thr Thr Thr Pro Leu Thr Gly Pro Gln Arg Leu Gln Trp
            20                  25                  30

Thr His Leu Pro Asp Ala Leu Tyr Pro Asp Ala Ser Tyr Asp Leu Asp
        35                  40                  45

Gly Cys Tyr Ser Gly Gly Ala Val Phe Thr Asp Gly Thr Leu Lys Leu
    50                  55                  60

Phe Tyr Thr Gly Asn Leu Lys Ile Asp Gly Lys Arg Arg Ala Thr Gln
65                  70                  75                  80

Asn Leu Val Glu Val Glu Asp Pro Thr Gly Leu Met Gly Gly Ile His
                85                  90                  95

Arg Arg Ser Pro Lys Asn Pro Leu Ile Asp Gly Pro Ala Ser Gly Phe
            100                 105                 110

Thr Pro His Tyr Arg Asp Pro Met Ile Ser Pro Asp Gly Asp Gly Trp
        115                 120                 125

Lys Met Val Leu Gly Ala Gln Arg Glu Asn Leu Thr Gly Ala Ala Val
    130                 135                 140

Leu Tyr Arg Ser Thr Asp Leu Glu Asn Trp Glu Phe Ser Gly Glu
145                 150                 155


<210> SEQ ID NO 15
<211> LENGTH: 490
<212> TYPE: DNA
<213> ORGANISM: Corynebacterium thermoaminogenes

<400> SEQUENCE: 15

atttaatgg atattatcta tattttatca atattatcct tatgcacctg aatggggacc      60

aatgcattgg ggacacgcac gtagtaaaga tttagttcat tgggaaacat taccgattgc    120

tttagaacct ggagatgaag aagaaaaatg gttgtttctc tggtacaggt atagtcaaag    180

atgataagtt gtatttattt tatacaggtc accattatta taatgacgat gatcccgatc    240

atttttggca aaatcaaaat atggcttata gtgaagatgg cattcatttt caaaaatata    300

aacaaaatgc aatcattcct accccacctg aagataatac acatcacttc agagatccaa    360

aggtatggga acatccatgg cttattatta catgatagta ggtagtcaaa atgatagaga    420

attaggacgt attatcttat atcgttctga ggatttatag aggggaattc tggtcctgag    480

atcaatccaa                                                           490


<210> SEQ ID NO 16
<211> LENGTH: 4254
<212> TYPE: DNA
<213> ORGANISM: Corynebacterium thermoaminogenes
<220> FEATURE:
<221> NAME/KEY: CDS
<222> LOCATION: (637)..(1362)
<223> OTHER INFORMATION:
<220> FEATURE:
<221> NAME/KEY: CDS
```

-continued

```
<222> LOCATION: (1434)..(2315)
<223> OTHER INFORMATION:
<220> FEATURE:
<221> NAME/KEY: CDS
<222> LOCATION: (2432)..(3115)
<223> OTHER INFORMATION:
<220> FEATURE:
<221> NAME/KEY: CDS
<222> LOCATION: (3235)..(4065)
<223> OTHER INFORMATION:

<400> SEQUENCE: 16

tcacggcgcg cagattaccc agtgtgccgt agagacgctg atcggcattc tcacgcaccg      60

cgcaggtgtt gaagacgatg agatcagggg tgtcaccctc ccccgccgcg gtgtaaccgg     120

cctcctcgag cagaccggag agacgctcgg aatcgtggac gttcatctgg cagccgaagg     180

tacgcacctc ataggtgcgg gcagtggtgc cctcccggtt cccccgcgcc gggagggtgt     240

cggcggggtg gtccgggtgg gatggatggg tgttcatctg gtgggtatca atctgctgcg     300

tcacgggagg taattgtatc ggccgcgggc accctgacat aaacgtccga tccagaggaa     360

cgcaaccccg tggagtgtcg cagccatgca ggttgggcaa caccgtaacg gaacctagca     420

gagtggtagg attgacttca cattctttac ctattgagct attgataaaa tccgggcgga     480

aatggaaatc acccccacaa atcaccccaa ctgacctgtg gaaagggcga gaaatccagg     540

gaaattcatt tcaaaatgga ctcaatcaca ggatttaccc cacatgaccc aacattcctt     600

tatgctatcc ccatgacgca gaccacaaat cacccg atg atc aag atg acg ggg       654
                                       Met Ile Lys Met Thr Gly
                                       1               5

gtg cag aag ttc ttc gat gac ttc cag gcc ctg acc gat atc aat ctt       702
Val Gln Lys Phe Phe Asp Asp Phe Gln Ala Leu Thr Asp Ile Asn Leu
            10                  15                  20

gag gtc ccc gcg gga cag gtc gtt gtt gtt ctc ggc ccg tcc ggt tcc       750
Glu Val Pro Ala Gly Gln Val Val Val Val Leu Gly Pro Ser Gly Ser
        25                  30                  35

gga aag tcg acg ctg tgc cgc acc atc aac cgc ctc gaa acc atc gag       798
Gly Lys Ser Thr Leu Cys Arg Thr Ile Asn Arg Leu Glu Thr Ile Glu
    40                  45                  50

gag gga acc atc gag atc gat gga aaa ctg ctt ccg gag gag ggc aag       846
Glu Gly Thr Ile Glu Ile Asp Gly Lys Leu Leu Pro Glu Glu Gly Lys
55                  60                  65                  70

gac ctg gcc aag atc cgt gcc gac gtg ggc atg gtg ttc cag tct ttc       894
Asp Leu Ala Lys Ile Arg Ala Asp Val Gly Met Val Phe Gln Ser Phe
                75                  80                  85

aac ctc ttc ccc cac ctc acc atc aag gac aat gtc acc ctc ggc ccg       942
Asn Leu Phe Pro His Leu Thr Ile Lys Asp Asn Val Thr Leu Gly Pro
            90                  95                  100

atg aag gtc cgg aag atg aag aag tcc gag gcc aat gag gtg gcc atg       990
Met Lys Val Arg Lys Met Lys Lys Ser Glu Ala Asn Glu Val Ala Met
        105                 110                 115

aag ctg ttg gaa cgc gtc ggc atc gcc aac cag gcc gag aaa tac ccg      1038
Lys Leu Leu Glu Arg Val Gly Ile Ala Asn Gln Ala Glu Lys Tyr Pro
    120                 125                 130

gca cag ctc tcg ggc ggg cag cag cag cgc gtg gcc atc gcc cgc gca      1086
Ala Gln Leu Ser Gly Gly Gln Gln Gln Arg Val Ala Ile Ala Arg Ala
135                 140                 145                 150

ctg gcg atg aac ccc aag atc atg ctt ttc gac gaa cca acc tcc gcc      1134
Leu Ala Met Asn Pro Lys Ile Met Leu Phe Asp Glu Pro Thr Ser Ala
                155                 160                 165

ctc gac ccc gag atg gtc aac gag gtt ctg gac gtc atg gcg agt ctg      1182
Leu Asp Pro Glu Met Val Asn Glu Val Leu Asp Val Met Ala Ser Leu
```

-continued

```
        170                 175                 180

gcc aag gaa ggc atg acc atg gtg tgt gtc acc cac gag atg ggt ttc      1230
Ala Lys Glu Gly Met Thr Met Val Cys Val Thr His Glu Met Gly Phe
    185                 190                 195

gca cgc agg gcc gca gac cgt gtg ctg ttc atg tct gac ggc gcc atc      1278
Ala Arg Arg Ala Ala Asp Arg Val Leu Phe Met Ser Asp Gly Ala Ile
    200                 205                 210

gtc gag gac tcc gac ccg gag acc ttc ttc acc aat cca caa acc gac      1326
Val Glu Asp Ser Asp Pro Glu Thr Phe Phe Thr Asn Pro Gln Thr Asp
215                 220                 225                 230

cgg gcg aag gat ttc ctg ggc aag atc ctc gcc cac tgacctcccc          1372
Arg Ala Lys Asp Phe Leu Gly Lys Ile Leu Ala His
                235                 240

tcactctgtg tccaactccc ccgctggcca aaatcagcga ccatgaccaa caggagcatc   1432

a atg tcg cac aaa cgc atg ttc acc cgt ctc gcc gca gcc acc agc gca    1481
  Met Ser His Lys Arg Met Phe Thr Arg Leu Ala Ala Ala Thr Ser Ala
          245                 250                 255

gct gtt ctc gcc ggc atc acc ctc acc gcc tgt ggt gat tcc gag ggt      1529
Ala Val Leu Ala Gly Ile Thr Leu Thr Ala Cys Gly Asp Ser Glu Gly
    260                 265                 270

ggt gac ggt ctg ctc gcc gcc atc gaa aat ggc aat gtc acc atc ggc      1577
Gly Asp Gly Leu Leu Ala Ala Ile Glu Asn Gly Asn Val Thr Ile Gly
275                 280                 285                 290

acc aag tac gat cag ccg ggt ctg gga ctg cgt aac ccg gac aat tcc      1625
Thr Lys Tyr Asp Gln Pro Gly Leu Gly Leu Arg Asn Pro Asp Asn Ser
                295                 300                 305

atg agc gga ctg gat gtc gac gtc gcg cag tac gtg gtc aac tcc atc      1673
Met Ser Gly Leu Asp Val Asp Val Ala Gln Tyr Val Val Asn Ser Ile
        310                 315                 320

gcc gat gac aac ggt tgg gat cac ccc acc gtg gaa tgg cgc gag acc      1721
Ala Asp Asp Asn Gly Trp Asp His Pro Thr Val Glu Trp Arg Glu Thr
    325                 330                 335

ccc tcc gcc cag cgc gag acc ctc atc cag aac ggt gag gtg gat atg      1769
Pro Ser Ala Gln Arg Glu Thr Leu Ile Gln Asn Gly Glu Val Asp Met
    340                 345                 350

atc gcc gca acc tac tcc atc aac ccc gga cgc tcc gaa tcg gtg aac      1817
Ile Ala Ala Thr Tyr Ser Ile Asn Pro Gly Arg Ser Glu Ser Val Asn
355                 360                 365                 370

ttc ggt gga cca tac ctc ctc acc cac cag gcc ctc ctg gtc cgc gag      1865
Phe Gly Gly Pro Tyr Leu Leu Thr His Gln Ala Leu Leu Val Arg Glu
                375                 380                 385

gac gat gac cgc atc cag acc ctc gag gac ctc gat gac ggc ctg atc      1913
Asp Asp Asp Arg Ile Gln Thr Leu Glu Asp Leu Asp Asp Gly Leu Ile
        390                 395                 400

ctg tgt tcc gtt acc gga tcc acc ccc gcc cag aag gtc aag gat gtc      1961
Leu Cys Ser Val Thr Gly Ser Thr Pro Ala Gln Lys Val Lys Asp Val
    405                 410                 415

ctc ccc ggc gtc cag ctg cag gaa tac gac acc tac tcc tcc tgt gtg      2009
Leu Pro Gly Val Gln Leu Gln Glu Tyr Asp Thr Tyr Ser Ser Cys Val
    420                 425                 430

gag gca ctg agc cag ggc aac gtc gat gca atg acc acc gac gcc acc      2057
Glu Ala Leu Ser Gln Gly Asn Val Asp Ala Met Thr Thr Asp Ala Thr
435                 440                 445                 450

atc ctc ttc ggc tac gcg cag cag cgc gaa ggt gaa ttc cgc gtc gtg      2105
Ile Leu Phe Gly Tyr Ala Gln Gln Arg Glu Gly Glu Phe Arg Val Val
                455                 460                 465

gag atg gaa cag gac ggc gag ccg ttc acc aat gag tac tac ggc atc      2153
Glu Met Glu Gln Asp Gly Glu Pro Phe Thr Asn Glu Tyr Tyr Gly Ile
        470                 475                 480
```

-continued

```
ggt atc acc aag gat gac acc gaa gcc acc gat gcg atc aac gca gcg     2201
Gly Ile Thr Lys Asp Asp Thr Glu Ala Thr Asp Ala Ile Asn Ala Ala
        485                 490                 495

ttg gag cgt atg tac gcc gac ggt tcc ttc cag cgt ttc ctc acc gag     2249
Leu Glu Arg Met Tyr Ala Asp Gly Ser Phe Gln Arg Phe Leu Thr Glu
    500                 505                 510

aac ctc ggc gag gat tcc cag gtt gtc cag gag ggc acc ccg ggt gac     2297
Asn Leu Gly Glu Asp Ser Gln Val Val Gln Glu Gly Thr Pro Gly Asp
515                 520                 525                 530

ctc tcc ttc ctg gac gag tgacctgacg gggccgaacg cccgatgagc            2345
Leu Ser Phe Leu Asp Glu
                535

atgcgtggcc cccgcatccc ggggtgccac gcatcatcac tttcaccact gatcccctac   2405

cgttccttac cgaggagaaa ttcccc atg agt aca tta tgg gcg gat ctg ggt    2458
                             Met Ser Thr Leu Trp Ala Asp Leu Gly
                                         540                 545

ccg tca ctc cta ccc gca ttc tgg gtg aca atc caa ctc acc gtc tat     2506
Pro Ser Leu Leu Pro Ala Phe Trp Val Thr Ile Gln Leu Thr Val Tyr
                550                 555                 560

tcc gcc atc gga tcc atg atc ctc ggt acc atc ctc acc gcc atg agg     2554
Ser Ala Ile Gly Ser Met Ile Leu Gly Thr Ile Leu Thr Ala Met Arg
            565                 570                 575

gtg tcc ccg gtg aag atc ctg cgc agc ata tcc acc gcc tac atc aac     2602
Val Ser Pro Val Lys Ile Leu Arg Ser Ile Ser Thr Ala Tyr Ile Asn
        580                 585                 590

acg gtc cgt aac acc cca ctg acc ctg gtg atc ctg ttc tgt tcc ttc     2650
Thr Val Arg Asn Thr Pro Leu Thr Leu Val Ile Leu Phe Cys Ser Phe
    595                 600                 605

ggc ctg tat cag aat ctc ggt ctc acc ctc gcc ggt cgc gac agt tcc     2698
Gly Leu Tyr Gln Asn Leu Gly Leu Thr Leu Ala Gly Arg Asp Ser Ser
610                 615                 620                 625

acc ttt ctg gcc gat aac aac ttc cgg ctc gcg gtg ctc gga ttc atc     2746
Thr Phe Leu Ala Asp Asn Asn Phe Arg Leu Ala Val Leu Gly Phe Ile
                630                 635                 640

ctg tac acc tcc gcc ttc gtt gcg gaa tca ctc cgg tca ggc atc aac     2794
Leu Tyr Thr Ser Ala Phe Val Ala Glu Ser Leu Arg Ser Gly Ile Asn
            645                 650                 655

acc gtg cac ttc ggg cag gcg gag gcc gcc cgg tcg ctg gga ctc ggt     2842
Thr Val His Phe Gly Gln Ala Glu Ala Ala Arg Ser Leu Gly Leu Gly
        660                 665                 670

ttc agt gac atc ttc cgg tcc atc atc ttc ccc cag gcg gtg cgt gcc     2890
Phe Ser Asp Ile Phe Arg Ser Ile Ile Phe Pro Gln Ala Val Arg Ala
    675                 680                 685

gcc atc atc ccg ctg ggc aac acc ctc atc gcc ctg acc aag aac acc     2938
Ala Ile Ile Pro Leu Gly Asn Thr Leu Ile Ala Leu Thr Lys Asn Thr
690                 695                 700                 705

acg atc gcg tcc gtg atc ggc gtc ggt gag gcc tcg ctg ctg atg aag     2986
Thr Ile Ala Ser Val Ile Gly Val Gly Glu Ala Ser Leu Leu Met Lys
                710                 715                 720

tcc acg att gaa aat cat gcc aac atg ctc ttc gtc gtg ttc gcc atc     3034
Ser Thr Ile Glu Asn His Ala Asn Met Leu Phe Val Val Phe Ala Ile
            725                 730                 735

ttc gcc gtc ggc ttc atg atc ctc acc ctc ccc atg ggc ctg ggg ctt     3082
Phe Ala Val Gly Phe Met Ile Leu Thr Leu Pro Met Gly Leu Gly Leu
        740                 745                 750

gga aaa ctc gct gag aaa atg gcg gtg aag aaa taatgtcctc ctccgtacgc   3135
Gly Lys Leu Ala Glu Lys Met Ala Val Lys Lys
    755                 760
```

-continued

```
gcaacagtcc tctacgacgc ccccggcccc cggggacgca ggtccaacac catcatcacc   3195

atcgccacca ccctggtggc agtggccgtc ctgttctgg gtg ggc agt gtt ctc      3249
                                         Val Gly Ser Val Leu
                                         765

cag gaa aac ggc cag ttg gac ggc gac aaa tgg acc ccg ttc ctc gat     3297
Gln Glu Asn Gly Gln Leu Asp Gly Asp Lys Trp Thr Pro Phe Leu Asp
770                 775                 780                 785

ccc cag acc tgg acc acc tat ctt ctg ccc ggc ctg tgg gga acc ctg     3345
Pro Gln Thr Trp Thr Thr Tyr Leu Leu Pro Gly Leu Trp Gly Thr Leu
                790                 795                 800

aag gca gcg gtg gcc tcc atc ctt ctc gcg ctg atc atg ggc acc ctg     3393
Lys Ala Ala Val Ala Ser Ile Leu Leu Ala Leu Ile Met Gly Thr Leu
            805                 810                 815

ctc ggg ctc gga cgc atc tcc gaa atc cgg ctc ctg cgc tgg ttc tgc     3441
Leu Gly Leu Gly Arg Ile Ser Glu Ile Arg Leu Leu Arg Trp Phe Cys
        820                 825                 830

ggg atc atc atc gag acc ttc cgt gcc atc ccg gtg ctg atc ctc atg     3489
Gly Ile Ile Ile Glu Thr Phe Arg Ala Ile Pro Val Leu Ile Leu Met
    835                 840                 845

atc ttc gcc tat cag ttg ttc gcc cgt tac cag ctc gtt cca tca cgc     3537
Ile Phe Ala Tyr Gln Leu Phe Ala Arg Tyr Gln Leu Val Pro Ser Arg
850                 855                 860                 865

cag ctg gcc ttc gcc gcg gtg gtc ttc ggt ctc acc atg tac aac ggc     3585
Gln Leu Ala Phe Ala Ala Val Val Phe Gly Leu Thr Met Tyr Asn Gly
                870                 875                 880

tcc gtc atc gcc gag atc ctt aga tcg ggt atc gcc tcc ctg ccg aag     3633
Ser Val Ile Ala Glu Ile Leu Arg Ser Gly Ile Ala Ser Leu Pro Lys
            885                 890                 895

gga cag cgt gag gcg gcg atc gcc ctg ggc atg tca acc cgc cag acc     3681
Gly Gln Arg Glu Ala Ala Ile Ala Leu Gly Met Ser Thr Arg Gln Thr
        900                 905                 910

acc tgg tcg atc ctg ctc ccc cag gcg gtg gca gcg atg ctg ccc gcc     3729
Thr Trp Ser Ile Leu Leu Pro Gln Ala Val Ala Ala Met Leu Pro Ala
    915                 920                 925

ctg atc gcg cag atg gtc atc gcg ctg aag gac tcc gcc ctc ggt tac     3777
Leu Ile Ala Gln Met Val Ile Ala Leu Lys Asp Ser Ala Leu Gly Tyr
930                 935                 940                 945

cag atc ggt tat atc gag gtg gta cgc tcc ggt atc cag tcc gca tcc     3825
Gln Ile Gly Tyr Ile Glu Val Val Arg Ser Gly Ile Gln Ser Ala Ser
                950                 955                 960

gtc aac cgg aac tac ctg gct gcc ctc gcg gtg gtc gcg gtc atc atg     3873
Val Asn Arg Asn Tyr Leu Ala Ala Leu Ala Val Val Ala Val Ile Met
            965                 970                 975

atc ctg atc aac ttc gca ctg acc gca ctg gca gag cgt atc cag cgt     3921
Ile Leu Ile Asn Phe Ala Leu Thr Ala Leu Ala Glu Arg Ile Gln Arg
        980                 985                 990

cag ctg cgt gcc gga cgt gcc  cgc agg aac att gtg  gca aag gtg ccc   3969
Gln Leu Arg Ala Gly Arg Ala  Arg Arg Asn Ile Val  Ala Lys Val Pro
    995                 1000                1005

gag  gaa ccc gat cag ggc  ctg gat acc aag gac  aat gtg aac gtg      4014
Glu  Glu Pro Asp Gln Gly  Leu Asp Thr Lys Asp  Asn Val Asn Val
1010                1015                1020

gat  tgg cac gat ccc gat  tac aag gaa gtc aaa  cac ccg gga ccg      4059
Asp  Trp His Asp Pro Asp  Tyr Lys Glu Val Lys  His Pro Gly Pro
1025                1030                1035

tca  ttc tgacaggtcc ctggatcccc gctgcggtca ggaggcgggt gcaacaatga     4115
Ser  Phe
1040

agtccggctg cccagatgtc tggggcagcc ggactttgtg gcagatcaat gctgactgag   4175
```

gtcctcgatg cgctcatcga gagcctcccg ggccaggtcc atcgacatac ccgcggggaa 4235 tccacgacgg gcaagtgct 4254

<210> SEQ ID NO 17
<211> LENGTH: 242
<212> TYPE: PRT
<213> ORGANISM: Corynebacterium thermoaminogenes

<400> SEQUENCE: 17

```
Met Ile Lys Met Thr Gly Val Gln Lys Phe Phe Asp Asp Phe Gln Ala
1               5                   10                  15

Leu Thr Asp Ile Asn Leu Glu Val Pro Ala Gly Gln Val Val Val Val
            20                  25                  30

Leu Gly Pro Ser Gly Ser Gly Lys Ser Thr Leu Cys Arg Thr Ile Asn
        35                  40                  45

Arg Leu Glu Thr Ile Glu Glu Gly Thr Ile Glu Ile Asp Gly Lys Leu
    50                  55                  60

Leu Pro Glu Glu Gly Lys Asp Leu Ala Lys Ile Arg Ala Asp Val Gly
65                  70                  75                  80

Met Val Phe Gln Ser Phe Asn Leu Phe Pro His Leu Thr Ile Lys Asp
                85                  90                  95

Asn Val Thr Leu Gly Pro Met Lys Val Arg Lys Met Lys Lys Ser Glu
            100                 105                 110

Ala Asn Glu Val Ala Met Lys Leu Leu Glu Arg Val Gly Ile Ala Asn
        115                 120                 125

Gln Ala Glu Lys Tyr Pro Ala Gln Leu Ser Gly Gly Gln Gln Gln Arg
    130                 135                 140

Val Ala Ile Ala Arg Ala Leu Ala Met Asn Pro Lys Ile Met Leu Phe
145                 150                 155                 160

Asp Glu Pro Thr Ser Ala Leu Asp Pro Glu Met Val Asn Glu Val Leu
                165                 170                 175

Asp Val Met Ala Ser Leu Ala Lys Glu Gly Met Thr Met Val Cys Val
            180                 185                 190

Thr His Glu Met Gly Phe Ala Arg Arg Ala Ala Asp Arg Val Leu Phe
        195                 200                 205

Met Ser Asp Gly Ala Ile Val Glu Asp Ser Asp Pro Glu Thr Phe Phe
    210                 215                 220

Thr Asn Pro Gln Thr Asp Arg Ala Lys Asp Phe Leu Gly Lys Ile Leu
225                 230                 235                 240

Ala His
```

<210> SEQ ID NO 18
<211> LENGTH: 294
<212> TYPE: PRT
<213> ORGANISM: Corynebacterium thermoaminogenes

<400> SEQUENCE: 18

```
Met Ser His Lys Arg Met Phe Thr Arg Leu Ala Ala Ala Thr Ser Ala
1               5                   10                  15

Ala Val Leu Ala Gly Ile Thr Leu Thr Ala Cys Gly Asp Ser Glu Gly
            20                  25                  30

Gly Asp Gly Leu Leu Ala Ala Ile Glu Asn Gly Asn Val Thr Ile Gly
        35                  40                  45

Thr Lys Tyr Asp Gln Pro Gly Leu Gly Leu Arg Asn Pro Asp Asn Ser
    50                  55                  60
```

-continued

```
Met Ser Gly Leu Asp Val Asp Val Ala Gln Tyr Val Val Asn Ser Ile
65                  70                  75                  80

Ala Asp Asp Asn Gly Trp Asp His Pro Thr Val Glu Trp Arg Glu Thr
                85                  90                  95

Pro Ser Ala Gln Arg Glu Thr Leu Ile Gln Asn Gly Glu Val Asp Met
            100                 105                 110

Ile Ala Ala Thr Tyr Ser Ile Asn Pro Gly Arg Ser Glu Ser Val Asn
        115                 120                 125

Phe Gly Gly Pro Tyr Leu Leu Thr His Gln Ala Leu Leu Val Arg Glu
    130                 135                 140

Asp Asp Asp Arg Ile Gln Thr Leu Glu Asp Leu Asp Asp Gly Leu Ile
145                 150                 155                 160

Leu Cys Ser Val Thr Gly Ser Thr Pro Ala Gln Lys Val Lys Asp Val
                165                 170                 175

Leu Pro Gly Val Gln Leu Gln Glu Tyr Asp Thr Tyr Ser Ser Cys Val
            180                 185                 190

Glu Ala Leu Ser Gln Gly Asn Val Asp Ala Met Thr Thr Asp Ala Thr
        195                 200                 205

Ile Leu Phe Gly Tyr Ala Gln Gln Arg Glu Gly Glu Phe Arg Val Val
    210                 215                 220

Glu Met Glu Gln Asp Gly Glu Pro Phe Thr Asn Glu Tyr Tyr Gly Ile
225                 230                 235                 240

Gly Ile Thr Lys Asp Asp Thr Glu Ala Thr Asp Ala Ile Asn Ala Ala
                245                 250                 255

Leu Glu Arg Met Tyr Ala Asp Gly Ser Phe Gln Arg Phe Leu Thr Glu
            260                 265                 270

Asn Leu Gly Glu Asp Ser Gln Val Val Gln Glu Gly Thr Pro Gly Asp
        275                 280                 285

Leu Ser Phe Leu Asp Glu
    290


<210> SEQ ID NO 19
<211> LENGTH: 228
<212> TYPE: PRT
<213> ORGANISM: Corynebacterium thermoaminogenes

<400> SEQUENCE: 19

Met Ser Thr Leu Trp Ala Asp Leu Gly Pro Ser Leu Leu Pro Ala Phe
1               5                   10                  15

Trp Val Thr Ile Gln Leu Thr Val Tyr Ser Ala Ile Gly Ser Met Ile
            20                  25                  30

Leu Gly Thr Ile Leu Thr Ala Met Arg Val Ser Pro Val Lys Ile Leu
        35                  40                  45

Arg Ser Ile Ser Thr Ala Tyr Ile Asn Thr Val Arg Asn Thr Pro Leu
    50                  55                  60

Thr Leu Val Ile Leu Phe Cys Ser Phe Gly Leu Tyr Gln Asn Leu Gly
65                  70                  75                  80

Leu Thr Leu Ala Gly Arg Asp Ser Ser Thr Phe Leu Ala Asp Asn Asn
                85                  90                  95

Phe Arg Leu Ala Val Leu Gly Phe Ile Leu Tyr Thr Ser Ala Phe Val
            100                 105                 110

Ala Glu Ser Leu Arg Ser Gly Ile Asn Thr Val His Phe Gly Gln Ala
        115                 120                 125

Glu Ala Ala Arg Ser Leu Gly Leu Gly Phe Ser Asp Ile Phe Arg Ser
```

-continued

```
    130                 135                 140

Ile Ile Phe Pro Gln Ala Val Arg Ala Ala Ile Ile Pro Leu Gly Asn
145                 150                 155                 160

Thr Leu Ile Ala Leu Thr Lys Asn Thr Thr Ile Ala Ser Val Ile Gly
                165                 170                 175

Val Gly Glu Ala Ser Leu Leu Met Lys Ser Thr Ile Glu Asn His Ala
            180                 185                 190

Asn Met Leu Phe Val Val Phe Ala Ile Phe Ala Val Gly Phe Met Ile
        195                 200                 205

Leu Thr Leu Pro Met Gly Leu Gly Leu Gly Lys Leu Ala Glu Lys Met
    210                 215                 220

Ala Val Lys Lys
225


<210> SEQ ID NO 20
<211> LENGTH: 277
<212> TYPE: PRT
<213> ORGANISM: Corynebacterium thermoaminogenes

<400> SEQUENCE: 20

Val Gly Ser Val Leu Gln Glu Asn Gly Gln Leu Asp Gly Asp Lys Trp
1               5                   10                  15

Thr Pro Phe Leu Asp Pro Gln Thr Trp Thr Thr Tyr Leu Leu Pro Gly
            20                  25                  30

Leu Trp Gly Thr Leu Lys Ala Ala Val Ala Ser Ile Leu Leu Ala Leu
        35                  40                  45

Ile Met Gly Thr Leu Leu Gly Leu Gly Arg Ile Ser Glu Ile Arg Leu
    50                  55                  60

Leu Arg Trp Phe Cys Gly Ile Ile Ile Glu Thr Phe Arg Ala Ile Pro
65                  70                  75                  80

Val Leu Ile Leu Met Ile Phe Ala Tyr Gln Leu Phe Ala Arg Tyr Gln
                85                  90                  95

Leu Val Pro Ser Arg Gln Leu Ala Phe Ala Ala Val Val Phe Gly Leu
            100                 105                 110

Thr Met Tyr Asn Gly Ser Val Ile Ala Glu Ile Leu Arg Ser Gly Ile
        115                 120                 125

Ala Ser Leu Pro Lys Gly Gln Arg Glu Ala Ala Ile Ala Leu Gly Met
    130                 135                 140

Ser Thr Arg Gln Thr Thr Trp Ser Ile Leu Leu Pro Gln Ala Val Ala
145                 150                 155                 160

Ala Met Leu Pro Ala Leu Ile Ala Gln Met Val Ile Ala Leu Lys Asp
                165                 170                 175

Ser Ala Leu Gly Tyr Gln Ile Gly Tyr Ile Glu Val Val Arg Ser Gly
            180                 185                 190

Ile Gln Ser Ala Ser Val Asn Arg Asn Tyr Leu Ala Ala Leu Ala Val
        195                 200                 205

Val Ala Val Ile Met Ile Leu Ile Asn Phe Ala Leu Thr Ala Leu Ala
    210                 215                 220

Glu Arg Ile Gln Arg Gln Leu Arg Ala Gly Arg Ala Arg Arg Asn Ile
225                 230                 235                 240

Val Ala Lys Val Pro Glu Glu Pro Asp Gln Gly Leu Asp Thr Lys Asp
                245                 250                 255

Asn Val Asn Val Asp Trp His Asp Pro Asp Tyr Lys Glu Val Lys His
            260                 265                 270
```

-continued

```
Pro Gly Pro Ser Phe
        275


<210> SEQ ID NO 21
<211> LENGTH: 3598
<212> TYPE: DNA
<213> ORGANISM: Corynebacterium thermoaminogenes
<220> FEATURE:
<221> NAME/KEY: CDS
<222> LOCATION: (454)..(3222)
<223> OTHER INFORMATION:

<400> SEQUENCE: 21

agcacggcca aacatgagag aaacttcaca ttttgaattt ccccttcct gcatatggaa      60

aaccgccggt gacacccctg ccatttgggc agctcccccc acctcaccat gtccacattt     120

tccataatgt ggcctgtaac acccttgggc tcaaggcttc cacgccccac cgggaccctc     180

atcagcaggt gaaacagacc ctcctgcaat gctttgttaa aaagaaccgc cctttgtgcg     240

tatccttgtg tcaattgtgc gcgcactgcc accagctttc ctcaggattg aacacggtcg     300

ggaaatcctc cccggatacc ctgcacgccc cacctcccac accgacaccg gcggggaggg     360

ccgggcacgt tttcagctgc gggtgatgga agcggtcgcc ggtcccccgg tcgcataaac     420

gaaatgaaaa acattccaac aggaggtgtg gaa atg gcc gat caa gca aaa ctt     474
                                     Met Ala Asp Gln Ala Lys Leu
                                     1               5

ggt ggc aaa ccc aca gat gac acc aac ttc gcg atg atc cgt gat ggc     522
Gly Gly Lys Pro Thr Asp Asp Thr Asn Phe Ala Met Ile Arg Asp Gly
        10                  15                  20

gtt gca tct tat ttg aac gac tcc gac ccg gag gag acc aag gag tgg     570
Val Ala Ser Tyr Leu Asn Asp Ser Asp Pro Glu Glu Thr Lys Glu Trp
    25                  30                  35

atg gac tcc cta gac ggt cta ctg cag gat tcc tct ccg gag cgc gcc     618
Met Asp Ser Leu Asp Gly Leu Leu Gln Asp Ser Ser Pro Glu Arg Ala
40                  45                  50                  55

cgt tac ctg atg ctg cgc ctg ctg gag cgg gca tcc gcc aag cgt gtc     666
Arg Tyr Leu Met Leu Arg Leu Leu Glu Arg Ala Ser Ala Lys Arg Val
                60                  65                  70

cca ctg ccc ccg atg acg tcc acc gat tac gtc aac acc atc ccc aca     714
Pro Leu Pro Pro Met Thr Ser Thr Asp Tyr Val Asn Thr Ile Pro Thr
            75                  80                  85

tcc atg gag ccc gat ttc ccg ggt gat gag gag atg gag aag cgc tac     762
Ser Met Glu Pro Asp Phe Pro Gly Asp Glu Glu Met Glu Lys Arg Tyr
        90                  95                  100

cgc cgc tgg atg cgc tgg aac gcc gcc atc atg gtg cac cgt gcc cag     810
Arg Arg Trp Met Arg Trp Asn Ala Ala Ile Met Val His Arg Ala Gln
    105                 110                 115

cgc ccg gga atc ggt gtg ggt ggg cac atc tcc acc tac gcc ggc gcc     858
Arg Pro Gly Ile Gly Val Gly Gly His Ile Ser Thr Tyr Ala Gly Ala
120                 125                 130                 135

gcc cca ctc tac gag gtc ggt ttc aac cac ttc ttc cgc ggc aag gac     906
Ala Pro Leu Tyr Glu Val Gly Phe Asn His Phe Phe Arg Gly Lys Asp
                140                 145                 150

cac ccg ggt ggc ggt gac cag gtc ttc ttc cag ggt cac gcc tcc ccg     954
His Pro Gly Gly Gly Asp Gln Val Phe Phe Gln Gly His Ala Ser Pro
            155                 160                 165

ggc atg tac gcc cgc gcc ttc ctc gag ggc cgt ctc acc gag agc gat    1002
Gly Met Tyr Ala Arg Ala Phe Leu Glu Gly Arg Leu Thr Glu Ser Asp
        170                 175                 180

ctg gac agc ttc cgc cag gag gtc tcc tac gaa ggt ggt ggc atc ccg    1050
Leu Asp Ser Phe Arg Gln Glu Val Ser Tyr Glu Gly Gly Gly Ile Pro
```

-continued

```
    185                 190                 195

tcc tac ccg cac ccg cac ggc atg ccg gac ttc tgg gag ttc ccg acc      1098
Ser Tyr Pro His Pro His Gly Met Pro Asp Phe Trp Glu Phe Pro Thr
200                 205                 210                 215

gtg tcc atg ggc ctc ggg ccc atg gat gcc atc tac cag gcg cgc ttc      1146
Val Ser Met Gly Leu Gly Pro Met Asp Ala Ile Tyr Gln Ala Arg Phe
                220                 225                 230

aac cgc tac ctg cac aac cgt ggc atc aag gac acc tcg gag cag cac      1194
Asn Arg Tyr Leu His Asn Arg Gly Ile Lys Asp Thr Ser Glu Gln His
            235                 240                 245

gtc tgg gca ttc ctc ggt gac ggc gag atg gat gag ccg gag tcc cgt      1242
Val Trp Ala Phe Leu Gly Asp Gly Glu Met Asp Glu Pro Glu Ser Arg
        250                 255                 260

ggt ctc atc cac cag gct gcg ctg aac aac ctg gac aac ctc acc ttc      1290
Gly Leu Ile His Gln Ala Ala Leu Asn Asn Leu Asp Asn Leu Thr Phe
    265                 270                 275

gtg atc aac tgc aac ctg cag cgt ctt gat ggc ccg gtc cgc ggt aac      1338
Val Ile Asn Cys Asn Leu Gln Arg Leu Asp Gly Pro Val Arg Gly Asn
280                 285                 290                 295

acc aag atc atc cag gaa ctc gag tcc ttc ttc cgt ggt gcc ggc tgg      1386
Thr Lys Ile Ile Gln Glu Leu Glu Ser Phe Phe Arg Gly Ala Gly Trp
                300                 305                 310

tcc gtc atc aag gtc atc tgg ggc cgt gag tgg gat gaa ctg ctg gag      1434
Ser Val Ile Lys Val Ile Trp Gly Arg Glu Trp Asp Glu Leu Leu Glu
            315                 320                 325

aag gac cag gac ggt gct ctt gtc gag gtc atg aac aac acc tcc gac      1482
Lys Asp Gln Asp Gly Ala Leu Val Glu Val Met Asn Asn Thr Ser Asp
        330                 335                 340

ggt gac tac cag acc ttc aag gcc aat gac ggt gcc tac gtc cgt gag      1530
Gly Asp Tyr Gln Thr Phe Lys Ala Asn Asp Gly Ala Tyr Val Arg Glu
    345                 350                 355

cac ttc ttc ggc cgt gac ccc cgc acc ctc aag ctc gtc gag gac atg      1578
His Phe Phe Gly Arg Asp Pro Arg Thr Leu Lys Leu Val Glu Asp Met
360                 365                 370                 375

acc gac gag gag atc tgg aag ctg ccc cgt ggt ggc cat gac tac cgt      1626
Thr Asp Glu Glu Ile Trp Lys Leu Pro Arg Gly Gly His Asp Tyr Arg
                380                 385                 390

aag gtc tac gcc gcc tac aag cgt gcg ctg gag acc aag gac cgc ccg      1674
Lys Val Tyr Ala Ala Tyr Lys Arg Ala Leu Glu Thr Lys Asp Arg Pro
            395                 400                 405

acc gtc att ctc gcc cat acc atc aag ggc tac ggc ctg ggc cac aac      1722
Thr Val Ile Leu Ala His Thr Ile Lys Gly Tyr Gly Leu Gly His Asn
        410                 415                 420

ttc gag ggc cgc aac gcg acc cac cag atg aag aag ctg acc ctg gat      1770
Phe Glu Gly Arg Asn Ala Thr His Gln Met Lys Lys Leu Thr Leu Asp
    425                 430                 435

gac ctg aag ctg ttc cgt gac aag cag ggt ctg ccc atc acc gat gag      1818
Asp Leu Lys Leu Phe Arg Asp Lys Gln Gly Leu Pro Ile Thr Asp Glu
440                 445                 450                 455

gag ctg gag aag gat ccc tac ctg cct ccg tac tac cac ccg ggt gag      1866
Glu Leu Glu Lys Asp Pro Tyr Leu Pro Pro Tyr Tyr His Pro Gly Glu
                460                 465                 470

gac gca ccg gag atc aag tac atg aag gag cgt cgc cag gcg ctc ggt      1914
Asp Ala Pro Glu Ile Lys Tyr Met Lys Glu Arg Arg Gln Ala Leu Gly
            475                 480                 485

ggt ttc ctg ccg gag cgc cgt gag aag tac gag cca ctg cag gtt ccc      1962
Gly Phe Leu Pro Glu Arg Arg Glu Lys Tyr Glu Pro Leu Gln Val Pro
        490                 495                 500

ccg ctg gac aag ctg cgg tcc gtg cgc aag ggt tcc ggc aag cag cag      2010
```

-continued

```
Pro Leu Asp Lys Leu Arg Ser Val Arg Lys Gly Ser Gly Lys Gln Gln
    505                 510                 515

gtg gcc acc acc atg gcc acg gtg cgt acc ttc aag gaa ctc atg cgg      2058
Val Ala Thr Thr Met Ala Thr Val Arg Thr Phe Lys Glu Leu Met Arg
520                 525                 530                 535

gac aag aac ctg gcc gac cgc ttg gtc ccg atc atc ccg gat gag gcc      2106
Asp Lys Asn Leu Ala Asp Arg Leu Val Pro Ile Ile Pro Asp Glu Ala
                540                 545                 550

cgc acc ttc ggc ctg gac tcc tgg ttc ccg acc ctg aaa atc tac aac      2154
Arg Thr Phe Gly Leu Asp Ser Trp Phe Pro Thr Leu Lys Ile Tyr Asn
            555                 560                 565

ccg cac ggt cag aac tac gtg ccg gtc gac cat gac ctc atg ctg tcc      2202
Pro His Gly Gln Asn Tyr Val Pro Val Asp His Asp Leu Met Leu Ser
        570                 575                 580

tac cgt gag gcc aag gac ggc cag atc ctg cat gag ggc atc aac gag      2250
Tyr Arg Glu Ala Lys Asp Gly Gln Ile Leu His Glu Gly Ile Asn Glu
    585                 590                 595

gcc ggt tcc gtg gca tcg ttt atc gcc gcc gga acc tcc tac gcc acc      2298
Ala Gly Ser Val Ala Ser Phe Ile Ala Ala Gly Thr Ser Tyr Ala Thr
600                 605                 610                 615

cat ggc gag gcc atg atc ccg ctg tac atc ttc tac tcg atg ttc ggc      2346
His Gly Glu Ala Met Ile Pro Leu Tyr Ile Phe Tyr Ser Met Phe Gly
                620                 625                 630

ttc cag cgc acc ggt gac ggc atc tgg gcc gca gcc gac cag atg acg      2394
Phe Gln Arg Thr Gly Asp Gly Ile Trp Ala Ala Ala Asp Gln Met Thr
            635                 640                 645

cgt ggt ttc ctc ctg ggc gcc acc gcc ggt cgc acc acc ctg acc ggt      2442
Arg Gly Phe Leu Leu Gly Ala Thr Ala Gly Arg Thr Thr Leu Thr Gly
        650                 655                 660

gag ggc ctc cag cac atg gat ggc cac tcc ccg atc ctg gcc tcc acc      2490
Glu Gly Leu Gln His Met Asp Gly His Ser Pro Ile Leu Ala Ser Thr
    665                 670                 675

aac ccc ggt gtg gag acc tat gac ccg gcg ttc tcc tac gag atc gcg      2538
Asn Pro Gly Val Glu Thr Tyr Asp Pro Ala Phe Ser Tyr Glu Ile Ala
680                 685                 690                 695

cac ctg gtc cac cgc ggc atc gac cgc atg tac gga ccg ggc aag ggt      2586
His Leu Val His Arg Gly Ile Asp Arg Met Tyr Gly Pro Gly Lys Gly
                700                 705                 710

gag aat gtc atc tac tac ctc acc atc tac aac gag cca acc ccg cag      2634
Glu Asn Val Ile Tyr Tyr Leu Thr Ile Tyr Asn Glu Pro Thr Pro Gln
            715                 720                 725

ccg gct gag cct gag gat ctg gac gtc gag ggc ctg cac aag ggc atc      2682
Pro Ala Glu Pro Glu Asp Leu Asp Val Glu Gly Leu His Lys Gly Ile
        730                 735                 740

tac ctc tac gac aag gcc gcc gag ggt gag ggc cat gag gcc tcg atc      2730
Tyr Leu Tyr Asp Lys Ala Ala Glu Gly Glu Gly His Glu Ala Ser Ile
    745                 750                 755

ctg gcc tcc ggc atc ggc atg cag tgg gca ctg cgc gcc cgt gac atc      2778
Leu Ala Ser Gly Ile Gly Met Gln Trp Ala Leu Arg Ala Arg Asp Ile
760                 765                 770                 775

ctc gcc gag gat tac ggc atc cgt gcc aac atc ttc tcc gcc acc tcg      2826
Leu Ala Glu Asp Tyr Gly Ile Arg Ala Asn Ile Phe Ser Ala Thr Ser
                780                 785                 790

tgg gtg gag ctg gcc cgc gac ggt gcc cgc cgt aac ctg gag gcg ctg      2874
Trp Val Glu Leu Ala Arg Asp Gly Ala Arg Arg Asn Leu Glu Ala Leu
            795                 800                 805

cgc aac ccg ggt gcg gat gtc ggt gag gca ttc gtg acc acc cag ctg      2922
Arg Asn Pro Gly Ala Asp Val Gly Glu Ala Phe Val Thr Thr Gln Leu
        810                 815                 820
```

-continued

```
aag aag ggt tcc ggc ccc tac gtc gcg gtg tcc gac ttc gcg acc gac     2970
Lys Lys Gly Ser Gly Pro Tyr Val Ala Val Ser Asp Phe Ala Thr Asp
    825                 830                 835

ctg ccg aac cag atc cgc gag tgg gtt ccc ggt gac tac atc gtc ctc     3018
Leu Pro Asn Gln Ile Arg Glu Trp Val Pro Gly Asp Tyr Ile Val Leu
840                 845                 850                 855

ggt gcc gac ggc ttc ggt ttc tcc gat acc cgt ccg gca gcc cgt cgt     3066
Gly Ala Asp Gly Phe Gly Phe Ser Asp Thr Arg Pro Ala Ala Arg Arg
                860                 865                 870

tac ttc aac atc gac gcc gag tcc atc gtc gtg gcg gtc ctg cgc ggc     3114
Tyr Phe Asn Ile Asp Ala Glu Ser Ile Val Val Ala Val Leu Arg Gly
            875                 880                 885

ctg gtc cgc gag ggt gtc atc gat gcc tcc gtg gcg gcg cac gcg gct     3162
Leu Val Arg Glu Gly Val Ile Asp Ala Ser Val Ala Ala His Ala Ala
        890                 895                 900

gag aag tac aag ctg tcc gac ccg acg gca cca cag gtc gat ccg gac     3210
Glu Lys Tyr Lys Leu Ser Asp Pro Thr Ala Pro Gln Val Asp Pro Asp
    905                 910                 915

gca ccg atc gag tagacctgct tgtcgacgaa aaacaccccc gccccctcac         3262
Ala Pro Ile Glu
920

atgatgaggg gggcgggggt gtgctcgttt acggcgggta caggggggta tcagcccagc   3322

atcgccttat cggagagcgt cgcgcccttg atcttggcga attcctgcag cagatcccgc   3382

acggtgagct tctgcttcac ctctgcgctg gcctcataga cgatccgtcc ctcgtgcatc   3442

atgatgaggc ggttacccag gcggatagcc tgttccatgt tgtgggtgac catgagggtg   3502

gtcagtttgc cgtcctcgac gatcttctcg gtcagggtgg tgaccagttc ggctcgctgg   3562

gggtccaggg cggcggtgtg ttcgtcgaga agcatg                             3598
```

<210> SEQ ID NO 22
<211> LENGTH: 923
<212> TYPE: PRT
<213> ORGANISM: Corynebacterium thermoaminogenes

<400> SEQUENCE: 22

```
Met Ala Asp Gln Ala Lys Leu Gly Gly Lys Pro Thr Asp Asp Thr Asn
1               5                   10                  15

Phe Ala Met Ile Arg Asp Gly Val Ala Ser Tyr Leu Asn Asp Ser Asp
            20                  25                  30

Pro Glu Glu Thr Lys Glu Trp Met Asp Ser Leu Asp Gly Leu Leu Gln
        35                  40                  45

Asp Ser Ser Pro Glu Arg Ala Arg Tyr Leu Met Leu Arg Leu Leu Glu
    50                  55                  60

Arg Ala Ser Ala Lys Arg Val Pro Leu Pro Pro Met Thr Ser Thr Asp
65                  70                  75                  80

Tyr Val Asn Thr Ile Pro Thr Ser Met Glu Pro Asp Phe Pro Gly Asp
                85                  90                  95

Glu Glu Met Glu Lys Arg Tyr Arg Arg Trp Met Arg Trp Asn Ala Ala
            100                 105                 110

Ile Met Val His Arg Ala Gln Arg Pro Gly Ile Gly Val Gly Gly His
        115                 120                 125

Ile Ser Thr Tyr Ala Gly Ala Ala Pro Leu Tyr Glu Val Gly Phe Asn
    130                 135                 140

His Phe Phe Arg Gly Lys Asp His Pro Gly Gly Gly Asp Gln Val Phe
145                 150                 155                 160

Phe Gln Gly His Ala Ser Pro Gly Met Tyr Ala Arg Ala Phe Leu Glu
```

-continued

```
                165                 170                 175

Gly Arg Leu Thr Glu Ser Asp Leu Asp Ser Phe Arg Gln Glu Val Ser
            180                 185                 190

Tyr Glu Gly Gly Gly Ile Pro Ser Tyr Pro His Pro His Gly Met Pro
        195                 200                 205

Asp Phe Trp Glu Phe Pro Thr Val Ser Met Gly Leu Gly Pro Met Asp
    210                 215                 220

Ala Ile Tyr Gln Ala Arg Phe Asn Arg Tyr Leu His Asn Arg Gly Ile
225                 230                 235                 240

Lys Asp Thr Ser Glu Gln His Val Trp Ala Phe Leu Gly Asp Gly Glu
                245                 250                 255

Met Asp Glu Pro Glu Ser Arg Gly Leu Ile His Gln Ala Ala Leu Asn
            260                 265                 270

Asn Leu Asp Asn Leu Thr Phe Val Ile Asn Cys Asn Leu Gln Arg Leu
        275                 280                 285

Asp Gly Pro Val Arg Gly Asn Thr Lys Ile Ile Gln Glu Leu Glu Ser
    290                 295                 300

Phe Phe Arg Gly Ala Gly Trp Ser Val Ile Lys Val Ile Trp Gly Arg
305                 310                 315                 320

Glu Trp Asp Glu Leu Leu Glu Lys Asp Gln Asp Gly Ala Leu Val Glu
                325                 330                 335

Val Met Asn Asn Thr Ser Asp Gly Asp Tyr Gln Thr Phe Lys Ala Asn
            340                 345                 350

Asp Gly Ala Tyr Val Arg Glu His Phe Phe Gly Arg Asp Pro Arg Thr
        355                 360                 365

Leu Lys Leu Val Glu Asp Met Thr Asp Glu Glu Ile Trp Lys Leu Pro
    370                 375                 380

Arg Gly Gly His Asp Tyr Arg Lys Val Tyr Ala Ala Tyr Lys Arg Ala
385                 390                 395                 400

Leu Glu Thr Lys Asp Arg Pro Thr Val Ile Leu Ala His Thr Ile Lys
                405                 410                 415

Gly Tyr Gly Leu Gly His Asn Phe Glu Gly Arg Asn Ala Thr His Gln
            420                 425                 430

Met Lys Lys Leu Thr Leu Asp Asp Leu Lys Leu Phe Arg Asp Lys Gln
        435                 440                 445

Gly Leu Pro Ile Thr Asp Glu Glu Leu Glu Lys Asp Pro Tyr Leu Pro
    450                 455                 460

Pro Tyr Tyr His Pro Gly Glu Asp Ala Pro Glu Ile Lys Tyr Met Lys
465                 470                 475                 480

Glu Arg Arg Gln Ala Leu Gly Gly Phe Leu Pro Glu Arg Arg Glu Lys
                485                 490                 495

Tyr Glu Pro Leu Gln Val Pro Pro Leu Asp Lys Leu Arg Ser Val Arg
            500                 505                 510

Lys Gly Ser Gly Lys Gln Gln Val Ala Thr Thr Met Ala Thr Val Arg
        515                 520                 525

Thr Phe Lys Glu Leu Met Arg Asp Lys Asn Leu Ala Asp Arg Leu Val
    530                 535                 540

Pro Ile Ile Pro Asp Glu Ala Arg Thr Phe Gly Leu Asp Ser Trp Phe
545                 550                 555                 560

Pro Thr Leu Lys Ile Tyr Asn Pro His Gly Gln Asn Tyr Val Pro Val
                565                 570                 575

Asp His Asp Leu Met Leu Ser Tyr Arg Glu Ala Lys Asp Gly Gln Ile
            580                 585                 590
```

```
Leu His Glu Gly Ile Asn Glu Ala Gly Ser Val Ala Ser Phe Ile Ala
        595                 600                 605

Ala Gly Thr Ser Tyr Ala Thr His Gly Glu Ala Met Ile Pro Leu Tyr
    610                 615                 620

Ile Phe Tyr Ser Met Phe Gly Phe Gln Arg Thr Gly Asp Gly Ile Trp
625                 630                 635                 640

Ala Ala Ala Asp Gln Met Thr Arg Gly Phe Leu Leu Gly Ala Thr Ala
                645                 650                 655

Gly Arg Thr Thr Leu Thr Gly Glu Gly Leu Gln His Met Asp Gly His
            660                 665                 670

Ser Pro Ile Leu Ala Ser Thr Asn Pro Gly Val Glu Thr Tyr Asp Pro
        675                 680                 685

Ala Phe Ser Tyr Glu Ile Ala His Leu Val His Arg Gly Ile Asp Arg
    690                 695                 700

Met Tyr Gly Pro Gly Lys Gly Glu Asn Val Ile Tyr Tyr Leu Thr Ile
705                 710                 715                 720

Tyr Asn Glu Pro Thr Pro Gln Pro Ala Glu Pro Glu Asp Leu Asp Val
                725                 730                 735

Glu Gly Leu His Lys Gly Ile Tyr Leu Tyr Asp Lys Ala Ala Glu Gly
            740                 745                 750

Glu Gly His Glu Ala Ser Ile Leu Ala Ser Gly Ile Gly Met Gln Trp
        755                 760                 765

Ala Leu Arg Ala Arg Asp Ile Leu Ala Glu Asp Tyr Gly Ile Arg Ala
    770                 775                 780

Asn Ile Phe Ser Ala Thr Ser Trp Val Glu Leu Ala Arg Asp Gly Ala
785                 790                 795                 800

Arg Arg Asn Leu Glu Ala Leu Arg Asn Pro Gly Ala Asp Val Gly Glu
                805                 810                 815

Ala Phe Val Thr Thr Gln Leu Lys Lys Gly Ser Gly Pro Tyr Val Ala
            820                 825                 830

Val Ser Asp Phe Ala Thr Asp Leu Pro Asn Gln Ile Arg Glu Trp Val
        835                 840                 845

Pro Gly Asp Tyr Ile Val Leu Gly Ala Asp Gly Phe Gly Phe Ser Asp
    850                 855                 860

Thr Arg Pro Ala Ala Arg Arg Tyr Phe Asn Ile Asp Ala Glu Ser Ile
865                 870                 875                 880

Val Val Ala Val Leu Arg Gly Leu Val Arg Glu Gly Val Ile Asp Ala
                885                 890                 895

Ser Val Ala Ala His Ala Ala Glu Lys Tyr Lys Leu Ser Asp Pro Thr
            900                 905                 910

Ala Pro Gln Val Asp Pro Asp Ala Pro Ile Glu
        915                 920
```

<210> SEQ ID NO 23
<211> LENGTH: 4012
<212> TYPE: DNA
<213> ORGANISM: Corynebacterium thermoaminogenes
<220> FEATURE:
<221> NAME/KEY: CDS
<222> LOCATION: (319)..(3735)
<223> OTHER INFORMATION:

<400> SEQUENCE: 23

```
tcctttttgc aaattctgca aagtgggtag aggtcagatg tcagcaggtc ggtccgattt     60

ctgtaggaaa gtggagccgt tgggggcaac attaaccttc cccctgggat gtagctaaac    120
```

-continued

```
ggcaatgggg gtctcgggcg gggggcattc ttttcacggc aaggtggtga aattccgcag    180

gtcactcccc ggccggcggt agagaacgga gcgaaaacgg aaagcaatac gtggttttcc    240

ggactggccg ttacgatgtt ctgaagagtg actgccatca cccaacaggc tggtcctcgt    300

cgaaaggaac aaaaactg tgg tta caa caa cac cct cca cgc tgc cgg cgt      351
                    Trp Leu Gln Gln His Pro Pro Arg Cys Arg Arg
                    1               5                   10

tca aaa aga tcc tgg tgg cca acc gag gtg aaa tcg cgg tgc gag cat      399
Ser Lys Arg Ser Trp Trp Pro Thr Glu Val Lys Ser Arg Cys Glu His
            15                  20                  25

tcc gcg ccg cct acg aga ccg ggg ccg caa ccg tgg cca tct acc ccc      447
Ser Ala Pro Pro Thr Arg Pro Gly Pro Gln Pro Trp Pro Ser Thr Pro
        30                  35                  40

ggg agg acc gtg gct cct tcc acc gct cct tcg cct ccg agg cgg tga      495
Gly Arg Thr Val Ala Pro Ser Thr Ala Pro Ser Pro Pro Arg Arg
    45                  50                  55

gga tcg gaa ccg agg gct cac ccg tca agg cgt acc tcg ata ttg atg      543
Gly Ser Glu Pro Arg Ala His Pro Ser Arg Arg Thr Ser Ile Leu Met
    60                  65                  70

aga tca tca acg ccg cca aga agg tga aag cgg acg cgg tct acc cgg      591
Arg Ser Ser Thr Pro Pro Arg Arg     Lys Arg Thr Arg Ser Thr Arg
75                  80                  85

ggt atg gtt tcc ttt cgg aaa atg ccc agc tcg cgc gtg aat gcg cgg      639
Gly Met Val Ser Phe Arg Lys Met Pro Ser Ser Arg Val Asn Ala Arg
90                  95                  100                 105

aga acg gca tta cct tca tcg gtc cca ccc cgg agg tgc tcg acc tca      687
Arg Thr Ala Leu Pro Ser Ser Val Pro Pro Arg Arg Cys Ser Thr Ser
                110                 115                 120

cgg gcg aca agt cca agg ctg tgt ccg ccg cga aga agg ccg ggc tgc      735
Arg Ala Thr Ser Pro Arg Leu Cys Pro Pro Arg Arg Arg Pro Gly Cys
            125                 130                 135

cgg tgc tgg cgg aat cca ccc cca gca ccg aca tcg atg aga tcg tca      783
Arg Cys Trp Arg Asn Pro Pro Pro Ala Pro Thr Ser Met Arg Ser Ser
        140                 145                 150

aga gtg ccg agg ggc aga cct acc cga tct tcg tca agg ccg tcg cag      831
Arg Val Pro Arg Gly Arg Pro Thr Arg Ser Ser Ser Arg Pro Ser Gln
    155                 160                 165

gtg gtg gcg ggc gtg gta tgc ggt tcg tcg aga agc ccg agg acc tgc      879
Val Val Ala Gly Val Val Cys Gly Ser Ser Arg Ser Pro Arg Thr Cys
170                 175                 180                 185

gtg agc tgg cca ggg agg cct ccc gcg agg cgg agg ccg ctt tcg gtg      927
Val Ser Trp Pro Gly Arg Pro Pro Ala Arg Arg Arg Pro Leu Ser Val
                190                 195                 200

acg gat ccg tct acg tcg aac ggg ccg tga tca aac ccc agc aca tcg      975
Thr Asp Pro Ser Thr Ser Asn Gly Pro     Ser Asn Pro Ser Thr Ser
            205                 210                 215

agg tgc aga tcc tcg gtg atc aca ccg gcg atg tca tcc acc tgt atg     1023
Arg Cys Arg Ser Ser Val Ile Thr Pro Ala Met Ser Ser Thr Cys Met
            220                 225                 230

aac gcg act gtt ccc tgc agc gcc gcc acc aga agg tcg tgg aga tcg     1071
Asn Ala Thr Val Pro Cys Ser Ala Ala Thr Arg Arg Ser Trp Arg Ser
        235                 240                 245

cac ctg ccc agc acc tcg acc cgg agc tgc gcg acc gca tct gtg ccg     1119
His Leu Pro Ser Thr Ser Thr Arg Ser Cys Ala Thr Ala Ser Val Pro
    250                 255                 260

atg ccg tga agt tct gca aat cca tcg gat acc agg gcg ccg gca ccg     1167
Met Pro     Ser Ser Ala Asn Pro Ser Asp Thr Arg Ala Pro Ala Pro
265                 270                 275
```

-continued

```
tgg agt tcc tcg tcg acg agg cgg gca acc acg tct tca ttg aga tga     1215
Trp Ser Ser Ser Ser Thr Arg Arg Ala Thr Thr Ser Ser Leu Arg
280                 285                 290

acc ccc gca tcc agg tgg aac aca ccg tga ccg agg agg tca cct ccg     1263
Thr Pro Ala Ser Arg Trp Asn Thr Pro     Pro Arg Arg Ser Pro Pro
295                 300                     305

tcg acc tgg tca agg cgc aga tgc acc tgg ccg ccg gtg cca ccc tga     1311
Ser Thr Trp Ser Arg Arg Arg Cys Thr Trp Pro Pro Val Pro Pro
310                 315                 320

agg aac tgg gcc tga ccc agg aca aga tca cca ccc acg gtg ccg ccc     1359
Arg Asn Trp Ala     Pro Arg Thr Arg Ser Pro Pro Thr Val Pro Pro
325                     330                 335

tgc agt gcc gca tca cca cgg agg acc cgt cca aca act tcc ggc ccg     1407
Cys Ser Ala Ala Ser Pro Arg Arg Thr Arg Pro Thr Thr Ser Gly Pro
340                 345                 350                 355

aca ccg gtg tga tca ccg cct acc gct ccc cgg gtg gtg cgg gtg tgc     1455
Thr Pro Val     Ser Pro Pro Thr Ala Pro Arg Val Val Arg Val Cys
                    360                 365                 370

gtc tcg acg gcg cag ccc agc tcg gcg gcg aga tca ccg cac att tcg     1503
Val Ser Thr Ala Gln Pro Ser Ser Ala Ala Arg Ser Pro His Ile Ser
                375                 380                 385

att cca tgc tgg tca aga tga cct gcc gcg gtt ccg att tcg aga ccg     1551
Ile Pro Cys Trp Ser Arg     Pro Ala Ala Val Pro Ile Ser Arg Pro
            390                     395                 400

ccg tgt ccc gag ccc agc gcg ccc tgg cgg agt tca acg tct ccg gcg     1599
Pro Cys Pro Glu Pro Ser Ala Pro Trp Arg Ser Ser Thr Ser Pro Ala
            405                 410                 415

tgg cca cca aca tcg gct tcc tgc gtg cgc tgc tgc gcg agg aag act     1647
Trp Pro Pro Thr Ser Ala Ser Cys Val Arg Cys Cys Ala Arg Lys Thr
        420                 425                 430

tca cca aga ggc gca tcg aca ccg gct tca tcg gct ccc acc agc acc     1695
Ser Pro Arg Gly Ala Ser Thr Pro Ala Ser Ser Ala Pro Thr Ser Thr
    435                 440                 445

tgc tcc agg ccc cac cgg ccg acg atg agc agg ggc gga tcc tgg aat     1743
Cys Ser Arg Pro His Arg Pro Thr Met Ser Arg Gly Gly Ser Trp Asn
450                 455                 460                 465

acc tgg cgg atg tca ccg tga aca aac ccc acg gtg aac gcc ccg aga     1791
Thr Trp Arg Met Ser Pro     Thr Asn Pro Thr Val Asn Ala Pro Arg
                470                     475                 480

cag ccc gtc cga tag aga agc tgc ccg agg tgg aga aca tcc cgc tgc     1839
Gln Pro Val Arg     Arg Ser Cys Pro Arg Trp Arg Thr Ser Arg Cys
                    485                 490                 495

cac gcg gct ccc gcg acc gcc tga agc agc tcg gcc cgg agg gtt tcg     1887
His Ala Ala Pro Ala Thr Ala     Ser Ser Ser Ala Arg Arg Val Ser
                500                     505                 510

ccc gcg atc tgc gcg aac agg atg ccc tgg ccg tca ccg aca cca cct     1935
Pro Ala Ile Cys Ala Asn Arg Met Pro Trp Pro Ser Pro Thr Pro Pro
                515                 520                 525

tcc gcg atg ccc acc agt ccc tcc tgg cca ccc gcg tgc gct cct tcg     1983
Ser Ala Met Pro Thr Ser Pro Ser Trp Pro Pro Ala Cys Ala Pro Ser
            530                 535                 540

cgc tga ccc cgg cgg cgc gcg ccg tcg caa agc tca ccc ccg agc tgc     2031
Arg     Pro Arg Arg Arg Ala Pro Ser Gln Ser Ser Pro Pro Ser Cys
            545                 550                 555

tgt cgg tgg agg cct ggg gcg gtg cca cct acg acg tgg cca tgc gct     2079
Cys Arg Trp Arg Pro Gly Ala Val Pro Pro Thr Thr Trp Pro Cys Ala
        560                 565                 570

tcc tct tcg agg atc cgt ggg cac gcc tgg atg agc tgc gtg agg cga     2127
Ser Ser Ser Arg Ile Arg Gly His Ala Trp Met Ser Cys Val Arg Arg
    575                 580                 585
```

-continued

```
tgc cga atg tga aca tcc aga tgc tgc tgc gtg gtc gca aca ccg tcg     2175
Cys Arg Met     Thr Ser Arg Cys Cys Cys Val Val Ala Thr Pro Ser
590                 595                     600

ggt aca ccc cgt acc ccg att cgg tgt gcc gcg cgt ttg tgc agg agg     2223
Gly Thr Pro Arg Thr Pro Ile Arg Cys Ala Ala Arg Leu Cys Arg Arg
605                 610                 615                 620

ccg cca agt ccg gtg tgg aca tct tcc gca tct tcg acg cgc tca acg     2271
Pro Pro Ser Pro Val Trp Thr Ser Ser Ala Ser Ser Thr Arg Ser Thr
                625                 630                 635

aca tct ccc aga tgc gcc cgg cca tcg acg ccg tcc tgg aga ccg gca     2319
Thr Ser Pro Arg Cys Ala Arg Pro Ser Thr Pro Ser Trp Arg Pro Ala
            640                 645                 650

cca gtg ttg ccg agg tcg cca tgg cgt act ccg gtg acc tgt cca atc     2367
Pro Val Leu Pro Arg Ser Pro Trp Arg Thr Pro Val Thr Cys Pro Ile
        655                 660                 665

cgg ggg aga agc tct aca ccc tgg act act acc tga acc tgg ccg agc     2415
Arg Gly Arg Ser Ser Thr Pro Trp Thr Thr Thr     Thr Trp Pro Ser
    670                 675                     680

aga tcg tcg act ccg gtg cac aca tcc tgg cca tca agg aca tgg ccg     2463
Arg Ser Ser Thr Pro Val His Thr Ser Trp Pro Ser Arg Thr Trp Pro
    685                 690                 695

gcc tgc tgc gcc gcg ccg cgg cgc cca aac tgg tca ccg ccc tgc gcc     2511
Ala Cys Cys Ala Ala Pro Arg Arg Pro Asn Trp Ser Pro Pro Cys Ala
700                 705                 710                 715

gtg aat tcg acc tgc ccg tgc atg tcc aca ccc acg aca ccg ccg gcg     2559
Val Asn Ser Thr Cys Pro Cys Met Ser Thr Pro Thr Thr Pro Pro Ala
                720                 725                 730

gtc agc tgg cca cct acc tgg ccg ccg cca acg ccg ggg ccg atg ccg     2607
Val Ser Trp Pro Pro Thr Trp Pro Pro Pro Thr Pro Gly Pro Met Pro
            735                 740                 745

tcg acg ccg cct ccg cac ccc tgt ccg gta cca cct ccc agc cgt cga     2655
Ser Thr Pro Pro Pro His Pro Cys Pro Val Pro Pro Pro Ser Arg Arg
        750                 755                 760

tgt ccg ctc tgg ttg ccg cgt ttg cgc aca ccc gac gcg aca ccg gcc     2703
Cys Pro Leu Trp Leu Pro Arg Leu Arg Thr Pro Asp Ala Thr Pro Ala
    765                 770                 775

tca acc tgc agg ccg tct ccg acc tgg aac cgt act ggg agg cgg tcc     2751
Ser Thr Cys Arg Pro Ser Pro Thr Trp Asn Arg Thr Gly Arg Arg Ser
780                 785                 790                 795

gcg gac tgt acc tgc cgt ttg aat ccg gca ccc cgg gcc cga ccg gac     2799
Ala Asp Cys Thr Cys Arg Leu Asn Pro Ala Pro Arg Ala Arg Pro Asp
                800                 805                 810

gcg ttt acc gcc acg aga tcc ccg gcg gtc agc tgt cca acc tgc gtg     2847
Ala Phe Thr Ala Thr Arg Ser Pro Ala Val Ser Cys Pro Thr Cys Val
            815                 820                 825

ccc agg ccg ttg cac tgg gtc tgg ccg acc gct tcg agc tca tcg agg     2895
Pro Arg Pro Leu His Trp Val Trp Pro Thr Ala Ser Ser Ser Ser Arg
        830                 835                 840

act act acg cgg ccg tca acg aga tgc tgg gtc gtc cga cca agg tca     2943
Thr Thr Thr Arg Pro Ser Thr Arg Cys Trp Val Val Arg Pro Arg Ser
    845                 850                 855

ccc cgt cct cca agg ttg tcg gtg acc tcg cac tgc acc tcg tcg gtg     2991
Pro Arg Pro Pro Arg Leu Ser Val Thr Ser His Cys Thr Ser Ser Val
860                 865                 870                 875

ccg gtg tga gcc cgg agg att tcg ccg ccg atc cgc aga agt acg aca     3039
Pro Val     Ala Arg Arg Ile Ser Pro Pro Ile Arg Arg Ser Thr Thr
                    880                 885                 890

tcc ccg att cgg tca tcg cct tcc tcc gcg gcg aac tgg gta ccc ctc     3087
Ser Pro Ile Arg Ser Ser Pro Ser Ser Ala Ala Asn Trp Val Pro Leu
```

-continued

```
                895                 900                 905

ccg gtg gct ggc ccg aac cgc tgc gca ccc gtg cac tcg agg gtc gct      3135
Pro Val Ala Gly Pro Asn Arg Cys Ala Pro Val His Ser Arg Val Ala
            910                 915                 920

ccc agg gta agg ccc cgc tgg cgg aga tcc ccg ccg agg agc agg ccc      3183
Pro Arg Val Arg Pro Arg Trp Arg Arg Ser Pro Pro Arg Ser Arg Pro
        925                 930                 935

acc tgg att ccg atg att ccg cgg agc gtc gcg gca ccc tca acc gcc      3231
Thr Trp Ile Pro Met Ile Pro Arg Ser Val Ala Ala Pro Ser Thr Ala
    940                 945                 950

tgc tgt tcc cga agc cga ccg agg agt tcc ttg agc acc gtc gcc gct      3279
Cys Cys Ser Arg Ser Arg Pro Arg Ser Ser Leu Ser Thr Val Ala Ala
955                 960                 965                 970

tcg gca aca cct ccg ccc tgg atg acc gcg agt tct tct acg gct tga      3327
Ser Ala Thr Pro Pro Pro Trp Met Thr Ala Ser Ser Ser Thr Ala
                975                 980                 985

agg agg gac gtg agg agc tga tcc gac tga ccg gtg tgt cca ccc cga      3375
Arg Arg Asp Val Arg Ser     Ser Asp     Pro Val Cys Pro Pro Arg
                990                             995

tgg  tgg tcc gcc tgg atg  cgg tgt ccg aac cgg  atg aca aag gca      3420
Trp  Trp Ser Ala Trp Met  Arg Cys Pro Asn Arg  Met Thr Lys Ala
1000                 1005                 1010

tgc  gca acg tgg tgg tca  acg tca acg gcc aga  tcc gcc cga tca      3465
Cys  Ala Thr Trp Trp Ser  Thr Ser Thr Ala Arg  Ser Ala Arg Ser
1015                 1020                 1025

agg  tgc gcg acc gtt ccg  tgg agt ccg tca ccg  cca ccg cgg aga      3510
Arg  Cys Ala Thr Val Pro  Trp Ser Pro Ser Pro  Pro Pro Arg Arg
1030                 1035                 1040

agg  ccg atg cca cca aca  agg gcc atg tcg ccg  cac cat tcg ccg      3555
Arg  Pro Met Pro Pro Thr  Arg Ala Met Ser Pro  His His Ser Pro
1045                 1050                 1055

gtg  tgg tca ccg tga ccg tcg  ccg agg gtg atg aga  tca agg ctg      3600
Val  Trp Ser Pro     Pro Ser  Pro Arg Val Met Arg  Ser Arg Leu
1060                     1065                 1070

gcg acg  ccg tgg cca tca ttg  agg cca tga aga tgg agg  cca cca      3645
Ala Thr  Pro Trp Pro Ser Leu  Arg Pro     Arg Trp Arg  Pro Pro
    1075                 1080                     1085

tca ccg cgc  ctg tcg acg gtg tca  tcg acc gcg tcg tgg  tgc ccg      3690
Ser Pro Arg  Leu Ser Thr Val Ser  Ser Thr Ala Ser Trp  Cys Pro
        1090                 1095                 1100

ccg cca cca  agg tcg agg gcg gcg  acc tca tcg tgg tcg  tgt cct      3735
Pro Pro Pro  Arg Ser Arg Ala Ala  Thr Ser Ser Trp Ser  Cys Pro
        1105                 1110                 1115

agcgactgag agccacaacc cgtcccgggt gccttgttat caacctcccc ctgatgatgt   3795

tctcaggggg aggctctacg tacctcaccg tgacggtgca tgtatatcgt cctgctggag   3855

agaatgctcc aggtaggaac gccaaccacc ccactccgtg atgtcccgtg ctgatcccag   3915

gcaggccggt tggaaagaaa aaccagtgat ggaacggcca tcggacagcg agacggaacc   3975

aagcgtcatc ggctccggta gagcggtgag gagcctg                            4012


<210> SEQ ID NO 24
<211> LENGTH: 58
<212> TYPE: PRT
<213> ORGANISM: Corynebacterium thermoaminogenes

<400> SEQUENCE: 24

Trp Leu Gln Gln His Pro Pro Arg Cys Arg Arg Ser Lys Arg Ser Trp
1               5                   10                  15
```

-continued

```
Trp Pro Thr Glu Val Lys Ser Arg Cys Glu His Ser Ala Pro Pro Thr
            20                  25                  30

Arg Pro Gly Pro Gln Pro Trp Pro Ser Thr Pro Gly Arg Thr Val Ala
        35                  40                  45

Pro Ser Thr Ala Pro Ser Pro Pro Arg Arg
    50                  55


<210> SEQ ID NO 25
<211> LENGTH: 24
<212> TYPE: PRT
<213> ORGANISM: Corynebacterium thermoaminogenes

<400> SEQUENCE: 25

Gly Ser Glu Pro Arg Ala His Pro Ser Arg Arg Thr Ser Ile Leu Met
1               5                   10                  15

Arg Ser Ser Thr Pro Pro Arg Arg
            20


<210> SEQ ID NO 26
<211> LENGTH: 128
<212> TYPE: PRT
<213> ORGANISM: Corynebacterium thermoaminogenes

<400> SEQUENCE: 26

Lys Arg Thr Arg Ser Thr Arg Gly Met Val Ser Phe Arg Lys Met Pro
1               5                   10                  15

Ser Ser Arg Val Asn Ala Arg Arg Thr Ala Leu Pro Ser Ser Val Pro
            20                  25                  30

Pro Arg Arg Cys Ser Thr Ser Arg Ala Thr Ser Pro Arg Leu Cys Pro
        35                  40                  45

Pro Arg Arg Arg Pro Gly Cys Arg Cys Trp Arg Asn Pro Pro Pro Ala
    50                  55                  60

Pro Thr Ser Met Arg Ser Ser Arg Val Pro Arg Gly Arg Pro Thr Arg
65                  70                  75                  80

Ser Ser Ser Arg Pro Ser Gln Val Val Ala Gly Val Val Cys Gly Ser
                85                  90                  95

Ser Arg Ser Pro Arg Thr Cys Val Ser Trp Pro Gly Arg Pro Pro Ala
            100                 105                 110

Arg Arg Arg Pro Leu Ser Val Thr Asp Pro Ser Thr Ser Asn Gly Pro
        115                 120                 125


<210> SEQ ID NO 27
<211> LENGTH: 56
<212> TYPE: PRT
<213> ORGANISM: Corynebacterium thermoaminogenes

<400> SEQUENCE: 27

Ser Asn Pro Ser Thr Ser Arg Cys Arg Ser Ser Val Ile Thr Pro Ala
1               5                   10                  15

Met Ser Ser Thr Cys Met Asn Ala Thr Val Pro Cys Ser Ala Ala Thr
            20                  25                  30

Arg Arg Ser Trp Arg Ser His Leu Pro Ser Thr Ser Thr Arg Ser Cys
        35                  40                  45

Ala Thr Ala Ser Val Pro Met Pro
    50                  55


<210> SEQ ID NO 28
<211> LENGTH: 28
<212> TYPE: PRT
```

-continued

<213> ORGANISM: Corynebacterium thermoaminogenes

<400> SEQUENCE: 28

```
Ser Ser Ala Asn Pro Ser Asp Thr Arg Ala Pro Ala Pro Trp Ser Ser
1               5                   10                  15

Ser Ser Thr Arg Arg Ala Thr Thr Ser Ser Leu Arg
            20                  25
```

<210> SEQ ID NO 29
<211> LENGTH: 9
<212> TYPE: PRT
<213> ORGANISM: Corynebacterium thermoaminogenes

<400> SEQUENCE: 29

```
Thr Pro Ala Ser Arg Trp Asn Thr Pro
1               5
```

<210> SEQ ID NO 30
<211> LENGTH: 21
<212> TYPE: PRT
<213> ORGANISM: Corynebacterium thermoaminogenes

<400> SEQUENCE: 30

```
Pro Arg Arg Ser Pro Pro Ser Thr Trp Ser Arg Arg Arg Cys Thr Trp
1               5                   10                  15

Pro Pro Val Pro Pro
            20
```

<210> SEQ ID NO 31
<211> LENGTH: 4
<212> TYPE: PRT
<213> ORGANISM: Corynebacterium thermoaminogenes

<400> SEQUENCE: 31

```
Arg Asn Trp Ala
1
```

<210> SEQ ID NO 32
<211> LENGTH: 30
<212> TYPE: PRT
<213> ORGANISM: Corynebacterium thermoaminogenes

<400> SEQUENCE: 32

```
Pro Arg Thr Arg Ser Pro Pro Thr Val Pro Pro Cys Ser Ala Ala Ser
1               5                   10                  15

Pro Arg Arg Thr Arg Pro Thr Thr Ser Gly Pro Thr Pro Val
            20                  25                  30
```

<210> SEQ ID NO 33
<211> LENGTH: 34
<212> TYPE: PRT
<213> ORGANISM: Corynebacterium thermoaminogenes

<400> SEQUENCE: 33

```
Ser Pro Pro Thr Ala Pro Arg Val Val Arg Val Cys Val Ser Thr Ala
1               5                   10                  15

Gln Pro Ser Ser Ala Ala Arg Ser Pro His Ile Ser Ile Pro Cys Trp
            20                  25                  30

Ser Arg
```

<210> SEQ ID NO 34
<211> LENGTH: 79

```
<212> TYPE: PRT
<213> ORGANISM: Corynebacterium thermoaminogenes

<400> SEQUENCE: 34

Pro Ala Ala Val Pro Ile Ser Arg Pro Pro Cys Pro Glu Pro Ser Ala
1               5                   10                  15

Pro Trp Arg Ser Ser Thr Ser Pro Ala Trp Pro Pro Thr Ser Ala Ser
            20                  25                  30

Cys Val Arg Cys Cys Ala Arg Lys Thr Ser Pro Arg Gly Ala Ser Thr
        35                  40                  45

Pro Ala Ser Ser Ala Pro Thr Ser Thr Cys Ser Arg Pro His Arg Pro
    50                  55                  60

Thr Met Ser Arg Gly Gly Ser Trp Asn Thr Trp Arg Met Ser Pro
65                  70                  75


<210> SEQ ID NO 35
<211> LENGTH: 13
<212> TYPE: PRT
<213> ORGANISM: Corynebacterium thermoaminogenes

<400> SEQUENCE: 35

Thr Asn Pro Thr Val Asn Ala Pro Arg Gln Pro Val Arg
1               5                   10


<210> SEQ ID NO 36
<211> LENGTH: 18
<212> TYPE: PRT
<213> ORGANISM: Corynebacterium thermoaminogenes

<400> SEQUENCE: 36

Arg Ser Cys Pro Arg Trp Arg Thr Ser Arg Cys His Ala Ala Pro Ala
1               5                   10                  15

Thr Ala


<210> SEQ ID NO 37
<211> LENGTH: 41
<212> TYPE: PRT
<213> ORGANISM: Corynebacterium thermoaminogenes

<400> SEQUENCE: 37

Ser Ser Ser Ala Arg Arg Val Ser Pro Ala Ile Cys Ala Asn Arg Met
1               5                   10                  15

Pro Trp Pro Ser Pro Thr Pro Pro Ser Ala Met Pro Thr Ser Pro Ser
            20                  25                  30

Trp Pro Pro Ala Cys Ala Pro Ser Arg
        35                  40


<210> SEQ ID NO 38
<211> LENGTH: 49
<212> TYPE: PRT
<213> ORGANISM: Corynebacterium thermoaminogenes

<400> SEQUENCE: 38

Pro Arg Arg Arg Ala Pro Ser Gln Ser Ser Pro Pro Ser Cys Cys Arg
1               5                   10                  15

Trp Arg Pro Gly Ala Val Pro Pro Thr Thr Trp Pro Cys Ala Ser Ser
            20                  25                  30

Ser Arg Ile Arg Gly His Ala Trp Met Ser Cys Val Arg Arg Cys Arg
        35                  40                  45

Met
```

<210> SEQ ID NO 39
<211> LENGTH: 87
<212> TYPE: PRT
<213> ORGANISM: Corynebacterium thermoaminogenes

<400> SEQUENCE: 39

```
Thr Ser Arg Cys Cys Cys Val Val Ala Thr Pro Ser Gly Thr Pro Arg
1               5                   10                  15

Thr Pro Ile Arg Cys Ala Ala Arg Leu Cys Arg Arg Pro Pro Ser Pro
            20                  25                  30

Val Trp Thr Ser Ser Ala Ser Ser Thr Arg Ser Thr Thr Ser Pro Arg
        35                  40                  45

Cys Ala Arg Pro Ser Thr Pro Ser Trp Arg Pro Ala Pro Val Leu Pro
    50                  55                  60

Arg Ser Pro Trp Arg Thr Pro Val Thr Cys Pro Ile Arg Gly Arg Ser
65                  70                  75                  80

Ser Thr Pro Trp Thr Thr Thr
                85
```

<210> SEQ ID NO 40
<211> LENGTH: 198
<212> TYPE: PRT
<213> ORGANISM: Corynebacterium thermoaminogenes

<400> SEQUENCE: 40

```
Thr Trp Pro Ser Arg Ser Ser Thr Pro Val His Thr Ser Trp Pro Ser
1               5                   10                  15

Arg Thr Trp Pro Ala Cys Cys Ala Ala Pro Arg Arg Pro Asn Trp Ser
            20                  25                  30

Pro Pro Cys Ala Val Asn Ser Thr Cys Pro Cys Met Ser Thr Pro Thr
        35                  40                  45

Thr Pro Pro Ala Val Ser Trp Pro Pro Thr Trp Pro Pro Pro Thr Pro
    50                  55                  60

Gly Pro Met Pro Ser Thr Pro Pro Pro His Pro Cys Pro Val Pro Pro
65                  70                  75                  80

Pro Ser Arg Arg Cys Pro Leu Trp Leu Pro Arg Leu Arg Thr Pro Asp
                85                  90                  95

Ala Thr Pro Ala Ser Thr Cys Arg Pro Ser Pro Thr Trp Asn Arg Thr
            100                 105                 110

Gly Arg Arg Ser Ala Asp Cys Thr Cys Arg Leu Asn Pro Ala Pro Arg
        115                 120                 125

Ala Arg Pro Asp Ala Phe Thr Ala Thr Arg Ser Pro Ala Val Ser Cys
    130                 135                 140

Pro Thr Cys Val Pro Arg Pro Leu His Trp Val Trp Pro Thr Ala Ser
145                 150                 155                 160

Ser Ser Ser Arg Thr Thr Thr Arg Pro Ser Thr Arg Cys Trp Val Val
                165                 170                 175

Arg Pro Arg Ser Pro Arg Pro Pro Arg Leu Ser Val Thr Ser His Cys
            180                 185                 190

Thr Ser Ser Val Pro Val
        195
```

<210> SEQ ID NO 41
<211> LENGTH: 108
<212> TYPE: PRT
<213> ORGANISM: Corynebacterium thermoaminogenes

<400> SEQUENCE: 41

```
Ala Arg Arg Ile Ser Pro Pro Ile Arg Arg Ser Thr Thr Ser Pro Ile
1               5                   10                  15

Arg Ser Ser Pro Ser Ser Ala Ala Asn Trp Val Pro Leu Pro Val Ala
            20                  25                  30

Gly Pro Asn Arg Cys Ala Pro Val His Ser Arg Val Ala Pro Arg Val
        35                  40                  45

Arg Pro Arg Trp Arg Arg Ser Pro Pro Arg Ser Arg Pro Thr Trp Ile
    50                  55                  60

Pro Met Ile Pro Arg Ser Val Ala Ala Pro Ser Thr Ala Cys Cys Ser
65                  70                  75                  80

Arg Ser Arg Pro Arg Ser Ser Leu Ser Thr Val Ala Ala Ser Ala Thr
                85                  90                  95

Pro Pro Pro Trp Met Thr Ala Ser Ser Ser Thr Ala
            100                 105
```

<210> SEQ ID NO 42
<211> LENGTH: 6
<212> TYPE: PRT
<213> ORGANISM: Corynebacterium thermoaminogenes

<400> SEQUENCE: 42

```
Arg Arg Asp Val Arg Ser
1               5
```

<210> SEQ ID NO 43
<211> LENGTH: 70
<212> TYPE: PRT
<213> ORGANISM: Corynebacterium thermoaminogenes

<400> SEQUENCE: 43

```
Pro Val Cys Pro Pro Arg Trp Trp Ser Ala Trp Met Arg Cys Pro Asn
1               5                   10                  15

Arg Met Thr Lys Ala Cys Ala Thr Trp Trp Ser Thr Ser Thr Ala Arg
            20                  25                  30

Ser Ala Arg Ser Arg Cys Ala Thr Val Pro Trp Ser Pro Ser Pro Pro
        35                  40                  45

Pro Arg Arg Arg Pro Met Pro Pro Thr Arg Ala Met Ser Pro His His
    50                  55                  60

Ser Pro Val Trp Ser Pro
65                  70
```

<210> SEQ ID NO 44
<211> LENGTH: 19
<212> TYPE: PRT
<213> ORGANISM: Corynebacterium thermoaminogenes

<400> SEQUENCE: 44

```
Pro Ser Pro Arg Val Met Arg Ser Arg Leu Ala Thr Pro Trp Pro Ser
1               5                   10                  15

Leu Arg Pro
```

<210> SEQ ID NO 45
<211> LENGTH: 35
<212> TYPE: PRT
<213> ORGANISM: Corynebacterium thermoaminogenes

<400> SEQUENCE: 45

-continued

```
Arg Trp Arg Pro Pro Ser Pro Arg Leu Ser Thr Val Ser Ser Thr Ala
1               5                   10                  15

Ser Trp Cys Pro Pro Pro Pro Arg Ser Arg Ala Ala Thr Ser Ser Trp
            20                  25                  30

Ser Cys Pro
        35


<210> SEQ ID NO 46
<211> LENGTH: 3306
<212> TYPE: DNA
<213> ORGANISM: Corynebacterium thermoaminogenes
<220> FEATURE:
<221> NAME/KEY: CDS
<222> LOCATION: (64)..(2820)
<223> OTHER INFORMATION:

<400> SEQUENCE: 46

gatcaaccta agccaggaga atccggcggg cggtttctac ttctacagga gctgaacccc     60

acc gtg aat gaa ctt ctc cgt gac gat atc cgt tat ctc ggc cgg atc      108
    Val Asn Glu Leu Leu Arg Asp Asp Ile Arg Tyr Leu Gly Arg Ile
    1               5                   10                  15

ctg ggc gag gtg atc tcc gag cag gag ggc cac cat gtc ttc gaa ctg      156
Leu Gly Glu Val Ile Ser Glu Gln Glu Gly His His Val Phe Glu Leu
                20                  25                  30

gtt gaa cgc gcc cgc cgg acc tcc ttc gac atc gcc aag gga cgc gcg      204
Val Glu Arg Ala Arg Arg Thr Ser Phe Asp Ile Ala Lys Gly Arg Ala
            35                  40                  45

gag atg gac agt ctg gtg gag gtg ttc gct ggc atc gac ccg gag gac      252
Glu Met Asp Ser Leu Val Glu Val Phe Ala Gly Ile Asp Pro Glu Asp
        50                  55                  60

gcc acg ccc gtg gcc cga gcc ttc acc cat ttc gcc ctg ttg gcc aac      300
Ala Thr Pro Val Ala Arg Ala Phe Thr His Phe Ala Leu Leu Ala Asn
    65                  70                  75

ctc gcg gag gat ttg cat gac gca gcc cag cgg gaa cag gcc ctg aac      348
Leu Ala Glu Asp Leu His Asp Ala Ala Gln Arg Glu Gln Ala Leu Asn
80                  85                  90                  95

tcg ggt gag ccc gcg ccg gac agc acc ctc gag gcc acc tgg gtg aaa      396
Ser Gly Glu Pro Ala Pro Asp Ser Thr Leu Glu Ala Thr Trp Val Lys
                100                 105                 110

ctg gat gat gcc ggg gtg ggc agc ggt gag gtc gcc gcg gtg atc cgc      444
Leu Asp Asp Ala Gly Val Gly Ser Gly Glu Val Ala Ala Val Ile Arg
            115                 120                 125

aat gcg ctc gtc gcc ccg gtg ctc acc gcg cac ccg acg gaa acc cga      492
Asn Ala Leu Val Ala Pro Val Leu Thr Ala His Pro Thr Glu Thr Arg
        130                 135                 140

cgt cgt acc gtg ttc gac gcg cag aag cac atc acc gcc ctg atg gag      540
Arg Arg Thr Val Phe Asp Ala Gln Lys His Ile Thr Ala Leu Met Glu
    145                 150                 155

gaa cgc cac ctc ctc ctg gcg ctg ccc acg cat gcc cgg acc cag tcc      588
Glu Arg His Leu Leu Leu Ala Leu Pro Thr His Ala Arg Thr Gln Ser
160                 165                 170                 175

aag ctg gat gac atc gag cgc aac atc cgg cga cgg atc acg atc ctg      636
Lys Leu Asp Asp Ile Glu Arg Asn Ile Arg Arg Arg Ile Thr Ile Leu
                180                 185                 190

tgg cag acg gcc ctc atc cgt gtg gcc cgt ccc cgc atc gag gat gag      684
Trp Gln Thr Ala Leu Ile Arg Val Ala Arg Pro Arg Ile Glu Asp Glu
            195                 200                 205

gtc gag gtt gga ctg cgc tac tac aag ctc agc ctg ttg gcc gag atc      732
Val Glu Val Gly Leu Arg Tyr Tyr Lys Leu Ser Leu Leu Ala Glu Ile
        210                 215                 220
```

-continued

```
ccc cgc atc aat cat gat gtg acc gtg gaa ctg gcc cgg cgt ttc ggc      780
Pro Arg Ile Asn His Asp Val Thr Val Glu Leu Ala Arg Arg Phe Gly
    225                 230                 235

ggg gat atc ccc acc acg gcg atg gtc agg ccg gga tcc tgg atc ggc      828
Gly Asp Ile Pro Thr Thr Ala Met Val Arg Pro Gly Ser Trp Ile Gly
240                 245                 250                 255

ggg gac cat gat ggc aac ccc ttc gtc acc gcg gag act gtc acc tac      876
Gly Asp His Asp Gly Asn Pro Phe Val Thr Ala Glu Thr Val Thr Tyr
                260                 265                 270

gcc acc cat cgg gcc gcg gag acc gtg ctc aag tac tac gtc aag caa      924
Ala Thr His Arg Ala Ala Glu Thr Val Leu Lys Tyr Tyr Val Lys Gln
            275                 280                 285

ctg cac gcc ctg gaa cac gaa ctc agt ctc tcc gac cgg atg aac gtc      972
Leu His Ala Leu Glu His Glu Leu Ser Leu Ser Asp Arg Met Asn Val
        290                 295                 300

atc agc gat gag ctg cgt gtg ctt gcc gat gcc ggc cag aat gac atg     1020
Ile Ser Asp Glu Leu Arg Val Leu Ala Asp Ala Gly Gln Asn Asp Met
    305                 310                 315

ccc agc cgg gtt gat gaa ccc tac cgg cgg gcc atc cac ggc atg cgt     1068
Pro Ser Arg Val Asp Glu Pro Tyr Arg Arg Ala Ile His Gly Met Arg
320                 325                 330                 335

ggc cgg atg ctg gcc acc acg gcc gcc ctg atc ggt gag gag gcg gtc     1116
Gly Arg Met Leu Ala Thr Thr Ala Ala Leu Ile Gly Glu Glu Ala Val
                340                 345                 350

gag ggc acc tgg ttc aag acc ttc acg ccc tat acc gat acc cac gag     1164
Glu Gly Thr Trp Phe Lys Thr Phe Thr Pro Tyr Thr Asp Thr His Glu
            355                 360                 365

ttc aaa cgc gac ctc gat atc gtg gat ggt tcc ctg aga atg tcc cgg     1212
Phe Lys Arg Asp Leu Asp Ile Val Asp Gly Ser Leu Arg Met Ser Arg
        370                 375                 380

gat gac atc atc gcc gat gac cgt ctg gcc atg ctg cgc tcg gcc ctg     1260
Asp Asp Ile Ile Ala Asp Asp Arg Leu Ala Met Leu Arg Ser Ala Leu
    385                 390                 395

gac agc ttc ggg ttc aac ctc tac tcc ctg gat ctg cgc cag aat tcc     1308
Asp Ser Phe Gly Phe Asn Leu Tyr Ser Leu Asp Leu Arg Gln Asn Ser
400                 405                 410                 415

gac ggt ttc gag gat gtc ctc acc gaa ttg ttc gcc acc gcc cag acc     1356
Asp Gly Phe Glu Asp Val Leu Thr Glu Leu Phe Ala Thr Ala Gln Thr
                420                 425                 430

gag aag aac tac cgc ggg ttg acg gag gcg gag aag ctg gac ctg ctg     1404
Glu Lys Asn Tyr Arg Gly Leu Thr Glu Ala Glu Lys Leu Asp Leu Leu
            435                 440                 445

atc cgc gaa ctg agc aca ccc cgc ccg ctc atc ccg cac ggg gac ccg     1452
Ile Arg Glu Leu Ser Thr Pro Arg Pro Leu Ile Pro His Gly Asp Pro
        450                 455                 460

gac tac tcc gag gcc acc aac cgt gaa ctg ggg att ttt tcg aag gcc     1500
Asp Tyr Ser Glu Ala Thr Asn Arg Glu Leu Gly Ile Phe Ser Lys Ala
    465                 470                 475

gcg gag gcc gtg cgt aaa ttc ggt cct ctc atg gtg ccg cac tgc atc     1548
Ala Glu Ala Val Arg Lys Phe Gly Pro Leu Met Val Pro His Cys Ile
480                 485                 490                 495

atc tcc atg gcc tct tcc gtc acg gac atc ctc gaa ccg atg gtg ctg     1596
Ile Ser Met Ala Ser Ser Val Thr Asp Ile Leu Glu Pro Met Val Leu
                500                 505                 510

ctc aag gag ttc ggt ctg atc cgg gcc aac ggg aag aac ccg acg ggc     1644
Leu Lys Glu Phe Gly Leu Ile Arg Ala Asn Gly Lys Asn Pro Thr Gly
            515                 520                 525

agc gtc gac gtg atc ccg ctg ttc gag acg atc gat gac ctc cag cgt     1692
Ser Val Asp Val Ile Pro Leu Phe Glu Thr Ile Asp Asp Leu Gln Arg
        530                 535                 540
```

-continued

```
ggc gcg ggc atc ctg gag gaa ttg tgg gac atc gac ctc tac cgc aat      1740
Gly Ala Gly Ile Leu Glu Glu Leu Trp Asp Ile Asp Leu Tyr Arg Asn
    545                 550                 555

tac ctt gag cag cgg gac aac gtc cag gag gtc atg ctg ggg tat tcc      1788
Tyr Leu Glu Gln Arg Asp Asn Val Gln Glu Val Met Leu Gly Tyr Ser
560                 565                 570                 575

gac tcc aac aag gac ggc ggg tac ttc gcc gcc aac tgg gcg ctt tac      1836
Asp Ser Asn Lys Asp Gly Gly Tyr Phe Ala Ala Asn Trp Ala Leu Tyr
                580                 585                 590

gac gcg gag tta cgc ctg gtc gaa cta tgc cgg ggc cgt aat gtc aag      1884
Asp Ala Glu Leu Arg Leu Val Glu Leu Cys Arg Gly Arg Asn Val Lys
            595                 600                 605

ctc cgt ctc ttc cac ggt cgt ggt ggc acg gtg ggt cgt ggc ggt ggc      1932
Leu Arg Leu Phe His Gly Arg Gly Gly Thr Val Gly Arg Gly Gly Gly
        610                 615                 620

ccc tcc tat gat gcg atc ctg gcc cag ccc aag ggc gcg gtc cgg ggt      1980
Pro Ser Tyr Asp Ala Ile Leu Ala Gln Pro Lys Gly Ala Val Arg Gly
    625                 630                 635

gcg gtg cgg gtg act gaa cag ggc gag atc atc tcc gcg aag tac ggt      2028
Ala Val Arg Val Thr Glu Gln Gly Glu Ile Ile Ser Ala Lys Tyr Gly
640                 645                 650                 655

aac ccg gat acg gca cgc cgc aac ctt gag gcc ctg gtg tcc gcg acg      2076
Asn Pro Asp Thr Ala Arg Arg Asn Leu Glu Ala Leu Val Ser Ala Thr
                660                 665                 670

ctg gag gca tcg ctt ctg gat gat gtg gaa ctg ccc aat cgg gaa cgc      2124
Leu Glu Ala Ser Leu Leu Asp Asp Val Glu Leu Pro Asn Arg Glu Arg
            675                 680                 685

gcg cac cag atc atg ggg gag atc tcg gag ttg agc ttc cgc agg tac      2172
Ala His Gln Ile Met Gly Glu Ile Ser Glu Leu Ser Phe Arg Arg Tyr
        690                 695                 700

tca tca ctg gtc cat gag gat ccc gga ttc atc cag tac ttc acc cag      2220
Ser Ser Leu Val His Glu Asp Pro Gly Phe Ile Gln Tyr Phe Thr Gln
    705                 710                 715

tcc acc ccc ctg cag gag atc gga tcc ctc aac atc ggt tcc cga ccc      2268
Ser Thr Pro Leu Gln Glu Ile Gly Ser Leu Asn Ile Gly Ser Arg Pro
720                 725                 730                 735

tcc tca cgt aaa cag acc aac acg gtg gag gat ctg cgt gcc atc ccg      2316
Ser Ser Arg Lys Gln Thr Asn Thr Val Glu Asp Leu Arg Ala Ile Pro
                740                 745                 750

tgg gtg ctc agc tgg tcc cag tcc cgt gtc atg ctg ccg ggc tgg ttc      2364
Trp Val Leu Ser Trp Ser Gln Ser Arg Val Met Leu Pro Gly Trp Phe
            755                 760                 765

ggt gtg ggt acc gca ctg cgt gag tgg atc ggt gag ggg gag ggg gct      2412
Gly Val Gly Thr Ala Leu Arg Glu Trp Ile Gly Glu Gly Glu Gly Ala
        770                 775                 780

gcg gag cgc atc gcg gag ctg cag gaa ctc aac cgg tgc tgg ccg ttc      2460
Ala Glu Arg Ile Ala Glu Leu Gln Glu Leu Asn Arg Cys Trp Pro Phe
    785                 790                 795

ttc acc tcg gtg ctg gac aac atg gcc cag gtg atg agc aag gcg gaa      2508
Phe Thr Ser Val Leu Asp Asn Met Ala Gln Val Met Ser Lys Ala Glu
800                 805                 810                 815

ctg cgc ctg gcc agg ttg tac gcc gat ctc atc ccg gat cgc gag gtg      2556
Leu Arg Leu Ala Arg Leu Tyr Ala Asp Leu Ile Pro Asp Arg Glu Val
                820                 825                 830

gcg gac cgg atc tat gag acc atc ttc ggg gag tat ttc ctg acc aag      2604
Ala Asp Arg Ile Tyr Glu Thr Ile Phe Gly Glu Tyr Phe Leu Thr Lys
            835                 840                 845

gag atg ttc tgc acc atc acc ggt tcc cag gac ctg ctc gat gac aac      2652
Glu Met Phe Cys Thr Ile Thr Gly Ser Gln Asp Leu Leu Asp Asp Asn
```

```
        850                 855                 860

ccg gcg ctg gcg cga tcg gtg cgc agt cgg ttc ccg tac ctg ctg ccg     2700
Pro Ala Leu Ala Arg Ser Val Arg Ser Arg Phe Pro Tyr Leu Leu Pro
    865                 870                 875

ctc aat gtc atc cag gtg gag atg atg cgc cgg tac cgg tcc ggt gat     2748
Leu Asn Val Ile Gln Val Glu Met Met Arg Arg Tyr Arg Ser Gly Asp
880                 885                 890                 895

gag ggc acg gct gtc cca cgt aat atc cgc ctg acc atg aat gga ttg     2796
Glu Gly Thr Ala Val Pro Arg Asn Ile Arg Leu Thr Met Asn Gly Leu
                900                 905                 910

tcc acg gcc ctg cgc aac tcg ggt tagggcgcca gacgccccgg gaacccgcac    2850
Ser Thr Ala Leu Arg Asn Ser Gly
            915

cctgtgtata ctgtctaaag ttgcccggtg tcatccgggc gtgatggata gacaacttaa   2910

cggcaaagga ttctccccac atggcactga cgcttcaaat cgtcctcgtt ctcgccagcg   2970

tgctcatgac ggtcttcgtc ctgctgcaca agggtaaggg cggaggtctg tcaagcctct   3030

tcggtggtgg cgtccagtcc aacctctccg gttccacggt ggtggagaag aacctggacc   3090

gcgtcaccat cctgaccgca gtcatctggt tgatctgcat tgtcgcgctc aacctcatcc   3150

aggcgtactc ctagcacctg atctttcaag gcctgccctt cggggcaggc ctttttttgca  3210

ttctccaggt gatgtccatc acccaccggt tttaaactat tgaccgatag aaacacctgc   3270

actaggttat ctgttatgca atagaaaata gtgcat                             3306


<210> SEQ ID NO 47
<211> LENGTH: 919
<212> TYPE: PRT
<213> ORGANISM: Corynebacterium thermoaminogenes

<400> SEQUENCE: 47

Val Asn Glu Leu Leu Arg Asp Asp Ile Arg Tyr Leu Gly Arg Ile Leu
1               5                   10                  15

Gly Glu Val Ile Ser Glu Gln Glu Gly His His Val Phe Glu Leu Val
            20                  25                  30

Glu Arg Ala Arg Arg Thr Ser Phe Asp Ile Ala Lys Gly Arg Ala Glu
        35                  40                  45

Met Asp Ser Leu Val Glu Val Phe Ala Gly Ile Asp Pro Glu Asp Ala
    50                  55                  60

Thr Pro Val Ala Arg Ala Phe Thr His Phe Ala Leu Leu Ala Asn Leu
65                  70                  75                  80

Ala Glu Asp Leu His Asp Ala Ala Gln Arg Glu Gln Ala Leu Asn Ser
                85                  90                  95

Gly Glu Pro Ala Pro Asp Ser Thr Leu Glu Ala Thr Trp Val Lys Leu
            100                 105                 110

Asp Asp Ala Gly Val Gly Ser Gly Glu Val Ala Ala Val Ile Arg Asn
        115                 120                 125

Ala Leu Val Ala Pro Val Leu Thr Ala His Pro Thr Glu Thr Arg Arg
    130                 135                 140

Arg Thr Val Phe Asp Ala Gln Lys His Ile Thr Ala Leu Met Glu Glu
145                 150                 155                 160

Arg His Leu Leu Leu Ala Leu Pro Thr His Ala Arg Thr Gln Ser Lys
                165                 170                 175

Leu Asp Asp Ile Glu Arg Asn Ile Arg Arg Arg Ile Thr Ile Leu Trp
            180                 185                 190

Gln Thr Ala Leu Ile Arg Val Ala Arg Pro Arg Ile Glu Asp Glu Val
```

```
        195                 200                 205

Glu Val Gly Leu Arg Tyr Tyr Lys Leu Ser Leu Leu Ala Glu Ile Pro
    210                 215                 220

Arg Ile Asn His Asp Val Thr Val Glu Leu Ala Arg Arg Phe Gly Gly
225                 230                 235                 240

Asp Ile Pro Thr Thr Ala Met Val Arg Pro Gly Ser Trp Ile Gly Gly
                245                 250                 255

Asp His Asp Gly Asn Pro Phe Val Thr Ala Glu Thr Val Thr Tyr Ala
            260                 265                 270

Thr His Arg Ala Ala Glu Thr Val Leu Lys Tyr Tyr Val Lys Gln Leu
        275                 280                 285

His Ala Leu Glu His Glu Leu Ser Leu Ser Asp Arg Met Asn Val Ile
    290                 295                 300

Ser Asp Glu Leu Arg Val Leu Ala Asp Ala Gly Gln Asn Asp Met Pro
305                 310                 315                 320

Ser Arg Val Asp Glu Pro Tyr Arg Arg Ala Ile His Gly Met Arg Gly
                325                 330                 335

Arg Met Leu Ala Thr Thr Ala Ala Leu Ile Gly Glu Glu Ala Val Glu
            340                 345                 350

Gly Thr Trp Phe Lys Thr Phe Thr Pro Tyr Thr Asp Thr His Glu Phe
        355                 360                 365

Lys Arg Asp Leu Asp Ile Val Asp Gly Ser Leu Arg Met Ser Arg Asp
    370                 375                 380

Asp Ile Ile Ala Asp Asp Arg Leu Ala Met Leu Arg Ser Ala Leu Asp
385                 390                 395                 400

Ser Phe Gly Phe Asn Leu Tyr Ser Leu Asp Leu Arg Gln Asn Ser Asp
                405                 410                 415

Gly Phe Glu Asp Val Leu Thr Glu Leu Phe Ala Thr Ala Gln Thr Glu
            420                 425                 430

Lys Asn Tyr Arg Gly Leu Thr Glu Ala Glu Lys Leu Asp Leu Leu Ile
        435                 440                 445

Arg Glu Leu Ser Thr Pro Arg Pro Leu Ile Pro His Gly Asp Pro Asp
    450                 455                 460

Tyr Ser Glu Ala Thr Asn Arg Glu Leu Gly Ile Phe Ser Lys Ala Ala
465                 470                 475                 480

Glu Ala Val Arg Lys Phe Gly Pro Leu Met Val Pro His Cys Ile Ile
                485                 490                 495

Ser Met Ala Ser Ser Val Thr Asp Ile Leu Glu Pro Met Val Leu Leu
            500                 505                 510

Lys Glu Phe Gly Leu Ile Arg Ala Asn Gly Lys Asn Pro Thr Gly Ser
        515                 520                 525

Val Asp Val Ile Pro Leu Phe Glu Thr Ile Asp Asp Leu Gln Arg Gly
    530                 535                 540

Ala Gly Ile Leu Glu Glu Leu Trp Asp Ile Asp Leu Tyr Arg Asn Tyr
545                 550                 555                 560

Leu Glu Gln Arg Asp Asn Val Gln Glu Val Met Leu Gly Tyr Ser Asp
                565                 570                 575

Ser Asn Lys Asp Gly Gly Tyr Phe Ala Ala Asn Trp Ala Leu Tyr Asp
            580                 585                 590

Ala Glu Leu Arg Leu Val Glu Leu Cys Arg Gly Arg Asn Val Lys Leu
        595                 600                 605

Arg Leu Phe His Gly Arg Gly Gly Thr Val Gly Arg Gly Gly Gly Pro
    610                 615                 620
```

-continued

Ser Tyr Asp Ala Ile Leu Ala Gln Pro Lys Gly Ala Val Arg Gly Ala
625 630 635 640

Val Arg Val Thr Glu Gln Gly Glu Ile Ile Ser Ala Lys Tyr Gly Asn
645 650 655

Pro Asp Thr Ala Arg Arg Asn Leu Glu Ala Leu Val Ser Ala Thr Leu
660 665 670

Glu Ala Ser Leu Leu Asp Asp Val Glu Leu Pro Asn Arg Glu Arg Ala
675 680 685

His Gln Ile Met Gly Glu Ile Ser Glu Leu Ser Phe Arg Arg Tyr Ser
690 695 700

Ser Leu Val His Glu Asp Pro Gly Phe Ile Gln Tyr Phe Thr Gln Ser
705 710 715 720

Thr Pro Leu Gln Glu Ile Gly Ser Leu Asn Ile Gly Ser Arg Pro Ser
725 730 735

Ser Arg Lys Gln Thr Asn Thr Val Glu Asp Leu Arg Ala Ile Pro Trp
740 745 750

Val Leu Ser Trp Ser Gln Ser Arg Val Met Leu Pro Gly Trp Phe Gly
755 760 765

Val Gly Thr Ala Leu Arg Glu Trp Ile Gly Glu Gly Glu Gly Ala Ala
770 775 780

Glu Arg Ile Ala Glu Leu Gln Glu Leu Asn Arg Cys Trp Pro Phe Phe
785 790 795 800

Thr Ser Val Leu Asp Asn Met Ala Gln Val Met Ser Lys Ala Glu Leu
805 810 815

Arg Leu Ala Arg Leu Tyr Ala Asp Leu Ile Pro Asp Arg Glu Val Ala
820 825 830

Asp Arg Ile Tyr Glu Thr Ile Phe Gly Glu Tyr Phe Leu Thr Lys Glu
835 840 845

Met Phe Cys Thr Ile Thr Gly Ser Gln Asp Leu Leu Asp Asp Asn Pro
850 855 860

Ala Leu Ala Arg Ser Val Arg Ser Arg Phe Pro Tyr Leu Leu Pro Leu
865 870 875 880

Asn Val Ile Gln Val Glu Met Met Arg Arg Tyr Arg Ser Gly Asp Glu
885 890 895

Gly Thr Ala Val Pro Arg Asn Ile Arg Leu Thr Met Asn Gly Leu Ser
900 905 910

Thr Ala Leu Arg Asn Ser Gly
915

<210> SEQ ID NO 48
<211> LENGTH: 3907
<212> TYPE: DNA
<213> ORGANISM: Corynebacterium thermoaminogenes
<220> FEATURE:
<221> NAME/KEY: CDS
<222> LOCATION: (686)..(3388)
<223> OTHER INFORMATION:

<400> SEQUENCE: 48
attacttcag ctgactcagc aacattcgta ttaggtatgc aaacaacatt tggttcgtta 60
aatccaagta gtatggttaa agtaacttgg ggtattgctc aagcacttat cgcctttgta 120
ttattattag ctggtggcgg agatggaact aaagctctca acgcaattca gagtgccgct 180
attattagtg cgtttccatt ctcctttgtc gtcatattaa tgatgatcag tttctacaaa 240
gatgctaata aagaacgtaa attcttagga ttaacattaa cgcctaataa acacagatta 300

-continued

```
gaagaatacg ttaaatatca acaagaggat tacgaatctg atattttaga aaaacgtgaa    360

tctagacgta atcgtgaaag agaagaataa ttgaatgaaa tatctactat aatggtgggt    420

ttaaagctat caacaatttt gttgatagct atttttatgt ttcaaacata taaatattat    480

ttacttgcga ttgataacca ttctcaatta ataaaaataa cttatagtac aaatgcgtta    540

taataagttt tacttatact acctgattaa aaatgcgaaa tgaaaaatga cccctttata    600

tacctataca gttgtgttcg aaaacatata ataatacaat ttaactaagg catataaata    660

tatagaaatt caagggggat atcaa atg gct tct aat ttt aaa gaa aca gcg     712
                            Met Ala Ser Asn Phe Lys Glu Thr Ala
                            1               5

aag aaa caa ttt gat tta aat ggc caa tca tac acg tac tat gat tta     760
Lys Lys Gln Phe Asp Leu Asn Gly Gln Ser Tyr Thr Tyr Tyr Asp Leu
10                  15                  20                  25

aaa tca tta gaa gaa caa ggt tta act aaa att tca aag tta cct tat     808
Lys Ser Leu Glu Glu Gln Gly Leu Thr Lys Ile Ser Lys Leu Pro Tyr
                30                  35                  40

tca atc cgt gta tta cta gaa tca gtg tta cgt cag gaa gat gat ttt     856
Ser Ile Arg Val Leu Leu Glu Ser Val Leu Arg Gln Glu Asp Asp Phe
            45                  50                  55

gta att act gat gat cac att aaa caa tta gca gaa ttt ggc aaa aaa     904
Val Ile Thr Asp Asp His Ile Lys Gln Leu Ala Glu Phe Gly Lys Lys
        60                  65                  70

ggt aac gaa ggt gaa gta cct ttc aaa cca tct cga gtt att tta caa     952
Gly Asn Glu Gly Glu Val Pro Phe Lys Pro Ser Arg Val Ile Leu Gln
    75                  80                  85

gac ttc act ggt gta cca gca gta gtt gac tta gcg tct tta cgt aaa    1000
Asp Phe Thr Gly Val Pro Ala Val Val Asp Leu Ala Ser Leu Arg Lys
90                  95                  100                 105

gca atg aat gat gtt ggt ggg gat att aat aaa att aac cct gaa gta    1048
Ala Met Asn Asp Val Gly Gly Asp Ile Asn Lys Ile Asn Pro Glu Val
                110                 115                 120

cca gtt gac tta gtt att gac cac tct gta caa gta gat agt tat gct    1096
Pro Val Asp Leu Val Ile Asp His Ser Val Gln Val Asp Ser Tyr Ala
            125                 130                 135

aat cca gat gca tta caa cgt aac atg aaa tta gaa ttt gaa cgt aac    1144
Asn Pro Asp Ala Leu Gln Arg Asn Met Lys Leu Glu Phe Glu Arg Asn
        140                 145                 150

tat gaa cgt tac caa ttc tta aac tgg gca aca aaa gca ttt gat aac    1192
Tyr Glu Arg Tyr Gln Phe Leu Asn Trp Ala Thr Lys Ala Phe Asp Asn
    155                 160                 165

tat aat gca gta cca cct gct aca ggt att gtc cac caa gta aac tta    1240
Tyr Asn Ala Val Pro Pro Ala Thr Gly Ile Val His Gln Val Asn Leu
170                 175                 180                 185

gaa tac tta gcg aat gtt gta cat gtt cgt gac gtt gac gga gaa caa    1288
Glu Tyr Leu Ala Asn Val Val His Val Arg Asp Val Asp Gly Glu Gln
                190                 195                 200

act gct ttc cca gat aca tta gtt ggt act gac tca cat act aca atg    1336
Thr Ala Phe Pro Asp Thr Leu Val Gly Thr Asp Ser His Thr Thr Met
            205                 210                 215

att aac ggt att ggt gta tta ggt tgg ggt gtc ggc ggt atc gaa gct    1384
Ile Asn Gly Ile Gly Val Leu Gly Trp Gly Val Gly Gly Ile Glu Ala
        220                 225                 230

gaa gca ggt atg tta gga caa cca tca tac ttc cca att cca gaa gtt    1432
Glu Ala Gly Met Leu Gly Gln Pro Ser Tyr Phe Pro Ile Pro Glu Val
    235                 240                 245

att ggt gtt aaa tta agt aat gaa tta cca caa ggt tca aca gca act    1480
Ile Gly Val Lys Leu Ser Asn Glu Leu Pro Gln Gly Ser Thr Ala Thr
```

-continued

```
250                 255                 260                 265

gac tta gca tta cgt gta act gaa gag tta cgt aaa cgt ggt gta gta      1528
Asp Leu Ala Leu Arg Val Thr Glu Glu Leu Arg Lys Arg Gly Val Val
                270                 275                 280

ggt aaa ttc gtt gag ttc ttt ggt cct ggt gta aca aac tta cca tta      1576
Gly Lys Phe Val Glu Phe Phe Gly Pro Gly Val Thr Asn Leu Pro Leu
            285                 290                 295

gct gac cgt gca aca att gcg aac atg gcg cct gaa tat ggt gca act      1624
Ala Asp Arg Ala Thr Ile Ala Asn Met Ala Pro Glu Tyr Gly Ala Thr
        300                 305                 310

tgt ggt ttc ttc cca gtt gat gaa gaa tca ctt aaa tac atg aaa tta      1672
Cys Gly Phe Phe Pro Val Asp Glu Glu Ser Leu Lys Tyr Met Lys Leu
    315                 320                 325

act ggt cgt aaa gat gat cat att gca cta gta aaa gaa tat tta caa      1720
Thr Gly Arg Lys Asp Asp His Ile Ala Leu Val Lys Glu Tyr Leu Gln
330                 335                 340                 345

caa aat aat atg ttc ttc caa gtt gaa aat gaa gat cct gaa tat act      1768
Gln Asn Asn Met Phe Phe Gln Val Glu Asn Glu Asp Pro Glu Tyr Thr
                350                 355                 360

gaa gtg att gat tta gat tta tct aca gtt caa gct tct tta tca ggt      1816
Glu Val Ile Asp Leu Asp Leu Ser Thr Val Gln Ala Ser Leu Ser Gly
            365                 370                 375

cca aaa cgt cca caa gat tta atc ttc tta agt gac atg aaa act gaa      1864
Pro Lys Arg Pro Gln Asp Leu Ile Phe Leu Ser Asp Met Lys Thr Glu
        380                 385                 390

ttc gaa aaa tca gtt aca gca cca gct ggt aac caa ggt cac ggt tta      1912
Phe Glu Lys Ser Val Thr Ala Pro Ala Gly Asn Gln Gly His Gly Leu
    395                 400                 405

gat gaa agt gaa ttt gat aag aaa gca gaa atc aaa ttt aat gat ggt      1960
Asp Glu Ser Glu Phe Asp Lys Lys Ala Glu Ile Lys Phe Asn Asp Gly
410                 415                 420                 425

aga act tca act atg aag act ggt gat gtt gcg att gca gcg att aca      2008
Arg Thr Ser Thr Met Lys Thr Gly Asp Val Ala Ile Ala Ala Ile Thr
                430                 435                 440

tca tgt aca aat aca tct aac cct tac gtt atg tta ggt gca ggt tta      2056
Ser Cys Thr Asn Thr Ser Asn Pro Tyr Val Met Leu Gly Ala Gly Leu
            445                 450                 455

gta gct aaa aaa gca att gaa aaa ggc tta aaa gta cct gat tat gta      2104
Val Ala Lys Lys Ala Ile Glu Lys Gly Leu Lys Val Pro Asp Tyr Val
        460                 465                 470

aaa act tca tta gca cca ggt tca aaa gtt gtt act gga tat tta aga      2152
Lys Thr Ser Leu Ala Pro Gly Ser Lys Val Val Thr Gly Tyr Leu Arg
    475                 480                 485

gat tca ggt tta caa gaa tat ctt gat gac tta ggt ttc aac tta gtt      2200
Asp Ser Gly Leu Gln Glu Tyr Leu Asp Asp Leu Gly Phe Asn Leu Val
490                 495                 500                 505

ggt tat ggt tgt aca act tgt atc ggt aac tca ggt cca tta tta cct      2248
Gly Tyr Gly Cys Thr Thr Cys Ile Gly Asn Ser Gly Pro Leu Leu Pro
                510                 515                 520

gaa att gaa aaa gca gta gct gac gaa gat tta tta gta act tct gta      2296
Glu Ile Glu Lys Ala Val Ala Asp Glu Asp Leu Leu Val Thr Ser Val
            525                 530                 535

ctt tct ggt aac cgt aac ttt gaa ggt cgt atc cat ccg tta gtt aaa      2344
Leu Ser Gly Asn Arg Asn Phe Glu Gly Arg Ile His Pro Leu Val Lys
        540                 545                 550

gct aac tac tta gct tca cca caa tta gtt gta gct tat gca tta gct      2392
Ala Asn Tyr Leu Ala Ser Pro Gln Leu Val Val Ala Tyr Ala Leu Ala
    555                 560                 565

gga acg gtt gat atc gat tta cac aat gaa cct atc ggt aaa ggt aaa      2440
```

-continued

```
Gly Thr Val Asp Ile Asp Leu His Asn Glu Pro Ile Gly Lys Gly Lys
570                 575                 580                 585

gat ggc gaa gat gta tac ctt aaa gat atc tgg cca agt atc aaa gaa      2488
Asp Gly Glu Asp Val Tyr Leu Lys Asp Ile Trp Pro Ser Ile Lys Glu
                590                 595                 600

gtt gca gac act gtt gat agt gtc gta acg cca gaa tta ttc tta gaa      2536
Val Ala Asp Thr Val Asp Ser Val Val Thr Pro Glu Leu Phe Leu Glu
            605                 610                 615

gaa tat gca aat gta tac gaa aat aat gaa atg tgg aat gaa atc gac      2584
Glu Tyr Ala Asn Val Tyr Glu Asn Asn Glu Met Trp Asn Glu Ile Asp
        620                 625                 630

gtt act gac gca cca tta tat gat ttc gat cca aat tca act tat att      2632
Val Thr Asp Ala Pro Leu Tyr Asp Phe Asp Pro Asn Ser Thr Tyr Ile
    635                 640                 645

caa aat cca tca ttc ttc caa ggt tta tct aaa gaa cca gga act att      2680
Gln Asn Pro Ser Phe Phe Gln Gly Leu Ser Lys Glu Pro Gly Thr Ile
650                 655                 660                 665

gaa cca tta aaa gat tta cgt att atg ggt aaa ttt ggt gat tca gtt      2728
Glu Pro Leu Lys Asp Leu Arg Ile Met Gly Lys Phe Gly Asp Ser Val
                670                 675                 680

aca act gac cac att tct cca gca ggt gcg atc ggt aaa gat aca cca      2776
Thr Thr Asp His Ile Ser Pro Ala Gly Ala Ile Gly Lys Asp Thr Pro
            685                 690                 695

gca ggt aaa tat tta tta gac cat gat gtt cca att aga gaa ttt aac      2824
Ala Gly Lys Tyr Leu Leu Asp His Asp Val Pro Ile Arg Glu Phe Asn
        700                 705                 710

tct tat ggt tca aga cgt ggt aac cat gaa gta atg gta cgt ggt act      2872
Ser Tyr Gly Ser Arg Arg Gly Asn His Glu Val Met Val Arg Gly Thr
    715                 720                 725

ttc gct aat atc cgt att aaa aac caa tta gca cca ggc act gaa ggt      2920
Phe Ala Asn Ile Arg Ile Lys Asn Gln Leu Ala Pro Gly Thr Glu Gly
730                 735                 740                 745

gga ttt aca aca tat tgg cct aca gaa gaa atc atg cct atc tat gat      2968
Gly Phe Thr Thr Tyr Trp Pro Thr Glu Glu Ile Met Pro Ile Tyr Asp
                750                 755                 760

gca gct atg aga tac aaa gaa aat ggt act ggt tta gct gtt tta gct      3016
Ala Ala Met Arg Tyr Lys Glu Asn Gly Thr Gly Leu Ala Val Leu Ala
            765                 770                 775

ggt aat gat tac ggt atg ggt tca tct cgt gac tgg gca gct aaa ggt      3064
Gly Asn Asp Tyr Gly Met Gly Ser Ser Arg Asp Trp Ala Ala Lys Gly
        780                 785                 790

act aac tta tta ggt gtt aaa act gtt att gca caa agt tat gaa cgt      3112
Thr Asn Leu Leu Gly Val Lys Thr Val Ile Ala Gln Ser Tyr Glu Arg
    795                 800                 805

atc cat cgt tca aac tta gta atg atg ggt gta tta cca tta caa ttt      3160
Ile His Arg Ser Asn Leu Val Met Met Gly Val Leu Pro Leu Gln Phe
810                 815                 820                 825

aaa caa ggt gag tca gct gat tct cta ggt tta gaa ggt aaa gaa gaa      3208
Lys Gln Gly Glu Ser Ala Asp Ser Leu Gly Leu Glu Gly Lys Glu Glu
                830                 835                 840

att tct gta gat atc gat gaa aat gtt aaa cca cat gat tta gta act      3256
Ile Ser Val Asp Ile Asp Glu Asn Val Lys Pro His Asp Leu Val Thr
            845                 850                 855

gtt cat gct aaa aaa gaa aac gga gaa gtt gtt gat ttt gaa gca atg      3304
Val His Ala Lys Lys Glu Asn Gly Glu Val Val Asp Phe Glu Ala Met
        860                 865                 870

gtt cgt ttc gat tca tta gta gaa tta gat tat tat cgt cat ggt ggt      3352
Val Arg Phe Asp Ser Leu Val Glu Leu Asp Tyr Tyr Arg His Gly Gly
    875                 880                 885
```

-continued

```
atc tta caa atg gta tta aga aac aaa tta gct caa taatcacaat         3398
Ile Leu Gln Met Val Leu Arg Asn Lys Leu Ala Gln
890                 895                 900

gtgacttttg acagtgctaa cgtttaggtt agcactgttt ttttatgcta aactatatat   3458

gtaatgttaa tagttaagga aggattggac ttaaatgatt tatagtttga ctgaaattga   3518

accaagatat caagagacag ataaaatggg cgtgatttat catggcaatt atgcaacatg   3578

gtttgaagta gcgcgtacag attacattag aaaactagga tttagttatg ctgatatgga   3638

aaagcaaggg atcatttctc cagttacaga cttaaatatc aaatataaaa aatcaatttt   3698

ttatcctgaa aaagtaacca ttaaaacatg ggtggaaaaa tattcaagat tacgttctgt   3758

gtatagatat gaaattttta atgaacaggg agaacttgca actacaggtt atactgagtt   3818

aatttgtatg aaagctgata cctttagacc aattagatta gatcgttatt tctcagattg   3878

gcatgaaacc tatagtaaag ttgaagctt                                     3907


<210> SEQ ID NO 49
<211> LENGTH: 901
<212> TYPE: PRT
<213> ORGANISM: Corynebacterium thermoaminogenes

<400> SEQUENCE: 49

Met Ala Ser Asn Phe Lys Glu Thr Ala Lys Lys Gln Phe Asp Leu Asn
1               5                   10                  15

Gly Gln Ser Tyr Thr Tyr Tyr Asp Leu Lys Ser Leu Glu Glu Gln Gly
            20                  25                  30

Leu Thr Lys Ile Ser Lys Leu Pro Tyr Ser Ile Arg Val Leu Leu Glu
        35                  40                  45

Ser Val Leu Arg Gln Glu Asp Asp Phe Val Ile Thr Asp Asp His Ile
    50                  55                  60

Lys Gln Leu Ala Glu Phe Gly Lys Lys Gly Asn Glu Gly Glu Val Pro
65                  70                  75                  80

Phe Lys Pro Ser Arg Val Ile Leu Gln Asp Phe Thr Gly Val Pro Ala
                85                  90                  95

Val Val Asp Leu Ala Ser Leu Arg Lys Ala Met Asn Asp Val Gly Gly
            100                 105                 110

Asp Ile Asn Lys Ile Asn Pro Glu Val Pro Val Asp Leu Val Ile Asp
        115                 120                 125

His Ser Val Gln Val Asp Ser Tyr Ala Asn Pro Asp Ala Leu Gln Arg
    130                 135                 140

Asn Met Lys Leu Glu Phe Glu Arg Asn Tyr Glu Arg Tyr Gln Phe Leu
145                 150                 155                 160

Asn Trp Ala Thr Lys Ala Phe Asp Asn Tyr Asn Ala Val Pro Pro Ala
                165                 170                 175

Thr Gly Ile Val His Gln Val Asn Leu Glu Tyr Leu Ala Asn Val Val
            180                 185                 190

His Val Arg Asp Val Asp Gly Glu Gln Thr Ala Phe Pro Asp Thr Leu
        195                 200                 205

Val Gly Thr Asp Ser His Thr Thr Met Ile Asn Gly Ile Gly Val Leu
    210                 215                 220

Gly Trp Gly Val Gly Gly Ile Glu Ala Glu Ala Gly Met Leu Gly Gln
225                 230                 235                 240

Pro Ser Tyr Phe Pro Ile Pro Glu Val Ile Gly Val Lys Leu Ser Asn
                245                 250                 255

Glu Leu Pro Gln Gly Ser Thr Ala Thr Asp Leu Ala Leu Arg Val Thr
```

-continued

```
            260                 265                 270

Glu Glu Leu Arg Lys Arg Gly Val Val Gly Lys Phe Val Glu Phe Phe
        275                 280                 285

Gly Pro Gly Val Thr Asn Leu Pro Leu Ala Asp Arg Ala Thr Ile Ala
    290                 295                 300

Asn Met Ala Pro Glu Tyr Gly Ala Thr Cys Gly Phe Phe Pro Val Asp
305                 310                 315                 320

Glu Glu Ser Leu Lys Tyr Met Lys Leu Thr Gly Arg Lys Asp Asp His
                325                 330                 335

Ile Ala Leu Val Lys Glu Tyr Leu Gln Gln Asn Asn Met Phe Phe Gln
            340                 345                 350

Val Glu Asn Glu Asp Pro Glu Tyr Thr Glu Val Ile Asp Leu Asp Leu
        355                 360                 365

Ser Thr Val Gln Ala Ser Leu Ser Gly Pro Lys Arg Pro Gln Asp Leu
    370                 375                 380

Ile Phe Leu Ser Asp Met Lys Thr Glu Phe Glu Lys Ser Val Thr Ala
385                 390                 395                 400

Pro Ala Gly Asn Gln Gly His Gly Leu Asp Glu Ser Glu Phe Asp Lys
                405                 410                 415

Lys Ala Glu Ile Lys Phe Asn Asp Gly Arg Thr Ser Thr Met Lys Thr
            420                 425                 430

Gly Asp Val Ala Ile Ala Ala Ile Thr Ser Cys Thr Asn Thr Ser Asn
        435                 440                 445

Pro Tyr Val Met Leu Gly Ala Gly Leu Val Ala Lys Lys Ala Ile Glu
    450                 455                 460

Lys Gly Leu Lys Val Pro Asp Tyr Val Lys Thr Ser Leu Ala Pro Gly
465                 470                 475                 480

Ser Lys Val Val Thr Gly Tyr Leu Arg Asp Ser Gly Leu Gln Glu Tyr
                485                 490                 495

Leu Asp Asp Leu Gly Phe Asn Leu Val Gly Tyr Gly Cys Thr Thr Cys
            500                 505                 510

Ile Gly Asn Ser Gly Pro Leu Leu Pro Glu Ile Glu Lys Ala Val Ala
        515                 520                 525

Asp Glu Asp Leu Leu Val Thr Ser Val Leu Ser Gly Asn Arg Asn Phe
    530                 535                 540

Glu Gly Arg Ile His Pro Leu Val Lys Ala Asn Tyr Leu Ala Ser Pro
545                 550                 555                 560

Gln Leu Val Val Ala Tyr Ala Leu Ala Gly Thr Val Asp Ile Asp Leu
                565                 570                 575

His Asn Glu Pro Ile Gly Lys Gly Lys Asp Gly Glu Asp Val Tyr Leu
            580                 585                 590

Lys Asp Ile Trp Pro Ser Ile Lys Glu Val Ala Asp Thr Val Asp Ser
        595                 600                 605

Val Val Thr Pro Glu Leu Phe Leu Glu Glu Tyr Ala Asn Val Tyr Glu
    610                 615                 620

Asn Asn Glu Met Trp Asn Glu Ile Asp Val Thr Asp Ala Pro Leu Tyr
625                 630                 635                 640

Asp Phe Asp Pro Asn Ser Thr Tyr Ile Gln Asn Pro Ser Phe Phe Gln
                645                 650                 655

Gly Leu Ser Lys Glu Pro Gly Thr Ile Glu Pro Leu Lys Asp Leu Arg
            660                 665                 670

Ile Met Gly Lys Phe Gly Asp Ser Val Thr Thr Asp His Ile Ser Pro
        675                 680                 685
```

```
Ala Gly Ala Ile Gly Lys Asp Thr Pro Ala Gly Lys Tyr Leu Leu Asp
    690                 695                 700

His Asp Val Pro Ile Arg Glu Phe Asn Ser Tyr Gly Ser Arg Arg Gly
705                 710                 715                 720

Asn His Glu Val Met Val Arg Gly Thr Phe Ala Asn Ile Arg Ile Lys
                725                 730                 735

Asn Gln Leu Ala Pro Gly Thr Glu Gly Gly Phe Thr Thr Tyr Trp Pro
            740                 745                 750

Thr Glu Glu Ile Met Pro Ile Tyr Asp Ala Ala Met Arg Tyr Lys Glu
        755                 760                 765

Asn Gly Thr Gly Leu Ala Val Leu Ala Gly Asn Asp Tyr Gly Met Gly
    770                 775                 780

Ser Ser Arg Asp Trp Ala Ala Lys Gly Thr Asn Leu Leu Gly Val Lys
785                 790                 795                 800

Thr Val Ile Ala Gln Ser Tyr Glu Arg Ile His Arg Ser Asn Leu Val
                805                 810                 815

Met Met Gly Val Leu Pro Leu Gln Phe Lys Gln Gly Glu Ser Ala Asp
            820                 825                 830

Ser Leu Gly Leu Glu Gly Lys Glu Glu Ile Ser Val Asp Ile Asp Glu
        835                 840                 845

Asn Val Lys Pro His Asp Leu Val Thr Val His Ala Lys Lys Glu Asn
    850                 855                 860

Gly Glu Val Val Asp Phe Glu Ala Met Val Arg Phe Asp Ser Leu Val
865                 870                 875                 880

Glu Leu Asp Tyr Tyr Arg His Gly Gly Ile Leu Gln Met Val Leu Arg
                885                 890                 895

Asn Lys Leu Ala Gln
            900


<210> SEQ ID NO 50
<211> LENGTH: 3006
<212> TYPE: DNA
<213> ORGANISM: Corynebacterium thermoaminogenes
<220> FEATURE:
<221> NAME/KEY: CDS
<222> LOCATION: (328)..(2514)
<223> OTHER INFORMATION:

<400> SEQUENCE: 50

gtcgacgacg aaccccccac cgccgaacca gccgccgatc tggtgtggga gacacccggg      60

ttctcctccc tgggtgaaca ggtgccacaa ccccgtccca acaggcacac ctaccactgg     120

atcgccgggg agagcagcat ggtcacacgc ctgcggcgtg ccctggtgaa ggatcacggc     180

ctggacagat cgcaggtggc attcatgggt tattggaggc agggagtggc catgaggggt     240

tgatatcgct tccctgaggg tccgcaggcg tgcctcaccc tgtattcttg atagttgaac     300

aaaagagccc acataacaag gagactc atg gct aag atc atc tgg acc cgc acc     354
                              Met Ala Lys Ile Ile Trp Thr Arg Thr
                              1               5

gac gaa gca ccg ctg ctc gcg acc tac tcg ctg aag ccg gtc gtc gag       402
Asp Glu Ala Pro Leu Leu Ala Thr Tyr Ser Leu Lys Pro Val Val Glu
10                  15                  20                  25

gct ttc gcc gcc acc gcg ggc atc gag gtg gag acc cgc gat atc tct       450
Ala Phe Ala Ala Thr Ala Gly Ile Glu Val Glu Thr Arg Asp Ile Ser
                30                  35                  40

ctc gcc ggt cgc atc ctc gca cag ttc gcg gac cag ctc ccc gag gag       498
Leu Ala Gly Arg Ile Leu Ala Gln Phe Ala Asp Gln Leu Pro Glu Glu
```

-continued

```
            45                  50                  55

cag aag gtc tcc gac gcc ctc gcc gag ctc ggc gaa ctg gct aag acc      546
Gln Lys Val Ser Asp Ala Leu Ala Glu Leu Gly Glu Leu Ala Lys Thr
        60                  65                  70

ccc gaa gcc aac atc atc aag ctt ccc aac atc tcc gca tcc gta ccg      594
Pro Glu Ala Asn Ile Ile Lys Leu Pro Asn Ile Ser Ala Ser Val Pro
    75                  80                  85

cag ctc aag gct gcc gta aag gaa ctg cag gaa cag ggc tac gac ctg      642
Gln Leu Lys Ala Ala Val Lys Glu Leu Gln Glu Gln Gly Tyr Asp Leu
90                  95                  100                 105

ccc gag tac gag gat gcc aag gac cgc tac gcc gct gtc atc ggc tcc      690
Pro Glu Tyr Glu Asp Ala Lys Asp Arg Tyr Ala Ala Val Ile Gly Ser
                110                 115                 120

aac gtc aac ccg gtc ctg cgc gag ggc aac tcc gac cgc cgc gca ccg      738
Asn Val Asn Pro Val Leu Arg Glu Gly Asn Ser Asp Arg Arg Ala Pro
            125                 130                 135

gtg gcc gtg aag aac ttc gtg aag aag ttc ccc cac cgc atg ggc gag      786
Val Ala Val Lys Asn Phe Val Lys Lys Phe Pro His Arg Met Gly Glu
        140                 145                 150

tgg tcc gcc gac tcc aag acc aac gtt gcc acc atg ggt gcc gac gac      834
Trp Ser Ala Asp Ser Lys Thr Asn Val Ala Thr Met Gly Ala Asp Asp
    155                 160                 165

ttc cgc agc aat gag aag tcc gtg atc atg gac gag gcc gac acc gtg      882
Phe Arg Ser Asn Glu Lys Ser Val Ile Met Asp Glu Ala Asp Thr Val
170                 175                 180                 185

gtg atc aag cat gtc gcc gcc gac ggc acc gag acc gtg ctc aag gac      930
Val Ile Lys His Val Ala Ala Asp Gly Thr Glu Thr Val Leu Lys Asp
                190                 195                 200

agc ctc ccc ctg ctc aag ggt gag gtc atc gac ggc acc ttc atc tcc      978
Ser Leu Pro Leu Leu Lys Gly Glu Val Ile Asp Gly Thr Phe Ile Ser
            205                 210                 215

gcc aag gca ctg gac gcc ttc ctg ctc gac cag gtc aaa cgc gcc aag     1026
Ala Lys Ala Leu Asp Ala Phe Leu Leu Asp Gln Val Lys Arg Ala Lys
        220                 225                 230

gag gag ggc atc ctc ttc tcc gcc cac atg aag gcc acc atg atg aag     1074
Glu Glu Gly Ile Leu Phe Ser Ala His Met Lys Ala Thr Met Met Lys
    235                 240                 245

gtc tcc gac ccg atc atc ttc ggc cac atc gtc cgc gcc tac ttc gcc     1122
Val Ser Asp Pro Ile Ile Phe Gly His Ile Val Arg Ala Tyr Phe Ala
250                 255                 260                 265

gat gtc tac gca cag tac ggt gag cag ctg ctc gcc gcc ggc ctc aac     1170
Asp Val Tyr Ala Gln Tyr Gly Glu Gln Leu Leu Ala Ala Gly Leu Asn
                270                 275                 280

ggt gag aac ggt ctc gcc gcc atc tac gcc ggc ctg gac aag ctg gac     1218
Gly Glu Asn Gly Leu Ala Ala Ile Tyr Ala Gly Leu Asp Lys Leu Asp
            285                 290                 295

aac ggt gcc gag atc aag gca gcc ttc gac aag ggc ctg gaa gag ggc     1266
Asn Gly Ala Glu Ile Lys Ala Ala Phe Asp Lys Gly Leu Glu Glu Gly
        300                 305                 310

ccc gac ctg gcc atg gtg aac tcc gcc aag ggc atc acc aac ctg cat     1314
Pro Asp Leu Ala Met Val Asn Ser Ala Lys Gly Ile Thr Asn Leu His
    315                 320                 325

gtg ccc tcc gat gtc atc atc gac gcc tcc atg ccc gcc atg atc cgc     1362
Val Pro Ser Asp Val Ile Ile Asp Ala Ser Met Pro Ala Met Ile Arg
330                 335                 340                 345

acc tcc ggc aag atg tgg aac aag gac gac cag acc cag gat gcc ctg     1410
Thr Ser Gly Lys Met Trp Asn Lys Asp Asp Gln Thr Gln Asp Ala Leu
                350                 355                 360

gct gtc atc ccg gac tcc tcc tac gcc ggt gtc tac cag acc gtc atc     1458
```

-continued

```
Ala Val Ile Pro Asp Ser Ser Tyr Ala Gly Val Tyr Gln Thr Val Ile
            365                 370                 375

gag gac tgc cgc aag aat ggc gcc ttc gat ccg acc acc atg ggc acc      1506
Glu Asp Cys Arg Lys Asn Gly Ala Phe Asp Pro Thr Thr Met Gly Thr
        380                 385                 390

gtc ccc aac gtc ggt ctg atg gca cag aag gcc gag gag tac ggc tcc      1554
Val Pro Asn Val Gly Leu Met Ala Gln Lys Ala Glu Glu Tyr Gly Ser
    395                 400                 405

cac gac aag acc ttc cgt atc gag gcc gac ggc aag gta cag gtc gtc      1602
His Asp Lys Thr Phe Arg Ile Glu Ala Asp Gly Lys Val Gln Val Val
410                 415                 420                 425

gcc tcc aac ggt gat gtc ctc atc gag cac gac gtg gag aag ggc gac      1650
Ala Ser Asn Gly Asp Val Leu Ile Glu His Asp Val Glu Lys Gly Asp
                430                 435                 440

atc tgg cgc gcc tgc cag acc aag gac gcc ccg atc cag gac tgg gtc      1698
Ile Trp Arg Ala Cys Gln Thr Lys Asp Ala Pro Ile Gln Asp Trp Val
            445                 450                 455

aag ctg gct gtc aac cgc gca cgt ctc tcc ggc atg ccc gct gtg ttc      1746
Lys Leu Ala Val Asn Arg Ala Arg Leu Ser Gly Met Pro Ala Val Phe
        460                 465                 470

tgg ctg gat ccc gcc cgc gca cac gac cgc aac ctg acc aca ctg gtg      1794
Trp Leu Asp Pro Ala Arg Ala His Asp Arg Asn Leu Thr Thr Leu Val
    475                 480                 485

gag aag tac ctg gca gac cac gac acc gag ggc ctg gac atc cag atc      1842
Glu Lys Tyr Leu Ala Asp His Asp Thr Glu Gly Leu Asp Ile Gln Ile
490                 495                 500                 505

ctc tcc ccc gtc gag gcc acc cag cac gcc atc gac cgc atc cgc cgc      1890
Leu Ser Pro Val Glu Ala Thr Gln His Ala Ile Asp Arg Ile Arg Arg
                510                 515                 520

ggc gag gac acc atc tcc gtc acc ggt aac gtc ctg cgt gac tac aac      1938
Gly Glu Asp Thr Ile Ser Val Thr Gly Asn Val Leu Arg Asp Tyr Asn
            525                 530                 535

acc gac ctc ttc ccg atc ctc gag ctg ggc acc tcc gcc aag atg ctc      1986
Thr Asp Leu Phe Pro Ile Leu Glu Leu Gly Thr Ser Ala Lys Met Leu
        540                 545                 550

tcc gtc gtg cca ctg atg gcc ggc ggt gga ctc ttc gag acc ggt gcc      2034
Ser Val Val Pro Leu Met Ala Gly Gly Gly Leu Phe Glu Thr Gly Ala
    555                 560                 565

ggt ggc tcc gcc ccg aag cac gtc cag cag gtc atc gag gaa aac cac      2082
Gly Gly Ser Ala Pro Lys His Val Gln Gln Val Ile Glu Glu Asn His
570                 575                 580                 585

ctg cgc tgg gat tcc ctc ggt gag ttc ctg gcc ctg gcc gag tcc ttc      2130
Leu Arg Trp Asp Ser Leu Gly Glu Phe Leu Ala Leu Ala Glu Ser Phe
                590                 595                 600

cgc cac gag ctc aac acc cgc aac aac acc aag gcc ggt gtc ctc gcc      2178
Arg His Glu Leu Asn Thr Arg Asn Asn Thr Lys Ala Gly Val Leu Ala
            605                 610                 615

gat gcc ctg gac cgt gcg acc gag aag ctc ctc aac gag gag aag tcc      2226
Asp Ala Leu Asp Arg Ala Thr Glu Lys Leu Leu Asn Glu Glu Lys Ser
        620                 625                 630

ccg tcc cgc aag gtc ggc gag atc gac aac cgt ggt tcc cac ttc tgg      2274
Pro Ser Arg Lys Val Gly Glu Ile Asp Asn Arg Gly Ser His Phe Trp
    635                 640                 645

ctg gcc acc tac tgg gcc gat gaa ctg gcc aac cag acc gag gac gcc      2322
Leu Ala Thr Tyr Trp Ala Asp Glu Leu Ala Asn Gln Thr Glu Asp Ala
650                 655                 660                 665

gag ctg gct gag acc ttc gcc cct gtc gcc gag gcc ctg aac aac cag      2370
Glu Leu Ala Glu Thr Phe Ala Pro Val Ala Glu Ala Leu Asn Asn Gln
                670                 675                 680
```

-continued

```
gct gcc gac atc gac gca gca ctc atc ggt gag cag ggc aag cct gtc      2418
Ala Ala Asp Ile Asp Ala Ala Leu Ile Gly Glu Gln Gly Lys Pro Val
            685                 690                 695

gac ctg ggt ggc tac tac gca ccc tcc gat gag aag acc tcc gcg atc      2466
Asp Leu Gly Gly Tyr Tyr Ala Pro Ser Asp Glu Lys Thr Ser Ala Ile
        700                 705                 710

atg cgc ccg gtg gcc gca ttc aac gag atc atc gac tcc ctg aag aag      2514
Met Arg Pro Val Ala Ala Phe Asn Glu Ile Ile Asp Ser Leu Lys Lys
    715                 720                 725

taacccccttc tccggagccg acagccgacg gccacgctcc cccgcccacg ggggatcgtg   2574

gccgtcggcc gtttctggca ctggagtgaa cacttcggtg ataatggtga gatgaacagc   2634

ccccgtgtcc ccgccatcct gtccgccgtt tccgccgtgg gtctgatcgc tgcgctgggc   2694

acccccgttg ccgtcgcaga caccatcacc gcggacaccg accgggaaac ctgcgtggcc   2754

agccagaatg acaactccag cgtgatcagg ttctgggatg acctggaggc cgatgtccgt   2814

gagcagcgcc tgaccgaact ggatgcacag gaccccggcc tcaagaacga catcgaggcc   2874

ttcatcgccg aggacccggt agccccctcc gcagccgatc tccagagacg gctggatgca   2934

aatgacgccg gtgagggcct ggccatgctg ctacctgaat cccgcaccga ccccgaggtg   2994

gtggacctgc ag                                                        3006


<210> SEQ ID NO 51
<211> LENGTH: 729
<212> TYPE: PRT
<213> ORGANISM: Corynebacterium thermoaminogenes

<400> SEQUENCE: 51

Met Ala Lys Ile Ile Trp Thr Arg Thr Asp Glu Ala Pro Leu Leu Ala
1               5                   10                  15

Thr Tyr Ser Leu Lys Pro Val Val Glu Ala Phe Ala Ala Thr Ala Gly
            20                  25                  30

Ile Glu Val Glu Thr Arg Asp Ile Ser Leu Ala Gly Arg Ile Leu Ala
        35                  40                  45

Gln Phe Ala Asp Gln Leu Pro Glu Glu Gln Lys Val Ser Asp Ala Leu
    50                  55                  60

Ala Glu Leu Gly Glu Leu Ala Lys Thr Pro Glu Ala Asn Ile Ile Lys
65                  70                  75                  80

Leu Pro Asn Ile Ser Ala Ser Val Pro Gln Leu Lys Ala Ala Val Lys
                85                  90                  95

Glu Leu Gln Glu Gln Gly Tyr Asp Leu Pro Glu Tyr Glu Asp Ala Lys
            100                 105                 110

Asp Arg Tyr Ala Ala Val Ile Gly Ser Asn Val Asn Pro Val Leu Arg
        115                 120                 125

Glu Gly Asn Ser Asp Arg Arg Ala Pro Val Ala Val Lys Asn Phe Val
    130                 135                 140

Lys Lys Phe Pro His Arg Met Gly Glu Trp Ser Ala Asp Ser Lys Thr
145                 150                 155                 160

Asn Val Ala Thr Met Gly Ala Asp Asp Phe Arg Ser Asn Glu Lys Ser
                165                 170                 175

Val Ile Met Asp Glu Ala Asp Thr Val Val Ile Lys His Val Ala Ala
            180                 185                 190

Asp Gly Thr Glu Thr Val Leu Lys Asp Ser Leu Pro Leu Leu Lys Gly
        195                 200                 205

Glu Val Ile Asp Gly Thr Phe Ile Ser Ala Lys Ala Leu Asp Ala Phe
    210                 215                 220
```

-continued

```
Leu Leu Asp Gln Val Lys Arg Ala Lys Glu Glu Gly Ile Leu Phe Ser
225                 230                 235                 240

Ala His Met Lys Ala Thr Met Met Lys Val Ser Asp Pro Ile Ile Phe
                245                 250                 255

Gly His Ile Val Arg Ala Tyr Phe Ala Asp Val Tyr Ala Gln Tyr Gly
            260                 265                 270

Glu Gln Leu Leu Ala Ala Gly Leu Asn Gly Glu Asn Gly Leu Ala Ala
        275                 280                 285

Ile Tyr Ala Gly Leu Asp Lys Leu Asp Asn Gly Ala Glu Ile Lys Ala
    290                 295                 300

Ala Phe Asp Lys Gly Leu Glu Glu Gly Pro Asp Leu Ala Met Val Asn
305                 310                 315                 320

Ser Ala Lys Gly Ile Thr Asn Leu His Val Pro Ser Asp Val Ile Ile
                325                 330                 335

Asp Ala Ser Met Pro Ala Met Ile Arg Thr Ser Gly Lys Met Trp Asn
            340                 345                 350

Lys Asp Asp Gln Thr Gln Asp Ala Leu Ala Val Ile Pro Asp Ser Ser
        355                 360                 365

Tyr Ala Gly Val Tyr Gln Thr Val Ile Glu Asp Cys Arg Lys Asn Gly
    370                 375                 380

Ala Phe Asp Pro Thr Thr Met Gly Thr Val Pro Asn Val Gly Leu Met
385                 390                 395                 400

Ala Gln Lys Ala Glu Glu Tyr Gly Ser His Asp Lys Thr Phe Arg Ile
                405                 410                 415

Glu Ala Asp Gly Lys Val Gln Val Val Ala Ser Asn Gly Asp Val Leu
            420                 425                 430

Ile Glu His Asp Val Glu Lys Gly Asp Ile Trp Arg Ala Cys Gln Thr
        435                 440                 445

Lys Asp Ala Pro Ile Gln Asp Trp Val Lys Leu Ala Val Asn Arg Ala
    450                 455                 460

Arg Leu Ser Gly Met Pro Ala Val Phe Trp Leu Asp Pro Ala Arg Ala
465                 470                 475                 480

His Asp Arg Asn Leu Thr Thr Leu Val Glu Lys Tyr Leu Ala Asp His
                485                 490                 495

Asp Thr Glu Gly Leu Asp Ile Gln Ile Leu Ser Pro Val Glu Ala Thr
            500                 505                 510

Gln His Ala Ile Asp Arg Ile Arg Arg Gly Glu Asp Thr Ile Ser Val
        515                 520                 525

Thr Gly Asn Val Leu Arg Asp Tyr Asn Thr Asp Leu Phe Pro Ile Leu
    530                 535                 540

Glu Leu Gly Thr Ser Ala Lys Met Leu Ser Val Val Pro Leu Met Ala
545                 550                 555                 560

Gly Gly Gly Leu Phe Glu Thr Gly Ala Gly Gly Ser Ala Pro Lys His
                565                 570                 575

Val Gln Gln Val Ile Glu Glu Asn His Leu Arg Trp Asp Ser Leu Gly
            580                 585                 590

Glu Phe Leu Ala Leu Ala Glu Ser Phe Arg His Glu Leu Asn Thr Arg
        595                 600                 605

Asn Asn Thr Lys Ala Gly Val Leu Ala Asp Ala Leu Asp Arg Ala Thr
    610                 615                 620

Glu Lys Leu Leu Asn Glu Glu Lys Ser Pro Ser Arg Lys Val Gly Glu
625                 630                 635                 640
```

-continued

```
Ile Asp Asn Arg Gly Ser His Phe Trp Leu Ala Thr Tyr Trp Ala Asp
                645                 650                 655

Glu Leu Ala Asn Gln Thr Glu Asp Ala Glu Leu Ala Glu Thr Phe Ala
            660                 665                 670

Pro Val Ala Glu Ala Leu Asn Asn Gln Ala Ala Asp Ile Asp Ala Ala
        675                 680                 685

Leu Ile Gly Glu Gln Gly Lys Pro Val Asp Leu Gly Gly Tyr Tyr Ala
    690                 695                 700

Pro Ser Asp Glu Lys Thr Ser Ala Ile Met Arg Pro Val Ala Ala Phe
705                 710                 715                 720

Asn Glu Ile Ile Asp Ser Leu Lys Lys
                725


<210> SEQ ID NO 52
<211> LENGTH: 2322
<212> TYPE: DNA
<213> ORGANISM: Corynebacterium thermoaminogenes
<220> FEATURE:
<221> NAME/KEY: CDS
<222> LOCATION: (806)..(2212)
<223> OTHER INFORMATION:

<400> SEQUENCE: 52

ggtacccccca cgtaccctag gccatcacag caatttttac atcggatatt ttaggtgtgc      60

tcataacgtc cttatgaatt tcgcagttat tagttattta aatagagaat caaactccga     120

cctagcctct gccgatgcta aaagtcagct gaccccttgg ggcgcttcat ttgaaactgc     180

gaccaagctc atgaatgcgc gaaagcattt ccattataag ggtaagctgt aagaatagtg     240

ggagaaaatg ttcagtcgtg ttctaactca cttgagaaat tccatttttc tgggcttctc     300

tcaaatagat taagtggccc gtatgctgga tttctagaat atttagaagc gcgccaactc     360

atgattatgt attgtataag cctcaaagac cgaatagatt actaacattt aagtggacca     420

gagcgttaga agctttgtag agtgctcatt ccttgctgac ggcaagggtt tcctaccatg     480

agatagatcg gcagatagtt ggtttgtaaa aatttttaag gacggtccgc aatgtcaatt     540

cttgaacaga tcatcttctt catcaacacc atcttgggtt atggtctgca cgctggttct     600

tccgcttcca gcaacctttc tcacacgatc ggcctgttct aggcctaatt ggtaataagg     660

ctgtgtaaca gtcgcccgcg tgattgtgtc tttttaggcg cccgcgcggg cgattttcgg     720

ttttcatctt ttttaaattg agtttggaag atcaagtgcc cccggatgca cgacaatgct     780

atgccgaaca cgtattgttg aaatc gtg act gaa cat tat gac gta gta gta       832
                            Val Thr Glu His Tyr Asp Val Val Val
                            1               5

ctc gga gct ggc ccc ggt ggc tat gtc tcc gcc atc cgc gcc gcg cag       880
Leu Gly Ala Gly Pro Gly Gly Tyr Val Ser Ala Ile Arg Ala Ala Gln
10                  15                  20                  25

ctc ggt aag aaa gtt gcg gtt atc gag aag cag tac tgg gga ggt gtc       928
Leu Gly Lys Lys Val Ala Val Ile Glu Lys Gln Tyr Trp Gly Gly Val
                30                  35                  40

tgc ctg aat gtg ggt tgt atc cca tct aag gcg ttg atc aag aac gct       976
Cys Leu Asn Val Gly Cys Ile Pro Ser Lys Ala Leu Ile Lys Asn Ala
            45                  50                  55

gag atc gcc cac atc ttc aac cat gag aag aag acc ttc ggc atc aac      1024
Glu Ile Ala His Ile Phe Asn His Glu Lys Lys Thr Phe Gly Ile Asn
        60                  65                  70

ggc gag gtc acc ttc aac tac gag gat gcc cac aag cgt tcc cgt ggt      1072
Gly Glu Val Thr Phe Asn Tyr Glu Asp Ala His Lys Arg Ser Arg Gly
    75                  80                  85
```

-continued

```
gtc tcc gac aag atc gtc ggc ggt gtt cac tac ttg atg aag aag aac     1120
Val Ser Asp Lys Ile Val Gly Gly Val His Tyr Leu Met Lys Lys Asn
90                  95                  100                 105

aag atc acc gag atc gac ggt ttc ggc acc ttc aag gat gcc aag acc     1168
Lys Ile Thr Glu Ile Asp Gly Phe Gly Thr Phe Lys Asp Ala Lys Thr
                110                 115                 120

atc gag gtg acc gat ggt aag gat gcc ggc aag acc gtc acc ttc gat     1216
Ile Glu Val Thr Asp Gly Lys Asp Ala Gly Lys Thr Val Thr Phe Asp
            125                 130                 135

gac tgc atc atc gcc acc ggt tcc gtg gtc aac tcc ctc cgt ggt gtt     1264
Asp Cys Ile Ile Ala Thr Gly Ser Val Val Asn Ser Leu Arg Gly Val
        140                 145                 150

gag ttc tcc gag aac gtg gtc tcc tac gag gag cag atc ctc aac ccg     1312
Glu Phe Ser Glu Asn Val Val Ser Tyr Glu Glu Gln Ile Leu Asn Pro
    155                 160                 165

gtg gcg cct aag aag atg gtc atc gtc ggt ggc ggc gcc atc ggt atg     1360
Val Ala Pro Lys Lys Met Val Ile Val Gly Gly Gly Ala Ile Gly Met
170                 175                 180                 185

gaa ttc gcc tac gtt ctg ggc aac tac ggt gtg gac gta acc ctc atc     1408
Glu Phe Ala Tyr Val Leu Gly Asn Tyr Gly Val Asp Val Thr Leu Ile
                190                 195                 200

gag ttc atg gac cgc gtt ctg ccg aac gag gat cca gag gtg tcc aag     1456
Glu Phe Met Asp Arg Val Leu Pro Asn Glu Asp Pro Glu Val Ser Lys
            205                 210                 215

gtt atc gcc aag gcc tac aag aag atg ggc atc aag ctc ctc ccg ggc     1504
Val Ile Ala Lys Ala Tyr Lys Lys Met Gly Ile Lys Leu Leu Pro Gly
        220                 225                 230

cac gca acc acc gcg gtg cgc gac aat ggc gat tcc gtt gag gtc gat     1552
His Ala Thr Thr Ala Val Arg Asp Asn Gly Asp Ser Val Glu Val Asp
    235                 240                 245

tac cag aag aag ggc tcg gac aag acc gag acc atc acc gtc gac cgt     1600
Tyr Gln Lys Lys Gly Ser Asp Lys Thr Glu Thr Ile Thr Val Asp Arg
250                 255                 260                 265

gtt ctt atc tcc gtc ggc ttc cgc cca cgc gtc gag ggc ttc ggc ctg     1648
Val Leu Ile Ser Val Gly Phe Arg Pro Arg Val Glu Gly Phe Gly Leu
                270                 275                 280

gag aac acc ggc gtc aag ctc acc gaa cgc ggt gcc atc gac att gat     1696
Glu Asn Thr Gly Val Lys Leu Thr Glu Arg Gly Ala Ile Asp Ile Asp
            285                 290                 295

gag cat atg cgc acc aac gtc gac ggc atc tac gcc atc ggt gac gtc     1744
Glu His Met Arg Thr Asn Val Asp Gly Ile Tyr Ala Ile Gly Asp Val
        300                 305                 310

acc gcc aag ctg cag ctg gca cac gtc gcc gag gca cag ggc att gtc     1792
Thr Ala Lys Leu Gln Leu Ala His Val Ala Glu Ala Gln Gly Ile Val
    315                 320                 325

gcc gcc gag aca ctc gcc ggc gca gaa acc cag acc ctg ggc gac tac     1840
Ala Ala Glu Thr Leu Ala Gly Ala Glu Thr Gln Thr Leu Gly Asp Tyr
330                 335                 340                 345

atg atg atg ccg cgt gcc acc ttc tgc aac cca cag gtt gcc tcc ttc     1888
Met Met Met Pro Arg Ala Thr Phe Cys Asn Pro Gln Val Ala Ser Phe
                350                 355                 360

ggt tac acc gag gag cag gcc aag gag aag tgg ccg gat cga gag atc     1936
Gly Tyr Thr Glu Glu Gln Ala Lys Glu Lys Trp Pro Asp Arg Glu Ile
            365                 370                 375

aag gtg tcc tcc ttc ccg ttc tcc gcg aac ggc aag gcc gtc ggc ctg     1984
Lys Val Ser Ser Phe Pro Phe Ser Ala Asn Gly Lys Ala Val Gly Leu
        380                 385                 390

gct gag acc gat ggt ttc gcc aag atc gtc gcc gac gct gag ttc ggt     2032
Ala Glu Thr Asp Gly Phe Ala Lys Ile Val Ala Asp Ala Glu Phe Gly
```

```
    395                 400                 405

gaa ctg ctg ggt ggc cac att gtc ggt gcc aac gcc tcc gag ctg ctc     2080
Glu Leu Leu Gly Gly His Ile Val Gly Ala Asn Ala Ser Glu Leu Leu
410                 415                 420                 425

aac gag ctg gtg ctg gcc cag aac tgg gat ctc acc acc gag gag atc     2128
Asn Glu Leu Val Leu Ala Gln Asn Trp Asp Leu Thr Thr Glu Glu Ile
                430                 435                 440

agc cgc agc gtc cac atc cac ccg acc ctg tcg gag gct gtc aag gaa     2176
Ser Arg Ser Val His Ile His Pro Thr Leu Ser Glu Ala Val Lys Glu
            445                 450                 455

gct gcc cac ggc gtc aac ggc cac atg atc aac ttc taaatcccgt          2222
Ala Ala His Gly Val Asn Gly His Met Ile Asn Phe
        460                 465

cagacaaatg caaatcccct caccgatggc atatcggtga ggggattttc tcatgcacgt   2282

aaaatcataa tccatggcaa ggaaagtcga caacagcgcc                         2322


<210> SEQ ID NO 53
<211> LENGTH: 469
<212> TYPE: PRT
<213> ORGANISM: Corynebacterium thermoaminogenes

<400> SEQUENCE: 53

Val Thr Glu His Tyr Asp Val Val Val Leu Gly Ala Gly Pro Gly Gly
1               5                   10                  15

Tyr Val Ser Ala Ile Arg Ala Ala Gln Leu Gly Lys Lys Val Ala Val
            20                  25                  30

Ile Glu Lys Gln Tyr Trp Gly Gly Val Cys Leu Asn Val Gly Cys Ile
        35                  40                  45

Pro Ser Lys Ala Leu Ile Lys Asn Ala Glu Ile Ala His Ile Phe Asn
    50                  55                  60

His Glu Lys Lys Thr Phe Gly Ile Asn Gly Glu Val Thr Phe Asn Tyr
65                  70                  75                  80

Glu Asp Ala His Lys Arg Ser Arg Gly Val Ser Asp Lys Ile Val Gly
                85                  90                  95

Gly Val His Tyr Leu Met Lys Lys Asn Lys Ile Thr Glu Ile Asp Gly
            100                 105                 110

Phe Gly Thr Phe Lys Asp Ala Lys Thr Ile Glu Val Thr Asp Gly Lys
        115                 120                 125

Asp Ala Gly Lys Thr Val Thr Phe Asp Asp Cys Ile Ile Ala Thr Gly
    130                 135                 140

Ser Val Val Asn Ser Leu Arg Gly Val Glu Phe Ser Glu Asn Val Val
145                 150                 155                 160

Ser Tyr Glu Glu Gln Ile Leu Asn Pro Val Ala Pro Lys Lys Met Val
                165                 170                 175

Ile Val Gly Gly Gly Ala Ile Gly Met Glu Phe Ala Tyr Val Leu Gly
            180                 185                 190

Asn Tyr Gly Val Asp Val Thr Leu Ile Glu Phe Met Asp Arg Val Leu
        195                 200                 205

Pro Asn Glu Asp Pro Glu Val Ser Lys Val Ile Ala Lys Ala Tyr Lys
    210                 215                 220

Lys Met Gly Ile Lys Leu Leu Pro Gly His Ala Thr Thr Ala Val Arg
225                 230                 235                 240

Asp Asn Gly Asp Ser Val Glu Val Asp Tyr Gln Lys Lys Gly Ser Asp
                245                 250                 255

Lys Thr Glu Thr Ile Thr Val Asp Arg Val Leu Ile Ser Val Gly Phe
```

-continued

```
        260                 265                 270

Arg Pro Arg Val Glu Gly Phe Gly Leu Glu Asn Thr Gly Val Lys Leu
    275                 280                 285

Thr Glu Arg Gly Ala Ile Asp Ile Asp Glu His Met Arg Thr Asn Val
    290                 295                 300

Asp Gly Ile Tyr Ala Ile Gly Asp Val Thr Ala Lys Leu Gln Leu Ala
305                 310                 315                 320

His Val Ala Glu Ala Gln Gly Ile Val Ala Ala Glu Thr Leu Ala Gly
                325                 330                 335

Ala Glu Thr Gln Thr Leu Gly Asp Tyr Met Met Met Pro Arg Ala Thr
            340                 345                 350

Phe Cys Asn Pro Gln Val Ala Ser Phe Gly Tyr Thr Glu Glu Gln Ala
        355                 360                 365

Lys Glu Lys Trp Pro Asp Arg Glu Ile Lys Val Ser Ser Phe Pro Phe
    370                 375                 380

Ser Ala Asn Gly Lys Ala Val Gly Leu Ala Glu Thr Asp Gly Phe Ala
385                 390                 395                 400

Lys Ile Val Ala Asp Ala Glu Phe Gly Glu Leu Leu Gly Gly His Ile
                405                 410                 415

Val Gly Ala Asn Ala Ser Glu Leu Leu Asn Glu Leu Val Leu Ala Gln
            420                 425                 430

Asn Trp Asp Leu Thr Thr Glu Glu Ile Ser Arg Ser Val His Ile His
        435                 440                 445

Pro Thr Leu Ser Glu Ala Val Lys Glu Ala Ala His Gly Val Asn Gly
    450                 455                 460

His Met Ile Asn Phe
465


<210> SEQ ID NO 54
<211> LENGTH: 4096
<212> TYPE: DNA
<213> ORGANISM: Corynebacterium thermoaminogenes
<220> FEATURE:
<221> NAME/KEY: CDS
<222> LOCATION: (250)..(3951)
<223> OTHER INFORMATION:

<400> SEQUENCE: 54

ccggatcatc gtggttgacg ggggacgtat catcgaggat ggttcccacg atgaacttct      60

gggagcgaat ggaacctacg caacaatgtg gcatttagta gggtgacagg atattttagg     120

aaagacttgt taccaaaagg tgctaatact ggggtgctag gtccccgcga ccggaaccag     180

cgttacagtg gataaaataa agcccattta gaaccctcaa caagcaagga aaagaggcga     240

gtacctgcc gtg agc agc gct agt act ttc ggc cag aac gcg tgg ctg gtg     291
          Val Ser Ser Ala Ser Thr Phe Gly Gln Asn Ala Trp Leu Val
          1               5                   10

gat gag atg ttc cag cag ttc aag aag gac ccc cag tcc gtg gac aag      339
Asp Glu Met Phe Gln Gln Phe Lys Lys Asp Pro Gln Ser Val Asp Lys
15                  20                  25                  30

gaa tgg aga gag ctc ttc gag tct cag ggg ggt ccc cag gct gaa aag      387
Glu Trp Arg Glu Leu Phe Glu Ser Gln Gly Gly Pro Gln Ala Glu Lys
                35                  40                  45

gct acc ccc gcc acc ccc gaa gcc aag aag gca gct tcg tcg cag tcc      435
Ala Thr Pro Ala Thr Pro Glu Ala Lys Lys Ala Ala Ser Ser Gln Ser
            50                  55                  60

tca act tcc gga cag tcc acc gcc aag gct gcc cct gcc gcc aag acc      483
Ser Thr Ser Gly Gln Ser Thr Ala Lys Ala Ala Pro Ala Ala Lys Thr
```

-continued

```
        65                  70                  75

gca ccg gcc tct gcg cca gcc aag gct gcc cct gtt aag caa aac cag      531
Ala Pro Ala Ser Ala Pro Ala Lys Ala Ala Pro Val Lys Gln Asn Gln
    80                  85                  90

gcg tcc aag cct gcc aag aag gcc aag gag tcc ccc ctg tcc aag cca      579
Ala Ser Lys Pro Ala Lys Lys Ala Lys Glu Ser Pro Leu Ser Lys Pro
95                  100                 105                 110

gct gcc atg cct gag ccg gga acc acc cca ctc agg ggc atc ttc aag      627
Ala Ala Met Pro Glu Pro Gly Thr Thr Pro Leu Arg Gly Ile Phe Lys
                115                 120                 125

tcc atc gcc aag aac atg gac ctc tcc ctc gag gtg ccc acc gcc acc      675
Ser Ile Ala Lys Asn Met Asp Leu Ser Leu Glu Val Pro Thr Ala Thr
            130                 135                 140

tcc gtc cgc gac atg ccc gcg cgc ctc atg ttc gag aac cgc gcc atg      723
Ser Val Arg Asp Met Pro Ala Arg Leu Met Phe Glu Asn Arg Ala Met
        145                 150                 155

gtc aac gac cag ctc aag cgc acc cgt ggc ggc aag atc tcc ttc acc      771
Val Asn Asp Gln Leu Lys Arg Thr Arg Gly Gly Lys Ile Ser Phe Thr
    160                 165                 170

cac atc atc ggc tac gcc atg gtg aag gct gtc atg gca cac ccg gac      819
His Ile Ile Gly Tyr Ala Met Val Lys Ala Val Met Ala His Pro Asp
175                 180                 185                 190

atg aac aac tcc tat gac atc gtc gac ggc aag ccg tcc ctg gtc gtc      867
Met Asn Asn Ser Tyr Asp Ile Val Asp Gly Lys Pro Ser Leu Val Val
                195                 200                 205

ccg gag cac atc aac ctc ggc ctg gcc atc gac ctc ccc cag aag gac      915
Pro Glu His Ile Asn Leu Gly Leu Ala Ile Asp Leu Pro Gln Lys Asp
            210                 215                 220

ggc tcc cgt gcc ctc gtg gtc gcc gcc atc aag gaa acc gag aag atg      963
Gly Ser Arg Ala Leu Val Val Ala Ala Ile Lys Glu Thr Glu Lys Met
        225                 230                 235

acc ttc tcc cag ttc ctg gag gcc tat gag gac gtt gtg gca cgc tcc     1011
Thr Phe Ser Gln Phe Leu Glu Ala Tyr Glu Asp Val Val Ala Arg Ser
    240                 245                 250

cgc gtc ggc aag ctc acc atg gat gac tac cag ggt gtc acc atc tcc     1059
Arg Val Gly Lys Leu Thr Met Asp Asp Tyr Gln Gly Val Thr Ile Ser
255                 260                 265                 270

ttg acc aac ccg ggt ggc atc ggt acc cgc cac tcc atc ccg cgt ctg     1107
Leu Thr Asn Pro Gly Gly Ile Gly Thr Arg His Ser Ile Pro Arg Leu
                275                 280                 285

acc aag ggc cag ggc acc atc atc ggt gtc ggt tcc atg gac tac ccg     1155
Thr Lys Gly Gln Gly Thr Ile Ile Gly Val Gly Ser Met Asp Tyr Pro
            290                 295                 300

gcc gag ttc cag ggt gcc tcc gag gac cgt ctc gcc gag ctc ggt gtg     1203
Ala Glu Phe Gln Gly Ala Ser Glu Asp Arg Leu Ala Glu Leu Gly Val
        305                 310                 315

ggc aag ctc gtc acc atc acc tcc acc tac gat cac cgc gtc atc cag     1251
Gly Lys Leu Val Thr Ile Thr Ser Thr Tyr Asp His Arg Val Ile Gln
    320                 325                 330

ggc gcg gaa tcc ggt gag ttc ctg cgc acc atg tcc cag ctg ctc gtg     1299
Gly Ala Glu Ser Gly Glu Phe Leu Arg Thr Met Ser Gln Leu Leu Val
335                 340                 345                 350

gac gat gcg ttc tgg gat cac atc ttc gag gag atg aac gtt ccc tac     1347
Asp Asp Ala Phe Trp Asp His Ile Phe Glu Glu Met Asn Val Pro Tyr
                355                 360                 365

acc ccg atg cgc tgg gca cag gac ctg ccc aac acc ggt gtg gac aag     1395
Thr Pro Met Arg Trp Ala Gln Asp Leu Pro Asn Thr Gly Val Asp Lys
            370                 375                 380

aac acc cgt gtc atg cag ctc atc gag gcc tac cgc tcc cgc ggt cac     1443
```

-continued

```
Asn Thr Arg Val Met Gln Leu Ile Glu Ala Tyr Arg Ser Arg Gly His
        385                 390                 395

ctc atc gcc gac acc aac cca ctg ccc tgg gtc cag ccc ggc atg ccc      1491
Leu Ile Ala Asp Thr Asn Pro Leu Pro Trp Val Gln Pro Gly Met Pro
    400                 405                 410

gtc ccg gat cac cgt gac ctc gac atc gag acc cac ggc ctg acc ctg      1539
Val Pro Asp His Arg Asp Leu Asp Ile Glu Thr His Gly Leu Thr Leu
415                 420                 425                 430

tgg gat ctg gac cgt acc ttc cac gtc ggt ggt ttc ggt ggc aag gag      1587
Trp Asp Leu Asp Arg Thr Phe His Val Gly Gly Phe Gly Gly Lys Glu
                435                 440                 445

acc atg acc ctg cgc gag gtg ctc agc cgc ctc cgc gcc gcc tac acc      1635
Thr Met Thr Leu Arg Glu Val Leu Ser Arg Leu Arg Ala Ala Tyr Thr
            450                 455                 460

ctc aag gtc ggc tcc gag tac acc cac atc ctc gac cgc gat gag cgc      1683
Leu Lys Val Gly Ser Glu Tyr Thr His Ile Leu Asp Arg Asp Glu Arg
        465                 470                 475

acc tgg ctg cag gac cgc ctc gag gcc ggt atg ccc aag ccc acc gcc      1731
Thr Trp Leu Gln Asp Arg Leu Glu Ala Gly Met Pro Lys Pro Thr Ala
    480                 485                 490

gcc gag cag aag tac atc ctg cag aag ctc aac gcc gcc gag gca ttc      1779
Ala Glu Gln Lys Tyr Ile Leu Gln Lys Leu Asn Ala Ala Glu Ala Phe
495                 500                 505                 510

gag aac ttc ctg cag acc aag tac gtc ggc cag aag cgt ttc tcc ctc      1827
Glu Asn Phe Leu Gln Thr Lys Tyr Val Gly Gln Lys Arg Phe Ser Leu
                515                 520                 525

gag ggt gcc gag tca ctg atc ccg ctg atg gac tcc gcc atc gac acc      1875
Glu Gly Ala Glu Ser Leu Ile Pro Leu Met Asp Ser Ala Ile Asp Thr
            530                 535                 540

gcc gca ggc cag ggc ctt gac gag gtc gtc atc ggc atg ccc cac cgt      1923
Ala Ala Gly Gln Gly Leu Asp Glu Val Val Ile Gly Met Pro His Arg
        545                 550                 555

ggt cgc ctc aac gtg ctg ttc aac atc gtc ggc aag cca ctg gcc tcg      1971
Gly Arg Leu Asn Val Leu Phe Asn Ile Val Gly Lys Pro Leu Ala Ser
    560                 565                 570

atc ttc aac gag ttc gag ggc cag atg gag cag ggc cag atc ggt ggc      2019
Ile Phe Asn Glu Phe Glu Gly Gln Met Glu Gln Gly Gln Ile Gly Gly
575                 580                 585                 590

tcc ggt gac gtg aag tac cac ctc ggt tcc gag ggc acc cac ctg cag      2067
Ser Gly Asp Val Lys Tyr His Leu Gly Ser Glu Gly Thr His Leu Gln
                595                 600                 605

atg ttc ggc gac ggc gag atc aag gtc tcc ctc acc gcc aac ccc tcc      2115
Met Phe Gly Asp Gly Glu Ile Lys Val Ser Leu Thr Ala Asn Pro Ser
            610                 615                 620

cac ctc gag gcc gtc aac ccg gtc gtg gag ggc atc gtc cgc gcc aag      2163
His Leu Glu Ala Val Asn Pro Val Val Glu Gly Ile Val Arg Ala Lys
        625                 630                 635

cag gac atc ctg gac aag ggc ccg gac ggc tac acc gtc gtc ccg ctg      2211
Gln Asp Ile Leu Asp Lys Gly Pro Asp Gly Tyr Thr Val Val Pro Leu
    640                 645                 650

ctg ctc cac ggt gac gcc gcc ttc gcc ggc ctg ggc atc gtg ccc gag      2259
Leu Leu His Gly Asp Ala Ala Phe Ala Gly Leu Gly Ile Val Pro Glu
655                 660                 665                 670

acc atc aac ctc gca gcc ctg cgt ggt tac gat gtc ggt ggc acc atc      2307
Thr Ile Asn Leu Ala Ala Leu Arg Gly Tyr Asp Val Gly Gly Thr Ile
                675                 680                 685

cac atc gtg gtc aac aac cag atc ggc ttc acc acc acc ccg gac tcc      2355
His Ile Val Val Asn Asn Gln Ile Gly Phe Thr Thr Thr Pro Asp Ser
            690                 695                 700
```

-continued

```
agc cgt tcc atg cac tac gcc acc gac tgc gcc aag gcc ttc ggt tgc      2403
Ser Arg Ser Met His Tyr Ala Thr Asp Cys Ala Lys Ala Phe Gly Cys
        705                 710                 715

ccg gtg ttc cac gtc aac ggt gac gac ccc gag gct gtg gtc tgg gtc      2451
Pro Val Phe His Val Asn Gly Asp Asp Pro Glu Ala Val Val Trp Val
    720                 725                 730

ggc cag ctg gcc acc gag tac cgt cgc cgc ttc ggc aag gat gtc ttc      2499
Gly Gln Leu Ala Thr Glu Tyr Arg Arg Arg Phe Gly Lys Asp Val Phe
735                 740                 745                 750

atc gac ctc atc tgc tac cgc ctg cgc ggc cac aac gag gct gat gac      2547
Ile Asp Leu Ile Cys Tyr Arg Leu Arg Gly His Asn Glu Ala Asp Asp
                755                 760                 765

cca tcc atg acc cag ccg aag atg tac gag ctg atc acc ggc cgc gac      2595
Pro Ser Met Thr Gln Pro Lys Met Tyr Glu Leu Ile Thr Gly Arg Asp
            770                 775                 780

tcc gtg cgt gcc acc tac acc gag gac ctc ctc ggc cgt ggt gac ctc      2643
Ser Val Arg Ala Thr Tyr Thr Glu Asp Leu Leu Gly Arg Gly Asp Leu
        785                 790                 795

tcc ccc gag gac gcc gag gcc gtt gtc cgc gac ttc cac gac cag atg      2691
Ser Pro Glu Asp Ala Glu Ala Val Val Arg Asp Phe His Asp Gln Met
    800                 805                 810

gaa tcc gtg ttc aac gag gtc aag gaa gcc ggc aag aag cag cct gat      2739
Glu Ser Val Phe Asn Glu Val Lys Glu Ala Gly Lys Lys Gln Pro Asp
815                 820                 825                 830

gag cag acc ggc atc acc ggt tcc cag gaa ctg acc cgt ggc ctg gac      2787
Glu Gln Thr Gly Ile Thr Gly Ser Gln Glu Leu Thr Arg Gly Leu Asp
                835                 840                 845

acc aac atc acc cgc gag gaa ctg gtc gaa ctc ggc cag gcc ttc gtc      2835
Thr Asn Ile Thr Arg Glu Glu Leu Val Glu Leu Gly Gln Ala Phe Val
            850                 855                 860

aac acc cca gag ggc ttc acc tac cac cca cgt gtg gca ccg gtg gcc      2883
Asn Thr Pro Glu Gly Phe Thr Tyr His Pro Arg Val Ala Pro Val Ala
        865                 870                 875

aag aag cgt gcc gag tcc gtc acc gag ggt ggc atc gac tgg gca tgg      2931
Lys Lys Arg Ala Glu Ser Val Thr Glu Gly Gly Ile Asp Trp Ala Trp
    880                 885                 890

ggc gag ctc atc gcc ttc ggc tcc ctg gcc acc tcc ggc agg ctg gtc      2979
Gly Glu Leu Ile Ala Phe Gly Ser Leu Ala Thr Ser Gly Arg Leu Val
895                 900                 905                 910

cgc ctc gcc ggt gag gat tcc cgc cgt ggt acc ttc acc cag cgt cac      3027
Arg Leu Ala Gly Glu Asp Ser Arg Arg Gly Thr Phe Thr Gln Arg His
                915                 920                 925

gcc gtg gcc atc gac ccg aac acc gcc gag gag ttc aac ccg ctc cac      3075
Ala Val Ala Ile Asp Pro Asn Thr Ala Glu Glu Phe Asn Pro Leu His
            930                 935                 940

gag ctg gca cag gcc aag ggc ggc ggc aag ttc ctc gtc tac aac tcc      3123
Glu Leu Ala Gln Ala Lys Gly Gly Gly Lys Phe Leu Val Tyr Asn Ser
        945                 950                 955

gcg ctg acc gag tac gcg ggt atg ggc ttc gaa tac ggc tac tcc gtg      3171
Ala Leu Thr Glu Tyr Ala Gly Met Gly Phe Glu Tyr Gly Tyr Ser Val
    960                 965                 970

ggc aac ccg gac gcc gtg gtg tcc tgg gag gca cag ttc ggt gac ttc      3219
Gly Asn Pro Asp Ala Val Val Ser Trp Glu Ala Gln Phe Gly Asp Phe
975                 980                 985                 990

gcc aac ggt gca cag acc atc atc gat gag  tac atc tcc tcc ggt  gag    3267
Ala Asn Gly Ala Gln Thr Ile Ile Asp Glu  Tyr Ile Ser Ser Gly  Glu
                995                 1000                1005

gcc aag tgg ggc  cag acc tcc tcg gtc  atc ctg ctg ctg ccc  cac       3312
Ala Lys Trp Gly  Gln Thr Ser Ser Val  Ile Leu Leu Leu Pro  His
            1010                1015                1020
```

-continued

```
ggt tac gag ggc  cag ggt ccg gac cac  tcc tcc gca cgc atc  gag      3357
Gly Tyr Glu Gly  Gln Gly Pro Asp His  Ser Ser Ala Arg Ile  Glu
            1025                 1030                 1035

cgt ttc ctg cag  ctg tgc gcc gag ggt  tcc atg acc atc gcc  cag      3402
Arg Phe Leu Gln  Leu Cys Ala Glu Gly  Ser Met Thr Ile Ala  Gln
            1040                 1045                 1050

ccg acc acc ccg  gcg aac tac ttc cac  ctg ctg cgt cgt cac  gca      3447
Pro Thr Thr Pro  Ala Asn Tyr Phe His  Leu Leu Arg Arg His  Ala
            1055                 1060                 1065

ctg ggc aag atg  aag cgc ccg ctg gtc  gtc ttc acc ccg aag  tcc      3492
Leu Gly Lys Met  Lys Arg Pro Leu Val  Val Phe Thr Pro Lys  Ser
            1070                 1075                 1080

atg ctg cgc aac  aag gcc gcc acc tcc  gct ccg gag gag ttc  acc      3537
Met Leu Arg Asn  Lys Ala Ala Thr Ser  Ala Pro Glu Glu Phe  Thr
            1085                 1090                 1095

gag gtc acc cgc  ttc aag tcc gtg atc  gac gat ccg aac gtg  gcg      3582
Glu Val Thr Arg  Phe Lys Ser Val Ile  Asp Asp Pro Asn Val  Ala
            1100                 1105                 1110

gat gcc tcc aag  gtg aag aag atc atg  ctg tgc tcc ggc aag  atc      3627
Asp Ala Ser Lys  Val Lys Lys Ile Met  Leu Cys Ser Gly Lys  Ile
            1115                 1120                 1125

tac tac gaa ctg  gcc aag cgc aag gag  aag gac aac cgc gac  gac      3672
Tyr Tyr Glu Leu  Ala Lys Arg Lys Glu  Lys Asp Asn Arg Asp  Asp
            1130                 1135                 1140

atc gcg atc gtg  cgc atc gag atg ctg  cac ccg atc ccg ttc  aac      3717
Ile Ala Ile Val  Arg Ile Glu Met Leu  His Pro Ile Pro Phe  Asn
            1145                 1150                 1155

cgt ctg cgc gac  gcc ttc gac ggc tac  ccc aac gcc gag gag  atc      3762
Arg Leu Arg Asp  Ala Phe Asp Gly Tyr  Pro Asn Ala Glu Glu  Ile
            1160                 1165                 1170

ctg ttc gtt cag  gac gag ccg gca aac  cag ggt gcc tgg ccg  ttc      3807
Leu Phe Val Gln  Asp Glu Pro Ala Asn  Gln Gly Ala Trp Pro  Phe
            1175                 1180                 1185

tac cag gag cac  ctg ccc aac ctc atc  gag ggc atg ctc ccg  atg      3852
Tyr Gln Glu His  Leu Pro Asn Leu Ile  Glu Gly Met Leu Pro  Met
            1190                 1195                 1200

cgt cgc atc tcg  cgc cgt tcc cag tcc  tcg act gcg acc ggt  atc      3897
Arg Arg Ile Ser  Arg Arg Ser Gln Ser  Ser Thr Ala Thr Gly  Ile
            1205                 1210                 1215

gcg aag gtg cac  acc atc gag cag cag  aag ctg ctg gat gat  gcg      3942
Ala Lys Val His  Thr Ile Glu Gln Gln  Lys Leu Leu Asp Asp  Ala
            1220                 1225                 1230

ttc aac gca taaacgttaa tacagcggtt gataccttga accccgccgc             3991
Phe Asn Ala

accctttaga tgcgggcggg gttttgcttt gcctgcatag gcgataatat tcatatacac   4051

ccatcacgtt taagttctgc atttggatcg tgcgagcatc ccggt                   4096


<210> SEQ ID NO 55
<211> LENGTH: 1234
<212> TYPE: PRT
<213> ORGANISM: Corynebacterium thermoaminogenes

<400> SEQUENCE: 55

Val Ser Ser Ala Ser Thr Phe Gly Gln Asn Ala Trp Leu Val Asp Glu
1               5                   10                  15

Met Phe Gln Gln Phe Lys Lys Asp Pro Gln Ser Val Asp Lys Glu Trp
            20                  25                  30

Arg Glu Leu Phe Glu Ser Gln Gly Gly Pro Gln Ala Glu Lys Ala Thr
```

-continued

```
        35                  40                  45

Pro Ala Thr Pro Glu Ala Lys Lys Ala Ala Ser Ser Gln Ser Ser Thr
    50                  55                  60

Ser Gly Gln Ser Thr Ala Lys Ala Ala Pro Ala Ala Lys Thr Ala Pro
65                  70                  75                  80

Ala Ser Ala Pro Ala Lys Ala Ala Pro Val Lys Gln Asn Gln Ala Ser
                85                  90                  95

Lys Pro Ala Lys Lys Ala Lys Glu Ser Pro Leu Ser Lys Pro Ala Ala
            100                 105                 110

Met Pro Glu Pro Gly Thr Thr Pro Leu Arg Gly Ile Phe Lys Ser Ile
        115                 120                 125

Ala Lys Asn Met Asp Leu Ser Leu Glu Val Pro Thr Ala Thr Ser Val
    130                 135                 140

Arg Asp Met Pro Ala Arg Leu Met Phe Glu Asn Arg Ala Met Val Asn
145                 150                 155                 160

Asp Gln Leu Lys Arg Thr Arg Gly Gly Lys Ile Ser Phe Thr His Ile
                165                 170                 175

Ile Gly Tyr Ala Met Val Lys Ala Val Met Ala His Pro Asp Met Asn
            180                 185                 190

Asn Ser Tyr Asp Ile Val Asp Gly Lys Pro Ser Leu Val Val Pro Glu
        195                 200                 205

His Ile Asn Leu Gly Leu Ala Ile Asp Leu Pro Gln Lys Asp Gly Ser
    210                 215                 220

Arg Ala Leu Val Val Ala Ala Ile Lys Glu Thr Glu Lys Met Thr Phe
225                 230                 235                 240

Ser Gln Phe Leu Glu Ala Tyr Glu Asp Val Val Ala Arg Ser Arg Val
                245                 250                 255

Gly Lys Leu Thr Met Asp Asp Tyr Gln Gly Val Thr Ile Ser Leu Thr
            260                 265                 270

Asn Pro Gly Gly Ile Gly Thr Arg His Ser Ile Pro Arg Leu Thr Lys
        275                 280                 285

Gly Gln Gly Thr Ile Ile Gly Val Gly Ser Met Asp Tyr Pro Ala Glu
    290                 295                 300

Phe Gln Gly Ala Ser Glu Asp Arg Leu Ala Glu Leu Gly Val Gly Lys
305                 310                 315                 320

Leu Val Thr Ile Thr Ser Thr Tyr Asp His Arg Val Ile Gln Gly Ala
                325                 330                 335

Glu Ser Gly Glu Phe Leu Arg Thr Met Ser Gln Leu Leu Val Asp Asp
            340                 345                 350

Ala Phe Trp Asp His Ile Phe Glu Glu Met Asn Val Pro Tyr Thr Pro
        355                 360                 365

Met Arg Trp Ala Gln Asp Leu Pro Asn Thr Gly Val Asp Lys Asn Thr
    370                 375                 380

Arg Val Met Gln Leu Ile Glu Ala Tyr Arg Ser Arg Gly His Leu Ile
385                 390                 395                 400

Ala Asp Thr Asn Pro Leu Pro Trp Val Gln Pro Gly Met Pro Val Pro
                405                 410                 415

Asp His Arg Asp Leu Asp Ile Glu Thr His Gly Leu Thr Leu Trp Asp
            420                 425                 430

Leu Asp Arg Thr Phe His Val Gly Gly Phe Gly Gly Lys Glu Thr Met
        435                 440                 445

Thr Leu Arg Glu Val Leu Ser Arg Leu Arg Ala Ala Tyr Thr Leu Lys
    450                 455                 460
```

-continued

Val Gly Ser Glu Tyr Thr His Ile Leu Asp Arg Asp Glu Arg Thr Trp
465 470 475 480

Leu Gln Asp Arg Leu Glu Ala Gly Met Pro Lys Pro Thr Ala Ala Glu
485 490 495

Gln Lys Tyr Ile Leu Gln Lys Leu Asn Ala Ala Glu Ala Phe Glu Asn
500 505 510

Phe Leu Gln Thr Lys Tyr Val Gly Gln Lys Arg Phe Ser Leu Glu Gly
515 520 525

Ala Glu Ser Leu Ile Pro Leu Met Asp Ser Ala Ile Asp Thr Ala Ala
530 535 540

Gly Gln Gly Leu Asp Glu Val Val Ile Gly Met Pro His Arg Gly Arg
545 550 555 560

Leu Asn Val Leu Phe Asn Ile Val Gly Lys Pro Leu Ala Ser Ile Phe
565 570 575

Asn Glu Phe Glu Gly Gln Met Glu Gln Gly Gln Ile Gly Gly Ser Gly
580 585 590

Asp Val Lys Tyr His Leu Gly Ser Glu Gly Thr His Leu Gln Met Phe
595 600 605

Gly Asp Gly Glu Ile Lys Val Ser Leu Thr Ala Asn Pro Ser His Leu
610 615 620

Glu Ala Val Asn Pro Val Val Glu Gly Ile Val Arg Ala Lys Gln Asp
625 630 635 640

Ile Leu Asp Lys Gly Pro Asp Gly Tyr Thr Val Val Pro Leu Leu Leu
645 650 655

His Gly Asp Ala Ala Phe Ala Gly Leu Gly Ile Val Pro Glu Thr Ile
660 665 670

Asn Leu Ala Ala Leu Arg Gly Tyr Asp Val Gly Gly Thr Ile His Ile
675 680 685

Val Val Asn Asn Gln Ile Gly Phe Thr Thr Thr Pro Asp Ser Ser Arg
690 695 700

Ser Met His Tyr Ala Thr Asp Cys Ala Lys Ala Phe Gly Cys Pro Val
705 710 715 720

Phe His Val Asn Gly Asp Asp Pro Glu Ala Val Val Trp Val Gly Gln
725 730 735

Leu Ala Thr Glu Tyr Arg Arg Arg Phe Gly Lys Asp Val Phe Ile Asp
740 745 750

Leu Ile Cys Tyr Arg Leu Arg Gly His Asn Glu Ala Asp Asp Pro Ser
755 760 765

Met Thr Gln Pro Lys Met Tyr Glu Leu Ile Thr Gly Arg Asp Ser Val
770 775 780

Arg Ala Thr Tyr Thr Glu Asp Leu Leu Gly Arg Gly Asp Leu Ser Pro
785 790 795 800

Glu Asp Ala Glu Ala Val Val Arg Asp Phe His Asp Gln Met Glu Ser
805 810 815

Val Phe Asn Glu Val Lys Glu Ala Gly Lys Lys Gln Pro Asp Glu Gln
820 825 830

Thr Gly Ile Thr Gly Ser Gln Glu Leu Thr Arg Gly Leu Asp Thr Asn
835 840 845

Ile Thr Arg Glu Glu Leu Val Glu Leu Gly Gln Ala Phe Val Asn Thr
850 855 860

Pro Glu Gly Phe Thr Tyr His Pro Arg Val Ala Pro Val Ala Lys Lys
865 870 875 880

-continued

```
Arg Ala Glu Ser Val Thr Glu Gly Gly Ile Asp Trp Ala Trp Gly Glu
                885                 890                 895

Leu Ile Ala Phe Gly Ser Leu Ala Thr Ser Gly Arg Leu Val Arg Leu
            900                 905                 910

Ala Gly Glu Asp Ser Arg Arg Gly Thr Phe Thr Gln Arg His Ala Val
        915                 920                 925

Ala Ile Asp Pro Asn Thr Ala Glu Glu Phe Asn Pro Leu His Glu Leu
    930                 935                 940

Ala Gln Ala Lys Gly Gly Gly Lys Phe Leu Val Tyr Asn Ser Ala Leu
945                 950                 955                 960

Thr Glu Tyr Ala Gly Met Gly Phe Glu Tyr Gly Tyr Ser Val Gly Asn
                965                 970                 975

Pro Asp Ala Val Val Ser Trp Glu Ala Gln Phe Gly Asp Phe Ala Asn
            980                 985                 990

Gly Ala Gln Thr Ile Ile Asp Glu  Tyr Ile Ser Ser Gly  Glu Ala Lys
        995                 1000                1005

Trp Gly  Gln Thr Ser Ser Val  Ile Leu Leu Leu Pro  His Gly Tyr
    1010                1015                1020

Glu Gly  Gln Gly Pro Asp His  Ser Ser Ala Arg Ile  Glu Arg Phe
    1025                1030                1035

Leu Gln  Leu Cys Ala Glu Gly  Ser Met Thr Ile Ala  Gln Pro Thr
    1040                1045                1050

Thr Pro  Ala Asn Tyr Phe His  Leu Leu Arg Arg His  Ala Leu Gly
    1055                1060                1065

Lys Met  Lys Arg Pro Leu Val  Val Phe Thr Pro Lys  Ser Met Leu
    1070                1075                1080

Arg Asn  Lys Ala Ala Thr Ser  Ala Pro Glu Glu Phe  Thr Glu Val
    1085                1090                1095

Thr Arg  Phe Lys Ser Val Ile  Asp Asp Pro Asn Val  Ala Asp Ala
    1100                1105                1110

Ser Lys  Val Lys Lys Ile Met  Leu Cys Ser Gly Lys  Ile Tyr Tyr
    1115                1120                1125

Glu Leu  Ala Lys Arg Lys Glu  Lys Asp Asn Arg Asp  Asp Ile Ala
    1130                1135                1140

Ile Val  Arg Ile Glu Met Leu  His Pro Ile Pro Phe  Asn Arg Leu
    1145                1150                1155

Arg Asp  Ala Phe Asp Gly Tyr  Pro Asn Ala Glu Glu  Ile Leu Phe
    1160                1165                1170

Val Gln  Asp Glu Pro Ala Asn  Gln Gly Ala Trp Pro  Phe Tyr Gln
    1175                1180                1185

Glu His  Leu Pro Asn Leu Ile  Glu Gly Met Leu Pro  Met Arg Arg
    1190                1195                1200

Ile Ser  Arg Arg Ser Gln Ser  Ser Thr Ala Thr Gly  Ile Ala Lys
    1205                1210                1215

Val His  Thr Ile Glu Gln Gln  Lys Leu Leu Asp Asp  Ala Phe Asn
    1220                1225                1230

Ala
```

```
<210> SEQ ID NO 56
<211> LENGTH: 20
<212> TYPE: DNA
<213> ORGANISM: Artificial Sequence
<220> FEATURE:
<223> OTHER INFORMATION: synthetic DNA
```

-continued

<400> SEQUENCE: 56
cctctaccca gcgaactccg 20

<210> SEQ ID NO 57
<211> LENGTH: 20
<212> TYPE: DNA
<213> ORGANISM: Artificial Sequence
<220> FEATURE:
<223> OTHER INFORMATION: synthetic DNA

<400> SEQUENCE: 57
ctgccttgaa ctcacggttc 20

<210> SEQ ID NO 58
<211> LENGTH: 20
<212> TYPE: DNA
<213> ORGANISM: Artificial Sequence
<220> FEATURE:
<223> OTHER INFORMATION: synthetic DNA

<400> SEQUENCE: 58
catccacccc ggctacggct 20

<210> SEQ ID NO 59
<211> LENGTH: 20
<212> TYPE: DNA
<213> ORGANISM: Artificial Sequence
<220> FEATURE:
<223> OTHER INFORMATION: synthetic DNA

<400> SEQUENCE: 59
cggtgactgg gtgttccacc 20

<210> SEQ ID NO 60
<211> LENGTH: 20
<212> TYPE: DNA
<213> ORGANISM: Artificial Sequence
<220> FEATURE:
<223> OTHER INFORMATION: synthetic DNA

<400> SEQUENCE: 60
acggcccagc cctgaccgac 20

<210> SEQ ID NO 61
<211> LENGTH: 20
<212> TYPE: DNA
<213> ORGANISM: Artificial Sequence
<220> FEATURE:
<223> OTHER INFORMATION: synthetic DNA

<400> SEQUENCE: 61
agcagcgccc atgacggcga 20

<210> SEQ ID NO 62
<211> LENGTH: 20
<212> TYPE: DNA
<213> ORGANISM: Artificial Sequence
<220> FEATURE:
<223> OTHER INFORMATION: synthetic DNA

<400> SEQUENCE: 62
acggcccagc cctgaccgac 20

<210> SEQ ID NO 63
<211> LENGTH: 20

<212> TYPE: DNA
<213> ORGANISM: Artificial Sequence
<220> FEATURE:
<223> OTHER INFORMATION: synthetic DNA

<400> SEQUENCE: 63
agcagcgccc atgacggcga 20

<210> SEQ ID NO 64
<211> LENGTH: 20
<212> TYPE: DNA
<213> ORGANISM: Artificial Sequence
<220> FEATURE:
<223> OTHER INFORMATION: synthetic DNA

<400> SEQUENCE: 64
cgtcatccga ggaatcgtcc 20

<210> SEQ ID NO 65
<211> LENGTH: 20
<212> TYPE: DNA
<213> ORGANISM: Artificial Sequence
<220> FEATURE:
<223> OTHER INFORMATION: synthetic DNA

<400> SEQUENCE: 65
cgtggcggcc catgacctcc 20

<210> SEQ ID NO 66
<211> LENGTH: 17
<212> TYPE: DNA
<213> ORGANISM: Artificial Sequence
<220> FEATURE:
<223> OTHER INFORMATION: synthetic DNA
<220> FEATURE:
<221> NAME/KEY: misc_feature
<222> LOCATION: (3)..(3)
<223> OTHER INFORMATION: n is a, g, c, or t

<400> SEQUENCE: 66
ggncghytba aygaycc 17

<210> SEQ ID NO 67
<211> LENGTH: 20
<212> TYPE: DNA
<213> ORGANISM: Artificial Sequence
<220> FEATURE:
<223> OTHER INFORMATION: synthetic DNA
<220> FEATURE:
<221> NAME/KEY: misc_feature
<222> LOCATION: (18)..(18)
<223> OTHER INFORMATION: n is a, g, c, or t

<400> SEQUENCE: 67
ggrcaytccc acatrtancc 20

<210> SEQ ID NO 68
<211> LENGTH: 20
<212> TYPE: DNA
<213> ORGANISM: Artificial Sequence
<220> FEATURE:
<223> OTHER INFORMATION: synthetic DNA

<400> SEQUENCE: 68
ccatccggat ccggcaagtc 20

<210> SEQ ID NO 69

-continued

<211> LENGTH: 20
<212> TYPE: DNA
<213> ORGANISM: Artificial Sequence
<220> FEATURE:
<223> OTHER INFORMATION: synthetic DNA

<400> SEQUENCE: 69
aatcccatct cgtgggtaac 20

<210> SEQ ID NO 70
<211> LENGTH: 23
<212> TYPE: DNA
<213> ORGANISM: Artificial Sequence
<220> FEATURE:
<223> OTHER INFORMATION: synthetic DNA

<400> SEQUENCE: 70
actgtgtcca tgggtcttgg ccc 23

<210> SEQ ID NO 71
<211> LENGTH: 20
<212> TYPE: DNA
<213> ORGANISM: Artificial Sequence
<220> FEATURE:
<223> OTHER INFORMATION: synthetic DNA

<400> SEQUENCE: 71
cgctggaatc cgaacatcga 20

<210> SEQ ID NO 72
<211> LENGTH: 26
<212> TYPE: DNA
<213> ORGANISM: Artificial Sequence
<220> FEATURE:
<223> OTHER INFORMATION: synthetic DNA

<400> SEQUENCE: 72
ggcgcaacct acgacgttgc aatgcg 26

<210> SEQ ID NO 73
<211> LENGTH: 20
<212> TYPE: DNA
<213> ORGANISM: Artificial Sequence
<220> FEATURE:
<223> OTHER INFORMATION: synthetic DNA

<400> SEQUENCE: 73
tggccgcctg ggatctcgtg 20

<210> SEQ ID NO 74
<211> LENGTH: 20
<212> TYPE: DNA
<213> ORGANISM: Artificial Sequence
<220> FEATURE:
<223> OTHER INFORMATION: synthetic DNA

<400> SEQUENCE: 74
ggttcctgga ttggtggaga 20

<210> SEQ ID NO 75
<211> LENGTH: 20
<212> TYPE: DNA
<213> ORGANISM: Artificial Sequence
<220> FEATURE:
<223> OTHER INFORMATION: synthetic DNA

<400> SEQUENCE: 75
ccgccatcct tgttggaatc 20

<210> SEQ ID NO 76
<211> LENGTH: 20
<212> TYPE: DNA
<213> ORGANISM: Artificial Sequence
<220> FEATURE:
<223> OTHER INFORMATION: synthetic DNA
<220> FEATURE:
<221> NAME/KEY: misc_feature
<222> LOCATION: (3)..(3)
<223> OTHER INFORMATION: n is inosine
<220> FEATURE:
<221> NAME/KEY: misc_feature
<222> LOCATION: (6)..(6)
<223> OTHER INFORMATION: n is inosine
<220> FEATURE:
<221> NAME/KEY: misc_feature
<222> LOCATION: (9)..(9)
<223> OTHER INFORMATION: n is inosine

<400> SEQUENCE: 76
gtnggnacng aytcscatac 20

<210> SEQ ID NO 77
<211> LENGTH: 20
<212> TYPE: DNA
<213> ORGANISM: Artificial Sequence
<220> FEATURE:
<223> OTHER INFORMATION: synthetic DNA
<220> FEATURE:
<221> NAME/KEY: misc_feature
<222> LOCATION: (3)..(3)
<223> OTHER INFORMATION: n is inosine
<220> FEATURE:
<221> NAME/KEY: misc_feature
<222> LOCATION: (9)..(9)
<223> OTHER INFORMATION: n is inosine
<220> FEATURE:
<221> NAME/KEY: misc_feature
<222> LOCATION: (18)..(18)
<223> OTHER INFORMATION: n is inosine

<400> SEQUENCE: 77
gcnggagana tgtgrtcngt 20

<210> SEQ ID NO 78
<211> LENGTH: 20
<212> TYPE: DNA
<213> ORGANISM: Artificial Sequence
<220> FEATURE:
<223> OTHER INFORMATION: synthetic DNA

<400> SEQUENCE: 78
gacatttcac tcgctggacg 20

<210> SEQ ID NO 79
<211> LENGTH: 20
<212> TYPE: DNA
<213> ORGANISM: Artificial Sequence
<220> FEATURE:
<223> OTHER INFORMATION: synthetic DNA

<400> SEQUENCE: 79
ccgtactctt cagccttctg 20

<210> SEQ ID NO 80
<211> LENGTH: 17
<212> TYPE: DNA

<213> ORGANISM: Artificial Sequence
<220> FEATURE:
<223> OTHER INFORMATION: synthetic DNA

<400> SEQUENCE: 80
atcatcgcaa ccggttc 17

<210> SEQ ID NO 81
<211> LENGTH: 19
<212> TYPE: DNA
<213> ORGANISM: Artificial Sequence
<220> FEATURE:
<223> OTHER INFORMATION: synthetic DNA

<400> SEQUENCE: 81
cgtcaccgat ggcgtaaat 19

<210> SEQ ID NO 82
<211> LENGTH: 20
<212> TYPE: DNA
<213> ORGANISM: Artificial Sequence
<220> FEATURE:
<223> OTHER INFORMATION: synthetic DNA

<400> SEQUENCE: 82
acaccgtggt cgcctcaacg 20

<210> SEQ ID NO 83
<211> LENGTH: 20
<212> TYPE: DNA
<213> ORGANISM: Artificial Sequence
<220> FEATURE:
<223> OTHER INFORMATION: synthetic DNA

<400> SEQUENCE: 83
tgctaacccg tcccacctgg 20

<210> SEQ ID NO 84
<211> LENGTH: 20
<212> TYPE: DNA
<213> ORGANISM: Artificial Sequence
<220> FEATURE:
<223> OTHER INFORMATION: synthetic DNA

<400> SEQUENCE: 84
tacgaggagc agatcctcaa 20

<210> SEQ ID NO 85
<211> LENGTH: 20
<212> TYPE: DNA
<213> ORGANISM: Artificial Sequence
<220> FEATURE:
<223> OTHER INFORMATION: synthetic DNA

<400> SEQUENCE: 85
ttgacgccgg tgttctccag 20

<210> SEQ ID NO 86
<211> LENGTH: 20
<212> TYPE: DNA
<213> ORGANISM: Artificial Sequence
<220> FEATURE:
<223> OTHER INFORMATION: synthetic DNA

<400> SEQUENCE: 86
ggtgaagcta agtagttagc 20

<210> SEQ ID NO 87
<211> LENGTH: 18
<212> TYPE: DNA
<213> ORGANISM: Artificial Sequence
<220> FEATURE:
<223> OTHER INFORMATION: synthetic DNA

<400> SEQUENCE: 87
agctactaaa cctgcacc 18

<210> SEQ ID NO 88
<211> LENGTH: 20
<212> TYPE: DNA
<213> ORGANISM: Artificial Sequence
<220> FEATURE:
<223> OTHER INFORMATION: synthetic DNA

<400> SEQUENCE: 88
ccgtactctt cagccttctg 20

<210> SEQ ID NO 89
<211> LENGTH: 18
<212> TYPE: DNA
<213> ORGANISM: Artificial Sequence
<220> FEATURE:
<223> OTHER INFORMATION: synthetic DNA

<400> SEQUENCE: 89
tcgtccttgt tccacatc 18

<210> SEQ ID NO 90
<211> LENGTH: 17
<212> TYPE: DNA
<213> ORGANISM: Artificial Sequence
<220> FEATURE:
<223> OTHER INFORMATION: synthetic DNA

<400> SEQUENCE: 90
atcatcgcaa ccggttc 17

<210> SEQ ID NO 91
<211> LENGTH: 20
<212> TYPE: DNA
<213> ORGANISM: Artificial Sequence
<220> FEATURE:
<223> OTHER INFORMATION: synthetic DNA

<400> SEQUENCE: 91
tacgaggagc agatcctcaa 20

<210> SEQ ID NO 92
<211> LENGTH: 20
<212> TYPE: DNA
<213> ORGANISM: Artificial Sequence
<220> FEATURE:
<223> OTHER INFORMATION: synthetic DNA

<400> SEQUENCE: 92
gctaactact tagcttcacc 20

<210> SEQ ID NO 93
<211> LENGTH: 20
<212> TYPE: DNA
<213> ORGANISM: Artificial Sequence
<220> FEATURE:

<223> OTHER INFORMATION: synthetic DNA

<400> SEQUENCE: 93
gaaccaggaa ctattgaacc 20

<210> SEQ ID NO 94
<211> LENGTH: 18
<212> TYPE: DNA
<213> ORGANISM: Artificial Sequence
<220> FEATURE:
<223> OTHER INFORMATION: synthetic DNA

<400> SEQUENCE: 94
tccgatgtca tcatcgac 18

<210> SEQ ID NO 95
<211> LENGTH: 18
<212> TYPE: DNA
<213> ORGANISM: Artificial Sequence
<220> FEATURE:
<223> OTHER INFORMATION: synthetic DNA

<400> SEQUENCE: 95
atgtggaaca aggacgac 18

<210> SEQ ID NO 96
<211> LENGTH: 35
<212> TYPE: DNA
<213> ORGANISM: Artificial Sequence
<220> FEATURE:
<223> OTHER INFORMATION: synthetic DNA

<400> SEQUENCE: 96
gtacatattg tcgttagaac gcgtaatacg actca 35

<210> SEQ ID NO 97
<211> LENGTH: 35
<212> TYPE: DNA
<213> ORGANISM: Artificial Sequence
<220> FEATURE:
<223> OTHER INFORMATION: synthetic DNA

<400> SEQUENCE: 97
cgttagaacg cgtaatacga ctcactatag ggaga 35

<210> SEQ ID NO 98
<211> LENGTH: 32
<212> TYPE: DNA
<213> ORGANISM: Artificial Sequence
<220> FEATURE:
<223> OTHER INFORMATION: synthetic DNA

<400> SEQUENCE: 98
gcgcctgcag gtccgagggt gtgcgttcgg ca 32

<210> SEQ ID NO 99
<211> LENGTH: 32
<212> TYPE: DNA
<213> ORGANISM: Artificial Sequence
<220> FEATURE:
<223> OTHER INFORMATION: synthetic DNA

<400> SEQUENCE: 99
gcgcctgcag ccaccaggat gccctcaacc ag 32

-continued

```
<210> SEQ ID NO 100
<211> LENGTH: 1344
<212> TYPE: DNA
<213> ORGANISM: Corynebacterium thermoaminogenes
<220> FEATURE:
<221> NAME/KEY: CDS
<222> LOCATION: (1)..(1341)
<223> OTHER INFORMATION:

<400> SEQUENCE: 100

atg act gta gat gag cag gtc tcc aac tac tac gac atg ctg ctg aag       48
Met Thr Val Asp Glu Gln Val Ser Asn Tyr Tyr Asp Met Leu Leu Lys
1               5                   10                  15

cgc aac gcc ggg gaa cct gag ttc cac cag gct gtc gcg gag gtt ctc       96
Arg Asn Ala Gly Glu Pro Glu Phe His Gln Ala Val Ala Glu Val Leu
            20                  25                  30

gaa tct ctg aag atc gtc ctg gag aag gac ccg cac tac gcc gac tac      144
Glu Ser Leu Lys Ile Val Leu Glu Lys Asp Pro His Tyr Ala Asp Tyr
        35                  40                  45

ggt ctg atc cag cgt ctc tgc gaa ccg gaa cgc cag ctg atc ttc cgt      192
Gly Leu Ile Gln Arg Leu Cys Glu Pro Glu Arg Gln Leu Ile Phe Arg
    50                  55                  60

gtg ccc tgg gtg gat gac aac ggt cag gtg cac gtc aac cgt ggt ttc      240
Val Pro Trp Val Asp Asp Asn Gly Gln Val His Val Asn Arg Gly Phe
65                  70                  75                  80

cgt gtc cag ttc aac tcc gca ctc ggc ccg tac aag ggt ggt ctg cgt      288
Arg Val Gln Phe Asn Ser Ala Leu Gly Pro Tyr Lys Gly Gly Leu Arg
                85                  90                  95

ttc cac ccc tcc gtc aac ctc ggc atc gtc aag ttc ctc ggc ttc gag      336
Phe His Pro Ser Val Asn Leu Gly Ile Val Lys Phe Leu Gly Phe Glu
            100                 105                 110

cag atc ttc aag aac tcc ctc acc ggt ctg ccg atc ggt ggc ggc aag      384
Gln Ile Phe Lys Asn Ser Leu Thr Gly Leu Pro Ile Gly Gly Gly Lys
        115                 120                 125

ggt ggt tcc gac ttc gac ccg aag ggc aag tcc gag ctg gag atc atg      432
Gly Gly Ser Asp Phe Asp Pro Lys Gly Lys Ser Glu Leu Glu Ile Met
    130                 135                 140

cgc ttc tgc cag tcc ttc atg acc gag ctg cac cgc cac atc ggc gag      480
Arg Phe Cys Gln Ser Phe Met Thr Glu Leu His Arg His Ile Gly Glu
145                 150                 155                 160

tac cgg gat gtc ccg gcc ggt gac atc gga gtc ggt ggc cgc gag atc      528
Tyr Arg Asp Val Pro Ala Gly Asp Ile Gly Val Gly Gly Arg Glu Ile
                165                 170                 175

ggt tac ctc ttc ggc cac tac cgc cgt ctg gcc aac cag cac gag tcc      576
Gly Tyr Leu Phe Gly His Tyr Arg Arg Leu Ala Asn Gln His Glu Ser
            180                 185                 190

ggt gtg ctc acc ggc aag ggc ctg acc tgg ggt ggt tcc ctg gtc cgc      624
Gly Val Leu Thr Gly Lys Gly Leu Thr Trp Gly Gly Ser Leu Val Arg
        195                 200                 205

acc gag gcc acc ggc ttc ggc acc gtc tac ttc gtc cag gag atg atc      672
Thr Glu Ala Thr Gly Phe Gly Thr Val Tyr Phe Val Gln Glu Met Ile
    210                 215                 220

aag gcg gaa ggg gag acc ctc gag ggc aag aag gtc atc gtc tcc ggt      720
Lys Ala Glu Gly Glu Thr Leu Glu Gly Lys Lys Val Ile Val Ser Gly
225                 230                 235                 240

tcc ggc aac gtg gcc acc tac gcc atc cag aag gtg cag gaa ctg ggt      768
Ser Gly Asn Val Ala Thr Tyr Ala Ile Gln Lys Val Gln Glu Leu Gly
                245                 250                 255

gcg gtt gtg gtc ggc ttc tcc gac tcc agc ggc tgg gtc tcc acc ccg      816
Ala Val Val Val Gly Phe Ser Asp Ser Ser Gly Trp Val Ser Thr Pro
            260                 265                 270
```

-continued

```
aac ggt gtt gac gtg gcc aag ctg cgt gag atc aag gag gtc cgt cgt      864
Asn Gly Val Asp Val Ala Lys Leu Arg Glu Ile Lys Glu Val Arg Arg
        275                 280                 285

gca cgc gtg tcc tcc tac gcc gac gag gtg gag ggt gcg gag tac cac      912
Ala Arg Val Ser Ser Tyr Ala Asp Glu Val Glu Gly Ala Glu Tyr His
    290                 295                 300

acc gac ggc tcc atc tgg gat ctg acc gcc gac atc gcg ctg ccc tgc      960
Thr Asp Gly Ser Ile Trp Asp Leu Thr Ala Asp Ile Ala Leu Pro Cys
305                 310                 315                 320

gcc acc cag aac gaa ctg gac ggc gac aac gcc cgc acc ctc gcg gac     1008
Ala Thr Gln Asn Glu Leu Asp Gly Asp Asn Ala Arg Thr Leu Ala Asp
                325                 330                 335

aac ggc tgc cgc ttc gtg gcg gag ggc gcc aac atg ccc tcc acc ccc     1056
Asn Gly Cys Arg Phe Val Ala Glu Gly Ala Asn Met Pro Ser Thr Pro
            340                 345                 350

gag gcc atc gac gtc ttc cgt gag cgt ggt gtt ctc ttc ggg ccg ggc     1104
Glu Ala Ile Asp Val Phe Arg Glu Arg Gly Val Leu Phe Gly Pro Gly
        355                 360                 365

aag gct gcc aac gcc ggt ggc gtg gcc acc tcc gcc ctg gag atg cag     1152
Lys Ala Ala Asn Ala Gly Gly Val Ala Thr Ser Ala Leu Glu Met Gln
    370                 375                 380

cag aac gcc tcc cgt gat tcc tgg agc ttc gag tac acc gat gag cgt     1200
Gln Asn Ala Ser Arg Asp Ser Trp Ser Phe Glu Tyr Thr Asp Glu Arg
385                 390                 395                 400

ctc cac cgc atc atg aag aac atc ttc aag tcc tgc gcc gat acc gcc     1248
Leu His Arg Ile Met Lys Asn Ile Phe Lys Ser Cys Ala Asp Thr Ala
                405                 410                 415

aag gag tac ggc cac gag aag aac tac gtg gtc ggt gcg aac atc gcc     1296
Lys Glu Tyr Gly His Glu Lys Asn Tyr Val Val Gly Ala Asn Ile Ala
            420                 425                 430

gga ttc aag aag gtc gct gac gcc atg ctc gcc cag ggt gtc atc taa     1344
Gly Phe Lys Lys Val Ala Asp Ala Met Leu Ala Gln Gly Val Ile
        435                 440                 445


<210> SEQ ID NO 101
<211> LENGTH: 447
<212> TYPE: PRT
<213> ORGANISM: Corynebacterium thermoaminogenes

<400> SEQUENCE: 101

Met Thr Val Asp Glu Gln Val Ser Asn Tyr Tyr Asp Met Leu Leu Lys
1               5                   10                  15

Arg Asn Ala Gly Glu Pro Glu Phe His Gln Ala Val Ala Glu Val Leu
            20                  25                  30

Glu Ser Leu Lys Ile Val Leu Glu Lys Asp Pro His Tyr Ala Asp Tyr
        35                  40                  45

Gly Leu Ile Gln Arg Leu Cys Glu Pro Glu Arg Gln Leu Ile Phe Arg
    50                  55                  60

Val Pro Trp Val Asp Asp Asn Gly Gln Val His Val Asn Arg Gly Phe
65                  70                  75                  80

Arg Val Gln Phe Asn Ser Ala Leu Gly Pro Tyr Lys Gly Gly Leu Arg
                85                  90                  95

Phe His Pro Ser Val Asn Leu Gly Ile Val Lys Phe Leu Gly Phe Glu
            100                 105                 110

Gln Ile Phe Lys Asn Ser Leu Thr Gly Leu Pro Ile Gly Gly Gly Lys
        115                 120                 125

Gly Gly Ser Asp Phe Asp Pro Lys Gly Lys Ser Glu Leu Glu Ile Met
    130                 135                 140
```

-continued

```
Arg Phe Cys Gln Ser Phe Met Thr Glu Leu His Arg His Ile Gly Glu
145                 150                 155                 160

Tyr Arg Asp Val Pro Ala Gly Asp Ile Gly Val Gly Gly Arg Glu Ile
                165                 170                 175

Gly Tyr Leu Phe Gly His Tyr Arg Arg Leu Ala Asn Gln His Glu Ser
            180                 185                 190

Gly Val Leu Thr Gly Lys Gly Leu Thr Trp Gly Gly Ser Leu Val Arg
        195                 200                 205

Thr Glu Ala Thr Gly Phe Gly Thr Val Tyr Phe Val Gln Glu Met Ile
    210                 215                 220

Lys Ala Glu Gly Glu Thr Leu Glu Gly Lys Lys Val Ile Val Ser Gly
225                 230                 235                 240

Ser Gly Asn Val Ala Thr Tyr Ala Ile Gln Lys Val Gln Glu Leu Gly
                245                 250                 255

Ala Val Val Val Gly Phe Ser Asp Ser Ser Gly Trp Val Ser Thr Pro
            260                 265                 270

Asn Gly Val Asp Val Ala Lys Leu Arg Glu Ile Lys Glu Val Arg Arg
        275                 280                 285

Ala Arg Val Ser Ser Tyr Ala Asp Glu Val Glu Gly Ala Glu Tyr His
    290                 295                 300

Thr Asp Gly Ser Ile Trp Asp Leu Thr Ala Asp Ile Ala Leu Pro Cys
305                 310                 315                 320

Ala Thr Gln Asn Glu Leu Asp Gly Asp Asn Ala Arg Thr Leu Ala Asp
                325                 330                 335

Asn Gly Cys Arg Phe Val Ala Glu Gly Ala Asn Met Pro Ser Thr Pro
            340                 345                 350

Glu Ala Ile Asp Val Phe Arg Glu Arg Gly Val Leu Phe Gly Pro Gly
        355                 360                 365

Lys Ala Ala Asn Ala Gly Gly Val Ala Thr Ser Ala Leu Glu Met Gln
    370                 375                 380

Gln Asn Ala Ser Arg Asp Ser Trp Ser Phe Glu Tyr Thr Asp Glu Arg
385                 390                 395                 400

Leu His Arg Ile Met Lys Asn Ile Phe Lys Ser Cys Ala Asp Thr Ala
                405                 410                 415

Lys Glu Tyr Gly His Glu Lys Asn Tyr Val Val Gly Ala Asn Ile Ala
            420                 425                 430

Gly Phe Lys Lys Val Ala Asp Ala Met Leu Ala Gln Gly Val Ile
        435                 440                 445


<210> SEQ ID NO 102
<211> LENGTH: 1344
<212> TYPE: DNA
<213> ORGANISM: Brevibacterium lactofermentum
<220> FEATURE:
<221> NAME/KEY: CDS
<222> LOCATION: (1)..(1341)
<223> OTHER INFORMATION:

<400> SEQUENCE: 102

atg aca gtt gat gag cag gtc tct aac tat tac gac atg ctt ctg aag       48
Met Thr Val Asp Glu Gln Val Ser Asn Tyr Tyr Asp Met Leu Leu Lys
1               5                   10                  15

cgc aat gct ggc gag cct gaa ttt cac cag gca gtg gca gag gtt ttg       96
Arg Asn Ala Gly Glu Pro Glu Phe His Gln Ala Val Ala Glu Val Leu
            20                  25                  30

gaa tct ttg aag atc gtc ctg gaa aag gac cct cat tac gct gat tac      144
Glu Ser Leu Lys Ile Val Leu Glu Lys Asp Pro His Tyr Ala Asp Tyr
```

-continued

```
        35                  40                  45

ggt ctc atc cag cgc ctg tgc gag cct gag cgt cag ctc atc ttc cgt      192
Gly Leu Ile Gln Arg Leu Cys Glu Pro Glu Arg Gln Leu Ile Phe Arg
    50                  55                  60

gtg cct tgg gtt gat gac cag ggc cag gtc cac gtc aac cgt ggt ttc      240
Val Pro Trp Val Asp Asp Gln Gly Gln Val His Val Asn Arg Gly Phe
65                  70                  75                  80

cgc gtg cag ttc aac tct gca ctt gga cca tac aag ggc ggc ctg cgc      288
Arg Val Gln Phe Asn Ser Ala Leu Gly Pro Tyr Lys Gly Gly Leu Arg
                85                  90                  95

ttc cac cca tct gta aac ctg ggc att gtg aag ttc ctg ggc ttt gag      336
Phe His Pro Ser Val Asn Leu Gly Ile Val Lys Phe Leu Gly Phe Glu
            100                 105                 110

cag atc ttt aaa aac tcc cta acc ggc ctg cca atc ggt ggt ggc aag      384
Gln Ile Phe Lys Asn Ser Leu Thr Gly Leu Pro Ile Gly Gly Gly Lys
        115                 120                 125

ggt gga tcc gac ttc gac cct aag ggc aag tcc gat ctg gaa atc atg      432
Gly Gly Ser Asp Phe Asp Pro Lys Gly Lys Ser Asp Leu Glu Ile Met
    130                 135                 140

cgt ttc tgc cag tcc ttc atg acc gag ctg cac cgc cac atc ggt gag      480
Arg Phe Cys Gln Ser Phe Met Thr Glu Leu His Arg His Ile Gly Glu
145                 150                 155                 160

tac cgc gac gtt cct gca ggt gac atc gga gtt ggt ggc cgc gag atc      528
Tyr Arg Asp Val Pro Ala Gly Asp Ile Gly Val Gly Gly Arg Glu Ile
                165                 170                 175

ggt tac ctg ttt ggc cac tac cgt cgc atg gct aac cag cac gag tcc      576
Gly Tyr Leu Phe Gly His Tyr Arg Arg Met Ala Asn Gln His Glu Ser
            180                 185                 190

ggc gtt ttg acc ggt aag ggc ctg acc tgg ggt gga tcc ctg gtc cgc      624
Gly Val Leu Thr Gly Lys Gly Leu Thr Trp Gly Gly Ser Leu Val Arg
        195                 200                 205

acc gag gca act ggc tac ggc tgc gtt tac ttc gtg agt gaa atg atc      672
Thr Glu Ala Thr Gly Tyr Gly Cys Val Tyr Phe Val Ser Glu Met Ile
    210                 215                 220

aag gct aag ggc gag agc atc agc ggc cag aag atc atc gtt tcc ggt      720
Lys Ala Lys Gly Glu Ser Ile Ser Gly Gln Lys Ile Ile Val Ser Gly
225                 230                 235                 240

tcc ggc aac gta gca acc tac gcg att gaa aag gct cag gaa ctc ggc      768
Ser Gly Asn Val Ala Thr Tyr Ala Ile Glu Lys Ala Gln Glu Leu Gly
                245                 250                 255

gca acc gtt att ggt ttc tcc gat tcc agc ggt tgg gtt cat acc cct      816
Ala Thr Val Ile Gly Phe Ser Asp Ser Ser Gly Trp Val His Thr Pro
            260                 265                 270

aac ggc gtt gac gtg gct aag ctc cgc gaa atc aag gaa gtt cgc cgc      864
Asn Gly Val Asp Val Ala Lys Leu Arg Glu Ile Lys Glu Val Arg Arg
        275                 280                 285

gca cgc gta tcc gtg tac gcc gac gaa att gaa ggc gca acc tac cac      912
Ala Arg Val Ser Val Tyr Ala Asp Glu Ile Glu Gly Ala Thr Tyr His
    290                 295                 300

acc gac ggt tcc atc tgg gat ctc aag tgc gat atc gct ctt cct tgt      960
Thr Asp Gly Ser Ile Trp Asp Leu Lys Cys Asp Ile Ala Leu Pro Cys
305                 310                 315                 320

gca act cag aac gag ctc aac ggc gag aac gct aag act ctt gca gac     1008
Ala Thr Gln Asn Glu Leu Asn Gly Glu Asn Ala Lys Thr Leu Ala Asp
                325                 330                 335

aac ggc tgc cgt ttc gtt gct gaa ggc gcg aac atg cct tcc acc cct     1056
Asn Gly Cys Arg Phe Val Ala Glu Gly Ala Asn Met Pro Ser Thr Pro
            340                 345                 350

gag gct gtt gag gtc ttc cgt gag cgc gac atc cgc ttc gga cca ggc     1104
```

-continued

```
Glu Ala Val Glu Val Phe Arg Glu Arg Asp Ile Arg Phe Gly Pro Gly
        355                 360                 365

aag gca gct aac gct ggt ggc gtt gca acc tcc gct ctg gag atg cag      1152
Lys Ala Ala Asn Ala Gly Gly Val Ala Thr Ser Ala Leu Glu Met Gln
    370                 375                 380

cag aac gct tcg cgc gat tcc tgg agc ttc gag tac acc gac gag cgc      1200
Gln Asn Ala Ser Arg Asp Ser Trp Ser Phe Glu Tyr Thr Asp Glu Arg
385                 390                 395                 400

ctc cag gtg atc atg aag aac atc ttc aag acc tgt gca gag acc gca      1248
Leu Gln Val Ile Met Lys Asn Ile Phe Lys Thr Cys Ala Glu Thr Ala
                405                 410                 415

gca gag tat gga cac gag aac gat tac gtt gtc ggc gct aac att gct      1296
Ala Glu Tyr Gly His Glu Asn Asp Tyr Val Val Gly Ala Asn Ile Ala
            420                 425                 430

ggc ttt aag aag gta gct gac gcg atg ctg gca cag ggc gtc atc taa      1344
Gly Phe Lys Lys Val Ala Asp Ala Met Leu Ala Gln Gly Val Ile
        435                 440                 445


<210> SEQ ID NO 103
<211> LENGTH: 447
<212> TYPE: PRT
<213> ORGANISM: Brevibacterium lactofermentum

<400> SEQUENCE: 103

Met Thr Val Asp Glu Gln Val Ser Asn Tyr Tyr Asp Met Leu Leu Lys
1               5                   10                  15

Arg Asn Ala Gly Glu Pro Glu Phe His Gln Ala Val Ala Glu Val Leu
            20                  25                  30

Glu Ser Leu Lys Ile Val Leu Glu Lys Asp Pro His Tyr Ala Asp Tyr
        35                  40                  45

Gly Leu Ile Gln Arg Leu Cys Glu Pro Glu Arg Gln Leu Ile Phe Arg
    50                  55                  60

Val Pro Trp Val Asp Asp Gln Gly Gln Val His Val Asn Arg Gly Phe
65                  70                  75                  80

Arg Val Gln Phe Asn Ser Ala Leu Gly Pro Tyr Lys Gly Gly Leu Arg
                85                  90                  95

Phe His Pro Ser Val Asn Leu Gly Ile Val Lys Phe Leu Gly Phe Glu
            100                 105                 110

Gln Ile Phe Lys Asn Ser Leu Thr Gly Leu Pro Ile Gly Gly Gly Lys
        115                 120                 125

Gly Gly Ser Asp Phe Asp Pro Lys Gly Lys Ser Asp Leu Glu Ile Met
    130                 135                 140

Arg Phe Cys Gln Ser Phe Met Thr Glu Leu His Arg His Ile Gly Glu
145                 150                 155                 160

Tyr Arg Asp Val Pro Ala Gly Asp Ile Gly Val Gly Gly Arg Glu Ile
                165                 170                 175

Gly Tyr Leu Phe Gly His Tyr Arg Arg Met Ala Asn Gln His Glu Ser
            180                 185                 190

Gly Val Leu Thr Gly Lys Gly Leu Thr Trp Gly Gly Ser Leu Val Arg
        195                 200                 205

Thr Glu Ala Thr Gly Tyr Gly Cys Val Tyr Phe Val Ser Glu Met Ile
    210                 215                 220

Lys Ala Lys Gly Glu Ser Ile Ser Gly Gln Lys Ile Ile Val Ser Gly
225                 230                 235                 240

Ser Gly Asn Val Ala Thr Tyr Ala Ile Glu Lys Ala Gln Glu Leu Gly
                245                 250                 255
```

-continued

```
Ala Thr Val Ile Gly Phe Ser Asp Ser Ser Gly Trp Val His Thr Pro
            260                 265                 270

Asn Gly Val Asp Val Ala Lys Leu Arg Glu Ile Lys Glu Val Arg Arg
        275                 280                 285

Ala Arg Val Ser Val Tyr Ala Asp Glu Ile Glu Gly Ala Thr Tyr His
    290                 295                 300

Thr Asp Gly Ser Ile Trp Asp Leu Lys Cys Asp Ile Ala Leu Pro Cys
305                 310                 315                 320

Ala Thr Gln Asn Glu Leu Asn Gly Glu Asn Ala Lys Thr Leu Ala Asp
                325                 330                 335

Asn Gly Cys Arg Phe Val Ala Glu Gly Ala Asn Met Pro Ser Thr Pro
            340                 345                 350

Glu Ala Val Glu Val Phe Arg Glu Arg Asp Ile Arg Phe Gly Pro Gly
        355                 360                 365

Lys Ala Ala Asn Ala Gly Gly Val Ala Thr Ser Ala Leu Glu Met Gln
    370                 375                 380

Gln Asn Ala Ser Arg Asp Ser Trp Ser Phe Glu Tyr Thr Asp Glu Arg
385                 390                 395                 400

Leu Gln Val Ile Met Lys Asn Ile Phe Lys Thr Cys Ala Glu Thr Ala
                405                 410                 415

Ala Glu Tyr Gly His Glu Asn Asp Tyr Val Val Gly Ala Asn Ile Ala
            420                 425                 430

Gly Phe Lys Lys Val Ala Asp Ala Met Leu Ala Gln Gly Val Ile
        435                 440                 445
```

```
<210> SEQ ID NO 104
<211> LENGTH: 20
<212> TYPE: DNA
<213> ORGANISM: Artificial Sequence
<220> FEATURE:
<223> OTHER INFORMATION: synthetic DNA
<220> FEATURE:
<221> NAME/KEY: misc_feature
<222> LOCATION: (9)..(9)
<223> OTHER INFORMATION: n is inosine

<400> SEQUENCE: 104

aagatcacnt acatcgaygg                                                 20


<210> SEQ ID NO 105
<211> LENGTH: 20
<212> TYPE: DNA
<213> ORGANISM: Artificial Sequence
<220> FEATURE:
<223> OTHER INFORMATION: synthetic DNA

<400> SEQUENCE: 105

tagaagtcta cgttcgggta                                                 20


<210> SEQ ID NO 106
<211> LENGTH: 21
<212> TYPE: DNA
<213> ORGANISM: Artificial Sequence
<220> FEATURE:
<223> OTHER INFORMATION: synthetic DNA

<400> SEQUENCE: 106

gtcgacaata gcctgaatct g                                               21


<210> SEQ ID NO 107
<211> LENGTH: 21
```

-continued

```
<212> TYPE: DNA
<213> ORGANISM: Artificial Sequence
<220> FEATURE:
<223> OTHER INFORMATION: synthetic DNA

<400> SEQUENCE: 107

cggtggaacc ggtgctgaca t                                               21


<210> SEQ ID NO 108
<211> LENGTH: 21
<212> TYPE: DNA
<213> ORGANISM: Artificial Sequence
<220> FEATURE:
<223> OTHER INFORMATION: synthetic DNA

<400> SEQUENCE: 108

gggtggggaa ttcggtcatg t                                               21


<210> SEQ ID NO 109
<211> LENGTH: 21
<212> TYPE: DNA
<213> ORGANISM: Artificial Sequence
<220> FEATURE:
<223> OTHER INFORMATION: synthetic DNA

<400> SEQUENCE: 109

tgtcgtagcc gcggtagcgc a                                               21


<210> SEQ ID NO 110
<211> LENGTH: 1293
<212> TYPE: DNA
<213> ORGANISM: Corynebacterium thermoaminogenes
<220> FEATURE:
<221> NAME/KEY: CDS
<222> LOCATION: (1)..(1290)
<223> OTHER INFORMATION:

<400> SEQUENCE: 110

gtg gct tct gat aac aac aag gct gta ctg cac tac cct ggc ggc gaa       48
Val Ala Ser Asp Asn Asn Lys Ala Val Leu His Tyr Pro Gly Gly Glu
1               5                   10                  15

ttc gag atg ggc atc aag cag gcc acc gag ggt aac tcc ggt gtc atc       96
Phe Glu Met Gly Ile Lys Gln Ala Thr Glu Gly Asn Ser Gly Val Ile
            20                  25                  30

ctg ggt aag atg ctg tcg gaa acc ggt ctg gtc acc ttc gac ccc ggt      144
Leu Gly Lys Met Leu Ser Glu Thr Gly Leu Val Thr Phe Asp Pro Gly
        35                  40                  45

tat gtc agc acc ggt tcc acc gaa tcc aag atc acc tac atc gat ggt      192
Tyr Val Ser Thr Gly Ser Thr Glu Ser Lys Ile Thr Tyr Ile Asp Gly
    50                  55                  60

gat gca ggc atc ctg cgc tac cgc ggc tac gac att gcg gat ctg gcc      240
Asp Ala Gly Ile Leu Arg Tyr Arg Gly Tyr Asp Ile Ala Asp Leu Ala
65                  70                  75                  80

gaa aat gcc acc ttc aat gag gtc tcc tac ctc ctg atc aag ggt gag      288
Glu Asn Ala Thr Phe Asn Glu Val Ser Tyr Leu Leu Ile Lys Gly Glu
                85                  90                  95

ctc ccg acc ccg gaa gag ctc cac aag ttc aac gac gag att cgt cac      336
Leu Pro Thr Pro Glu Glu Leu His Lys Phe Asn Asp Glu Ile Arg His
            100                 105                 110

cac acc ctg ctg gac gag gac ttc aag tcc cag ttc aat gtc ttc cct      384
His Thr Leu Leu Asp Glu Asp Phe Lys Ser Gln Phe Asn Val Phe Pro
        115                 120                 125

cgc gat gcc cac ccg atg gcc acc ctg gcc tcc tcg gtt aac atc ctc      432
Arg Asp Ala His Pro Met Ala Thr Leu Ala Ser Ser Val Asn Ile Leu
```

-continued

```
    130                 135                 140

tcc acc tac tac cag gat cag ctg gat ccc ctg gat gag gct cag ctg      480
Ser Thr Tyr Tyr Gln Asp Gln Leu Asp Pro Leu Asp Glu Ala Gln Leu
145                 150                 155                 160

gac aag gca acc gtc cgc ctg atg gcg aag gtt ccg atg ctg gct gca      528
Asp Lys Ala Thr Val Arg Leu Met Ala Lys Val Pro Met Leu Ala Ala
                165                 170                 175

tac gca cac cgt gcc cgc aag ggt gcg ccg tac atg tac ccg gac aac      576
Tyr Ala His Arg Ala Arg Lys Gly Ala Pro Tyr Met Tyr Pro Asp Asn
            180                 185                 190

tcc ctc aat gcc cgt gag aac ttc ctg cgc atg atg ttc ggt tac ccg      624
Ser Leu Asn Ala Arg Glu Asn Phe Leu Arg Met Met Phe Gly Tyr Pro
        195                 200                 205

acc gag ccg tac gag gtt gat ccg atc atg gtc aaa gcc ctc gac aag      672
Thr Glu Pro Tyr Glu Val Asp Pro Ile Met Val Lys Ala Leu Asp Lys
    210                 215                 220

ctg ctc atc ctg cac gca gac cac gag cag aac tgc tcc acc tcc act      720
Leu Leu Ile Leu His Ala Asp His Glu Gln Asn Cys Ser Thr Ser Thr
225                 230                 235                 240

gtc cgc atg atc ggc tcc gcg cag gcg aac atg ttc gtc tcc atc gcc      768
Val Arg Met Ile Gly Ser Ala Gln Ala Asn Met Phe Val Ser Ile Ala
                245                 250                 255

ggc ggc atc aac gca ctc tcc ggc ccg ctg cac ggt ggc gcc aac cag      816
Gly Gly Ile Asn Ala Leu Ser Gly Pro Leu His Gly Gly Ala Asn Gln
            260                 265                 270

gct gtc ctc gag atg ctc gag gag atc gca gcc aac ggc ggc gac gca      864
Ala Val Leu Glu Met Leu Glu Glu Ile Ala Ala Asn Gly Gly Asp Ala
        275                 280                 285

acc gac ttc atg aac cgc gtg aag aac aag gag aag ggt gtc cgc ctc      912
Thr Asp Phe Met Asn Arg Val Lys Asn Lys Glu Lys Gly Val Arg Leu
    290                 295                 300

atg ggc ttc gga cac cgc gtc tac aag aac tac gat ccg cgt gca gcc      960
Met Gly Phe Gly His Arg Val Tyr Lys Asn Tyr Asp Pro Arg Ala Ala
305                 310                 315                 320

atc gtc aag gac acc gcc cac gag atc ctc gag cac ctc ggt ggc gac     1008
Ile Val Lys Asp Thr Ala His Glu Ile Leu Glu His Leu Gly Gly Asp
                325                 330                 335

cca ctg ctg gat ctg gct ctc aag ctg gaa gaa atc gca ctc aac gac     1056
Pro Leu Leu Asp Leu Ala Leu Lys Leu Glu Glu Ile Ala Leu Asn Asp
            340                 345                 350

gat tac ttc atc tcc cgc aag ctg tac ccg aac gtg gac ttc tac acc     1104
Asp Tyr Phe Ile Ser Arg Lys Leu Tyr Pro Asn Val Asp Phe Tyr Thr
        355                 360                 365

ggc ctg atc tac cgc gcc atg ggc ttc ccg acg gac ttc ttc acc gtc     1152
Gly Leu Ile Tyr Arg Ala Met Gly Phe Pro Thr Asp Phe Phe Thr Val
    370                 375                 380

ctg ttc gcc atc ggc cgc ctc ccg ggc tgg atc gcc cac tac cgc gag     1200
Leu Phe Ala Ile Gly Arg Leu Pro Gly Trp Ile Ala His Tyr Arg Glu
385                 390                 395                 400

cag ctc gcc gat ccg ggc gcc aag atc aac cgt cct cgc cag atc tac     1248
Gln Leu Ala Asp Pro Gly Ala Lys Ile Asn Arg Pro Arg Gln Ile Tyr
                405                 410                 415

acc ggt gag acc gca cgc aag atc atc ccc cgc gaa gag cgc tag         1293
Thr Gly Glu Thr Ala Arg Lys Ile Ile Pro Arg Glu Glu Arg
            420                 425                 430


<210> SEQ ID NO 111
<211> LENGTH: 430
<212> TYPE: PRT
<213> ORGANISM: Corynebacterium thermoaminogenes
```

<400> SEQUENCE: 111

```
Val Ala Ser Asp Asn Asn Lys Ala Val Leu His Tyr Pro Gly Gly Glu
1               5                   10                  15

Phe Glu Met Gly Ile Lys Gln Ala Thr Glu Gly Asn Ser Gly Val Ile
            20                  25                  30

Leu Gly Lys Met Leu Ser Glu Thr Gly Leu Val Thr Phe Asp Pro Gly
        35                  40                  45

Tyr Val Ser Thr Gly Ser Thr Glu Ser Lys Ile Thr Tyr Ile Asp Gly
    50                  55                  60

Asp Ala Gly Ile Leu Arg Tyr Arg Gly Tyr Asp Ile Ala Asp Leu Ala
65                  70                  75                  80

Glu Asn Ala Thr Phe Asn Glu Val Ser Tyr Leu Leu Ile Lys Gly Glu
                85                  90                  95

Leu Pro Thr Pro Glu Glu Leu His Lys Phe Asn Asp Glu Ile Arg His
            100                 105                 110

His Thr Leu Leu Asp Glu Asp Phe Lys Ser Gln Phe Asn Val Phe Pro
        115                 120                 125

Arg Asp Ala His Pro Met Ala Thr Leu Ala Ser Ser Val Asn Ile Leu
    130                 135                 140

Ser Thr Tyr Tyr Gln Asp Gln Leu Asp Pro Leu Asp Glu Ala Gln Leu
145                 150                 155                 160

Asp Lys Ala Thr Val Arg Leu Met Ala Lys Val Pro Met Leu Ala Ala
                165                 170                 175

Tyr Ala His Arg Ala Arg Lys Gly Ala Pro Tyr Met Tyr Pro Asp Asn
            180                 185                 190

Ser Leu Asn Ala Arg Glu Asn Phe Leu Arg Met Met Phe Gly Tyr Pro
        195                 200                 205

Thr Glu Pro Tyr Glu Val Asp Pro Ile Met Val Lys Ala Leu Asp Lys
    210                 215                 220

Leu Leu Ile Leu His Ala Asp His Glu Gln Asn Cys Ser Thr Ser Thr
225                 230                 235                 240

Val Arg Met Ile Gly Ser Ala Gln Ala Asn Met Phe Val Ser Ile Ala
                245                 250                 255

Gly Gly Ile Asn Ala Leu Ser Gly Pro Leu His Gly Gly Ala Asn Gln
            260                 265                 270

Ala Val Leu Glu Met Leu Glu Glu Ile Ala Ala Asn Gly Gly Asp Ala
        275                 280                 285

Thr Asp Phe Met Asn Arg Val Lys Asn Lys Glu Lys Gly Val Arg Leu
    290                 295                 300

Met Gly Phe Gly His Arg Val Tyr Lys Asn Tyr Asp Pro Arg Ala Ala
305                 310                 315                 320

Ile Val Lys Asp Thr Ala His Glu Ile Leu Glu His Leu Gly Gly Asp
                325                 330                 335

Pro Leu Leu Asp Leu Ala Leu Lys Leu Glu Glu Ile Ala Leu Asn Asp
            340                 345                 350

Asp Tyr Phe Ile Ser Arg Lys Leu Tyr Pro Asn Val Asp Phe Tyr Thr
        355                 360                 365

Gly Leu Ile Tyr Arg Ala Met Gly Phe Pro Thr Asp Phe Phe Thr Val
    370                 375                 380

Leu Phe Ala Ile Gly Arg Leu Pro Gly Trp Ile Ala His Tyr Arg Glu
385                 390                 395                 400

Gln Leu Ala Asp Pro Gly Ala Lys Ile Asn Arg Pro Arg Gln Ile Tyr
```

-continued

```
            405                 410                 415

Thr Gly Glu Thr Ala Arg Lys Ile Ile Pro Arg Glu Glu Arg
        420                 425                 430


<210> SEQ ID NO 112
<211> LENGTH: 1314
<212> TYPE: DNA
<213> ORGANISM: Brevibacterium lactofermentum
<220> FEATURE:
<221> NAME/KEY: CDS
<222> LOCATION: (1)..(1311)
<223> OTHER INFORMATION:

<400> SEQUENCE: 112

atg ttt gaa agg gat atc gtg gct act gat aac aac aag gct gtc ctg       48
Met Phe Glu Arg Asp Ile Val Ala Thr Asp Asn Asn Lys Ala Val Leu
1               5                   10                  15

cac tac ccc ggt ggc gag ttc gaa atg gac atc atc gag gct tct gag       96
His Tyr Pro Gly Gly Glu Phe Glu Met Asp Ile Ile Glu Ala Ser Glu
            20                  25                  30

ggt aac aac ggt gtt gtc ctg ggc aag atg ctg tct gag act gga ctg      144
Gly Asn Asn Gly Val Val Leu Gly Lys Met Leu Ser Glu Thr Gly Leu
        35                  40                  45

atc act ttt gac cca ggt tat gtg agc act ggc tcc acc gag tcg aag      192
Ile Thr Phe Asp Pro Gly Tyr Val Ser Thr Gly Ser Thr Glu Ser Lys
    50                  55                  60

atc acc tac atc gat ggc gat gcg gga atc ctg cgt tac cgc ggc tat      240
Ile Thr Tyr Ile Asp Gly Asp Ala Gly Ile Leu Arg Tyr Arg Gly Tyr
65                  70                  75                  80

gac atc gct gat ctg gct gag aat gcc acc ttc aac gag gtt tct tac      288
Asp Ile Ala Asp Leu Ala Glu Asn Ala Thr Phe Asn Glu Val Ser Tyr
                85                  90                  95

cta ctt atc aac ggt gaa cta cca acc cca gat gag ctt cac aag ttt      336
Leu Leu Ile Asn Gly Glu Leu Pro Thr Pro Asp Glu Leu His Lys Phe
            100                 105                 110

aac gac gag att cgc cac cac acc ctt ctg gac gag gac ttc aag tcc      384
Asn Asp Glu Ile Arg His His Thr Leu Leu Asp Glu Asp Phe Lys Ser
        115                 120                 125

cag ttc aac gtg ttc cca cgc gac gct cac cca atg gca acc ttg gct      432
Gln Phe Asn Val Phe Pro Arg Asp Ala His Pro Met Ala Thr Leu Ala
    130                 135                 140

tcc tcg gtt aac att ttg tct acc tac tac cag gat cag ctg aac cca      480
Ser Ser Val Asn Ile Leu Ser Thr Tyr Tyr Gln Asp Gln Leu Asn Pro
145                 150                 155                 160

ctc gat gag gca cag ctt gat aag gca acc gtt cgc ctc atg gca aag      528
Leu Asp Glu Ala Gln Leu Asp Lys Ala Thr Val Arg Leu Met Ala Lys
                165                 170                 175

gtt cca atg ctg gct gcg tac gca cac cgc gca cgc aag ggt gct cct      576
Val Pro Met Leu Ala Ala Tyr Ala His Arg Ala Arg Lys Gly Ala Pro
            180                 185                 190

tac atg tac cca gac aac tcc ctc aac gcg cgt gag aac ttc ctg cgc      624
Tyr Met Tyr Pro Asp Asn Ser Leu Asn Ala Arg Glu Asn Phe Leu Arg
        195                 200                 205

atg atg ttc ggt tac cca acc gag cca tac gag atc gac cca atc atg      672
Met Met Phe Gly Tyr Pro Thr Glu Pro Tyr Glu Ile Asp Pro Ile Met
    210                 215                 220

gtc aag gct ctg gac aag ctg ctc atc ctg cac gct gac cac gag cag      720
Val Lys Ala Leu Asp Lys Leu Leu Ile Leu His Ala Asp His Glu Gln
225                 230                 235                 240

aac tgc tcc acc tcc acc gtt cgt atg atc ggt tcc gca cag gcc aac      768
Asn Cys Ser Thr Ser Thr Val Arg Met Ile Gly Ser Ala Gln Ala Asn
```

```
                245                 250                 255

atg ttt gtc tcc atc gct ggt ggc atc aac gct ctg tcc ggc cca ctg      816
Met Phe Val Ser Ile Ala Gly Gly Ile Asn Ala Leu Ser Gly Pro Leu
            260                 265                 270

cac ggt ggc gca aac cag gct gtt ctg gag atg ctc gaa gac atc aag      864
His Gly Gly Ala Asn Gln Ala Val Leu Glu Met Leu Glu Asp Ile Lys
        275                 280                 285

aac aac cac ggt ggc gac gca acc gcg ttc atg aac aag gtc aag aac      912
Asn Asn His Gly Gly Asp Ala Thr Ala Phe Met Asn Lys Val Lys Asn
    290                 295                 300

aag gaa gac ggc gtc cgc ctc atg ggc ttc gga cac cgc gtt tac aag      960
Lys Glu Asp Gly Val Arg Leu Met Gly Phe Gly His Arg Val Tyr Lys
305                 310                 315                 320

aac tac gat cca cgt gca gca atc gtc aag gag acc gca cac gag atc     1008
Asn Tyr Asp Pro Arg Ala Ala Ile Val Lys Glu Thr Ala His Glu Ile
                325                 330                 335

ctc gag cac ctc ggt ggc gac gat ctt ctg gat ctg gca atc aag ctg     1056
Leu Glu His Leu Gly Gly Asp Asp Leu Leu Asp Leu Ala Ile Lys Leu
            340                 345                 350

gaa gaa att gca ctg gct gat gat tac ttc atc tcc cgc aag ctc tac     1104
Glu Glu Ile Ala Leu Ala Asp Asp Tyr Phe Ile Ser Arg Lys Leu Tyr
        355                 360                 365

ccg aac gta gac ttc tac acc ggc ctg atc tac cgc gca atg ggc ttc     1152
Pro Asn Val Asp Phe Tyr Thr Gly Leu Ile Tyr Arg Ala Met Gly Phe
    370                 375                 380

cca act gac ttc ttc acc gta ttg ttc gca atc ggt cgt ctg cca gga     1200
Pro Thr Asp Phe Phe Thr Val Leu Phe Ala Ile Gly Arg Leu Pro Gly
385                 390                 395                 400

tgg atc gct cac tac cgc gag cag ctc ggt gca gca ggc aac aag atc     1248
Trp Ile Ala His Tyr Arg Glu Gln Leu Gly Ala Ala Gly Asn Lys Ile
                405                 410                 415

aac cgc cca cgc cag gtc tac acc ggc aag gaa tcc cgc aag ttg gtt     1296
Asn Arg Pro Arg Gln Val Tyr Thr Gly Lys Glu Ser Arg Lys Leu Val
            420                 425                 430

cct cgc gag gag cgc taa                                             1314
Pro Arg Glu Glu Arg
        435


<210> SEQ ID NO 113
<211> LENGTH: 437
<212> TYPE: PRT
<213> ORGANISM: Brevibacterium lactofermentum

<400> SEQUENCE: 113

Met Phe Glu Arg Asp Ile Val Ala Thr Asp Asn Asn Lys Ala Val Leu
1               5                   10                  15

His Tyr Pro Gly Gly Glu Phe Glu Met Asp Ile Ile Glu Ala Ser Glu
            20                  25                  30

Gly Asn Asn Gly Val Val Leu Gly Lys Met Leu Ser Glu Thr Gly Leu
        35                  40                  45

Ile Thr Phe Asp Pro Gly Tyr Val Ser Thr Gly Ser Thr Glu Ser Lys
    50                  55                  60

Ile Thr Tyr Ile Asp Gly Asp Ala Gly Ile Leu Arg Tyr Arg Gly Tyr
65                  70                  75                  80

Asp Ile Ala Asp Leu Ala Glu Asn Ala Thr Phe Asn Glu Val Ser Tyr
                85                  90                  95

Leu Leu Ile Asn Gly Glu Leu Pro Thr Pro Asp Glu Leu His Lys Phe
            100                 105                 110
```

-continued

```
Asn Asp Glu Ile Arg His His Thr Leu Leu Asp Glu Asp Phe Lys Ser
        115                 120                 125

Gln Phe Asn Val Phe Pro Arg Asp Ala His Pro Met Ala Thr Leu Ala
    130                 135                 140

Ser Ser Val Asn Ile Leu Ser Thr Tyr Tyr Gln Asp Gln Leu Asn Pro
145                 150                 155                 160

Leu Asp Glu Ala Gln Leu Asp Lys Ala Thr Val Arg Leu Met Ala Lys
                165                 170                 175

Val Pro Met Leu Ala Ala Tyr Ala His Arg Ala Arg Lys Gly Ala Pro
            180                 185                 190

Tyr Met Tyr Pro Asp Asn Ser Leu Asn Ala Arg Glu Asn Phe Leu Arg
        195                 200                 205

Met Met Phe Gly Tyr Pro Thr Glu Pro Tyr Glu Ile Asp Pro Ile Met
    210                 215                 220

Val Lys Ala Leu Asp Lys Leu Leu Ile Leu His Ala Asp His Glu Gln
225                 230                 235                 240

Asn Cys Ser Thr Ser Thr Val Arg Met Ile Gly Ser Ala Gln Ala Asn
                245                 250                 255

Met Phe Val Ser Ile Ala Gly Gly Ile Asn Ala Leu Ser Gly Pro Leu
            260                 265                 270

His Gly Gly Ala Asn Gln Ala Val Leu Glu Met Leu Glu Asp Ile Lys
        275                 280                 285

Asn Asn His Gly Gly Asp Ala Thr Ala Phe Met Asn Lys Val Lys Asn
    290                 295                 300

Lys Glu Asp Gly Val Arg Leu Met Gly Phe Gly His Arg Val Tyr Lys
305                 310                 315                 320

Asn Tyr Asp Pro Arg Ala Ala Ile Val Lys Glu Thr Ala His Glu Ile
                325                 330                 335

Leu Glu His Leu Gly Gly Asp Asp Leu Leu Asp Leu Ala Ile Lys Leu
            340                 345                 350

Glu Glu Ile Ala Leu Ala Asp Asp Tyr Phe Ile Ser Arg Lys Leu Tyr
        355                 360                 365

Pro Asn Val Asp Phe Tyr Thr Gly Leu Ile Tyr Arg Ala Met Gly Phe
    370                 375                 380

Pro Thr Asp Phe Phe Thr Val Leu Phe Ala Ile Gly Arg Leu Pro Gly
385                 390                 395                 400

Trp Ile Ala His Tyr Arg Glu Gln Leu Gly Ala Ala Gly Asn Lys Ile
                405                 410                 415

Asn Arg Pro Arg Gln Val Tyr Thr Gly Lys Glu Ser Arg Lys Leu Val
            420                 425                 430

Pro Arg Glu Glu Arg
        435
```

```
<210> SEQ ID NO 114
<211> LENGTH: 1656
<212> TYPE: DNA
<213> ORGANISM: Corynebacterium thermoaminogenes
<220> FEATURE:
<221> NAME/KEY: CDS
<222> LOCATION: (309)..(1595)
<223> OTHER INFORMATION:

<400> SEQUENCE: 114

acgcccgatt cttcaacact atcgaagagg tcccaaccca cgcgttgacc cagggcttgg      60

gtactttgtc ccgcgcgcaa aatatcgtgt tggtggcaac tggccaagga aaagcagaca     120
```

-continued

```
gccatccgcg gaactgtgga aggtccagtg actgcttctt gcccaggttc cattctgcaa    180

atgcacaaca acgccaccat catcgttgat gaagcagcag catccaagct gaaaaatgct    240

gaccattacc gtctcatgga gcaattaaag ctgcgctaga aacaaaaagg aaagtactgt    300

gtggggct atg cac aca gaa ctt tcc agt ttg cgc cct gcg tac cat gtg     350
         Met His Thr Glu Leu Ser Ser Leu Arg Pro Ala Tyr His Val
         1               5                   10

act cct ccg cag ggc aga ctc aat gat ccc aat gga atg tac gtc gat      398
Thr Pro Pro Gln Gly Arg Leu Asn Asp Pro Asn Gly Met Tyr Val Asp
15                  20                  25                  30

gga gat acc ctc cac gtc tac tac cag cac gat cca ggt ttc ccc ttc      446
Gly Asp Thr Leu His Val Tyr Tyr Gln His Asp Pro Gly Phe Pro Phe
                35                  40                  45

gca cca aag cgc acc ggt tgg gct cac acc acc acg ccg ttg acc gga      494
Ala Pro Lys Arg Thr Gly Trp Ala His Thr Thr Thr Pro Leu Thr Gly
            50                  55                  60

ccg cag cga ttg cag tgg acg cac ctg ccc gat gct ctt tac ccg gat      542
Pro Gln Arg Leu Gln Trp Thr His Leu Pro Asp Ala Leu Tyr Pro Asp
        65                  70                  75

gta tcc tat gac ctg gat gga tgc tat tcc ggc gga gcc gta ttt tct      590
Val Ser Tyr Asp Leu Asp Gly Cys Tyr Ser Gly Gly Ala Val Phe Ser
    80                  85                  90

gac ggc acg ctt aaa ctt ttc tac acc ggc aac cga aaa att gac ggc      638
Asp Gly Thr Leu Lys Leu Phe Tyr Thr Gly Asn Arg Lys Ile Asp Gly
95                  100                 105                 110

aag cgc cgc gcc acc caa aac ctc gtc gaa gtc gag gac cca act ggg      686
Lys Arg Arg Ala Thr Gln Asn Leu Val Glu Val Glu Asp Pro Thr Gly
                115                 120                 125

ctg atg ggc ggc att cat cgc cgc tcg cct aaa aat ccg ctt atc gac      734
Leu Met Gly Gly Ile His Arg Arg Ser Pro Lys Asn Pro Leu Ile Asp
            130                 135                 140

gga ccc gcc agc ggt ttt acg ccc cac tac cgc gat ccc atg atc agc      782
Gly Pro Ala Ser Gly Phe Thr Pro His Tyr Arg Asp Pro Met Ile Ser
        145                 150                 155

cct gat ggg gat ggt tgg aag atg gtt ctt ggg gct cag cgc gaa aac      830
Pro Asp Gly Asp Gly Trp Lys Met Val Leu Gly Ala Gln Arg Glu Asn
    160                 165                 170

ctc acc ggt gca gcg gtt cta tac cgc tcg gca gat ctt gaa aac tgg      878
Leu Thr Gly Ala Ala Val Leu Tyr Arg Ser Ala Asp Leu Glu Asn Trp
175                 180                 185                 190

gaa ttc tcc ggt gaa atc acc ttt gac ctc agc gac gca caa cct ggt      926
Glu Phe Ser Gly Glu Ile Thr Phe Asp Leu Ser Asp Ala Gln Pro Gly
                195                 200                 205

tct gcc cct gat ctc gtt cct ggc ggc tac atg tgg gaa tgc ccc aac      974
Ser Ala Pro Asp Leu Val Pro Gly Gly Tyr Met Trp Glu Cys Pro Asn
            210                 215                 220

ctt ttt acg ctt cgc gat gaa aaa acc ggc gaa gac ctc gat gtg ctg     1022
Leu Phe Thr Leu Arg Asp Glu Lys Thr Gly Glu Asp Leu Asp Val Leu
        225                 230                 235

att ttc tgt cca caa gga ttg gac cgt atc gat gat gag gtt act cac     1070
Ile Phe Cys Pro Gln Gly Leu Asp Arg Ile Asp Asp Glu Val Thr His
    240                 245                 250

tac gca agc tct gac cag tgc gga tat gtc gtc ggc aag ctt gaa gaa     1118
Tyr Ala Ser Ser Asp Gln Cys Gly Tyr Val Val Gly Lys Leu Glu Glu
255                 260                 265                 270

acg acc ttc cgt gtc ctg cga gga ttc agc gag ctg gat ttc ggt cat     1166
Thr Thr Phe Arg Val Leu Arg Gly Phe Ser Glu Leu Asp Phe Gly His
                275                 280                 285

gaa ttc tac gcg ccg cag gtt gca gtc aac ggt tcc gat gcc tgg ctt     1214
```

```
Glu Phe Tyr Ala Pro Gln Val Ala Val Asn Gly Ser Asp Ala Trp Leu
            290                 295                 300

gtg ggc tgg atg gga ttg cct gca cag gat gat cac cca aca gtt gcg      1262
Val Gly Trp Met Gly Leu Pro Ala Gln Asp Asp His Pro Thr Val Ala
        305                 310                 315

cag gaa gga tgg gtg cac tgc ctg acc gtt cct cgc agg ctt cat ttg      1310
Gln Glu Gly Trp Val His Cys Leu Thr Val Pro Arg Arg Leu His Leu
    320                 325                 330

cgt aac cat gcg atc tat caa gag ctt ctt ctc cca gaa ggg gag tcg      1358
Arg Asn His Ala Ile Tyr Gln Glu Leu Leu Leu Pro Glu Gly Glu Ser
335                 340                 345                 350

ggg gta act aga tct gta tta ggt tct gaa cct gtc cga gta gac atc      1406
Gly Val Thr Arg Ser Val Leu Gly Ser Glu Pro Val Arg Val Asp Ile
                355                 360                 365

cga gac aat gtt tcc ctc gag tgg gat ggt gtc cgg ttg tct gtg gat      1454
Arg Asp Asn Val Ser Leu Glu Trp Asp Gly Val Arg Leu Ser Val Asp
            370                 375                 380

cgc gat ggc gat cgt cgt gta gct gaa gta aaa cct ggc gaa tta gtg      1502
Arg Asp Gly Asp Arg Arg Val Ala Glu Val Lys Pro Gly Glu Leu Val
        385                 390                 395

atc gcg gac gat aat aca gcg att gag ata aca gca ggt cat ggc cag      1550
Ile Ala Asp Asp Asn Thr Ala Ile Glu Ile Thr Ala Gly His Gly Gln
    400                 405                 410

gtt tcc ttc gct ttc cgc acc ttc aaa ggt gac act att gag aga          1595
Val Ser Phe Ala Phe Arg Thr Phe Lys Gly Asp Thr Ile Glu Arg
415                 420                 425

taagtcataa aaaagggcct tctgtggcgg attgtacaaa tacttcgcaa aatcccttga    1655

t                                                                    1656


<210> SEQ ID NO 115
<211> LENGTH: 429
<212> TYPE: PRT
<213> ORGANISM: Corynebacterium thermoaminogenes

<400> SEQUENCE: 115

Met His Thr Glu Leu Ser Ser Leu Arg Pro Ala Tyr His Val Thr Pro
1               5                   10                  15

Pro Gln Gly Arg Leu Asn Asp Pro Asn Gly Met Tyr Val Asp Gly Asp
            20                  25                  30

Thr Leu His Val Tyr Tyr Gln His Asp Pro Gly Phe Pro Phe Ala Pro
        35                  40                  45

Lys Arg Thr Gly Trp Ala His Thr Thr Thr Pro Leu Thr Gly Pro Gln
    50                  55                  60

Arg Leu Gln Trp Thr His Leu Pro Asp Ala Leu Tyr Pro Asp Val Ser
65                  70                  75                  80

Tyr Asp Leu Asp Gly Cys Tyr Ser Gly Gly Ala Val Phe Ser Asp Gly
                85                  90                  95

Thr Leu Lys Leu Phe Tyr Thr Gly Asn Arg Lys Ile Asp Gly Lys Arg
            100                 105                 110

Arg Ala Thr Gln Asn Leu Val Glu Val Glu Asp Pro Thr Gly Leu Met
        115                 120                 125

Gly Gly Ile His Arg Arg Ser Pro Lys Asn Pro Leu Ile Asp Gly Pro
    130                 135                 140

Ala Ser Gly Phe Thr Pro His Tyr Arg Asp Pro Met Ile Ser Pro Asp
145                 150                 155                 160

Gly Asp Gly Trp Lys Met Val Leu Gly Ala Gln Arg Glu Asn Leu Thr
                165                 170                 175
```

```
Gly Ala Ala Val Leu Tyr Arg Ser Ala Asp Leu Glu Asn Trp Glu Phe
            180                 185                 190

Ser Gly Glu Ile Thr Phe Asp Leu Ser Asp Ala Gln Pro Gly Ser Ala
        195                 200                 205

Pro Asp Leu Val Pro Gly Gly Tyr Met Trp Glu Cys Pro Asn Leu Phe
    210                 215                 220

Thr Leu Arg Asp Glu Lys Thr Gly Glu Asp Leu Asp Val Leu Ile Phe
225                 230                 235                 240

Cys Pro Gln Gly Leu Asp Arg Ile Asp Asp Glu Val Thr His Tyr Ala
                245                 250                 255

Ser Ser Asp Gln Cys Gly Tyr Val Val Gly Lys Leu Glu Glu Thr Thr
            260                 265                 270

Phe Arg Val Leu Arg Gly Phe Ser Glu Leu Asp Phe Gly His Glu Phe
        275                 280                 285

Tyr Ala Pro Gln Val Ala Val Asn Gly Ser Asp Ala Trp Leu Val Gly
    290                 295                 300

Trp Met Gly Leu Pro Ala Gln Asp Asp His Pro Thr Val Ala Gln Glu
305                 310                 315                 320

Gly Trp Val His Cys Leu Thr Val Pro Arg Arg Leu His Leu Arg Asn
                325                 330                 335

His Ala Ile Tyr Gln Glu Leu Leu Leu Pro Glu Gly Glu Ser Gly Val
            340                 345                 350

Thr Arg Ser Val Leu Gly Ser Glu Pro Val Arg Val Asp Ile Arg Asp
        355                 360                 365

Asn Val Ser Leu Glu Trp Asp Gly Val Arg Leu Ser Val Asp Arg Asp
    370                 375                 380

Gly Asp Arg Arg Val Ala Glu Val Lys Pro Gly Glu Leu Val Ile Ala
385                 390                 395                 400

Asp Asp Asn Thr Ala Ile Glu Ile Thr Ala Gly His Gly Gln Val Ser
                405                 410                 415

Phe Ala Phe Arg Thr Phe Lys Gly Asp Thr Ile Glu Arg
            420                 425
```

<210> SEQ ID NO 116
<211> LENGTH: 35
<212> TYPE: DNA
<213> ORGANISM: Artificial Sequence
<220> FEATURE:
<223> OTHER INFORMATION: synthetic DNA

<400> SEQUENCE: 116
gtacatattg tcgttagaac gcgtaatacg actca 35

<210> SEQ ID NO 117
<211> LENGTH: 35
<212> TYPE: DNA
<213> ORGANISM: Artificial Sequence
<220> FEATURE:
<223> OTHER INFORMATION: synthetic DNA

<400> SEQUENCE: 117
cgttagaacg cgtaatacga ctcactatag ggaga 35

<210> SEQ ID NO 118
<211> LENGTH: 30
<212> TYPE: DNA
<213> ORGANISM: Artificial Sequence
<220> FEATURE:

<223> OTHER INFORMATION: synthetic DNA

<400> SEQUENCE: 118
gtaaagagcg tcgggcaggt gcgtccactg 30

<210> SEQ ID NO 119
<211> LENGTH: 30
<212> TYPE: DNA
<213> ORGANISM: Artificial Sequence
<220> FEATURE:
<223> OTHER INFORMATION: synthetic DNA

<400> SEQUENCE: 119
ggtgtgagcc cagccggtgc gctttggtgc 30

<210> SEQ ID NO 120
<211> LENGTH: 30
<212> TYPE: DNA
<213> ORGANISM: Artificial Sequence
<220> FEATURE:
<223> OTHER INFORMATION: synthetic DNA

<400> SEQUENCE: 120
atcagccctg atggtgatgg ttggaaaatg 30

<210> SEQ ID NO 121
<211> LENGTH: 30
<212> TYPE: DNA
<213> ORGANISM: Artificial Sequence
<220> FEATURE:
<223> OTHER INFORMATION: synthetic DNA

<400> SEQUENCE: 121
ggtgcagcgg ttctataccg ctcgacagat 30

<210> SEQ ID NO 122
<211> LENGTH: 32
<212> TYPE: DNA
<213> ORGANISM: Artificial Sequence
<220> FEATURE:
<223> OTHER INFORMATION: synthetic DNA

<400> SEQUENCE: 122
ggcccgggac gcccgattct tcaacactat cg 32

<210> SEQ ID NO 123
<211> LENGTH: 32
<212> TYPE: DNA
<213> ORGANISM: Artificial Sequence
<220> FEATURE:
<223> OTHER INFORMATION: synthetic DNA

<400> SEQUENCE: 123
ggcccgggga tcaagggatt ttgcgaagta tt 32

<210> SEQ ID NO 124
<211> LENGTH: 30
<212> TYPE: DNA
<213> ORGANISM: Artificial Sequence
<220> FEATURE:
<223> OTHER INFORMATION: synthetic DNA

<400> SEQUENCE: 124
gaagatctct atgaccagcg catcaagctg 30

-continued

```
<210> SEQ ID NO 125
<211> LENGTH: 30
<212> TYPE: DNA
<213> ORGANISM: Artificial Sequence
<220> FEATURE:
<223> OTHER INFORMATION: synthetic DNA

<400> SEQUENCE: 125

gaagatctgg tcatcccaga acctgatcac                                        30


<210> SEQ ID NO 126
<211> LENGTH: 32
<212> TYPE: DNA
<213> ORGANISM: Artificial Sequence
<220> FEATURE:
<223> OTHER INFORMATION: synthetic DNA

<400> SEQUENCE: 126

gcgcctgcag gtccgagggt gtgcgttcgg ca                                     32


<210> SEQ ID NO 127
<211> LENGTH: 32
<212> TYPE: DNA
<213> ORGANISM: Artificial Sequence
<220> FEATURE:
<223> OTHER INFORMATION: synthetic DNA

<400> SEQUENCE: 127

gcgcctgcag gcaccaggat gccctcaacc ag                                     32


<210> SEQ ID NO 128
<211> LENGTH: 30
<212> TYPE: DNA
<213> ORGANISM: Artificial Sequence
<220> FEATURE:
<223> OTHER INFORMATION: synthetic DNA

<400> SEQUENCE: 128

ggggtaccga tcactataac cccacagcac                                        30


<210> SEQ ID NO 129
<211> LENGTH: 30
<212> TYPE: DNA
<213> ORGANISM: Artificial Sequence
<220> FEATURE:
<223> OTHER INFORMATION: synthetic DNA

<400> SEQUENCE: 129

ggggtaccct ggctgatctg aactaggcgc                                        30
```

GENES FOR HEAT RESISTANT ENZYMES OF AMINO ACID BIOSYNTHETIC PATHWAY DERIVED FROM THERMOPHILIC CORYNEFORM BACTERIA

CROSS-REFERENCE TO RELATED APPLICATIONS

The present application is a divisional of U.S. application Ser. No. 10/089,057, filed on Apr. 3, 2002 now U.S. Pat. No. 6,995,250, which is a National Stage (371) of International Application PCT/JP00/06913, filed on Oct. 4, 2000, which claims priority to Japanese patent application JP 11-282716, filed on Oct. 4, 1999, JP 11-311147, filed on Nov. 1, 1999, and JP 2000-120687, filed on Apr. 21, 2000.

TECHNICAL FIELD

The present invention relates to heat resistant enzyme genes, in particular, genes for enzymes of biosynthetic pathway and uptake system of L-amino acids such as L-glutamic acid, of *Corynebacterium thermoaminogenes*, which is a thermophilic coryneform bacterium.

BACKGROUND ART

The current main stream of the production of L-amino acids such as L-glutamic acid is the fermentative production utilizing coryneform bacteria. As for the fermentative production of L-amino acids, it has been attempted to reduce the cost based on breeding of strains with superior productivity and development of fermentation techniques. Although conventional attempts for realizing the cost reduction were mainly directed to achieving higher yield, energy required for cooling the fermentation heat generated during the culture cannot be ignored in addition to the raw material as the factors concerning the fermentation cost. That is, as for usual microorganisms used for the fermentation, the temperature of the medium rises due to fermentation heat generated by the microorganism themselves during the fermentation, and hence enzymes required for the fermentation may be inactivated or the productive bacteria may be killed. Therefore, it is necessary to cool the medium during the fermentation. Accordingly, in order to reduce the cooling cost, fermentation at high temperatures has been studied for many years. Moreover, if high temperature fermentation becomes possible, the reaction rate may also be improved. However, as for the L-amino acid fermentation, effective high temperature culture has not been realized so far.

*Corynebacterium thermoaminogenes* is a bacterium classified into coryneform bacteria like *Corynebacterium glutamicum* (*Brevibacterium lactofermentum*), which is commonly used for the fermentation of L-amino acids. However, it shows the optimum growth temperature of 37–43° C., which is higher than that of *Corynebacterium glutamicum*, i.e., 30–35° C., and shows the optimum temperature for L-glutamic acid production of 42–45° C., which is considerably shifted to the high temperature region (Japanese Patent Laid-open (Kokai) No. 63-240779/1988).

Meanwhile, there have been developed techniques for enhancing L-amino acid producing ability of *Corynebacterium* and *Brevibacterium* bacteria by introducing a gene coding for an L-amino acid synthesis system enzyme derived from *Escherichia coli* or *Corynebacterium glutamicum* into them. Examples of such an enzyme include, for example, citrate synthase (Japanese Patent Publication. (Kokoku) No. 7-121228/1995), which is an enzyme of the L-glutamic acid biosynthetic pathway, glutamate dehydrogenase (Japanese Patent Laid-open No. 61-268185/1986), isocitrate dehydrogenase, aconitate hydratase (Japanese Patent Laid-open No. 63-214189) and so forth.

However, any L-amino acid biosynthesis enzymes and genes coding for them derived from thermophilic coryneform bacteria have not been reported.

DISCLOSURE OF THE INVENTION

An object of the present invention is to provide genes coding for enzymes derived from *Corynebacterium thermoaminogenes*, preferably enzymes that function at a temperature higher than those of *Corynebacterium glutamicum*.

The inventors of the present invention extensively studied in order to achieve the aforementioned object. As a result, they successfully isolated genes coding for enzymes of the amino acid biosynthetic pathway of *Corynebacterium thermoaminogenes*, or genes coding for proteins involved in the uptake of amino acids into cells, and thus achieved the present invention.

That is, the present invention provides the followings.

(1) A protein having the amino acid sequence of SEQ ID NO: 2 or the amino acid sequence of SEQ ID NO: 2 including substitution, deletion, insertion, addition or inversion of one or several amino acids residues, which has isocitrate lyase activity and shows 30% or more of residual activity after a heat treatment at 50° C. for 5 minutes.

(2) A protein having the amino acid sequence of SEQ ID NO: 4 or the amino acid sequence of SEQ ID NO: 4 including substitution, deletion, insertion, addition or inversion of one or several amino acids residues, which is involved in acyl Co-A carboxylase activity derived from *Corynebacterium thermoaminogenes.*

(3) A protein having the amino acid sequence of SEQ ID NO: 6 or the amino acid sequence of SEQ ID NO: 6 including substitution, deletion, insertion, addition or inversion of one or several amino acids residues, which has DtsR activity derived from *Corynebacterium thermoaminogenes.*

(4) A protein having the amino acid sequence of SEQ ID NO: 8 or the amino acid sequence of SEQ ID NO: 8 including substitution, deletion, insertion, addition or inversion of one or several amino acids residues, which has DtsR activity derived from *Corynebacterium thermoaminogenes.*

(5) A protein having the amino acid sequence of SEQ ID NO: 10 or the amino acid sequence of SEQ ID NO: 10 including substitution, deletion, insertion, addition or inversion of one or several amino acids residues, which shows phosphofructokinase activity at 60° C. in an equivalent or higher degree compared with the activity at 30° C.

(6) A protein having the amino acid sequence of SEQ ID NO: 94 or the amino acid sequence of SEQ ID NO: 94 including substitution, deletion, insertion, addition or inversion of one or several amino acids residues, which has activity for imparting sucrose assimilating ability to *Corynebacterium thermoaminogenes.*

(7) A protein having any one of the amino acid sequences of SEQ ID NOS: 17–20 or the amino acid sequence of any one of SEQ ID NOS: 17–20 including substitution, deletion, insertion, addition or inversion of one or several amino acids residues, which has a function involved in glutamic acid uptake and derived from *Corynebacterium thermoaminogenes.*

(8) A protein having the amino acid sequence of SEQ ID NO: 22 or the amino acid sequence of SEQ ID NO: 22 including substitution, deletion, insertion, addition or inversion of one or several amino acids residues, which has pyruvate dehydrogenase activity derived from *Corynebacterium thermoaminogenes.*

(9) A protein having the amino acid sequence of SEQ ID NO: 24 or the amino acid sequence of SEQ ID NO: 24 including substitution, deletion, insertion, addition or inversion of one or several amino acids residues, which has pyruvate carboxylase activity derived from *Corynebacterium thermoaminogenes.*

(10) A protein having the amino acid sequence of SEQ ID NO: 26 or the amino acid sequence of. SEQ ID NO: 26 including substitution, deletion, insertion, addition or inversion of one or several amino acids residues, which has phosphoenolpyruvate carboxylase activity and shows 50% or more of residual activity after a heat treatment at 45° C. for 5 minutes.

(11) A protein having the amino acid sequence of SEQ ID NO: 28 or the amino acid sequence of SEQ ID NO: 28 including substitution, deletion, insertion, addition or inversion of one or several amino acids residues, which has aconitase activity and shows 30% or more of residual activity after a heat treatment at 50° C. for 3 minutes.

(12) A protein having the amino acid sequence of SEQ ID NO: 30 or the amino acid sequence of SEQ ID NO: 30 including substitution, deletion, insertion, addition or inversion of one or several amino acids residues, which has isocitrate dehydrogenase activity and shows 50% or more of residual activity after a heat treatment at 45° C. for 10 minutes.

(13) A protein having the amino acid sequence of SEQ ID NO: 32 or the amino acid sequence of SEQ ID NO: 32 including substitution, deletion, insertion, addition or inversion of one or several amino acids residues, which has dihydrolipoamide dehydrogenase activity derived from *Corynebacterium thermoaminogenes.*

(14) A protein having the amino acid sequence of SEQ ID NO: 34 or the amino acid sequence of SEQ ID NO: 34 including substitution, deletion, insertion, addition or inversion of one or several amino acids residues, which has 2-oxoglutarate dehydrogenase activity and shows 30% or more of residual activity after a heat treatment at 50° C. for 10 minutes.

(15) A protein having the amino acid sequence of SEQ ID NO: 80 in Sequence Listing or the amino acid sequence of SEQ ID NO: 80 including substitution, deletion, insertion, addition or inversion of one or several amino acids residues, which shows glutamate dehydrogenase activity at 42° C. in an equivalent or higher degree compared with the activity at 37° C.

(16) A protein having the amino acid sequence of SEQ ID NO: 90 in Sequence Listing or the amino acid sequence of SEQ ID NO: 90 including substitution, deletion, insertion, addition or inversion of one or several amino acids residues, which shows citrate synthase activity at 37° C. in an equivalent or higher degree compared with the activity at 23° C.

(17) A DNA which codes for a protein having the amino acid sequence of SEQ ID NO: 2 or the amino acid sequence of SEQ ID NO: 2 including substitution, deletion, insertion, addition or inversion of one or several amino acids residues, and having isocitrate lyase activity.

(18) The DNA according to (17), which is a DNA defined in the following (a1) or (b1):

(a1) a DNA which comprises the nucleotide sequence of SEQ ID NO: 1 in Sequence Listing, (b1) a DNA which is hybridizable with the nucleotide sequence of SEQ ID NO: 1 in Sequence Listing or a primer prepared based on the nucleotide sequence under a stringent condition, and codes for a protein having isocitrate lyase activity.

(19) A DNA which codes for a protein having the amino acid sequence of SEQ ID NO: 4 or the amino acid sequence of SEQ ID NO: 4 including substitution, deletion, insertion, addition or inversion of one or several amino acids residues, and involved in acyl Co-A carboxylase activity.

(20) The DNA according to (19), which is a DNA defined in the following (a2) or (b2):

(a2) a DNA which comprises the nucleotide sequence of SEQ ID NO: 3 in Sequence Listing, (b2) a DNA which is hybridizable with the nucleotide sequence of SEQ ID NO: 3 in Sequence Listing or a primer prepared based on the nucleotide sequence under a stringent condition, and codes for a protein involved in acyl Co-A carboxylase activity.

(21) A DNA which codes for a protein having the amino acid sequence of SEQ ID NO: 6 or the amino acid sequence of SEQ ID NO: 6 including substitution, deletion, insertion, addition or inversion of one or several amino acids residues, and having DtsR activity.

(22) The DNA according to (21), which is a DNA defined in the following (a3) or (b3):

(a3) a DNA which comprises the nucleotide sequence of SEQ ID NO: 5 in Sequence Listing, (b3) a DNA which is hybridizable with the nucleotide sequence of SEQ ID NO: 5 in Sequence Listing or a primer prepared based on the nucleotide sequence under a stringent condition, and codes for a protein having DtsR activity.

(23) A DNA which codes for a protein having the amino acid sequence of SEQ ID NO: 8 or the amino acid sequence of SEQ ID NO: 8 including substitution, deletion, insertion, addition or inversion of one or several amino acids residues, and having DtsR activity.

(24) The DNA according to (23), which is a DNA defined in the following (a4) or (b4):

(a4) a DNA which comprises the nucleotide sequence of SEQ ID NO: 7 in Sequence Listing, (b4) a DNA which is hybridizable with the nucleotide sequence of SEQ ID NO: 7 in Sequence Listing or a primer prepared based on the nucleotide sequence under a stringent condition, and codes for a protein having DtsR activity.

(25) A DNA which codes for a protein having the amino acid sequence of SEQ ID NO: 10 or the amino acid sequence of SEQ ID NO: 10 including substitution, deletion, insertion, addition or inversion of one or several amino acids residues, and having phosphofructokinase activity.

(26) The DNA according to (25), which is a DNA defined in the following (a5) or (b5):

(a5) a DNA which comprises the nucleotide sequence of SEQ ID NO: 9 in Sequence Listing, (b5) a DNA which is hybridizable with the nucleotide sequence of SEQ ID NO: 9 in Sequence Listing or a primer prepared based on the nucleotide sequence under a stringent condition, and codes for a protein having phosphofructokinase activity.

(27) A DNA which codes for a protein having the amino acid sequence of SEQ ID NO: 93 or the amino acid sequence of SEQ ID NO: 93 including substitution, deletion, insertion, addition or inversion of one or several amino acids residues, and having invertase activity.

(28) The DNA according to (27), which is a DNA defined in the following (a6) or (b6):

(a6) a DNA which comprises the nucleotide sequence of SEQ ID NO: 93 in Sequence Listing, (b6) a DNA which is hybridizable with the nucleotide sequence of SEQ ID NO: 93 in Sequence Listing or a primer prepared based on the nucleotide sequence under a stringent condition, and codes for a protein having invertase activity.

(29) A DNA which codes for a protein having any one of the amino acid sequences of SEQ ID NOS: 17–20 or the amino acid sequence of any one of SEQ ID NOS: 17–20 including substitution, deletion, insertion, addition or inversion of one or several amino acids residues, and having a function involved in glutamic acid uptake.

(30) The DNA according to (29), which is a DNA defined in the following (a7) or (b7):

(a7) a DNA which comprises the nucleotide sequence of SEQ ID NO: 16 in Sequence Listing, (b7) a DNA which is hybridizable with the nucleotide sequence of SEQ ID NO: 16 in Sequence Listing or a primer prepared based on the nucleotide sequence under a stringent condition, and codes for a protein having a function involved in glutamic acid uptake.

(31) A DNA which codes for a protein having the amino acid sequence of SEQ ID NO: 22 or the amino acid sequence of SEQ ID NO: 22 including substitution, deletion, insertion, addition or inversion of one or several amino acids residues, and having pyruvate dehydrogenase activity.

(32) The DNA according to (31), which is a DNA defined in the following (a8) or (b8):

(a8) a DNA which comprises the nucleotide sequence of SEQ ID NO: 21 in Sequence Listing, (b8) a DNA which is hybridizable with the nucleotide sequence of SEQ ID NO: 21 in Sequence Listing or a primer prepared based on the nucleotide sequence under a stringent condition, and codes for a protein having pyruvate dehydrogenase activity.

(33) A DNA which codes for a protein having the amino acid sequence of SEQ ID NO: 24 or the amino acid sequence of SEQ ID NO: 24 including substitution, deletion, insertion, addition or inversion of one or several amino acids residues, and having pyruvate carboxylase activity.

(34) A DNA according to (33), which is a DNA defined in the following (a9) or (b9):

(a9) a DNA which comprises the nucleotide sequence of SEQ ID NO: 23 in Sequence Listing, (b9) a DNA which is hybridizable with the nucleotide sequence of SEQ ID NO: 23 in Sequence Listing or a primer prepared based on the nucleotide sequence under a stringent condition, and codes for a protein having pyruvate carboxylase activity.

(35) A DNA which codes for a protein having the amino acid sequence of SEQ ID NO: 26 or the amino acid sequence of SEQ ID NO: 26 including substitution, deletion, insertion, addition or inversion of one or several amino acids residues, and having phosphoenolpyruvate carboxylase activity.

(36) The DNA according to (35), which is a DNA defined in the following (a10) or (b10):

(a10) a DNA which comprises the nucleotide sequence of SEQ ID NO: 25 in Sequence Listing, (b10) a DNA which is hybridizable with the nucleotide sequence of SEQ ID NO: 25 in Sequence Listing or a primer prepared based on the nucleotide sequence under a stringent condition, and codes for a protein having phosphoenolpyruvate carboxylase activity.

(37) A DNA which codes for a protein having the amino acid sequence of SEQ ID NO: 28 or the amino acid sequence of SEQ ID NO: 28 including substitution, deletion, insertion, addition or inversion of one or several amino acids residues, and having aconitase activity.

(38) The DNA according to (37), which is a DNA defined in the following (a11) or (b11):

(a11) a DNA which comprises the nucleotide sequence of SEQ ID NO: 27 in Sequence Listing, (b11) a DNA which is hybridizable with the nucleotide sequence of SEQ ID NO: 27 in Sequence Listing or a primer prepared based on the nucleotide sequence under a stringent condition, and codes for a protein having aconitase activity.

(39) A DNA which codes for a protein having the amino acid sequence of SEQ ID NO: 30 or the amino acid sequence of SEQ ID NO: 30 including substitution, deletion, insertion, addition or inversion of one or several amino acids residues, and having isocitrate dehydrogenase activity.

(40) The DNA according to (39), which is a DNA defined in the following (a12) or (b12):

(a12) a DNA which comprises the nucleotide sequence of SEQ ID NO: 27 in Sequence Listing, (b12) a DNA which is hybridizable with the nucleotide sequence of SEQ ID NO: 27 in Sequence Listing or a primer prepared based on the nucleotide sequence under a stringent condition, and codes for a protein having isocitrate dehydrogenase activity.

(41) A DNA which codes for a protein having the amino acid sequence of SEQ ID NO: 32 or the amino acid sequence of SEQ ID NO: 32 including substitution, deletion, insertion, addition or inversion of one or several amino acids residues, and having dihydrolipoamide dehydrogenase activity.

(42) The DNA according to (41), which is a DNA defined in the following (a13) or (b13):

(a13) a DNA which comprises the nucleotide sequence of SEQ ID NO: 31 in Sequence Listing, (b13) a DNA which is hybridizable with the nucleotide sequence of SEQ ID NO: 31 in Sequence Listing or a primer prepared based on the nucleotide sequence under a stringent condition, and codes for a protein having dihydrolipoamide dehydrogenase activity.

(43) A DNA which codes for a protein having the amino acid sequence of SEQ ID NO: 34 or the amino acid sequence of SEQ ID NO: 34 including substitution, deletion, insertion, addition or inversion of one or several amino acids residues, and having 2-oxoglutarate dehydrogenase activity.

(44) The DNA according to (43), which is a DNA defined in the following (a14) or (b14):

(a14) a DNA which comprises the nucleotide sequence of SEQ ID NO: 33 in Sequence Listing, (b14) a DNA which is hybridizable with the nucleotide sequence of SEQ ID NO: 33 in Sequence Listing or a primer prepared based on the nucleotide sequence under a stringent condition, and codes for a protein having 2-oxoglutarate dehydrogenase activity.

(45) A DNA which codes for a protein having the amino acid sequence of SEQ ID NO: 80 in Sequence Listing or the amino acid sequence of SEQ ID NO: 80 including substitution, deletion, insertion, addition or inversion of one or several amino acids residues, and showing glutamate dehydrogenase activity at 42° C. in an equivalent or higher degree compared with the activity at 37° C.

(46) The DNA according to (45), which is a DNA defined in the following (a15) or (b15):

(a15) a DNA which comprises the nucleotide sequence of SEQ ID NO: 79 in Sequence Listing, (b15) a DNA which is hybridizable with the nucleotide sequence of SEQ ID NO: 79 in Sequence Listing or a primer prepared based on the nucleotide sequence under a stringent condition, and codes for a protein showing glutamate dehydrogenase activity at 42° C. in an equivalent or higher degree compared with the activity at 37° C.

(47) A DNA which codes for a protein having the amino acid sequence of SEQ ID NO: 90 in Sequence Listing or the amino acid sequence of SEQ ID NO: 90 including substitution, deletion, insertion, addition or inversion of one or several amino acids residues, and showing citrate synthase activity at 37° C. in an equivalent or higher degree compared with the activity at 23° C.

(48) The DNA according to (47), which is a DNA defined. in the following (a16) or (b16):

(a16) a DNA which comprises the nucleotide sequence of SEQ ID NO: 89 in Sequence Listing, (b16) a DNA which is hybridizable with the nucleotide sequence of SEQ ID NO: 89 in Sequence Listing or a primer prepared based on the nucleotide sequence under a stringent condition, and codes for a protein showing citrate synthase activity at 37° C. in an equivalent or higher degree compared with the activity at 23° C.

(49) A method for producing L-amino acid, which comprises culturing a microorganism introduced with a DNA according to any one of (17) to (48) in a medium to produce and accumulate L-amino acid in the medium, and collecting the L-amino acid from the medium.

The term "DNA of the present invention" is used hereinafter for referring to either one or all of the aforementioned DNAS.

Hereafter, the present invention will be explained in detail.

The nucleotide sequences of the DNA of the present invention, names of the genes, and the proteins encoded by the DNA of the present invention are shown in Table 1.

TABLE 1

| Nucleotide sequence | Name of gene | Encoded protein (abbreviation) |
|---|---|---|
| SEQ ID NO: 1 | aceA | Isocitrate lyase (ICL) |
| SEQ ID NO: 3 | accBC | acyl Co-A carboxylase BC subunit |
| SEQ ID NO: 5 | dtsR1 | DTSR1 protein |
| SEQ ID NO: 7 | dtsR2 | DTSR2 protein |
| SEQ ID NO: 9 | pfk | Phosphofructokinase |
| SEQ ID NOS: 11, 13, 15, 93 | scrB | Invertase |
| SEQ ID NO: 16 | gluABCD | glutamic acid uptake system |
| SEQ ID NO: 21 | pdhA | pyruvate dehydrogenase |
| SEQ ID NO: 23 | pc | pyruvate carboxylase |
| SEQ ID NO: 25 | ppc | phosphoenolpyruvate carboxylase |
| SEQ ID NO: 27 | acn | aconitase |
| SEQ ID NO: 29 | icd | isocitrate dehydrogenase |
| SEQ ID NO: 31 | lpd | dihydrolipoamide dehydrogenase |
| SEQ ID NO: 33 | odha | 2-oxoglutarate dehydrogenase |
| SEQ ID NO: 79 | gdh | glutamate dehydrogenase |
| SEQ ID NO: 89 | gltA | citrate synthase |

The open reading frames (ORFS) of SEQ ID NOS: 3, 23, 25, 31 and 33 and the fourth ORF of SEQ ID NO: 16 all start from GTG. Although the amino acids encoded by these GTG are indicated as valine in Sequence Listing, they may be methionine.

The sequence of SEQ ID NO: 16 contains four ORFs, which correspond to gluA, glub, gluc and gluD in this order from the 5' end side.

The aforementioned DNA sequences were isolated from chromosomal DNA of the *Corynebacterium thermoaminogenes* AJ12310 strain (FERM BP-1542). However, the DNA sequences shown in SEQ ID NOS: 11 and 13 were isolated from *Corynebacterium thermoaminogenes* AJ12340 strain (FERM BP-1539) and AJ12309 strain (FERM BP-1541), respectively, which had invertase activity and sucrose assimilating property, because the AJ12310 strain did not have invertase activity and sucrose assimilating property, and the scrB gene isolated from the strain had not any open reading frame.

The *Corynebacterium thermoaminogenes* AJ12310 strain (also referred to as YS-314 strain) and AJ12309 strain (also referred to as YS-155 strain) were deposited at the National Institute of Bioscience and Human-Technology, Agency of Industrial Science and Technology, Ministry of International Trade and Industry (postal code: 305-8566, 1-3, Higashi 1-chome, Tsukuba-shi, Ibaraki-ken, Japan) on Mar. 13, 1987 and given deposition numbers of FERM P-9246 and FERM P-9245, respectively. Then, they were transferred to international depositions under the provisions of the Budapest Treaty on Oct. 27, 1987, and given deposition numbers of FERM BP-1542 and FERM BP-1541, respectively.

The AJ12340 strain (also referred to as YS-40 strain) was deposited at the National Institute of Bioscience and Human-Technology, Agency of Industrial Science and Technology, Ministry of International Trade and Industry (postal code: 305-8566, 1-3, Higashi 1-chome, Tsukuba-shi, Ibaraki-ken, Japan) on Mar. 10, 1987 and given a deposition number of FERM P-9277. Then, it was transferred to an international deposition under the provisions of the Budapest Treaty on Oct. 27, 1987, and given a deposition number of FERM BP-1539.

The nucleotide sequences shown in SEQ ID NOS: 11, 13 and 15 are partial sequences of scrB, and the sequences of SEQ ID NOS: 11 and 13 code for partial amino acid sequences of invertase shown in SEQ ID NOS: 12 and 14.

A DNA sequence containing a partial fragment of a target gene can be obtained by comparing already reported nucleotide sequences for the target gene of various microorganisms such as *Brevibacterium lactofermentum* to select a region containing a well-conserved nucleotide sequence, and carrying out PCR using primers designed based on the nucleotide sequence of the region and chromosomal DNA of *Corynebacterium thermoaminogenes* as a template. Further, by performing hybridization using the obtained DNA fragment or a probe prepared based on the sequence of the fragment to screen a chromosomal DNA library of *Corynebacterium thermoaminogenes*, a DNA fragment containing the gene in its full length can be obtained. A DNA fragment containing the gene in its full length can also be obtained by performing genome walking using the obtained partial fragment of the gene. The genome walking can be carried out by using a commercially available kit, for example, TaKaRa LA PCR in vitro Cloning Kit (produced by Takara Shuzo).

For example, a partial sequence of DNA coding for glutamate dehydrogenase (henceforth the DNA is also referred to as "gdh", and the enzyme is also referred to as "GDH") can be obtained from chromosomal DNA of *Corynebacterium thermoaminogenes* such as the *Corynebacterium thermoaminogenes* AJ12310 strain by PCR (polymerase chain reaction) using the chromosomal DNA as a template and primers having the nucleotide sequences shown in SEQ ID NOS: 77 and 78 of Sequence Listing. Further, by performing genome walking using the obtained partial fragment, the whole gdh gene can be obtained.

Further, a partial sequence of DNA coding for citrate synthase (henceforth the DNA is also referred to as "gltA", and the enzyme is also referred to as "CS") can be obtained from chromosomal DNA of *Corynebacterium thermoaminogenes* such as the *Corynebacterium thermoaminogenes* AJ12310 strain by PCR (polymerase chain reaction) using the chromosomal DNA as a template and primers having the nucleotide sequences shown in SEQ ID NOS: 83 and 84 of Sequence Listing. Further, by performing genome walking using the obtained partial fragment, the whole gltA gene can be obtained.

The nucleotide sequences of the aforementioned primers were designed based on a nucleotide sequence in a region containing a well-conserved nucleotide sequence among the already reported gdh genes or gltA genes of various microorganisms, which region was found by comparison of the genes.

As for DNA sequences coding for the other enzymes, partial fragments coding for those enzymes can be similarly obtained by using the primers mentioned in Table 1, and the genes in full length can be obtained by using the obtained partial fragments.

While the DNA of the present invention was obtained as described above, it can also be obtained from a chromosomal DNA library of *Corynebacterium thermoaminogenes* by hybridization using an oligonucleotide prepared based on the nucleotide sequences of the DNA of the present invention as a probe.

Methods for preparation of chromosomal DNA, construction of chromosomal DNA library, hybridization, PCR, preparation of plasmid DNA, digestion and ligation of DNA, transformation and so forth are described in Sambrook, J., Fritsch, E. F., Maniatis, T., Molecular Cloning, Cold Spring Harbor Laboratory Press, 1.21 (1989). Further, genome walking can be performed by using a commercially available kit, for example, TaKaRa LA PCR in vitro Cloning Kit (produced by Takara Shuzo).

Specific methods for obtaining the DNA of the present invention will be explained hereafter.

First, chromosomal DNA of *Corynebacterium thermoaminogenes* is digested with a suitable restriction enzyme, for example, Sau3AI, and fractionated by agarose gel electrophoresis to obtain a DNA fragment of about 4 to 6 kb. The obtained DNA fragment is inserted into a cloning vector such as pHSG399, and *Escherichia coli* is transformed with the obtained recombinant plasmid to produce a plasmid library of the chromosomal DNA.

Separately, primers are produced for use in selecting a clone containing a target gene from a plasmid library by PCR. These primers are designed based on conserved amino acid regions from various microorganisms corresponding to the gene of interest. In the design of primers, a plurality of primer sets are designed considering the codon usage of coryneform bacteria.

Then, in order to investigate propriety of the produced primers, PCR is performed by using these primers and chromosomal DNA of *Corynebacterium thermoaminogenes* as a template. Further, PCR is performed by using primers from which an amplification fragment has been obtained as primers for screening and a recombinant plasmid prepared from the plasmid library as a template to select a clone containing the target DNA fragment. This operation can be quickly carried out by performing the PCR for every batch including several tens of transformant strains as primary screening and performing colony PCR for the batch with which an amplification fragment was obtained as secondary screening. The fragment lengths of the amplified genes are shown in Tables 2 to 7.

If a transformant selected as described above contains a target gene is confirmed by preparing a recombinant DNA from the transformant selected as described above, determining the nucleotide sequence of the inserted fragment by the dideoxy termination method, and comparing the nucleotide sequence with a known gene sequence.

When the obtained DNA fragment contains a part of the target gene, the deleted part is obtained by genome walking.

The DNA of the present invention may code for a protein including substitution, deletion, insertion, addition or inversion of one or several amino acids residues, so long as the encoded protein has its original function. The number meant by the term "several" may vary depending on positions in the three-dimensional structure of protein or kinds of amino acid residues. However, in general, such a protein preferably shows homology of 30 to 40% or more, more preferably 55 to 65% or more, with respect to a corresponding whole amino acid sequence of the protein.

More specifically, the term "several" means a number of 2 to several hundreds, preferably 2 to several tens, more preferably 2 to 10.

Nucleotide and amino acid sequence were analyzed by, for exmaple, the method developed by Lipman and Peason (Science, 227, 1435–1441, 1985) by using commercially available softoware such as Genetyx-Mac computer program (Software Development Co., Tokyo, Japan).

GDH may be one showing homology of 40 to 80% or more, preferably 80 to 90% or more, for the total amino acid sequence constituting GDH, and showing GDH activity at 42° C. equivalent to or higher than the activity at 37° C. In this case, the term "several" means a number of 2 to 30, preferably 2 to 50, more preferably 2 to 10.

CS may be one showing homology of 40 to 80% or more, preferably 80 to 90% or more, for the total amino acid sequence constituting CS, and showing CS activity at 37° C. equivalent to or higher than the activity at 23° C. In this case, the term "several" means a number of 2 to 300, preferably 2 to 50, more preferably 2 to 10.

A DNA, which codes for the substantially same protein as the original protein as described above, can be obtained by, for example, modifying the nucleotide sequence, for example, by means of the site-directed mutagenesis so that one or more amino acid residues at a specific site should involve substitution, deletion, insertion, addition or inversion. A DNA modified as described above may also be obtained by a conventionally known mutation treatment. The mutation treatment includes a method for treating DNA coding for a target gene in vitro, for example, with hydroxylamine, and a method for treating a microorganism, for example, a bacterium belonging to the genus *Escherichia*, harboring DNA coding for the target gene with ultraviolet irradiation or a mutating agent usually used for the mutation treatment such as N-methyl-N'-nitro-N-nitrosoguanidine (NTG) and nitrous acid.

The substitution, deletion, insertion, addition, or inversion of nucleotides as described above also includes mutant or variant that naturally occurs due to the difference of strains of *Corynebacterium thermoaminogenes* or the like.

A DNA coding for substantially the same protein as the original protein can be obtained by expressing DNA having a mutation in an appropriate cell, and investigating activity or function of the expressed product protein. The DNA coding for substantially the same protein as the original protein can also be obtained by, for example, isolating a DNA which is hybridizable with a DNA having each of the nucleotide sequences of the sequences of which sequence numbers are mentioned in Table 1 or a coding region thereof, or a probe designed based on the nucleotide sequence under a stringent condition, and which codes for a protein having the activity originally possessed by the protein, from DNA coding for a protein having a mutation or from a cell harboring it. The activity preferably means each enzymatic activity at 42° C. for GDH or 37° C. for CS.

The aforementioned probe can be prepared from a DNA having any one of the nucleotide sequences of which sequence numbers are shown in Table 1 or a DNA having any one of the nucleotide sequences by PCR using suitable primers.

The "stringent condition" referred to herein is a condition under which so-called specific hybrid is formed, and non-specific hybrid is not formed. It is difficult to clearly express this condition by using any numerical value. However, for example, the stringent condition includes a condition under which DNAs having high homology, for example, DNAs having homology of not less than 50% are hybridized with each other, and DNAs having homology lower than the above are not hybridized with each other. Alternatively, the stringent condition is exemplified by a condition under which DNAs are hybridized with each other at a salt concentration corresponding to an ordinary condition of washing in Southern hybridization, i.e., 60° C., 1×SSC, 0.1% SDS, preferably 0.1×SSC, 0.1% SDS.

The gene, which is hybridizable under the condition as described above, includes those having a stop codon generated in the gene, and those having no activity due to mutation of active site. However, such genes can be easily removed by ligating the genes with a commercially available activity expression vector, and measuring the activity or function.

A protein corresponding to each DNA of the present invention can be produced by expressing the DNA in a suitable host-vector system.

As the host used for the expression of a gene, there can be mentioned various prokaryotic cells including *Brevibacterium lactofermentum* (*Corynebacterium glutamicum*), coryneform bacteria such as *Corynebacterium thermoaminogenes, Escherichia coli, Bacillus subtilis* and so forth, and various eucaryocytic cells including *Saccharomyces cerevisiae*, animal cells and plant cells. Among these, prokaryotic cells, in particular, coryneform bacteria and *Escherichia coli* are preferred.

If the DNA of the present invention is ligated to a vector DNA autonomously replicable in cells of *Escherichia coli* and/or coryneform bacteria and so forth to form a recombinant DNA, and this recombinant DNA is introduced into an *Escherichia coli* cell, the subsequent procedure becomes easy. The vector autonomously replicable in *Escherichia coli* cells is preferably a plasmid vector autonomously replicable in the host cell, and examples thereof include pUC19, pUC18, pBR322, pHSG299, pHSG399, pHSG398, RSF1010 and so forth.

As the vector autonomously replicable in coryneform bacterium cells, there can be mentioned pAM330 (refer to Japanese Patent Laid-open No. 58-67699/1983), pHM1519 (refer to Japanese Patent Laid-open No. 58-77895/1983) and so forth. Moreover, if a DNA fragment having an ability to make a plasmid autonomously replicable in coryneform bacteria is taken out from these vectors and inserted into the aforementioned vectors for *Escherichia coli*, they can be used as a so-called shuttle vector autonomously replicable in both of *Escherichia coli* and coryneform bacteria.

Examples of such a shuttle vector include those mentioned below. There are also indicated microorganisms that harbor each vector, and accession numbers thereof at international depositories are shown in the parentheses, respectively.

pAJ655 *Escherichia coli* AJ11882 (FERM BP-136) *Corynebacterium glutamicum* SR8201 (ATCC39135)

pAJ1844 *Escherichia coli* AJ11883 (FERM BP-137) *Corynebacterium glutamicum* SR8202 (ATCC39136)

pAJ611 *Escherichia coli* AJ11884 (FERM BP-138)

pAJ3148 *Corynebacterium glutamicum* SR8203 (ATCC39137)

pAJ440 *Bacillus subtilis* AJ11901 (FERM BP-140)

pHC4 *Escherichia coli* AJ12617 (FERM BP-3532)

In order to prepare a recombinant DNA by ligating the DNA of the present invention and a vector that functions in coryneform bacteria, the vector is digested with a restriction enzyme that provides an end corresponding to an end of the DNA of the present invention. The ligation is normally attained by using a ligase such as T4 DNA ligase.

To introduce the recombinant DNA prepared as described above into a host such as coryneform bacteria, any known transformation methods that have hitherto been reported can be employed. For instance, employable are a method of treating recipient cells with calcium chloride so as to increase the permeability for DNA, which has been reported for *Escherichia coli* K-12 (Mandel, M. and Higa, A., *J. Mol. Biol.,* 53, 159 (1970)), and a method of preparing competent cells from cells which are at the growth phase followed by introducing the DNA thereinto, which has been reported for *Bacillus subtilis* (Duncan, C. H., Wilson, G. A. and Young, F. E., *Gene,* 1, 153 (1977)). In addition to these, also employable is a method of making DNA-recipient cells into protoplasts or spheroplasts, which can easily take up recombinant DNA, followed by introducing the recombinant DNA into the cells, which is known to be applicable to *Bacillus subtilis*, actinomycetes and yeasts (Chang, S. and Choen, S. N., *Molec. Gen. Genet.,* 168, 111 (1979); Bibb, M. J., Ward, J. M. and Hopwood, O. A., *Nature,* 274, 398 (1978); Hinnen, A., Hicks, J. B. and Fink, G. R., *Proc. Natl. Sci. USA,* 75, 1929 (1978)). The transformation of coryneform bacteria can be effectively performed by the electric pulse method (refer to Japanese Patent Laid-open No. 2-207791).

As for the transformation of thermophilic coryneform bacteria such as *Corynebacterium thermoaminogenes*, it can be efficiently performed by treating cells with an agent that changes the structure of cell walls of the host cells, and applying an electric pulse to a solution containing DNA and the cells of which structure of the cell walls have been changed. The aforementioned agent is an agent that can change the structure of cell walls so that the cells can uptake the DNA when an electric pulse is applied to a solution containing the cells treated with the agent and the DNA (henceforth also referred to as a "cell wall treatment agent"). Examples of such an agent include agents that inhibit normal synthesis of bacterial cell wall and agents that lyse bacterial cell walls. Specific examples thereof include lysozyme, penicillin G, glycine and so forth.

Those cell wall treatment agents may be used each alone, or two or more kinds of them may be used in combination. Among the aforementioned agents, lysozyme and penicillin G are preferred, and lysozyme is particularly preferred.

Furthermore, the transformation of *Corynebacterium thermoaminogenes* can also be performed by applying an electric pulse to a solution containing DNA and the host cells of which cell walls has been weakened by a physical method such as ultrasonication (*FEMS Microbiology Letters,* 151, 135–138 (1987)).

In order to efficiently express a gene contained in the DNA of the present invention, a promoter that functions in the host cell such as lac, trp and $P_L$ may be ligated upstream from the coding region of the gene. If a vector containing a promoter is used as the vector, ligation of each gene, vector and promoter can be attained by one step.

The proteins of the present invention, which can be produced as described above, can be purified as required from a cell extract or medium by using usual methods for purifying enzymes such as ion exchange chromatography, gel filtration chromatography, adsorption chromatography, salting out and solvent precipitation.

It is expected that the proteins of the present invention are excellent in thermal stability or exhibit higher activity at high temperatures compared with the corresponding proteins of *Corynebacterium glutamicum* and so forth. For example, GDH of *Brevibacterium lactofermentum* shows the highest GDH specific activity around 37° C., and the activity is markedly reduced around 42° C. However, GDH of the present invention shows at 42° C. the GDH activity equivalent to or higher than the activity at 37° C. In a preferred embodiment, GDH of the present invention shows the highest specific activity around 42° C., and shows the activity even at 45° C.

The GDH activity can be measured by, for example, adding the enzyme to 100 mM Tris-HCl (pH 8.0), 20 mM $NH_4Cl$, 10 mM sodium α-ketoglutarate, 0.25 mM NADPH, and determining change of absorbance at 340 nm (Molecular Microbiology 6, 317–326 (1992)).

Further, CS of *Brevibacterium lactofermentum* shows the highest CS specific activity around 23° C., and the activity is markedly reduced around 33° C. To the contrary, CS of the present invention shows at 37° C. the CS activity equivalent to or higher than the activity at 23° C. In a preferred embodiment, CS of the present invention shows reaction temperature-dependently higher activity up to around 37° C., and shows, even at 40° C., about 40% of the activity with respect to the activity at 37° C.

The CS activity can be measured by, for example, the method described in Methods in Enzymol., 13, 3–11 (1969).

Further, other proteins of the present invention typically have the following characteristics. The isocitrate lyase has 30% or more of residual activity after a heat treatment at 50° C. for 5 minutes. The phosphofructokinase has, at 60° C., the activity equivalent to or higher than the activity at 30° C. The phosphoenolpyruvate carboxylase has 50% or more of residual activity after a heat treatment at 45° C. for 5 minutes. The aconitase has 30% or more of residual activity after a heat treatment at 50° C. for 3 minutes. The isocitrate dehydrogenase has 50% or more of residual activity after a heat treatment at 45° C. for 10 minutes. The 2-oxoglutarate dehydrogenase has 30% or more of residual activity after a heat treatment at 50° C. for 10 minutes.

The proteins of the present invention can also be obtained from cell extracts of *Corynebacterium thermoaminogenes* such as the *Corynebacterium thermoaminogenes* AJ12310 strain by using each activity as an index and usual purification methods for purifying enzymes such as ion exchange chromatography, gel filtration chromatography, adsorption chromatography, salting out and solvent precipitation.

Among the DNA of the present invention, pfk, pdhA, pc, ppc, acn, icd, gdh and gltA (names of the enzymes encoded by these are shown in Table 1) can be introduced into L-amino acid production bacteria such as coryneform bacteria to enhance their L-amino acid producing ability. It is also expected that coryneform bacteria introduced with the DNA of the present invention become possible to produce L-amino acid at a temperature higher than usual. The L-amino acid includes L-glutamic acid, L-aspartic acid, L-lysine, L-arginine, L-proline, L-glutamine and so forth.

For example, it is expected that L-glutamic acid production bacteria such as coryneform bacteria introduced with the gdh gene or gltA gene come to be able to produce L-glutamic acid at a temperature higher than usual. Further, although CS of *Brevibacterium lactofermentum* may not fully function at a usual culture temperature, for example, 31.5° C., the activity can be enhanced by introducing the gltA gene of the present invention.

Further, dtsR1 and dtsR2 are genes that code for proteins imparting resistance to surfactant to coryneform bacteria (DTSR protein), and coryneform L-glutamic acid producing bacteria of which these genes are disrupted produce a marked amount of L-glutamic acid even under a condition where biotin is present in such an amount that a wild strain becomes to be substantially unable to produce L-glutamic acid. Further, if dtsR1 and dtsR2 genes of coryneform L-glutamic acid producing bacteria having L-lysine producing ability are amplified, the bacteria are imparted with an ability to produce a marked amount of L-lysine (WO95/23224, Japanese Patent Laid-open (Kokai) No. 10-234371/1998).

The scrB gene can be used for improvement of coryneform bacteria for use in the production of L-amino acids by using coryneform bacteria in a medium containing sucrose.

By deleting aceA, accBC, lpd or odhA of L-glutamic acid producing coryneform bacteria and so forth, their L-glutamic acid productivity can be enhanced. Further, gluABCD is a gene cluster of the L-glutamic acid uptake system, and by deleting one to four of gluA, gluB, gluC and gluD in coryneform L-glutamic acid producing bacteria, the amount of L-glutamic acid accumulated in the medium can be increased. aceA, accBC, lpd, odhA and gluABCD of the present invention can be used for disruption of these genes on chromosome.

The medium used for producing L-amino acids by utilizing a microorganism introduced with the DNA of the present invention may be a usual medium that contains a carbon source, a nitrogen source, inorganic ions and other organic trace nutrients as required. As the carbon source, there can be used hydrocarbons such as glucose, lactose, galactose, fructose, sucrose, blackstrap molasses and starch hydrolysate; alcohols such as ethanol and inositol; or organic acids such as acetic acid, fumaric acid, citric acid and succinic acid.

As the nitrogen source, there can be used inorganic ammonium salts such as ammonium sulfate, ammonium nitrate, ammonium chloride, ammonium phosphate and ammonium acetate, ammonia, organic nitrogen such as peptone, meat extract, yeast extract, corn steep liquor and soybean hydrolysate, ammonia gas, aqueous ammonia and so forth.

As the inorganic ions (or sources thereof), added is a small amount of potassium phosphate, magnesium sulfate, iron ions, manganese ions and so forth. As for the organic trace nutrients, it is desirable to add required substances such as vitamin $B_1$, yeast extract and so forth in a suitable amount as required.

The culture is preferably performed under an aerobic condition attained by shaking, stirring for aeration or the like for 16 to 72 hours. The culture temperature is controlled to be at 30° C. to 47° C., and pH is controlled to be 5 to 9 during the culture. As for the culture temperature, the culture may be performed at a temperature suitable for culture of a microorganism not introduced with the DNA of the present invention or a temperature higher than that. For adjustment of pH, inorganic or organic acidic or alkaline substances, ammonia gas and so forth can be used.

Collection of L-amino acids from fermentation broth can be attained by a combination of known methods such as techniques utilizing ion exchange resin, precipitation, crystallization and so forth depending on the kind of the L-amino acids.

BEST MODE FOR CARRYING OUT THE INVENTION

Figure 1:
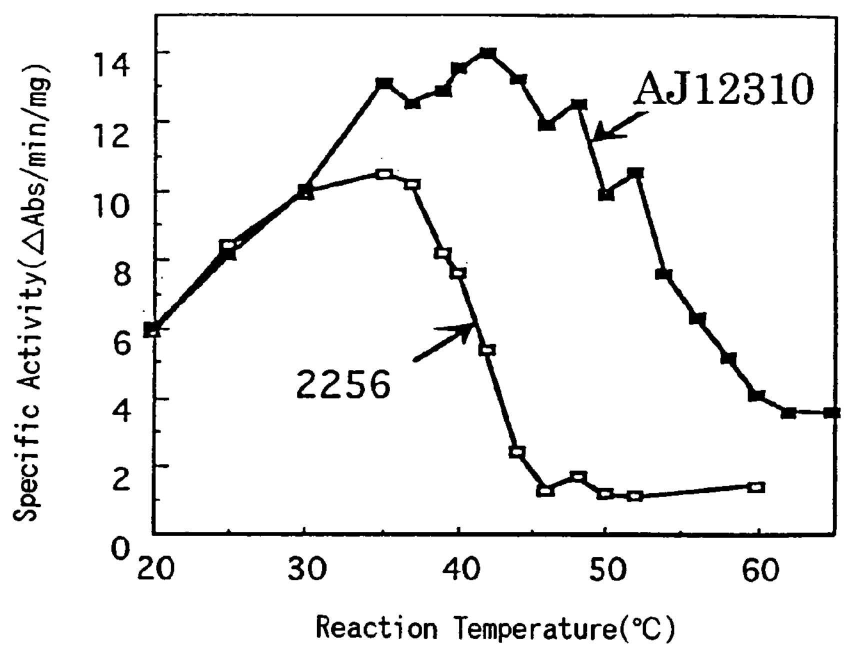
FIG. 1 shows variation with temperature in activity of glutamate dehydrogenases derived from the *Corynebacterium thermoaminogenes* AJ12310 strain and the *Brevibacterium lactofermentum* 2256 strain.

Hereafter, the present invention will be further specifically explained with reference to the following examples.

EXAMPLE 1

<1> Production of Plasmid Library of *Corynebacterium thermoaminogenes*

The *Corynebacterium thermoaminogenes* AJ12310 strain was cultured in CM2B liquid medium (1 g/dl of yeast extract (produced by Difco), 1 g/dl of polypeptone (produced by Nippon Seiyaku), 0.5 g/dl of NaCl, 10 μg/dl of biotin, pH 7.0 (adjusted with KOH)) at 37° C. for 15 hours, and its chromosomal DNA was prepared from the 10 ml of the medium by using a chromosomal DNA extraction kit (Bacterial Genome DNA Purification Kit (produced by Advanced Genetic Technologies)). The obtained DNA was partially digested with a restriction enzyme Sau3AI, and subjected to 0.8% agarose gel electrophoresis to fractionate the DNA. Then, a band corresponding to a DNA fragment of about 4 to 6 kb was excised from the gel, and a DNA fragment of the objective size was obtained by using a DNA gel extraction kit (GIBCO BRL, Concert™ Rapid Gel Extraction System).

The plasmid pHSG399 (produced by Takara Shuzo) was fully digested with BamHI, and its end was dephosphorylated by using alkaline phosphatase (CIAP; produced by Takara Shuzo). This vector fragment and the aforementioned chromosomal DNA fragment were ligated by using a DNA ligation kit produced by Takara Shuzo, and *Escherichia coli* JM109 was the transformed with the obtained recombinant vector. Selection of transformants was performed on LB agar medium (containing 1.5 g/dl of agar) containing 30 μg/ml of chloramphenicol, 0.04 mg/ml of IPTG (isopropyl-β-D-thiogalactopyranoside) and 0.04 mg/ml of X-Gal (5-bromo-4-chloro-3-indolyl-β-D-galactoside) to obtain about 4000 white colonies.

<2> Design of Primers for Amplification of each Gene

Primers for use in selection of a clone containing each target gene by PCR from the plasmid library obtained above were designed. The target genes were mentioned above.

The primers were designed based on a known gene sequence of coryneform bacteria, i.e., its sequence of a region where conservation at the amino acid level was observed when compared with corresponding genes of other microorganisms. Considering the codon usage of coryneform bacteria, a plurality of primer sets were designed for each gene.

To examine propriety of the prepared primers, PCR was performed by using these primers and chromosomal DNA of the *Corynebacterium thermoaminogenes* AJ12310 strain as a template to amplify each gene fragment. As a result, when the PCR was performed by using the primers shown in the upper rows of Tables 2 to 7 under the conditions indicated as "PCR conditions for obtaining partial fragment" in the tables, an amplified fragment was observed for all of the genes. The parenthesized numbers after the primer sequences indicate the sequence numbers in Sequence Listing. These primers were used as primers for screening mentioned below.

TABLE 2

| Gene | aceA | accBC | dtsR1 |
| --- | --- | --- | --- |
| 5'→3' Primer | CCTCTACCCAGCGAACTCCG (35) | CATCCACCCCGGCTACGGCT (37) | ACGGCCCAGCCCTGACCGAC (39) |
| 3'→5' Primer | CTGCCTTGAACTCACGGTTC (36) | CGGTGACTGGGTGTTCCACC (38) | AGCAGCGCCCATGACGGCGA (40) |
| PCR conditions for obtaining partial fragment and PCR conditions for screening | 94° C., 5 min<br>98° C., 5 sec<br>66° C., 2 sec, 30 cycles<br>Z-Taq | 94° C., 5 min<br>98° C., 5 sec<br>66° C., 2 sec, 30 cycles<br>Z-Taq | 94° C., 5 min<br>98° C., 5 sec<br>66° C., 2 sec, 30 cycles<br>Z-Taq |
| Conditions of colony PCR | 94° C., 7 min<br>91° C., 30 sec<br>55° C., 1 sec<br>72° C., 2.5 min, 30 cycles<br>Ex-Taq | 94° C., 7 min<br>91° C., 30 sec<br>55° C., 1 sec<br>72° C., 2.5 min, 30 cycles<br>Ex-Taq | 94° C., 7 min<br>91° C., 30 sec<br>55° C., 1 sec<br>72° C., 2.5 min, 30 cycles<br>Ex-Taq |
| Amplified fragment | 824 bp | 673 bp | 805 bp |

TABLE 3

| Gene | dtsR2 | pfk | scrR |
| --- | --- | --- | --- |
| 5' → 3' Primer | ACGGCCCAGCCCTGACCGAC (41) | CGTCATCCGAGGAATCGTCC (43) | GGNCGHYTBAAYGAYCC (45) |
| 3' → 5' Primer | AGCAGCGCCCATGACGGCGA (42) | CGTGGCGGCCCATGACCTCC (44) | GGRCAYTCCCACATRTANCC (46) |
| PCR conditions for obtaining partial fragment and PCR conditions for screening | 94° C., 5 min<br>98° C., 5 sec<br>66° C., 2 sec,<br>30 cycles Z-Tag | 94° C., 5 min<br>98° C., 5 sec<br>66° C., 2 sec,<br>30 cycles Z-Taq | 94° C., 5 min<br>98° C., 5 sec<br>50° C., 10 sec<br>72° C., 20 sec,<br>40 cycles Z-Taq |
| Conditions of colony PCR | 94° C., 7 min<br>91° C., 30 sec<br>55° C., 1 sec<br>72° C., 2.5 min,<br>30 cycles Ex-Tag | 94° C. 7 min<br>91° C. 30 sec<br>55° C. 1 sec<br>72° C. 2.5 min<br>30 cycles Ex-Tag | 94° C., 7 min<br>91° C., 30 sec<br>55° C., 1 sec<br>72° C., 2.5 min,<br>30 cycles Ex-Taq |
| Amplified fragment | 805 bp | 472 bp | 500 bp |

TABLE 4

| Gene | gluABCD | pdhA |
| --- | --- | --- |
| 5' → 3' Primer | CCATCCGGATCCGGCAAGTC (47) | ACTGTGTCCATGGGTCTTGGCCC (49) |
| 3' → 5' Primer | AATCCCATCTCGTGGGTAAC (48) | CGCTGGAATCCGAACATCGA (50) |
| PCR conditions for obtaining partial fragment | 94° C., 5 min<br>98° C., 5 sec<br>50° C., 10 sec<br>72° C., 20 sec,<br>30 cycles Z-Taq | 94° C., 5 min<br>98° C., 5 sec<br>50° C., 10 sec<br>72° C., 20 sec,<br>30 cycles Z-Taq |
| Amplified fragment | 500 bp | 1200 bp |
| Conditions for screening PCR and colony PCR | 94° C., 5 min<br>94° C., 30 sec<br>50° C., 1 min<br>72° C., 2 min,<br>30 cycles EX-Taq | 94° C., 5 min<br>94° C., 30 sec<br>50° C., 1 min<br>72° C., 2 min,<br>30 cycles EX-Taq |

TABLE 5

| Gene | pc | ppc |
| --- | --- | --- |
| 5' → 3' Primer | GGCGCAACCTACGACGTTGCAATGCG (51) | GGTTCCTGGATTGGTGGAGA (53) |
| 3' → 5' Primer | TGGCCGCCTGGGATCTCGTG (52) | CCGCCATCCTTGTTGGAATC (54) |
| PCR | 94° C., 5 min | 94° C. 5 min |

TABLE 5-continued

| Gene | pc | ppc |
| --- | --- | --- |
| conditions for obtaining partial fragment | 98° C., 5 sec<br>55° C., 80 sec 30 cycles Z-Taq | 98° C. 5 sec<br>50° C. 5 sec<br>72° C. 10 sec 30 cycles Z-Taq |
| Amplified fragment | 781 bp | 1000 bp |
| Conditions for screening PCR | 94° C., 5 min<br>98° C., 5 sec<br>55° C., 80 sec 30 cycles Z-Taq | 94° C., 5 min<br>98° C., 5 sec<br>50° C., 5 sec<br>72° C., 10 sec, 30 cycles Z-Taq |
| Conditions for colony PCR | 94° C., 5 min, 1 cycles<br>98° C., 5 sec<br>55° C., 80 sec, 50 cycles Z-Taq | 94° C., 5 min<br>98° C., 5 sec<br>50° C., 10 sec<br>72° C., 20 sec, 50 cycles Z-Taq |

TABLE 6

| Gene | acn | icd | lpd |
| --- | --- | --- | --- |
| 5' → 3' Primer | GTIGGIACIGAYTCSCATAC (55) | GACATTTCACTCGCTGGACG (57) | ATCATCGCAACCGGTTC (59) |
| 3' → 5' Primer | GCIGGAGAIATGTGRTCIGT (56) | CCGTACTCTTCAGCCTTCTG (58) | CGTCACCGATGGCGTAAAT (60) |
| PCR conditions for obtaining partial fragment | 94° C., 1 min<br>96° C., 20 sec<br>45° C., 1 min<br>68° C., 2 min, 30 cycles EX-Taq | 94° C., 5 min<br>98° C., 5 sec<br>55° C., 80 sec, 30 cycles Z-Taq | 94° C., 5 min<br>98° C., 5 sec<br>50° C., 10 sec<br>72° C., 20 sec, 30 cycles Z-Taq |
| Amplified fragment | 1500 bp | 1500 bp | 500 bp |
| Conditions for screening PCR and colony PCR | Same as above | Same as above | 94° C., 5 min<br>94° C., 30 sec<br>57° C., 1 min<br>72° C., 1 min, 30 cycles Ex-Taq |
| Screening PCR 5' → 3' Primer | | | TACGAGGAGCAGATCCTCAA (63) |
| 3' → 5' Primer | | | TTGACGCCGGTGTTCTCCAG (64) |
| Gene | acn | icd | Lpd |
| LA cloning (N') 3' → 5' Primer | S1: GGTGAAGCTAAGTAGTTAGC (65)<br>S2: AGCTACTAAACCTGCACC (66) | S1: CCGTACTCTTCAGCCTTCTG (67)<br>S2: TCGTCCTTGTTCCACATC (68) | S1: ATCATCGCAACCGGTTC (69)<br>S2: TACGAGGAGCAGATCCTCAA (70) |
| LA Cloning (C') 5' → 3' Primer | S1: GCTAACTACTTAGCTTCACC (71)<br>S2: GAACCAGGAACTATTGAACC (72) | S1: TCCGATGTCATCATCGAC (73)<br>S2: ATGTGGAACAAGGACGAC (74) | |
| Restrictione enzyme | PstI(N') HindIII(C') | SalI(N') PstI(C') | HindIII |
| Conditions for LA cloning | N' 94° C., 1 min<br>94° C., 30 sec<br>57° C., 2 min<br>72° C., 2 min, 30 cycles LA-Taq<br>C' 94° C., 1 min<br>94° C., 30 sec<br>57° C., 2 min<br>72° C., 2.5 min, 30 cycles LA-Taq | 94° C., 1 min<br>94° C., 30 sec<br>57° C., 2 min<br>72° C., 2.5 min, 30 cycles LA-Taq | 94° C., 1 min<br>94° C., 30 sec<br>57° C., 2 min<br>72° C., 1 min, 30 cycles LA-Taq |

TABLE 7

| Gene | odhA |
| --- | --- |
| 5'→3' Primer | ACACCGTGGTCGCCTCAACG (61) |
| 3'→5' Primer | TGCTAACCCGTCCCACCTGG (62) |
| PCR conditions for obtaining partial fragment | 94° C., 5 min<br>98° C., 5 sec<br>66° C., 2 sec, 30 cycles Z-Taq |
| Amplified fragment | 1306 bp |
| LA cloning (N') 5'→3' Primer | S1: GTACATATTGTCGTTAGAACGCGTAATACGACTCA (75)<br>S2: |

TABLE 7-continued

| Gene | odhA | |
|---|---|---|
| | CGTTAGAACGCGTAATACGACTCACTATAGGGAGA (76) | |
| Restriction | XbaI | |
| Conditions for | First time | 94° C., 30 sec |
| LA cloning | | 55° C., 2 min |
| | | 72° C., 1 min 30 cycles |
| | | LA-Taq |
| | Second time | 94° C., 1 min |
| | | 98° C., 20 sec |
| | | 68° C., 15 min, 30 cycles |
| | | 72° C. 10 min |
| | | LA-Taq |

<3> Screening of Plasmid Library by PCR

A clone containing a target gene was selected from the plasmid library by PCR. Sixty colonies were picked up from each plasmid library, and replicated onto two LB agar medium plates. The 60 colonies of each plate were combined, inoculated to a test tube containing 4 ml of LB liquid medium and cultured for 15 hours. Then, a plasmid mixture was respectively obtained by using a plasmid DNA extraction kit produced by Promega. By using this plasmid mixture as a template and primers for screening prepared for each target gene, PCR was performed with the conditions shown as "conditions for screening PCR" in each table to select a clone from which a DNA fragment of the same size as that obtained by PCR using chromosomal DNA as a template had been amplified.

The nucleotide sequence of the amplified DNA fragment was determined by using a Big Dye dye terminator cycle sequencing kit produced by Perkin-Elmer, and investigating its homology to known gene information to determine if the target gene was obtained or not.

As for lpd, since any DNA fragment was not amplified with the primers produced in <2>, other primers for screening were prepared based on the determined nucleotide sequence.

<4> Selection of Clone Harboring Target Gene by Colony PCR

By using a plate that was an origin of a plasmid mixture for which amplification of the target gene fragment was confirmed, colony PCR was performed to select a clone containing the gene fragment. The colony PCR was performed with the conditions shown in Tables 2–7.

Plasmid DNA was collected from a selected transformant and the nucleotide sequence of the inserted DNA fragment was determined. When the full length of the target gene was not inserted in the inserted DNA fragment, and a upstream region, downstream region or the both were deleted, primers were prepared based on the determined nucleotide sequence, with which a gene fragment comprising the nucleotide sequence of the target gene in its full length was obtained by using TaKaRa LA PCR in vitro Cloning Kit (Takara Shuzo). Then, its nucleotide sequence was determined.

The outline of LA PCR cloning was as follows. Two kinds of primers each having one of the nucleotide sequences of two regions of the inserted DNA fragment were produced. Chromosomal DNA of *Corynebacterium thermoaminogenes* AJ12310 strain was digested with various restriction enzymes, and ligated to a cassette primer corresponding to each of the restriction enzymes. By using this as a template, PCR was performed with a primer (S1) corresponding to a position distant from the deletion region and a cassette primer (C1) corresponding to a position outside the cassette primer among the prepared primers. Then, another PCR was performed with a primer (S2) corresponding to a position near the deletion region and a cassette primer (C2) corresponding to a position inside the cassette primer among the prepared primers. In this way, a DNA fragment containing the deleted region was obtained. By ligating the obtained DNA fragment with the already obtained DNA fragment, a DNA fragment containing the target gene in full length could be obtained. Since 5' end of the cassette did not have a phosphate group, a nick was formed at the ligation site of the 3' end of the DNA fragment and the 5' end of the cassette. Therefore, the DNA synthesis from the primer C1 stopped at this ligation site in the first PCR, and thus non-specific amplification did not occur. Therefore, specific amplification could be attained.

The primers and the reaction conditions used for the LA PCR cloning are shown in Tables 2–7. In the tables, the primers mentioned with "(N')" are primers used for the cloning of an upstream deleted portion, and the primers mentioned with "(C')" are primers used for the cloning of a downstream deleted portion. PCR was performed twice according to the instruction attached to the LA PCR cloning kit. Among the primers mentioned in the tables, the primers (S1) used for the first reaction are shown in the upper row, and the primers. (S2) used for the second reaction are shown in the lower row.

The nucleotide sequences of the DNA fragments containing each gene obtained as described above were determined in the same manner as mentioned above. Those nucleotide sequences and amino acid sequences that can be encoded by those nucleotide sequences are shown in SEQ ID NOS: 1–34. The sequences shown with the sequence numbers are summarized in Explanation of Sequence Listing mentioned hereinafter.

As for scrB, any open reading frame was not found. Since the *Corynebacterium thermoaminogenes* AJ12310 strain did not have the invertase activity and did not have sucrose assimilating property, an scrB gene fragment was obtained in a similar manner from. *Corynebacterium thermoaminogenes* AJ12340 and AJ12309 strains having the sucrose assimilating property. As a result, a DNA fragment having an open reading frame was obtained from the both strains.

EXAMPLE 2

Acquisition of gdh and gltA Gene

<1> Investigation of GDH Activity of *Corynebacterium thermoaminogenes*

Cells of a wild strain of *Corynebacterium thermoaminogenes*, the AJ12310 strain, was grown on CM-2B agar medium (1 g/dl of yeast extract (produced by Difco), 1 g/dl of polypeptone (produced by Nippon Seiyaku), 0.5 g/dl of NaCl, 10 μg/dl of biotin, 1.5 g/dl of agar, adjusted to pH 7.0 with KOH). The cells were inoculated to a 500-ml volume flask containing 20 ml of a medium for flask having the following composition and cultured at 37° C. for 17 hours (until the residual sugar reached about 1 g/dl).

Similarly, cells of the 2256 strain (ATCC13869) of *Brevibacterium lactofermentum* grown on CM-2B agar medium were cultured at 31.5° C. for 17 hours.

| [Medium for flask] | |
|---|---|
| Glucose | 3 g/dl |
| $KH_2PO_4$ | 0.1 g/dl |
| $MgSO_4.H_2O$ | 0.04 g/dl |
| $FeSO_4.7H_2O$ | 1 mg/dl |
| $MnSO_4.4H_2O$ | 1 mg/dl |
| Vitamin $B_1$-HCl | 200 μg/L |
| Biotin | 50 μg/L |
| $(NH_4)_2SO_4$ | 1.5 g/dl |

Soybean protein hydrolysis solution 48 mg/dl (Memeno (T-N)

$CaCO_3$ (Official regent) 5 g/dl (separately sterilized) pH 8.0 (adjusted with KOH)

About 1 ml of the above culture medium was centrifuged at 1000 rpm for 1 minute to remove $CaCO_3$, and the cells were washed twice with 200 mM K-phosphate buffer (pH 6.9) and suspended in 300 μl of the same buffer. The obtained cell suspension was sonicated for 5 minutes to disrupt the cells, centrifuged at 1000 rpm for 30 minutes to obtain a crude enzyme solution as the supernatant.

The optimum reaction temperature and the thermal stability of GDH activity were investigated using the aforementioned crude enzyme solution. The measurement of GDH activity was performed by adding the crude enzyme solution to a reaction mixture (100 mM Tris-HCl (pH 8.0), 20 mM $NH_4Cl$, 10 mM sodium a-ketoglutarate, 0.25 mM NADPH) and measuring change of absorbance at 340 nm. The protein concentration of the crude enzyme solution was quantified by the Bradford method (Bio-Rad Protein Assay Kit was used) using bovine serum albumin as the standard through measurement of absorbance at 595 nm. The absorbance was measured by using HITACHI U-2000 (produced by Hitachi).

The GDH activity measured at various reaction temperatures is shown in FIG. 1. While the ATCC13869 strain showed the highest specific activity of GDH around 37° C. and the activity markedly decreased around 42° C., the AJ12310 strain showed the highest specific activity around 42° C. and it showed the activity even at 45° C.

Figure 2:
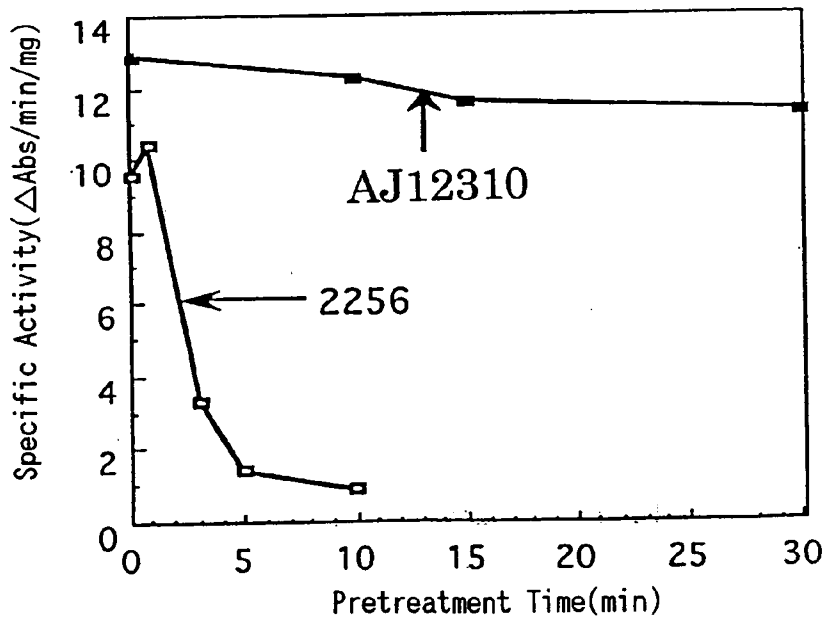
FIG. 2 shows thermal stability of glutamate dehydrogenases derived from the AJ12310 strain and the 2256 strain.

Then, the thermal stability of GDH was investigated. The crude enzyme solution was left at 65° C. for 0 to 30 minutes before the reaction, and then the enzyme activity was measured at 30° C. The results are shown in FIG. 2. As clearly seen from the results, while GDH of the ATCC13869 strain was inactivated by the heat treatment for 5 minutes, GDH of the AJ12310 strain maintained the activity even after the heat treatment for 30 minutes. In addition, the crude enzyme solution of the AJ12310 strain showed substantially no change in the GDH activity even after the heat treatment at 65° C. for 90 minutes (data are not shown).

<2> Examination of CS Activity of *Corynebacterium thermoaminogenes*

The optimum reaction temperature and thermal stability of CS were investigated by using crude enzyme solutions prepared from the cells of the *Corynebacterium thermoaminogenes* AJ12310 strain and the *Brevibacterium lactofermentum* ATCC13869 strain in the same manner as in Example 1. The measurement of CS activity was performed by adding each crude enzyme solution to a reaction mixture (100, mM Tris-HCl (pH 8.0), 0.1 mM DTNB (5,5'-dithiobis-(2-nitrobenzoic acid)), 200 mM sodium L-glutamate, 0.3 mM acetyl CoA), and measuring change of the absorbance at 412 nm.

Figure 3:
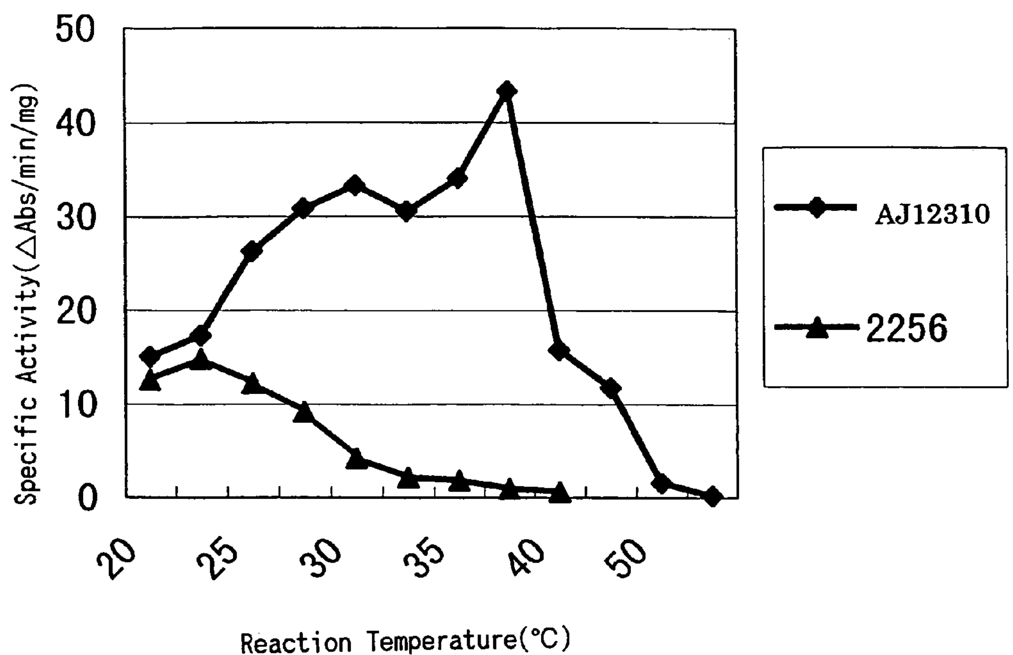
FIG. 3 shows variation with temperature in activity of citrate synthases derived from the AJ12310 strain and the 2256 strain.

The CS activity measured at various reaction temperatures is shown in FIG. 3. The ATCC13869 strain showed the highest specific activity of CS around 23° C. and the activity markedly decreased around 33° C. However, the AJ12310 strain showed high specific activity in a reaction temperature-dependent manner up to around 37° C. and it showed the activity even at 40° C. in a degree corresponding to about 40% of the activity at 37° C.

Figure 4:
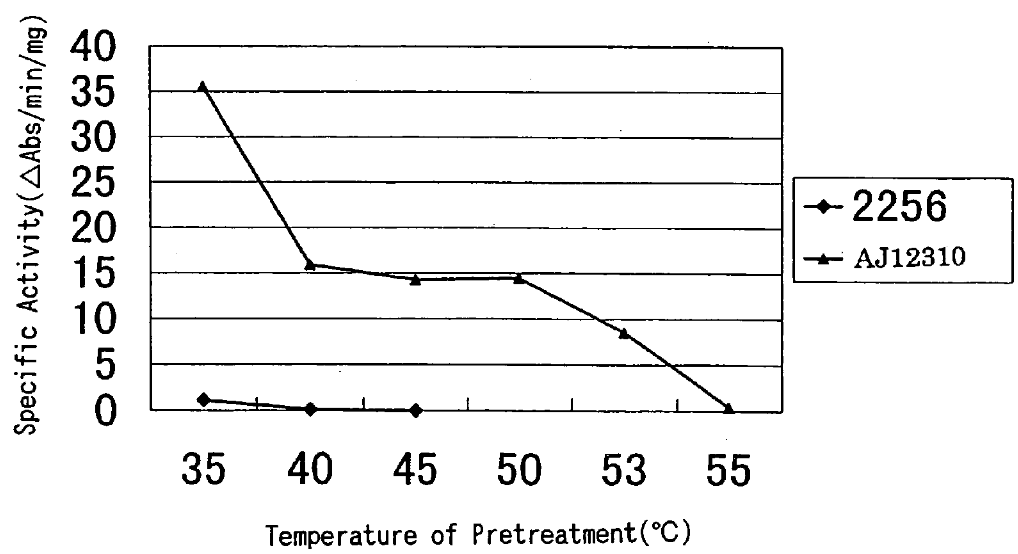
FIG. 4 shows thermal stability of citrate synthases derived from the AJ12310 strain and the 2256 strain.

Then, thermal stability of CS was investigated. The crude enzyme solution was left at 33–55° C. for 5 minutes before the reaction, and then the enzyme activity was measured at 30° C. The results are shown in FIG. 4. Whereas CS of the ATCC13869 strain was inactivated by the heat treatment at 35–40° C., CS of the AJ12310 strain maintained about 40% of the activity even after the heat treatment at 50° C.

<3> Acquisition of gdh Gene of *Corynebacterium thermoaminogenes*

The already reported nucleotide sequences of gdh gene of various microorganisms were compared. A region in which nucleotide sequences were well conserved was selected, and primers having the nucleotide sequences shown in SEQ ID NOS: 77 and 78 were prepared based on the nucleotide sequence of the region.

PCR was performed by using chromosomal DNA prepared from the *Corynebacterium thermoaminogenes* AJ12310 strain using Bacterial Genome DNA Purification Kit (produced by Advanced Genetic Technologies) as a template and the aforementioned primers. Based on the obtained DNA fragment, genome walking was performed by using TaKaRa LA PCR in vitro Cloning Kit (produced by Takara Shuzo) to obtain the whole gdh gene, of which whole nucleotide sequence was determined. The result is shown in SEQ ID NO: 79. Further, the amino acid sequence deduced from this nucleotide sequence is shown in SEQ ID NO: 80.

The gdh gene of the *Brevibacterium lactofermentum* ATCC13869 strain was obtained in a similar manner, and its nucleotide sequence was determined. The result is shown in SEQ ID NO: 81. The amino acid sequence encoded by this nucleotide sequence is shown in SEQ ID NO: 82.

Homology was investigated for the nucleotide sequences of the gdh gene and the amino acid sequences of GDH of the *Corynebacterium thermoaminogenes* AJ12310 strain and the *Brevibacterium lactofermentum* ATCC13869 strain determined as described above, and the known gdh gene and amino acid sequence of GDH of the *Corynebacterium glutamicum* (*C. glutamicum*) ATCC13032 strain (Molecular Microbiology 6, 317–326 (1992)). The results are shown in Table 8 (for nucleotide sequences) and Table 9 (for amino acid sequences).

TABLE 8

| | Homology of nucleotide sequences of various gdh genes | | |
|---|---|---|---|
| | ATCC13869 | ATCC13032 | AJ12310 |
| ATCC13869 | — | 94.5% | 82.4% |
| ATCC13032 | — | — | 78.1% |
| AJ12310 | — | — | — |

TABLE 9

| | Homology of amino acid sequences of various GDH | | |
|---|---|---|---|
| | ATCC13869 | ATCC13032 | AJ12310 |
| ATCC13869 | — | 90.8% | 91.7% |
| ATCC13032 | — | — | 83.4% |
| AJ12310 | — | — | — |

<4> Acquisition of gltA gene of *Corynebacterium thermoaminogenes*

The already reported nucleotide sequences of gltA gene of various microorganisms were compared. A region in which nucleotide sequences were well conserved was selected, and primers having the nucleotide sequences shown in SEQ ID NOS: 83 and 84 were prepared based on the nucleotide sequence of the region.

PCR was performed by using chromosomal DNA prepared from the *Corynebacterium thermoaminogenes* AJ12310 strain (FERM BP-1542) using Bacterial Genome DNA Purification Kit (produced by Advanced Genetic Technologies) as a template and the aforementioned primers 7 and 8, and the nucleotide sequence of the amplified nucleotide sequence of about 0.9 kb was determined.

On the basis of the obtained nucleotide sequence of gltA gene of *Corynebacterium glutamicum* (Microbiol., 140, 1817–1828 (1994)), the primers of SEQ ID NOS: 85, 86, 87 and 88 were prepared. PCR was performed in a manner similar to the above by using chromosomal DNA of AJ12310 as a template and the primers of SEQ ID NOS: 85, 86, 87 and 88, and the nucleotide sequence of the amplified DNA fragment was specified to determine the whole nucleotide sequence of the gltA gene. The result is shown in SEQ ID NO: 89. Further, an amino acid sequence expected from this nucleotide sequence is shown in SEQ ID NO: 90.

The gltA gene of the *Brevibacterium lactofermentum* 2256 strain was obtained in a similar manner, and its nucleotide sequence was determined. The result is shown in SEQ ID NO: 91. The amino acid sequence encoded by this nucleotide sequence is shown in SEQ ID NO: 92.

Homology was investigated for the nucleotide sequences of the gltA gene and the amino acid sequences of CS of the *Corynebacterium thermoaminogenes* AJ12310 strain and the *Brevibacterium lactofermentum* ATCC13032 strain determined as described above, and the known gltA gene and amino acid sequence of CS of the *Corynebacterium glutamicum* ATCC13032 strain (*Microbiol.,* 140, 1817–1828 (1994)). The results are shown in Table 10 (for nucleotide sequences) and Table 11 (for amino acid sequences).

TABLE 10

| | Homology of nucleotide sequences of various gltA genes | | |
|---|---|---|---|
| | ATCC13869 | ATCC13032 | AJ12310 |
| ATCC13869 | — | 99.5% | 85.7% |
| ATCC13032 | — | — | 85.6% |
| AJ12310 | — | — | — |

TABLE 11

| | Homology of amino acid sequences of various CS | | |
|---|---|---|---|
| | ATCC13869 | ATCC13032 | AJ12310 |
| ATCC13869 | — | 99.3% | 92.1% |
| ATCC13032 | — | — | 92.1% |
| AJ12310 | — | — | — |

EXAMPLE 3

Acquisition of scrB Gene of *Corynebacterium thermoaminogenes*

Since an scrB gene fragment was obtained from the *Corynebacterium thermoaminogenes* AJ12309 strain as shown in Example 1, it was attempted to obtain the total sequence of the gene. First, a partial fragment was obtained in the same manner as in Example 1 using the primers shown in SEQ ID NO: 45 and SEQ ID NO: 46. These primers were synthesized based on the scrB sequence of the *Brevibacterium lactofermentum* 2256 strain (Japanese Patent Laid-open No. 08-196280/1996).

Separately, chromosomal DNA was prepared from the AJ12309 strain by using Bacterial Genome DNA Purification Kit (Advanced Genetic Technologies Corp.). Sterilized water was added to 0.5 μg of this chromosomal DNA, 50 pmol each of the aforementioned primers, 4 μl of dNTP mixture (2.5 mM each), 5 μl of 10×Z-Taq Buffer (Takara Shuzo) and 2 U of Z-Taq (Takara Shuzo) to prepare a PCR reaction mixture in a total volume of 50 μl. PCR was performed with a cycle of denaturation at 98° C. for 5 seconds, association at 50° C. for 10 seconds and extension reaction at 72° C. for 20 seconds, which was repeated for 30 cycles, by using the above reaction mixture and a thermal cycler GeneAmp PCR System 9600 (PE) to amplify a partial fragment of scrB of about 600 bp.

Then, the total sequence of scrB was determined by using an LA PCR in vitro Cloning Kit (Takara Shuzo). All of the procedure was performed in accordance with the protocol attached to the LA PCR in vitro Cloning Kit. Based on the obtained partial sequence, primers shown in SEQ ID NOS: 97, 98, 99 and 100 were synthesized. For the first PCR reaction for sequencing an upstream region, the primers shown in SEQ ID NOS: 95 and 97 and chromosomal DNA of AJ12309 strain digested with EcoT14I as a template DNA were used. For the second PCR reaction, the primers shown in SEQ ID NOS: 96 and 98 were used. For the first PCR reaction for sequencing a downstream region, the primers shown in SEQ ID NOS: 95 and 99 and chromosomal DNA of AJ12309 strain digested with SalI (Takara Shuzo) as a template DNA were used. For the second PCR reaction, the primers shown in SEQ ID NOS: 96 and 100 were used. By the above procedure, a sequence of a full length of 1656 bp containing ORF of scrB was determined. This nucleotide sequence is shown in SEQ ID NO: 93, and a deduced amino acid sequence is shown in SEQ ID NO: 94.

EXAMPLE 4

Examination of Thermal Stability of Isocitrate Lyase, Phosphofructokinase, Phosphoenolpyruvate Carboxylase, Aconitase, Isocitrate Dehydrogenase and 2-oxoglutarate Dehydrogenase Thermal stability was investigated for the following enzymes derived from *Corynebacterium thermoaminogenes*. In this Example, protein concentrations were measured by the Bradford method (Bio-Rad Protein Assay Kit was used) using bovine serum albumin as a standard protein. Further, measurement of absorbance was performed by using HITACHI U-2000 (Hitachi) unless otherwise indicated.

<1> Isocitrate Lyase

Thermal stability of activity of isocitrate lyase (henceforth also referred to as "ICL") derived from the *Corynebacterium thermoaminogenes* AJ12310 strain and ICL derived from the *Brevibacterium lactofermentum* 2256 strain (ATCC13869) was investigated. For the activity measurement, used were cells of which culture in a medium having the composition mentioned in Table 2 was terminated before all of the carbon source was completely consumed. The method of the activity measurement was one described in Dieter J. Reinscheid et al., *J. Bacteriol.,* 176 (12), 3474 (1994). Specifically, the cells were washed with 50 mM Tris buffer (pH 7.3), suspended in the same buffer, and disrupted by sonication (INSONATOR 201M produced by KUBOTA was used, 200 W, 5 minutes). After the sonication, the suspension was centrifuged (13000×g, 30 minutes) to remove undisrupted cells to prepare a crude enzyme solution.

Figure 5:
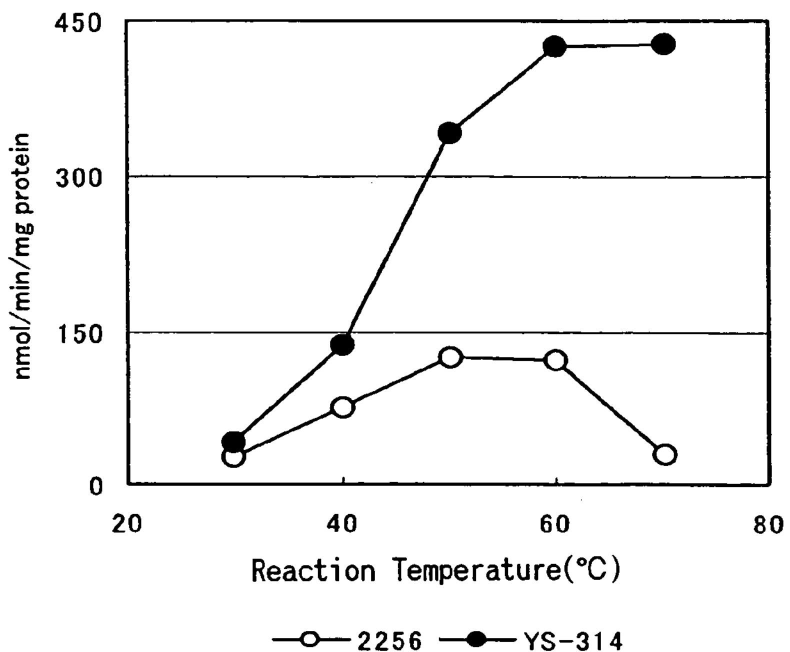
FIG. 5 shows variation with temperature in activity of isocitrate lyases derived from the AJ12310 strain and the 2256 strain.
Figure 6:
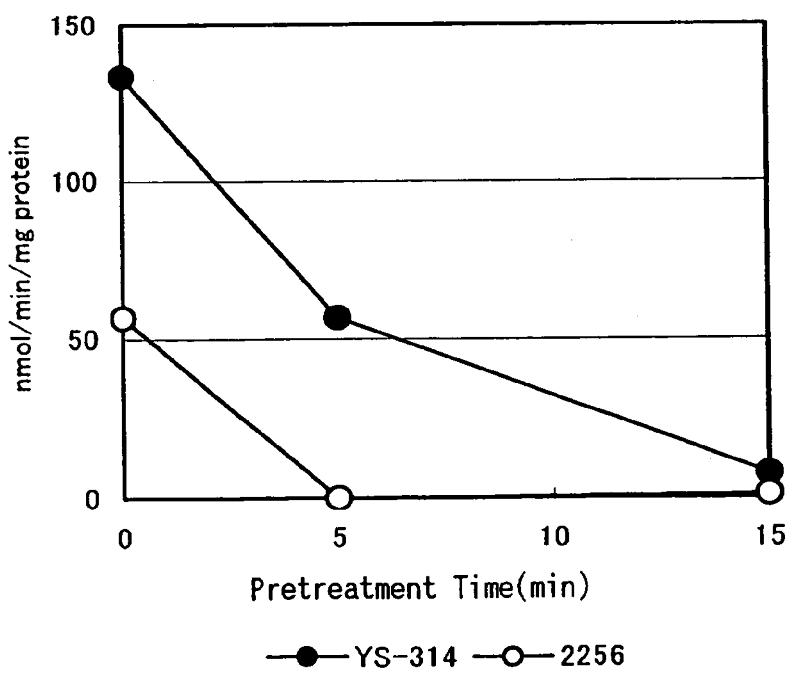
FIG. 6 shows thermal stability of isocitrate lyases derived from the AJ12310 strain and the 2256 strain.

The crude enzyme solution was added to a reaction system containing 50 mM MOPS-NaOH (pH 7.3), 5 mM dithiothreitol, 15 mM $MgCl_2$, 1 mM EDTA, 5 mM D-threo-isocitrate, 0.2 mM NADH and 18 U of LDH (lactate dehydrogenase), and absorbance at 340 nm at various temperatures (30, 40, 50, 60 or 70° C.) was measured by a Hitachi spectrophotometer U-3210. The measurement results for various reaction temperatures were shown in FIG. 5. Further, the crude enzyme solution was pretreated at 50° C. (pretreatment time: 5 minutes or 15 minutes), and the activity was measured at 37° C. The results are shown in FIG. 6.

As a result, ICL of the AJ12310 strain showed the maximum activity at 60° C., whereas ICL of the 2256 strain showed the maximum activity around 50° C. Further, while ICL of the 2256 strain was completely inactivated after the pretreatment for 5 minutes, ICL of the AJ12310 strain maintained half of the activity after the pretreatment for 5 minutes. Thus, the stability of ICL of the AJ12310 strain at high temperatures was confirmed.

TABLE 12

| Composition of medium for ICL activity measurement | |
|---|---|
| Component | Concentration |
| $(NH_4)_2SO_4$ | 5 g/l |
| Urea | 5 g/l |
| $KH_2PO_4$ | 0.5 g/l |
| $K_2HPO_4$ | 0.5 g/l |
| MOPS | 20.9 g/l |
| $MgSO_4.7H_2O$ | 0.25 g/l |
| $CaCl_2.7H_2O$ | 10 mM |
| $CuSO_4.7H_2O$ | 0.2 mg/l |
| Biotin | 0.2 mg/l |
| $MnSO_4.7H_2O$ | 10 mg/l |
| $FeSO_4.7H_2O$ | 10 mg/l |
| $ZnSO_4.7H_2O$ | 1 mg/l |
| Acetic acid | 4% |

<2> Phosphofructokinase

Thermal stability of activity of phosphofructokinase (henceforth also referred to as "PKF") derived from the *Corynebacterium thermoaminogenes* AJ12310 strain and PKF derived from the *Brevibacterium lactofermentum* 2256 strain was investigated. For the activity measurement, used were cells of which culture in a medium having the composition mentioned in Table 13 was terminated before all of the saccharide was completely consumed. The method of the activity measurement was one described in Michiko Mori et al., *Agric. Biol. Chem.,* 51 (10), 2671 (1994). Specifically, the cells were washed with 0.1 M Tris buffer (pH 7.5), suspended in the same buffer, and disrupted by sonication (INSONATOR 201M produced by KUBOTA was used, 200 W, 5 minutes). After the sonication, the suspension was centrifuged (13000×g, 30 minutes) to remove undisrupted cells to obtain a crude enzyme solution.

Figure 7:
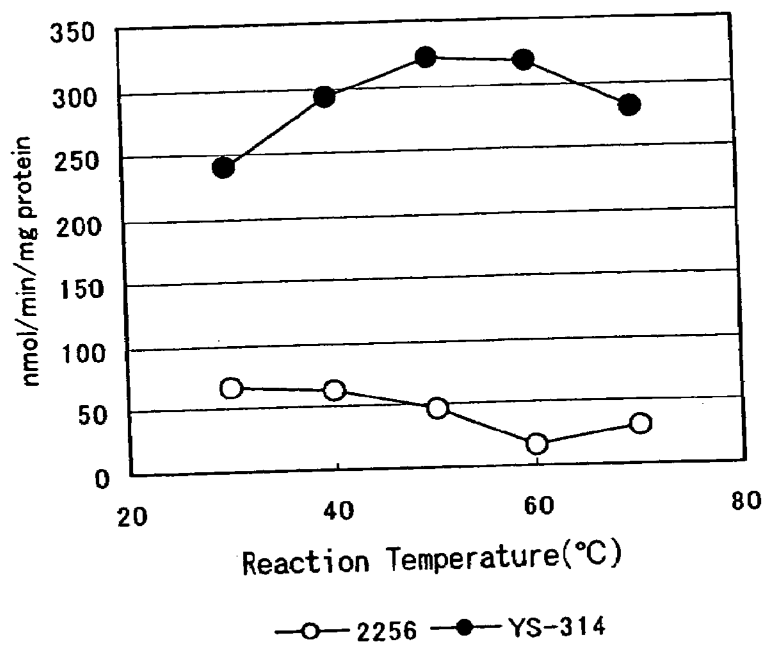
FIG. 7 shows variation with temperature in activity of phosphofructokinases derived from the AJ12310 strain and the 2256 strain.
Figure 8:
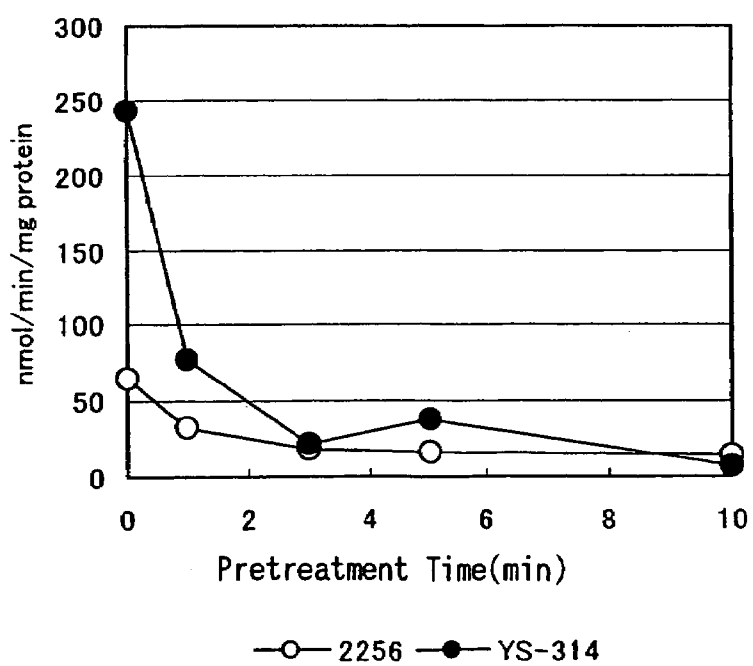
FIG. 8 shows thermal stability of phosphofructokinases derived from the AJ12310 strain and the 2256 strain.

The crude enzyme solution was added to a reaction system containing 100 mM Tris buffer (pH 7.5), 0.2 mM NADH, 10 MM $MgCl_2$, 2 mM $NH_4Cl$, 10 mM KCl, 0.2 mM phosphoenolpyruvic acid, 6.4 mM fructose-6-phosphate, 1 mM ATP and 40 μg of LDH/PK (pyruvate kinase), and absorbance at 340 nm was measured at various temperatures (30, 40, 50, 60 or 70° C.) by a Hitachi spectrophotometer U-3210. The measurement results for various reaction temperatures were shown in FIG. 7. Further, the crude enzyme solution was pretreated at 50° C. (pretreatment time: 1, 3, 5 or 10 minutes), and the activity was measured at 37° C. The results are shown in FIG. 8.

As a result, PKF of the AJ12310 strain showed the maximum activity around 50° C., whereas PKF of the 2256 strain showed the maximum activity around 30° C. Thus, it was confirmed that the optimum temperature of PKF of the AJ12310 strain resided in a high temperature region.

TABLE 13

| Composition of medium for PFK activity measurement | |
|---|---|
| Component | Concentration |
| Polypeptone | 20 g/l |
| Yeast extract | 20 g/l |
| Sodium chloride | 5 g/l |
| Glucose | 20 g/l |

<3> Phosphoenolpyruvate Carboxylase

Thermal stability of activity of phosphoenolpyruvate carboxylase (henceforth also referred to as "PEPC") derived from the *Corynebacterium thermoaminogenes* AJ12310 strain and PEPC of the *Brevibacterium lactofermentum* 2256 strain was examined.

Cells of the AJ12310 strain grown on CM-2B agar medium were inoculated to a 500-ml volume flask containing 20 ml of a medium for flask (8 g/dl of Glucose, 0.1 g/dl of $KH_2PO_4$, 0.04 g/dl of $MgSO_4.H_2O$, 1 mg/dl of $FeSO_4.7H_2O$, 5 mg/dl of $MnSO_4.4H_2O$, 3 g/dl of $(NH_4)_2SO_4$, 48 mg/dl of TN (soybean protein hydrolysis solution), 200 μg/L of vitamin $B_1$, 300 μg/L of biotin, 50 μl/l of GD-113 (antifoaming agent), 5 g/dl of $CaCO_3$ (Official regent, separately sterilized), pH 8.0 (adjusted with KOH)), and cultured at 37° C. Cells of the 2256 strain grown on CM-2B agar medium were similarly cultured at 31.5° C.

The above culture broth in which the cells were grown to the logarithmic growth phase was centrifuged at 1000 rpm for 1 minute to remove $CaCO_3$, and the cells were washed 3 times with washing buffer (100 mM Tris/HCl pH 8.0, 10 mM $MgSO_4$, 1 mM DTT, 20% glycerol), sonicated to disrupt the cells, and centrifuged at 15 krpm for 10 minutes to remove cell debris. The supernatant was further centrifuged at 60 krpm for 1 hour to obtain a crude enzyme solution as the supernatant.

By using the above crude enzyme solution, optimum reaction temperature and thermal stability of the PEPC activity were investigated. The measurement of PEPC activity was performed by adding the crude enzyme solution to a reaction mixture (100 mM $Tris/H_2SO_4$ (pH 8.5), 5 mM phosphoenolpyruvic acid, 10 MM $KHCO_3$, 0.1 mM acetyl-CoA, 0.15 mM NADH, 10 mM $MgSO_4$, 10 U of malate dehydrogenase, 0.1 mM DTT), and measuring change of the absorbance at 340 nm in 800 μl of reaction volume.

Figure 9:
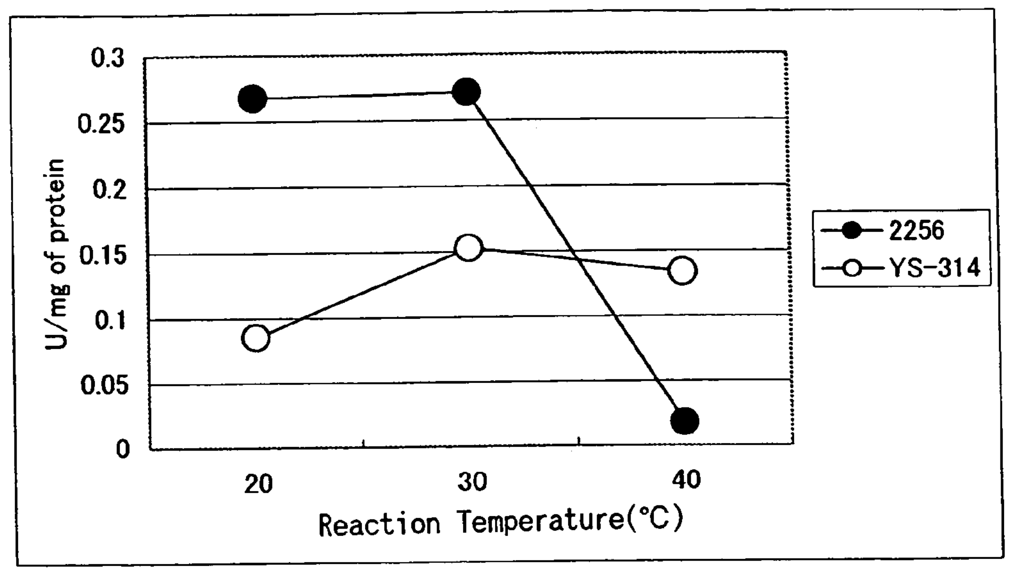
FIG. 9 shows variation with temperature in activity of phosphoenolpyruvate carboxylases derived from the AJ12310 strain and the 2256 strain.

The PEPC activity measured at various reaction temperatures is shown in FIG. 9. While the activity of the 2256 strain markedly decreased at 40° C., the AJ12310 strain showed substantially no decrease of the activity even at 40° C.

Figure 10:
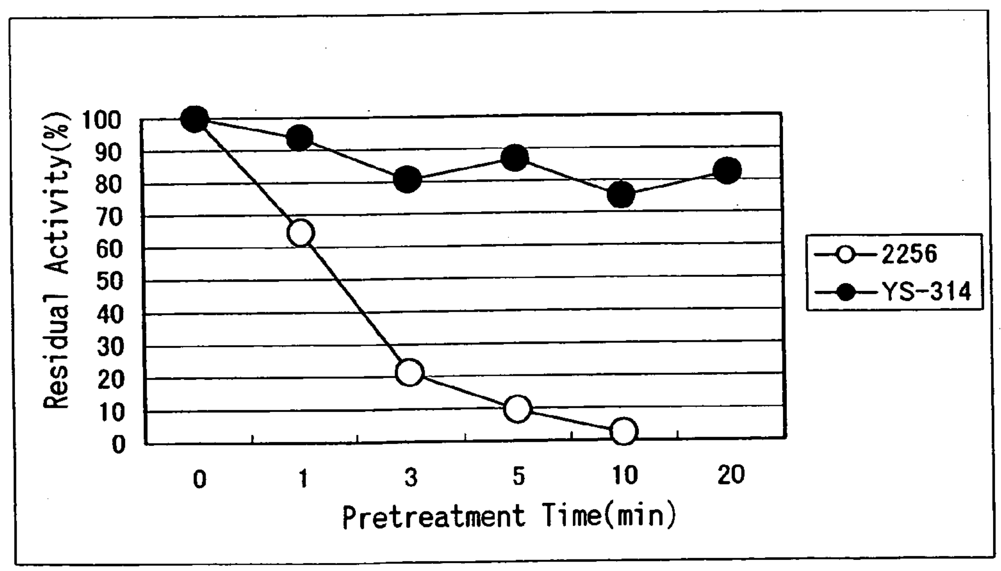
FIG. 10 shows thermal stability of phosphoenolpyruvate carboxylases derived from the AJ12310 strain and the 2256 strain.

Then, the thermal stability of PEPC was investigated. The crude enzyme solution was left at 45° C. for 0–20 minutes before the reaction, and then the enzyme activity was measured at 20° C. The results are shown in FIG. 10. As clearly seen from the results, whereas the PEPC activity of the 2256 strain was substantially lost after the heat treatment for 10 minutes, PEPC of the AJ12310 strain maintained the activity even after the heat treatment for 20 minutes.

These results demonstrated the stability of PEPC of the AJ12310 strain at a high temperature.

<4> Aconitase

Aconitase (henceforth also referred to as "ACN") derived from the *Corynebacterium thermoaminogenes* AJ12310 strain and ACN derived from the *Brevibacterium lactofermentum* 2256 strain were measured, and thermal stability thereof was examined.

Cells of the AJ12310 strain grown on CM-2B agar medium were inoculated to a 500-ml volume flask containing 20 ml of a medium for flask having the same composition as mentioned in <3>, and cultured at 37° C. Cells of the 2256 strain grown on CM-2B agar medium were similarly cultured at 31.5° C.

The above culture broth in which the cells were grown to the logarithmic growth phase was centrifuged at 1000 rpm for 1 minute to remove $CaCO_3$, and the cells were washed 3 times with 50 mM Tris/HCl pH 7.5, sonicated to disrupt the cells, and centrifuged at 15 krpm for 10 minutes to obtain a crude enzyme solution as the supernatant.

By using the above crude enzyme solution, optimum reaction temperature and thermal stability of ACN activity were investigated. The measurement of ACN activity was performed by adding the crude enzyme solution to a reaction mixture (20 mM Tris/HCl (pH7.5), 50 mM NaCl, 20 mM isocitrate.3Na), and measuring change of the absorbance at 240 nm in 800 μl of reaction volume.

Figure 11:
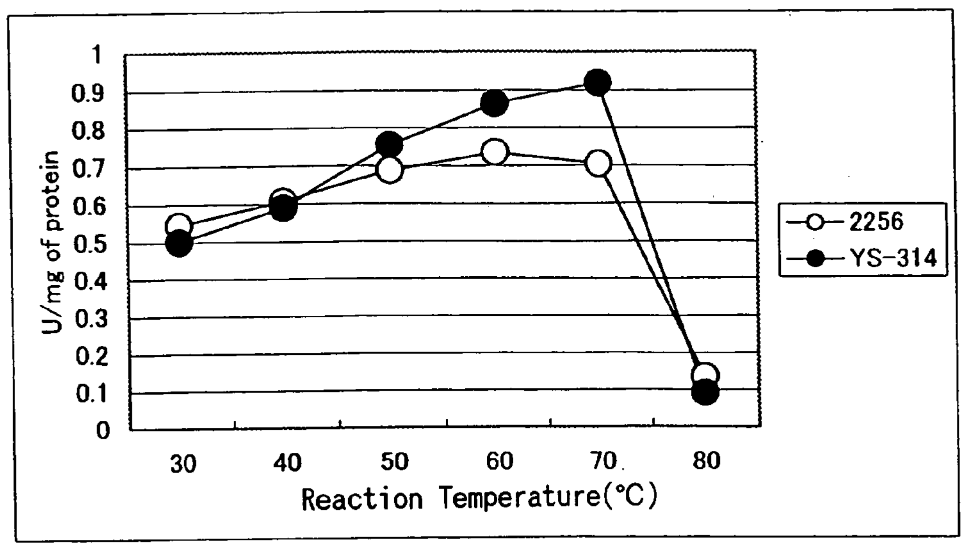
FIG. 11 shows variation with temperature in activity of aconitases derived from the AJ12310 strain and the 2256 strain.

The ACN activity measured at various reaction temperatures is shown in FIG. 11. The AJ12310 strain showed higher activity at a higher temperature compared with the 2256 strain.

Figure 12:
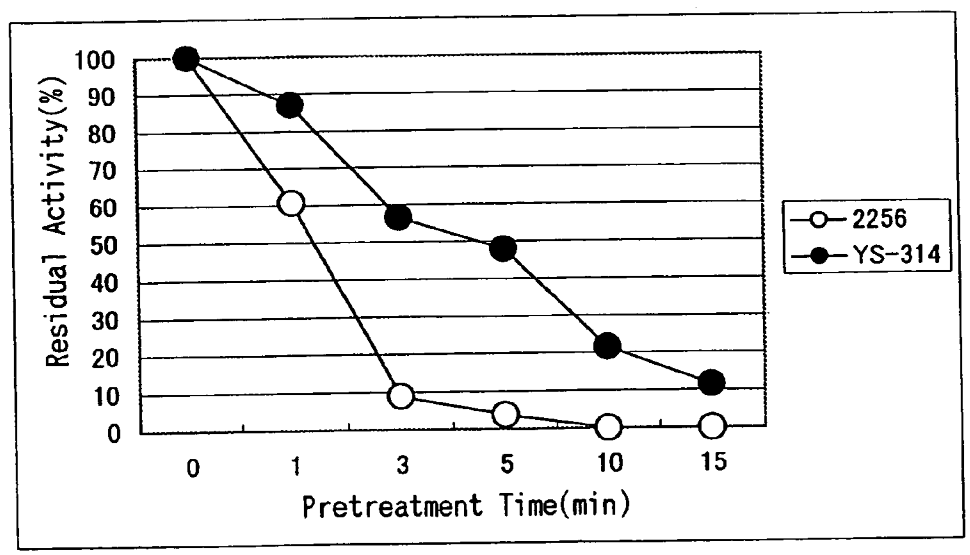
FIG. 12 shows thermal stability of aconitases derived from the AJ12310 strain and the 2256 strain.

Then, the thermal stability of ACN was investigated. The crude enzyme solution was left at 50° C. for 0–15 minutes before the reaction, and then the enzyme activity was measured at 30° C. The results are shown in FIG. 12. As clearly seen from the results, ACN of the AJ12310 strain showed less activity decrease due to the heat treatment compared with ACN of the 2256 strain.

These results demonstrated the stability of ACN of the AJ12310 strain at a high temperature.

<5> Isocitrate Dehydrogenase

Thermal stability of activity of isocitrate dehydrogenase (henceforth also referred to as "ICDH") derived from the *Corynebacterium thermoaminogenes* AJ12310 strain and ICDH derived from the *Brevibacterium lactofermentum* 2256 strain was examined.

Cells of the AJ12310 strain grown on CM-2B agar medium were inoculated to a 500-ml volume flask containing 20 ml of a medium for flask having the same composition as mentioned in <3>, and cultured at 37° C. Cells of the 2256 strain grown on CM-2B agar medium were similarly cultured at 31.5° C.

The above culture broth in which the cells were grown to the logarithmic growth phase was centrifuged at 1000 rpm for 1 minute to remove $CaCO_3$, and the cells were washed 3 times with 50 mM Tris/HCl pH 7.5, sonicated to disrupt the cells, and centrifuged at 15 krpm for 10 minutes to obtain a crude enzyme solution as the supernatant.

By using the above crude enzyme solution, optimum reaction temperature and thermal stability of ICDH activity were investigated. The measurement of ICDH activity was performed by adding the crude enzyme solution to a reaction mixture (35 mM Tris/HCl, 0.35 mM EDTA (pH 7.5), 1.5 mM $MnSO_4$, 0.1 mM NADP, 1.3 mM isocitrate.3Na), and measuring change of the absorbance at 340 nm in 800 μl of reaction volume.

Figure 13:
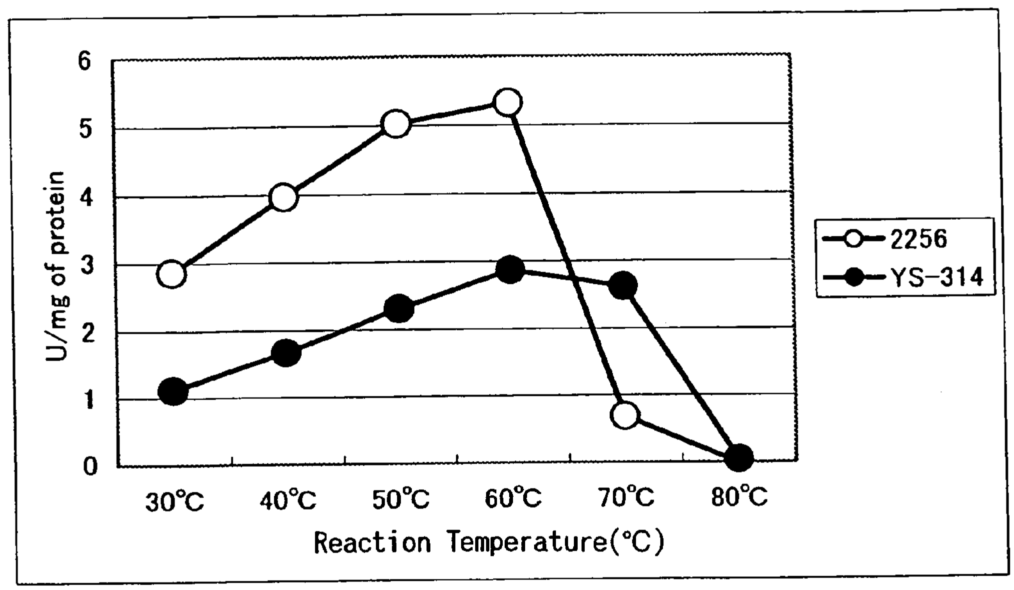
FIG. 13 shows variation with temperature in activity of isocitrate dehydrogenases derived from the AJ12310 strain and the 2256 strain.

The ICDH activity measured at various reaction temperatures is shown in FIG. 13. While the activity of the 2256 strain markedly decreased at 70° C., substantially no activity decrease was observed even at 70° C. for the AJ12310 strain.

Figure 14:
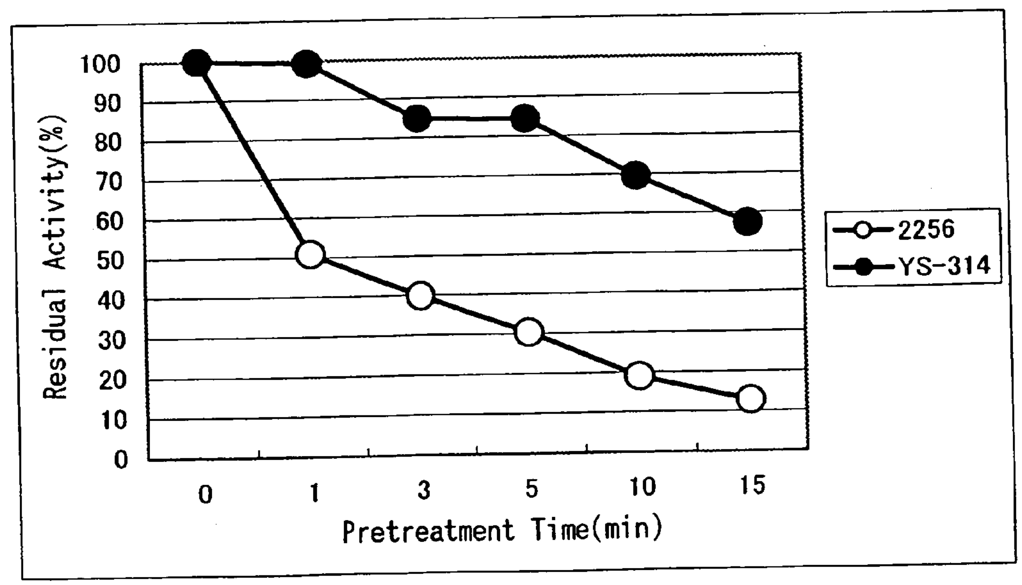
FIG. 14 shows thermal stability of isocitrate dehydrogenases derived from the AJ12310 strain and the 2256 strain.

Then, the thermal stability of ICDH was investigated. The crude enzyme solution was left at 45° C. for 0–15 minutes before the reaction, and then the enzyme activity was measured at 30° C. The results are shown in FIG. 14. As clearly seen from the results, while only about 15% of residual activity was observed after the heat treatment for 15 minutes for the 2256 strain, about 60% of residual ICDH activity was observed for the AJ12310 strain.

These results demonstrated the stability of ICDH of the AJ12310 strain at a high temperature.

<6> 2-Oxoglutarate dehydrogenase

2-Oxoglutarate dehydrogenase (henceforth also referred to as "ODHC") derived from the *Corynebacterium thermoaminogenes* AJ12310 strain and ODHC derived from the *Brevibacterium lactofermentum* 2256 strain were measured, and thermal stability thereof was examined.

For the activity measurement, used were cells of which culture in a medium having the composition mentioned in Table 14 was terminated before all of the saccharide was completely consumed. The method of the activity measurement was one described in Isamu Shiio et al., Agric. Biol. Chem., 44 (8), 1897 (1980). Specifically, the cells were washed with 0.2% potassium chloride, suspended in 100 mM TES-NaOH (pH 7.5), 30% glycerol solution, and disrupted by sonication (INSONATOR 201M produced by KUBOTA was used, 200 W, 5 minutes). After the disruption by sonication, the suspension was centrifuged (13000×g, 30 minutes) to remove undisrupted cells, and subjected to gel filtration using the same buffer and Sephadex-G25 to prepare a crude enzyme solution.

Figure 15:
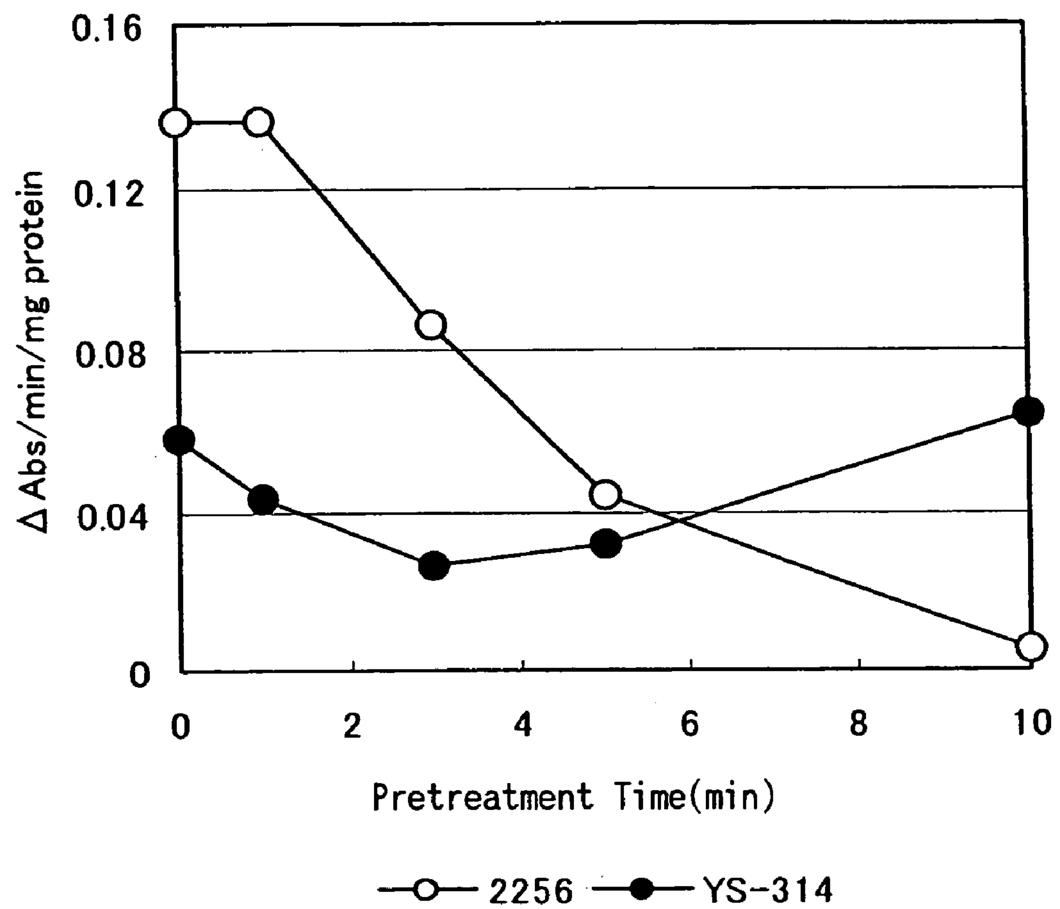
FIG. 15 shows thermal stability of 2-oxoglutarate dehydrogenases derived from the AJ12310 strain and the 2256 strain.

The crude enzyme solution was added to a reaction system containing 100 mM TES-NaOH (pH 7.7), 5 mM $MgCl_2$, 0.2 mM Coenzyme A, 0.3 mM cocarboxylase, 1 mM α-ketoglutaric acid, 3 mM L-cysteine and 1 mM acetylpyridine-adenine dinucleotide, and absorbance at 365 nm was measured at various temperatures (30, 40, 50, 60 or 70° C.) by a Hitachi spectrophotometer U-3210. The crude enzyme solution was pretreated at 50° C. (pretreatment time: 1, 3, 5 or 10 minutes), and the activity was measured at 37° C. The results are shown in FIG. 15.

As a result, while ODHC of the 2256 strain was completely inactivated by the pretreatment for 10 minutes, ODHC of the AJ12310 strain showed substantially constant activity irrespective of the pretreatment time, and thus its stability against high temperature treatment was confirmed.

TABLE 14

Composition of medium for ODHC activity measurement

| Component | Concentration |
|---|---|
| Glucose | 80 g/l |
| $KH_2PO_4$ | 1 g/l |
| $MgSO_4.7H_2O$ | 0.4 g/l |
| $FeSO_4.7H_2O$ | 0.01 g/l |
| $MnSO_4.7H_2O$ | 0.05 g/l |
| $(NH_4)_2SO_4$ | 30 g/l |
| Soybean protein hydrolysate | 480 mg/l |
| Thiamin hydrochloride | 200 μg/l |
| Biotin | 300 μg/l |

EXAMPLE 5

Impartation of Sucrose Assimilating Ability by Gene Transfer of scrB Gene

Since the *Corynebacterium thermoaminogenes* AJ12310 strain did not have invertase activity and sucrose assimilating property, it was investigated if sucrose assimilating ability could be imparted to it by transferring the scrB gene of the AJ12309 strain to the strain.

<1> Production of Plasmid Carrying scrB Derived from *Corynebacterium thermoaminogenes* AJ12309 Strain To obtain an scrB gene fragment, the primers shown in SEQ ID NOS: 101 and 102 were synthesized, of which both ends were ligated with SmaI sequences, based on the nucleotide sequence shown in SEQ ID NO: 93. Sterilized water was added to 0.5 μg of chromosomal DNA of the 12309 strain, 50 pmol each of the aforementioned oligonucleotides, 4 μl of dNTP mixture (2.5 mM each), 5 μl of 10×Pyrobest Buffer (Takara Shuzo) and 2 U of Pyrobest polymerase (Takara Shuzo) to prepare a PCR reaction mixture in a total volume of 50 μl. PCR was performed with a cycle of denaturation at 98° C. for 10 seconds, association at 55° C. for 30 seconds and extension reaction at 72° C. for 2 minutes, which was repeated for 30 cycles, by using the above reaction mixture and a thermal cycler GeneAmp PCR System 9600 (PE) to amplify a fragment of about 1.7 kb containing scrB ORF.

Figure 16:
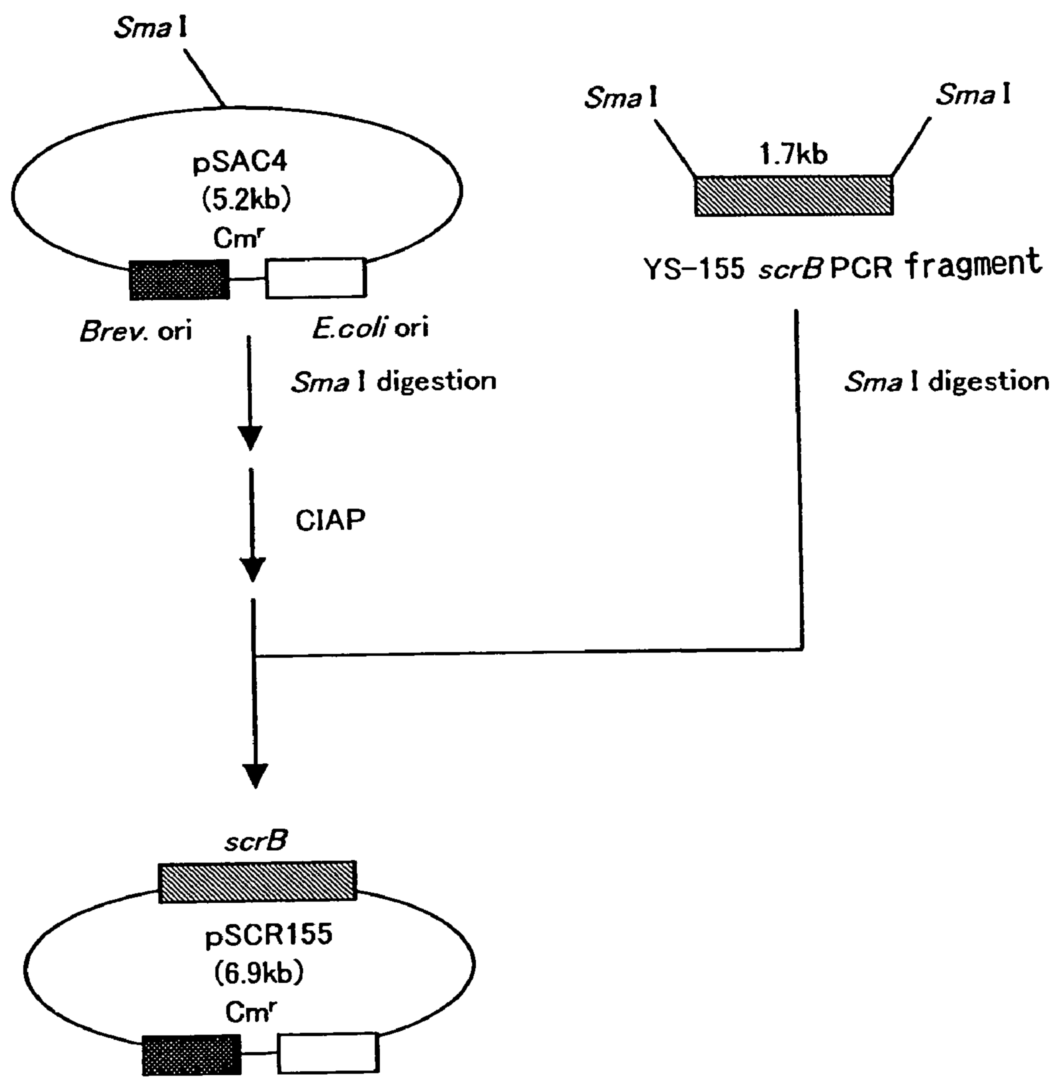
FIG. 16 shows construction of plasmid pSCR155 carrying scrB gene.

Then, the above amplified fragment was digested with SmaI (Takara Shuzo), and ligated to plasmid pSAC4 containing a dephosphorylated replication origin functioning in coryneform bacteria, which had been digested with SmaI, to prepare pSCR155. The construction of pSCR155 is shown in FIG. 16. pSAC4 was produced as follows. In order to make the vector for *Escherichia coli* pHSG399 (Takara Shuzo) autonomously replicable in coryneform bacteria, the replication origin (Japanese Patent Laid-open No. 5-7491/1993) derived from the already obtained plasmid pHM1519 autonomously replicable in coryneform bacteria (Miwa, k.et al., Agric. Biol. Chem., 48 (1984) 2901–2903) was introduced into it. Specifically, pHM1519 was digested with restriction enzymes BamHI and KpnI, and the obtained fragment containing the replication origin was blunt-ended by using a Blunting kit produced by Takara Shuzo and inserted into pHSG399 at the SalI site by using an SalI linker (produced by Takara Shuzo) to obtain pSAC4.

<2> Transfer of Plasmid Carrying scrB Gene into AJ12310 Strain pSCR155 produced above and plasmid pSSM30BS (Japanese Patent Laid-open No. 08-196280/1996) carrying the scrB gene derived from *Brevibacterium lactofermentum* were introduced into the *Corynebacterium thermoaminogenes* AJ12310 strain. The transformation was performed according to the following procedure. The cells were inoculated to CM-2B medium containing 20% sucrose in such an amount that $OD_{660}$ of the medium should become 0.1, and cultured at 37° C. with shaking until the $OD_{660}$ become 0.3. Lysozyme was added to the medium at a concentration of 100 μg/ml, and the cells were further cultured for 2 hours. The cells were washed three times with 20% sucrose, suspended in 20% sucrose, added with the plasmid collected from *Escherichia coli* JM110, mixed sufficiently, and applied with an electric pulse (18 kV/cm, 300 msec) to be introduced with the DNA. After the cells were subjected to restoration culture overnight in CM-2B medium containing 20% sucrose, transformants were selected on CM-2B agar medium containing 5 μg/ml of chloramphenicol. Specifically, the transformation was performed by the electric pulse method (Japanese Patent Laid-open No. 12-204236/2000, and the selection of transformants was performed on CM2B plate medium containing 5 μg/ml of chloramphenicol at 37° C. As a result, any transformant harboring the plasmid pSSM30BS carrying scrB derived from *Brevibacterium lactofermentum* was not obtained, but only a transformant harboring the plasmid pSCR155 carrying scrB derived from *Corynebacterium thermoaminogenes* was obtained. This strain was designated as AJ12310/pSCR155.

<3> Evaluation of Culture of AJ12310/pSCR155 Strain using Sucrose as Sugar Source AJ12310/pSCR155 prepared above was inoculated to a medium having the composition shown in Table 15, and cultured at 37° C. for 22 hours with shaking. The absorbance (OD) and residual sugar (RS) of the medium were measured after the culture. The results are shown in Table 16. As a result, it was confirmed that, while the AJ12310 strain could not assimilate sucrose and hence could not grow, the scrB gene introduced strain, the AJ12310/pSCR155 strain, became to be able to assimilate sucrose.

TABLE 15

| Medium composition | |
|---|---|
| Medium composition | Concentration |
| Sucrose | 60 g/l |
| $KH_2PO_4$ | 1 g/l |
| $MgSO_4.7H_2O$ | 0.4 g/l |
| $FeSO_4.7H_2O$ | 0.01 g/l |
| $MnSO_4.7H_2O$ | 0.01 g/l |
| $(NH_4)_2SO_4$ | 30 g/l |
| Soybean protein hydrolysate | 480 mg/l |
| Thiamin hydrochloride | 200 μg/l |
| Biotin | 300 μg/l |

TABLE 16

| Result of sucrose culture | | |
|---|---|---|
| | OD (×51) | RS (g/l) |
| 2256 | 1.292 | 0.00 |
| AJ12310 | 0.058 | 60.00 |
| AJ12310/pSCR155 | 1.571 | 0.84 |

EXAMPLE 6

L-glutamic Acid Production by pdhA Gene-Amplified Strain

<1> Construction of Plasmid pPDHA-2 Carrying pdha

Figure 17:
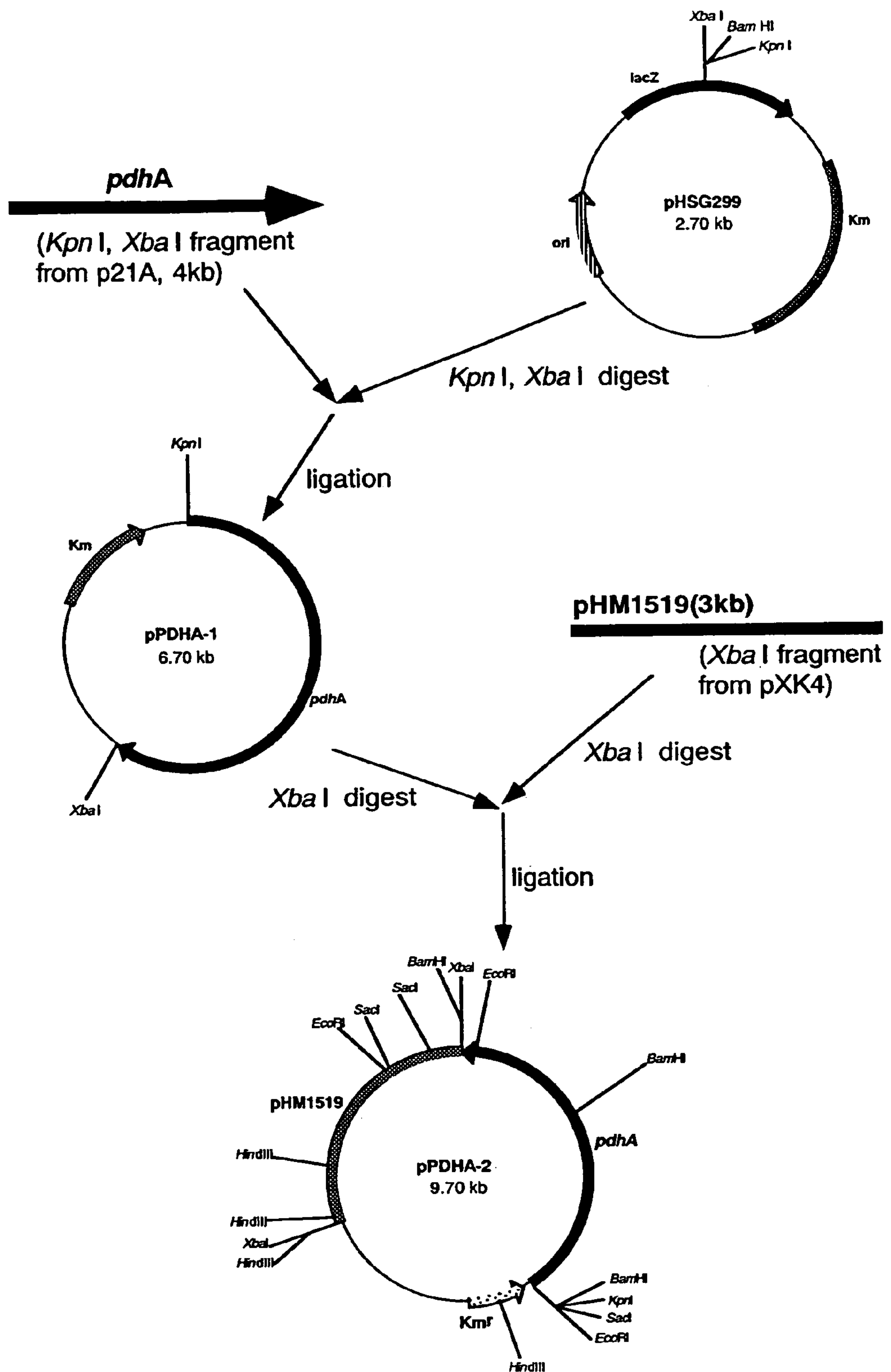
FIG. 17 shows construction of plasmid pPDHA-2 carrying pdhA gene.

The pdhA gene derived from the *Corynebacterium thermoaminogenes* AJ12310 strain was obtained by screening of a plasmid library. Specifically, PCR was performed with the conditions shown in Example 1, Table 4, using a plasmid library mixture as a template, and a clone p21A was selected, from which a DNA fragment of the same size is amplified as obtained in PCR using chromosomal DNA as a template. The DNA sequence of this plasmid was determined to confirm that the full length of pdhA was contained in it.

p21A was digested with XbaI and KpnI to excise a DNA fragment of 4 kb containing the full length of the pdhA gene and a promoter region. This DNA fragment containing the pdha gene was inserted into the XbaI and KpnI sites of pHSG299 (Takara Shuzo). Then, this plasmid was digested with XbaI, and a fragment obtained by digesting pXK4 with XbaI was inserted to prepare pPDHA-2. The construction process of pPDHA-2 is shown in FIG. 17. A DNA Ligation Kit Ver.2 (Takara Shuzo) was used for the ligation reaction, and *Escherichia coli* JM109 strain (Takara Shuzo) was used as the host of genetic manipulation. The aforementioned pXK4 was produced as follows. A shuttle vector pHK4 for coryneform bacteria and *Escherichia coli* (Japanese Patent Laid-open No. 5-7491/1993) was digested with restriction enzymes BamHI and KpnI to obtain a DNA fragment containing the replication origin, and the obtained fragment was blunt-ended by using a DNA blunting kit (Blunting Kit produced by Takara Shuzo), ligated to an XbaI linker (produced by Takara Shuzo) and inserted into pHSG299 at the XbaI site to obtain the plasmid pKX4.

<2> Transfer of Plasmid Carrying pdhA Gene into AJ12310 Strain

The plasmid pPDHA-2 produced above was introduced into the *Corynebacterium thermoaminogenes* AJ12310 strain to prepare a pdhA gene-amplified strain. The transformation was performed in the same manner as Example 5, and a transformant was selected on CM-2B agar medium containing 25 μg/ml kanamycin to obtain AJ12310/pPDHA-2 strain.

<3> L-glutamic Acid Production by pdhA-amplified Strain

Figure 18:
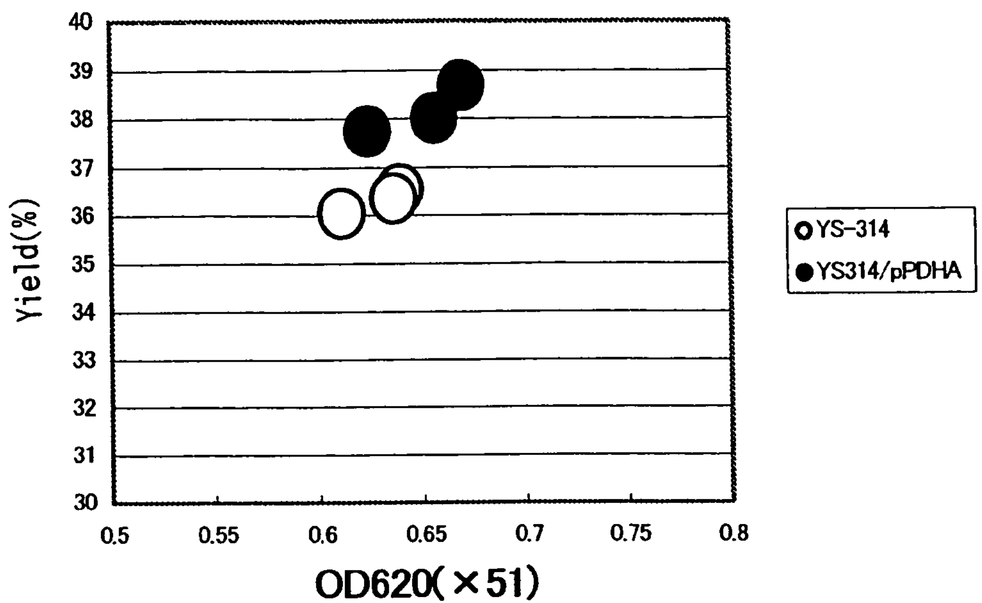
FIG. 18 shows L-glutamic acid productivity of a pdhA gene-amplified strain: (a) 37° C. and (b) 44° C.
Figure 18:
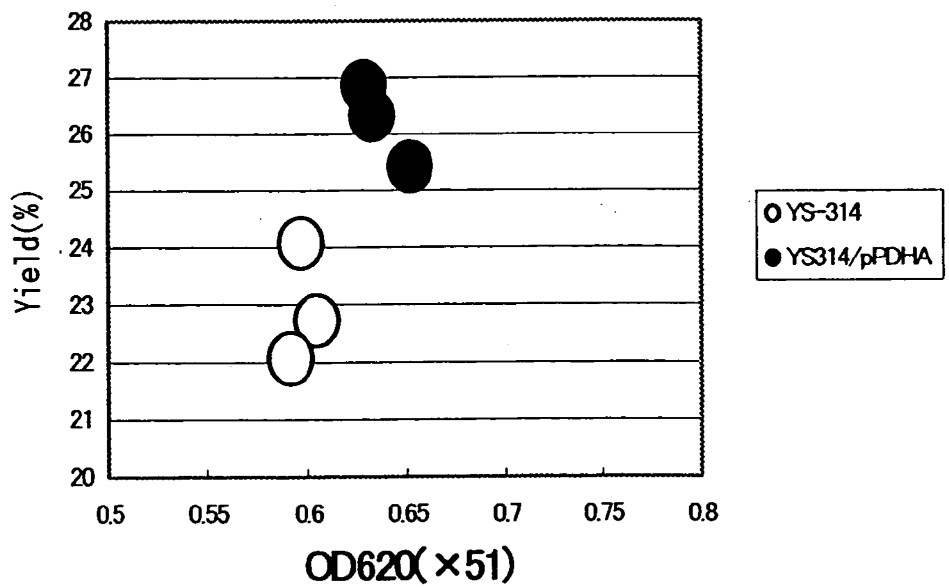

The AJ12310 strain and the pdhA gene-amplified strain obtained above, AJ12310/pPDHA-2 strain, both of which were grown on CM-2B agar medium, were each inoculated to a 500-ml volume flask containing 20 ml of a medium for seed culture flask shown in Table 17, and cultured at 37° C. with shaking until glucose was completely consumed. 2 ml of this culture broth was inoculated into 500 ml-volume flask containing 20 ml of a medium for main culture flask shown in Table 17, and cultured as main culture at 37° C. and 44° C. The main culture was continued until glucose was completely consumed. After the culture, $OD_{620}$ of the medium and accumulated amount of L-glutamic acid were measured to examine the effect of the gene amplification on the cell formation and production of glutamic acid. The measurement of OD was performed by using a spectrophotometer HITACHI U-2000 (Hitachi), and L-glutamic acid concentration was measured by using a glutamic acid analyzer AS-210 (Asahi Chemical Industry). The results are shown in FIG. 18.

The pdhA gene-amplified strain, AJ12310/pPDHA-2 strain, showed increased L-glutamic acid accumulation and increased OD compared with the AJ12310 strain, and thus it became clear that the amplification of the pdhA gene was effective for L-glutamic acid production.

TABLE 17

| Medium for evaluation of pdhA-amplified strain | | |
|---|---|---|
| Medium composition | Seed culture | Main culture |
| Sucrose | 30 g/l | 60 g/l |
| $KH_2PO_4$ | 1 g/l | 1 g/l |
| $MgSO_4.7H_2O$ | 0.4 g/l | 0.4 g/l |
| $FeSO_4.7H_2O$ | 0.01 g/l | 0.01 g/l |
| $MnSO_4.7H_2O$ | 0.01 g/l | 0.01 g/l |
| $(NH_4)_2SO_4$ | 15 g/l | 30 g/l |
| Soybean protein hydrolysate | 480 mg/l | 480 mg/l |
| Thiamin hydrochloride | 200 μg/l | 200 μg/l |
| Biotin | 10 μg/l | |
| AZ-20R (anti-foaming agent) | 20 μg/l | 20 μg/l |
| $CaCO_3$ (separately sterilized) | 50 g/L | 50 g/L |

pH 8.0 (adjusted with KOH)

EXAMPLE 7

L-glutamic Acid Production by icd Gene-Amplified Strain

<1> Construction of plasmid pICD-4 carrying icd derived from *Corynebacterium thermoaminogenes* AJ12310 Strain Based on the icd gene sequence of the AJ12310 strain shown in SEQ ID NO: 29, the primers shown in SEQ ID NO: 103 and SEQ ID NO: 104 were synthesized. A BglII site was introduced into 5' end of the both primers. Separately, genomic DNA of the *Corynebacterium thermoaminogenes* AJ12310 strain was prepared by using a Genomic DNA Purif. Kit (Edge BioSystems). Sterilized water was added to the genome DNA as a template, 100 pmol each of the aforementioned primers, 8 μl of dNTP mixture (2.5 mM each), 10 μl of 10× Pyrobest Buffer II (Takara Shuzo) and 2.5 U of Pyrobest polymerase (Takara Shuzo) to prepare a PCR reaction mixture in a total volume of 100 μl. PCR was performed with a cycle of denaturation at 98° C. for 10 seconds, association at 55° C. for 1 minute and extension reaction at 72° C. for 4 minutes, which was repeated for 30 cycles, by using the above reaction mixture and a thermal cycler TP240 (Takara Shuzo) to amplify a DNA fragment of about 3.3 kb containing the icd gene and its promoter.

Figure 19:
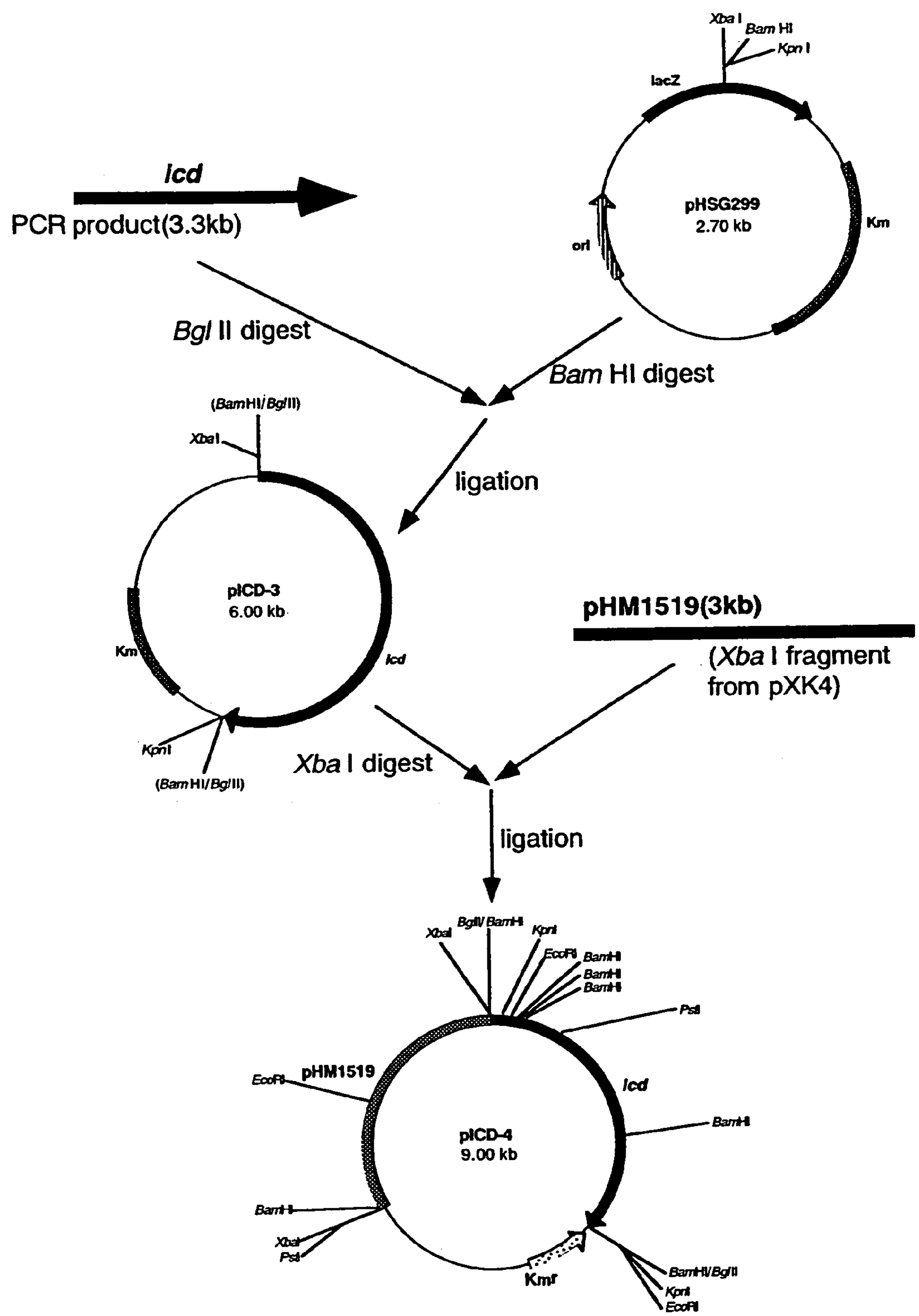
FIG. 19 shows is construction of a plasmid pICD-4 carrying icd gene.

Then, this DNA fragment containing the icd gene was digested with BglII, and ligated to pHSG299 (Takara Shuzo) at the BamHI site. This plasmid was then treated with XbaI, and a fragment obtained by digesting pXK4 with XbaI was inserted into the plasmid to construct pICD-4. The construction procedure of pICD-4 is shown in FIG. 19. A DNA Ligation Kit Ver.2 (Takara Shuzo) was used for the ligation reaction, and *Escherichia coli* JM109 strain (Takara Shuzo) was used as the host of genetic manipulation.

<2> Transfer of Plasmid Carrying icd Gene into AJ12310 Strain

The plasmid pICD-4 produced above was introduced into the *Corynebacterium thermoaminogenes* AJ12310 strain to prepare an icd gene-amplified strain. The transformation was performed in the same manner as Example 5, and a transformant was selected on CM-2B agar medium containing 25 μg/ml kanamycin to obtain AJ12310/pICD-4 strain.

<3> L-glutamic Acid Production by icd-Amplified Strain

Figure 20:
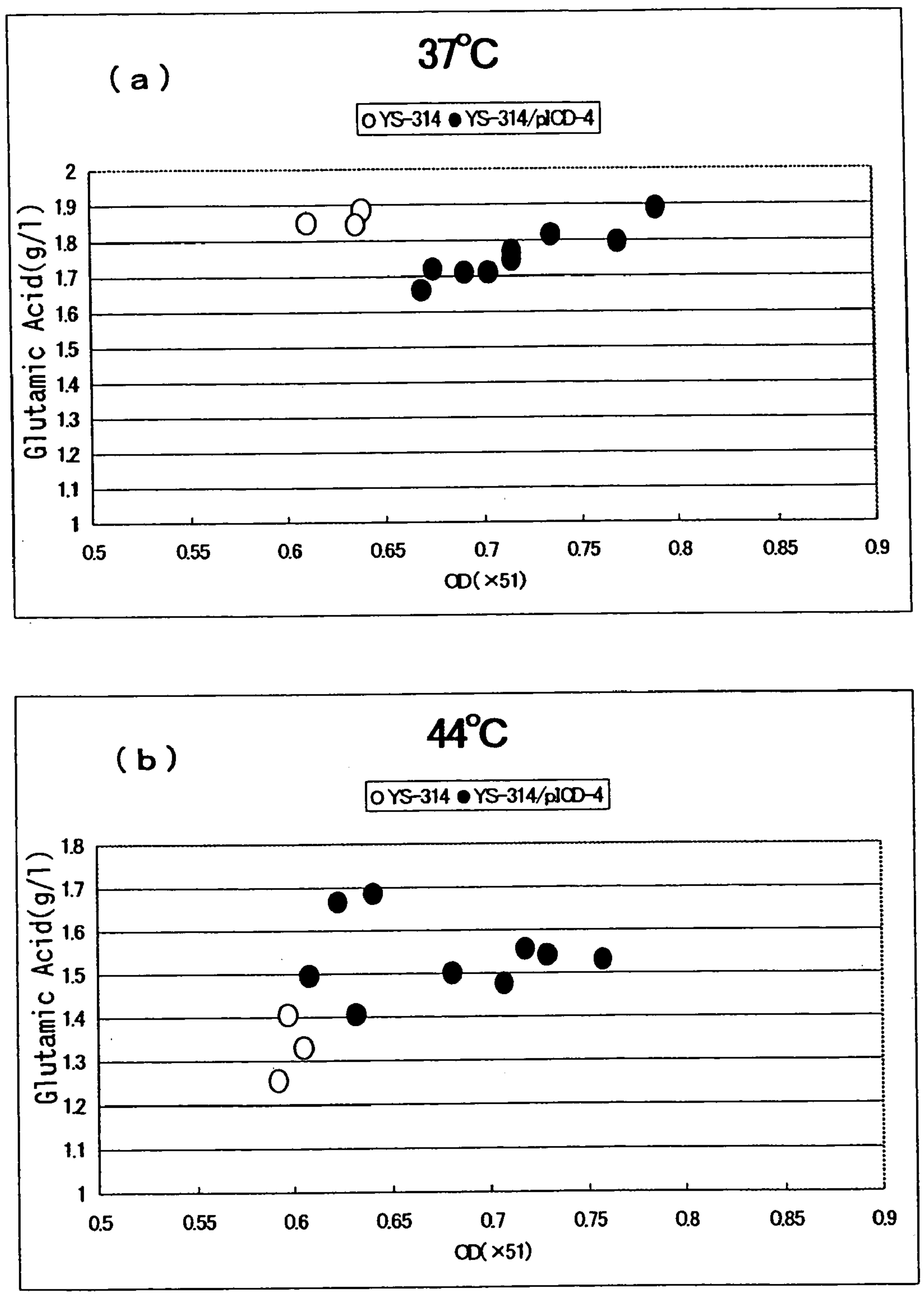
FIG. 20 shows L-glutamic acid productivity of an icd gene-amplified strain: (a) 37° C. and (b) 44° C.

Culture evaluation was performed for the AJ12310 strain and the icd-amplified strain thereof, AJ12310/pICD, by the culture method described in Example 6. The results are shown in FIG. 20. The icd gene-amplified strain AJ12310/pICD-4 strain showed increased L-glutamic acid accumulation and increased OD compared with the AJ12310 strain, and thus it became clear that the amplification of the icd gene was effective for L-glutamic acid production.

EXAMPLE 8

L-glutamic Acid Production by gdh Gene-Amplified Strain

<1> Construction of Plasmid Carrying gdh Derived from *Corynebacterium thermoaminogenes* AJ12310 Strain Based on the gdh gene sequence of the AJ12310 strain shown in SEQ ID NO: 79, the primers shown in SEQ ID NO: 105 and SEQ ID NO: 106 were synthesized.

Separately, chromosomal DNA of the AJ12310 strain was prepared by using a Bacterial Genome DNA Purification Kit (Advanced Genetic Technologies Corp.). Sterilized water was added to 0.5 μg of this chromosomal DNA, 10 pmol each of the aforementioned oligonucleotides, 8 μl of dNTP mixture (2.5 mM each), 5 μl of 10×LA Taq Buffer (Takara Shuzo) and 2 U of LA Taq (Takara Shuzo) to prepare a PCR reaction mixture in a total volume of 50 μl. PCR was performed with a cycle of denaturation at 94° C. for 30 seconds, association at 55° C. for 1 second and extension reaction at 72° C. for 3 minutes, which was repeated for 30 cycles, by using the above reaction mixture and a thermal cycler TP240 (Takara Shuzo) to amplify a DNA fragment of about 2 kb containing the gdh gene and its promoter. The obtained amplified fragment was digested with PstI (Takara Shuzo), mixed with pHSG299 (Takara Shuzo) fully digested with PstI and ligated to it. A DNA Ligation Kit Ver. 2 produced by Takara Shuzo was used for the ligation reaction. After the ligation, competent cells of *Escherichia coli* JM109 (produced by Takara Shuzo) were transformed with the ligation product, plated on L medium (10 g/l of Bacto-trypton, 5 g/l of Bacto-yeast extract, 5 g/l of NaCl, 15 g/l of agar, pH 7.2) containing 10 μg/ml of IPTG (isopropyl-β-D-thiogalactopyranoside), 40 μg/ml of X-Gal (5-bromo-4-chloro-3-indolyl-β-D-galactoside) and 40 μg/ml of chloramphenicol, and cultured overnight. The emerged white colonies were picked up and subjected to single colony separation to obtain transformants.

Figure 21:
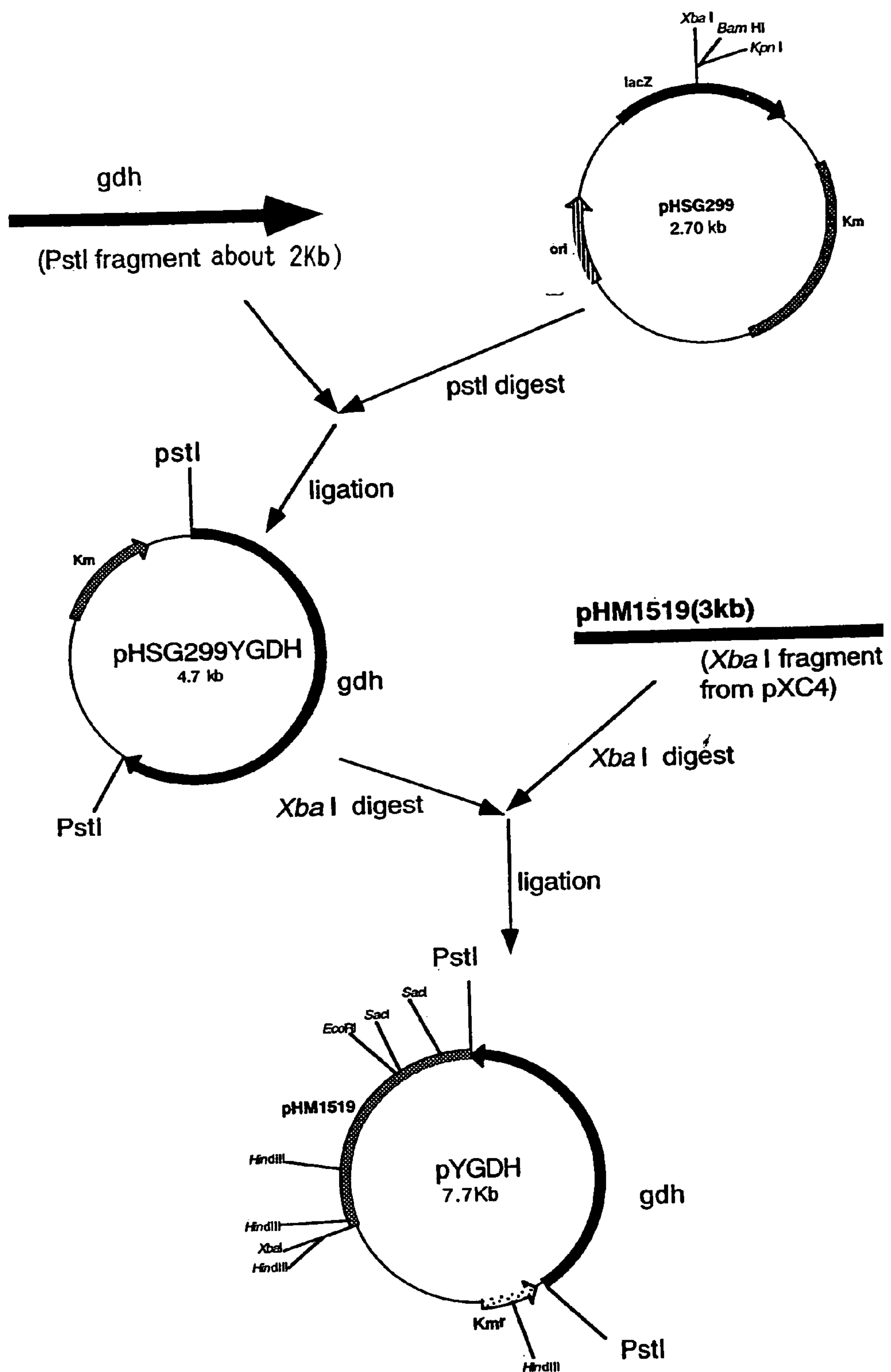
FIG. 21 shows construction of plasmids pHSG299YGDH and PYGDH.

Plasmids were prepared from the transformants by the alkali method (Text for Bioengineering Experiments, Edited by the Society for Bioscience and Bioengineering, Japan, p. 105, Baifukan, 1992) and their restriction maps were prepared. A plasmid having a restriction map equivalent to that shown in FIG. 21 was designated as pHSG299YGDH.

A replication origin that functions in coryneform bacteria was introduced into this pHSG299YGDH. Specifically, pXC4 was digested with a restriction enzyme XbaI to obtain a fragment containing a replication origin derived from pHM1519, and it was mixed with pHSG299YGDH fully digested with XbaI and ligated to it. Plasmids were prepared in the same manner as above and a plasmid having a restriction map equivalent to that shown in FIG. 21 was designated as pYGDH. pXC4 was constructed in the same manner as that for pXK4 mentioned in Example 6 except that pHSG399 ($Cm^r$) was used instead of pHSG299.

<2> Transfer of Plasmid Carrying gdh Gene into AJ12310

The plasmid produced above was introduced into the *Corynebacterium thermoaminogenes* AJ12310 strain to prepare a gdh gene-amplified strain. The transformation was performed in the same manner as Example 5, and a transformant was selected on CM-2B agar medium containing 25 μg/ml kanamycin at 31° C. to obtain AJ12310/pYGDH.

<3> L-glutamic Acid Production by gdh-Amplified Strain

The AJ12310 strain and the gdh gene-amplified strain obtained above, AJ12310/pYGDH strain, both of which were grown on CM-2B agar medium, were each inoculated to a 500-ml volume flask containing 20 ml of a medium for seed culture flask shown in Table 18, and cultured at 37° C. with shaking until glucose was completely consumed. 2 ml of this culture broth was inoculated into 500 ml-volume flask containing 20 ml of a medium for main culture flask shown in Table 19, and cultured as main culture at 37° C. and 44° C. The main culture was continued until glucose was completely consumed. After completion of the culture, $OD_{620}$ of the medium and accumulated amount of L-glutamic acid were measured to examine the effect of the gene amplification on the cell formation and production of glutamic acid. The measurement of OD was performed by using a spectrophotometer HITACHI U-2000 (Hitachi), and L-glutamic acid concentration was measured by using a glutamic acid analyzer AS-210 (Asahi Chemical Industry).

TABLE 18

Composition of medium for seed culture

| Medium composition | Concentration |
| --- | --- |
| Glucose | 30 g/l |
| Ammonium sulfate | 15 g/l |
| $KH_2PO_4$ | 1 g/l |
| $MgSO_4.7H_2O$ | 0.4 g/l |
| $FeSO_4.7H_2O$ | 0.01 g/l |

TABLE 18-continued

| Composition of medium for seed culture | |
|---|---|
| Medium composition | Concentration |
| $MnSO_4.7H_2O$ | 0.01 g/l |
| Soybean protein hydrolysate | 0.48 g/l |
| Thiamin hydrochloride | 200 μg/l |
| Biotin | 10 μg/l |
| AZ20R | 0.02 ml/l |
| $CaCO_3$ (separately sterilized) | 1 g/L |

pH 8.0 (adjusted with KOH)

TABLE 19

| Composition of medium for main culture | |
|---|---|
| Medium composition | Concentration |
| Glucose | 60 g/l |
| Ammonium sulfate | 30 g/l |
| $KH_2PO_4$ | 1 g/l |
| $MgSO_4.7H_2O$ | 0.4 g/l |
| $FeSO_4.7H_2O$ | 0.01 g/l |
| $MnSO_4.7H_2O$ | 0.01 g/l |
| Soybean protein hydrolysate | 0.48 g/l |
| Thiamin hydrochloride | 200 μg/l |
| AZ20R | 0.02 ml/l |
| $CaCO_3$ (separately sterilized) | 1 g/L |

PH 8.0 (adjusted with KOH)

The results of the culture are shown in Table 20 and Table 21. At 37° C., the gdh-amplified strain showed higher saccharide consuming rate, better growth and higher attained OD compared with the parent strain, the AJ12310 strain. Moreover, both of the L-glutamic acid accumulation and the yield were markedly improved, i.e., 5–7%, at 37° C. Also at 44° C., the yield was improved, and the attained OD increased. On the other hand, it was confirmed that accumulation of α-ketoglutaric acid was decreased in the gdh-amplified strain. These results demonstrate that the amplification of gdh is effective for improvement in L-glutamic acid yield and reduction of byproduct.

TABLE 20

Culture result of gdh-amplified strain (37° C.)

| | $OD_{620}$ (51×) | L-Glu accumulation (g/dl) | L-Glu yield (%) | α-KG (mg/dl) |
|---|---|---|---|---|
| AJ12310 | 0.58 | 1.74 | 30.7 | 53.9 |
| AJ12310/PYGDH | 0.65 | 2.23 | 39.3 | 4.1 |

TABLE 21

Culture result of gdh-amplified strain (44° C.)

| | $OD_{620}$ (51×) | L-Glu accumulation (g/dl) | L-Glu yield (%) |
|---|---|---|---|
| AJ12310 | 0.63 | 1.70 | 26.7 |
| AJ12310/pYGDH | 0.71 | 1.79 | 27.8 |

EXAMPLE 9

L-glutamic Acid Production by gltA Gene-Amplified Strain

<1> Construction of Plasmid Carrying gltA Gene Derived from *Corynebacterium thermoaminogenes*

Based on the gltA gene sequence of the AJ12310 strain shown in SEQ ID NO: 89, the primers shown in SEQ ID NO: 107 and SEQ ID NO: 108 were synthesized.

Separately, chromosomal DNA of the AJ12310 strain was prepared by using a Bacterial Genome DNA Purification Kit (Advanced Genetic Technologies Corp.). Sterilized water was added to 0.5 μg of this chromosomal DNA, 10 pmol each of the aforementioned oligonucleotides, 8 μl of dNTP mixture (2.5 mM each), 10 μl of 10× Pyrobest-Taq Buffer (Takara Shuzo) and 2 U of Pyrobest Taq (Takara Shuzo) to prepare a PCR reaction mixture in a total volume of 100 μl. PCR was performed with a cycle of denaturation at 94° C. for 30 seconds, association at 45° C. for 30 seconds and extension reaction at 72° C. for 3 minutes, which was repeated for 30 cycles, by using the above reaction mixture and a thermal cycler TP240 (Takara Shuzo) to amplify a DNA fragment of about 2 kb containing the gltA gene and its promoter. The obtained amplified fragment was digested with KpnI (Takara Shuzo), mixed with pHSG299 (Takara Shuzo) fully digested with KpnI and ligated to it. A DNA Ligation Kit Ver.2 produced by Takara Shuzo was used for the ligation reaction. After the ligation, competent cells of *Escherichia coli* JM109 (produced by Takara Shuzo) were transformed with the ligation product, plated on L medium (10 g/l of Bacto-trypton, 5 g/l of Bacto-yeast extract, 5 g/l of NaCl, 15 g/l of agar, pH 7.2) containing 10 μg/ml of IPTG (isopropyl-β-D-thiogalactopyranoside), 40 μg/ml of X-Gal (5-bromo-4-chloro-3-indolyl-β-D-galactoside) and 40 μg/ml of chloramphenicol, and cultured overnight. The emerged white colonies were picked up and subjected to single colony separation to obtain transformants.

Figure 22:
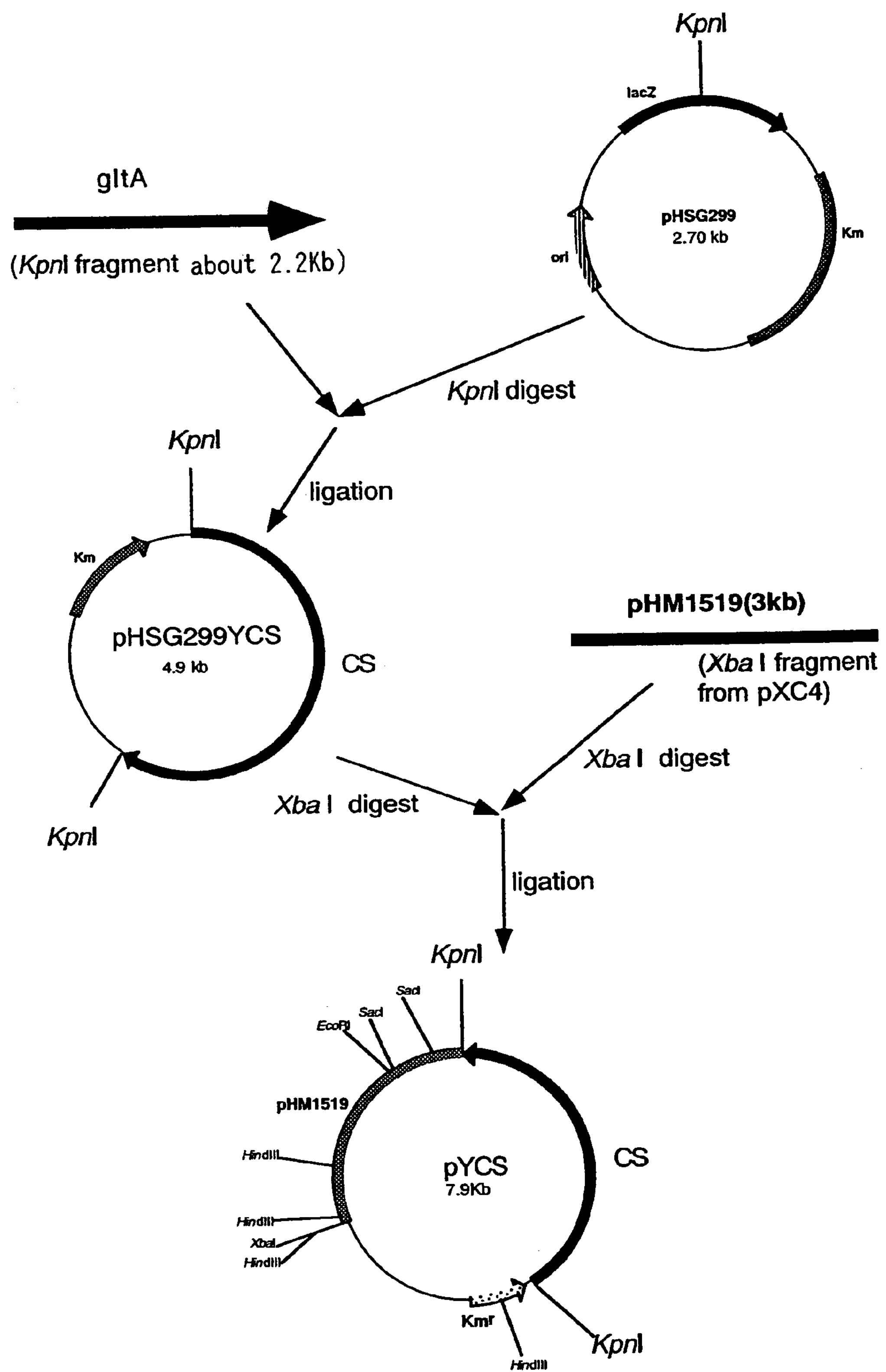
FIG. 22 shows construction of plasmids pHSG299YCS and pYCS.

Plasmids were prepared from the transformants by the alkali method (Text for Bioengineering Experiments, Edited by the Society for Bioscience and Bioengineering, Japan, p. 105, Baifukan, 1992) and their restriction maps were prepared. A plasmid having a restriction map equivalent to that shown in FIG. 22 was designated as pHSG299YCS.

A replication origin that is replicable in coryneform bacteria was introduced into this pHSG299YCS. Specifically, pXC4 was digested with a restriction enzyme XbaI to obtain a fragment containing a replication origin derived from pHM1519, and it was mixed with pHSG299YCS fully digested with XbaI and ligated to it. Plasmids were prepared in the same manner as above and a plasmid having a restriction map equivalent to that shown in FIG. 22 was designated as pYCS.

<2> Transfer of Plasmid Carrying gltA Gene into AJ12310 Strain

The plasmid produced above was introduced into the *Corynebacterium thermoaminogenes* AJ12310 strain to prepare a gltA gene-amplified strain. The transformation was performed in the same manner as Example 5, and a transformant was selected on CM-2B agar medium containing 25 μg/ml kanamycin to obtain AJ12310/pYCS.

<3> L-glutamic Acid Production by gltA-Amplified Strain

The AJ12310 strain and the gltA gene-amplified strain obtained above, AJ12310/pYCS strain, both of which were grown on CM-2B agar medium, were cultured in the same manner as in Example 8. The results of the culture are shown in Table 22 and Table 23. Both at the culture temperatures, 37° C. and 44° C., the CS-enhanced strain showed improved glutamic acid accumulation compared with the parent strain. Further, the gltA-amplified strain showed decreased L-aspartic acid and L-lysine, which are synthesized from oxaloacetic acid.

These results demonstrate that the amplification of gltA is effective for improvement of L-glutamic acid yield and reduction of byproduct.

TABLE 22

Culture result of gltA-amplified strain (37° C.)

| | L-Glu accumulation (g/dl) | Yield (%) | L-Asp accumulation (mg/dl) | L-Lys accumulation (mg/dl) |
|---|---|---|---|---|
| AJ12310 | 1.79 | 31.9 | 11.8 | 11.0 |
| AJ12310/pYCS | 2.04 | 36.5 | 8.1 | 7.3 |

TABLE 23

Culture result of gltA-amplified strain (44° C.)

| | OD | L-Glu accumulation (g/dl) | Yield (%) | L-Asp accumulation (mg/dl) | L-Lys Accumulation (mg/dl) |
|---|---|---|---|---|---|
| AJ12310 | 0.58 | 1.38 | 21.8 | 23.3 | 29.2 |
| AJ12310/pYCS | 0.65 | 1.84 | 28.8 | 14.1 | 17.2 |

Explanation of Sequence Listing

SEQ ID NO: 1: aceA, nucleotide sequence
SEQ ID NO: 2: aceA, amino acid sequence
SEQ ID NO: 3: accBC, nucleotide sequence
SEQ ID NO: 4: accBC, amino acid sequence
SEQ ID NO: 5: dtsR1, nucleotide sequence
SEQ ID NO: 6: dtsR1, amino acid sequence
SEQ ID NO: 7: dtsR2, nucleotide sequence
SEQ ID NO: 8: dtsR2, amino acid sequence
SEQ ID NO: 9: pfk, nucleotide sequence
SEQ ID NO: 10: pfk, amino acid sequence
SEQ ID NO: 11: scrB (AJ12340), nucleotide sequence
SEQ ID NO: 12: scrB (AJ12340), amino acid sequence
SEQ ID NO: 13: scrB (AJ12309), nucleotide sequence
SEQ ID NO: 14: scrB (AJ12309), amino acid sequence
SEQ ID NO: 15: scrB (AJ12310), nucleotide sequence
SEQ ID NO: 16: gluABCD, nucleotide sequence
SEQ ID NO: 17: gluABCD, amino acid sequence
SEQ ID NO: 18: gluABCD, amino acid sequence
SEQ ID NO: 19: gluABCD, amino acid sequence
SEQ ID NO: 20: gluABCD, amino acid sequence
SEQ ID NO: 21: pdhA, nucleotide sequence
SEQ ID NO: 22: pdhA, amino acid sequence
SEQ ID NO: 23: pc, nucleotide sequence
SEQ ID NO: 24: pc, amino acid sequence
SEQ ID NO: 25: ppc, nucleotide sequence
SEQ ID NO: 26: ppc, amino acid sequence
SEQ ID NO: 27: acn, nucleotide sequence
SEQ ID NO: 28: acn, amino acid sequence
SEQ ID NO: 29: icd, nucleotide sequence
SEQ ID NO: 30: icd, amino acid sequence
SEQ ID NO: 31: lpd, nucleotide sequence
SEQ ID NO: 32: lpd, amino acid sequence
SEQ ID NO: 33: odhA, nucleotide sequence
SEQ ID NO: 34: odhA, amino acid sequence
SEQ ID NO: 79: gdh (AJ12310), nucleotide sequence
SEQ ID NO: 80: gdh (AJ12310), amino acid sequence
SEQ ID NO: 81: gdh (2256), nucleotide sequence
SEQ ID NO: 82: gdh (2256), amino acid sequence
SEQ ID NO: 89: gltA (AJ12310), nucleotide sequence
SEQ ID NO: 90: gltA (AJ12310), amino acid sequence
SEQ ID NO: 91: gltA (2256), nucleotide sequence
SEQ ID NO: 92: gltA (2256), amino acid sequence
SEQ ID NO: 93: scrB (AJ12309), nucleotide sequence
SEQ ID NO: 94: scrB (AJ12309), amino acid sequence

INDUSTRIAL APPLICABILITY

According to the present invention, genes coding for enzymes of amino acid biosynthetic pathway derived from *Corynebacterium thermoaminogenes*, or genes coding for proteins involved in the amino acid uptake into cells.

The genes of the present invention can be utilized for the production of the aforementioned enzymes or proteins, or the breeding of amino acid producing bacteria.

What is claimed is:

1. An isolated DNA which codes for a protein consisting of the amino acid sequence of SEQ ID NO: 90 wherein said protein has citrate synthase activity at 37° C. in an equivalent or higher degree compared with the activity at 23° C.

2. An isolated DNA which consists of the nucleotide sequence of SEQ ID NO: 89 wherein said isolated DNA codes a protein having citrate synthase activity at 37° C. in an equivalent or higher degree compared with the activity at 23° C.

3. An isolated DNA which is hybridizable with the nucleotide sequence of SEQ ID NO: 89 under a stringent condition, and codes for a protein showing citrate synthase activity at 37° C. in an equivalent or higher degree compared with the activity at 23° C., and having the amino acid sequence of SEQ ID NO: 90 or the amino acid sequence of SEQ ID NO: 90 including substitution, deletion, insertion, addition, or inversion of one to ten amino acid residues, wherein the stringent condition is 60° C., 1×SSC and 0.1% SDS.

4. A method for producing L-amino acid, which comprises culturing a microorganism introduced with a DNA according to claim 1 in a medium to produce and accumulate L-amino acid in the medium, and collecting the L-amino acid from the medium.

5. A method for producing L-amino acid, which comprises culturing a microorganism introduced with a DNA according to claim 2 in a medium to produce and accumulate L-amino acid in the medium, and collecting the L-amino acid from the medium.

6. A method for producing L-amino acid, which comprises culturing a microorganism introduced with a DNA according to claim 3 in a medium to produce and accumulate L-amino acid in the medium, and collecting the L-amino acid from the medium.

7. The method according to claim 4, wherein the microorganism is a coryneform bacterium.

8. The method according to claim 7, wherein said microorganism is *Corynebacterium glutamicum.*

9. The method according to claim 5, wherein the microorganism is a coryneform bacterium.

10. The method according to claim 9, wherein said microorganism is *Corynebacterium glutamicum.*

11. The method according to claim 6, wherein the microorganism is a coryneform bacterium.

12. The method according to claim 11, wherein said microorganism is *Corynebacterium glutamicum.*

13. The method according to claim 4, wherein the L-amino acid is L-glutamic acid.

14. The method according to claim 5, wherein the L-amino acid is L-glutamic acid.

15. The method according to claim 6, wherein the L-amino acid is L-glutamic acid.

16. The method according to claim 7, wherein said microorganism is *Corynebacterium thermoaminogenes.*

17. The method according to claim 16, wherein the L-amino acid is L-glutamic acid.

18. The method according to claim 9, wherein said microorganism is *Corynebacterium thermoaminogenes.*

19. The method according to claim 18, wherein the L-amino acid is L-glutamic acid.

20. The method according to claim 11, wherein said microorganism is *Corynebacterium thermoaminogenes.*

21. The method according to claim 20, wherein the L-amino acid is L-glutamic acid.

* * * * *